US012446880B2

United States Patent
(12) United States Patent
Shelton, IV et al.

(10) Patent No.: US 12,446,880 B2
(45) Date of Patent: Oct. 21, 2025

(54) ROBOTIC TOOL COMPRISING AN ARTICULATION LOCK

(71) Applicant: Cilag GmbH International, Zug (CH)

(72) Inventors: Frederick E. Shelton, IV, Hillsboro, OH (US); Jerome R. Morgan, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/659,609

(22) Filed: May 9, 2024

(65) Prior Publication Data

US 2024/0350139 A1 Oct. 24, 2024

Related U.S. Application Data

(63) Continuation of application No. 17/032,279, filed on Sep. 25, 2020, now Pat. No. 12,059,154, which is a (Continued)

(51) Int. Cl.

| | |
|---|---|
| ***A61B 17/10*** | (2006.01) |
| ***A61B 17/00*** | (2006.01) |
| ***A61B 17/068*** | (2006.01) |
| ***A61B 17/072*** | (2006.01) |
| ***A61B 34/00*** | (2016.01) |

(Continued)

(52) U.S. Cl.

CPC .......... *A61B 17/105* (2013.01); *A61B 17/068* (2013.01); *A61B 17/072* (2013.01); *A61B 17/07207* (2013.01); *A61B 34/30* (2016.02); *A61B 34/35* (2016.02); *A61B 34/37* (2016.02); *A61B 2017/00115* (2013.01); *A61B 2017/00398* (2013.01); *A61B 2017/00473* (2013.01); *A61B 2017/00477* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 34/71* (2016.02); *A61B 34/76* (2016.02); *Y10T 29/53404* (2015.01); *Y10T 29/53417* (2015.01); *Y10T 29/53687* (2015.01)

(58) Field of Classification Search

CPC ... A61B 17/105; A61B 17/068; A61B 17/072; A61B 17/07207; A61B 34/30; A61B 34/35; A61B 34/37; A61B 34/71; A61B 34/76; A61B 2017/00115; A61B 2017/00398; A61B 2017/00473; A61B 2017/00477; A61B 2017/07214; A61B 2017/07257; A61B 2017/07271; A61B 2017/07278; A61B 2017/07285; Y10T 29/53404; Y10T 29/53417; Y10T 29/53687

See application file for complete search history.

(56) References Cited

U.S. PATENT DOCUMENTS 5,219,111 A 6/1993 Bilotti et al.
5,632,432 A 5/1997 Schulze et al.

(Continued)

*Primary Examiner* — Eronica Martin

(57) ABSTRACT

A surgical stapling instrument. Various embodiments include an actuation system for selectively generating a plurality of control motions. A surgical end effector is operably coupled to the actuation system. The actuation system interfaces with an actuation member configured to operably engage rotatable camming members to fire staples within the end effector into forming contact with an anvil portion of the end effector.

18 Claims, 88 Drawing Sheets

Related U.S. Application Data continuation of application No. 15/796,257, filed on Oct. 27, 2017, now Pat. No. 11,129,616, which is a continuation of application No. 14/725,181, filed on May 29, 2015, now Pat. No. 10,130,366, which is a continuation of application No. 13/118,241, filed on May 27, 2011, now Pat. No. 9,072,535.

(51) Int. Cl.

| | |
|---|---|
| ***A61B 34/30*** | (2016.01) |
| ***A61B 34/35*** | (2016.01) |
| ***A61B 34/37*** | (2016.01) |

(56) References Cited

U.S. PATENT DOCUMENTS

| | | | |
|---|---|---|---|
| 5,673,841 | A | 10/1997 | Schulze et al. |
| 5,688,270 | A | 11/1997 | Yates et al. |
| 5,709,680 | A | 1/1998 | Yates et al. |
| 5,779,130 | A | 7/1998 | Alesi et al. |
| 5,792,135 | A | 8/1998 | Madhani et al. |
| 5,878,193 | A | 3/1999 | Wang et al. |
| 5,954,259 | A | 9/1999 | Viola et al. |
| 6,132,368 | A | 10/2000 | Cooper |
| 6,231,565 | B1 | 5/2001 | Tovey et al. |
| 6,364,888 | B1 | 4/2002 | Niemeyer et al. |
| 6,488,196 | B1 | 12/2002 | Fenton, Jr. |
| 6,722,552 | B2 | 4/2004 | Fenton, Jr. |
| 6,783,524 | B2 | 8/2004 | Anderson et al. |
| 6,835,199 | B2 | 12/2004 | McGuckin, Jr. et al. |
| 6,978,921 | B2 | 12/2005 | Shelton, IV et al. |
| 7,461,767 | B2 | 12/2008 | Viola et al. |
| 7,524,320 | B2 | 4/2009 | Tierney et al. |
| 7,568,603 | B2 | 8/2009 | Shelton, IV et al. |
| 7,607,557 | B2 | 10/2009 | Shelton, IV et al. |
| 7,617,961 | B2 | 11/2009 | Viola |
| 7,641,095 | B2 | 1/2010 | Viola |
| 7,673,781 | B2 | 3/2010 | Swayze et al. |
| 7,673,783 | B2 | 3/2010 | Morgan et al. |
| 7,691,098 | B2 | 4/2010 | Wallace et al. |
| 7,695,485 | B2 | 4/2010 | Whitman et al. |
| 7,721,936 | B2 | 5/2010 | Shalton, IV et al. |
| 7,726,537 | B2 | 6/2010 | Olson et al. |
| 7,780,055 | B2 | 8/2010 | Scirica et al. |
| 7,806,891 | B2 | 10/2010 | Nowlin et al. |
| 7,824,401 | B2 | 11/2010 | Manzo et al. |
| 7,959,051 | B2 | 6/2011 | Smith et al. |
| 7,963,433 | B2 | 6/2011 | Whitman et al. |
| 8,020,743 | B2 | 9/2011 | Shelton, IV |
| 8,083,119 | B2 | 12/2011 | Prommersberger |
| 8,167,185 | B2 | 5/2012 | Shelton, IV et al. |
| 8,241,322 | B2 | 8/2012 | Whitman et al. |
| 8,360,297 | B2 | 1/2013 | Shelton, IV et al. |
| 8,459,520 | B2 | 6/2013 | Giordano et al. |
| 8,584,921 | B2 | 11/2013 | Scirica |
| 8,684,253 | B2 | 4/2014 | Giordano et al. |
| 8,752,749 | B2 | 6/2014 | Moore et al. |
| 8,822,934 | B2 | 9/2014 | Sayeh et al. |
| 8,876,857 | B2 | 11/2014 | Burbank |
| 8,931,682 | B2 | 1/2015 | Timm et al. |
| 8,992,422 | B2 | 3/2015 | Spivey et al. |
| 9,060,770 | B2 | 6/2015 | Shelton, IV et al. |
| 9,072,535 | B2 | 7/2015 | Shelton, IV et al. |
| 9,179,912 | B2 | 11/2015 | Yates et al. |
| 9,237,891 | B2 | 1/2016 | Shelton, IV |
| 9,386,983 | B2 | 7/2016 | Swensgard et al. |
| 10,071,452 | B2 | 9/2018 | Shelton, IV et al. |
| 10,130,366 | B2 | 11/2018 | Shelton, IV et al. |
| 10,271,847 | B2 | 4/2019 | Racenet et al. |
| 2003/0083673 | A1* | 5/2003 | Tierney .............. H01H 36/0046 606/130 |
| 2005/0131390 | A1 | 6/2005 | Heinrich et al. |
| 2007/0225562 | A1* | 9/2007 | Spivey ................. A61B 1/0057 600/121 |
| 2008/0308603 | A1* | 12/2008 | Shelton ............ A61B 17/07207 227/175.1 |
| 2009/0206131 | A1 | 8/2009 | Weisenburgh, II et al. |
| 2011/0290856 | A1 | 12/2011 | Shelton, IV et al. |
| 2011/0295295 | A1 | 12/2011 | Shelton, IV et al. |
| 2021/0085325 | A1 | 3/2021 | Shelton, IV et al. |

* cited by examiner

ROBOTIC TOOL COMPRISING AN ARTICULATION LOCK

CROSS REFERENCE TO RELATED APPLICATIONS

This application is a continuation application claiming priority under 35 U.S.C. § 120 to U.S. patent application Ser. No. 17/032,279, entitled SURGICAL INSTRUMENT WITH DETACHABLE MOTOR CONTROL UNIT, filed Sep. 25, 2020, which issued on Aug. 13, 2024 as U.S. Pat. No. 12,059,154, which is a continuation application claiming priority under 35 U.S.C. § 120 to U.S. patent application Ser. No. 15/796,257, entitled SURGICAL STAPLING SYSTEM, filed Oct. 27, 2017, which issued on Sep. 28, 2021 as U.S. Pat. No. 11,129,616, which is a continuation application claiming priority under 35 U.S.C. § 120 to U.S. patent application Ser. No. 14/725,181, entitled AUTOMATED RELOADING DEVICES FOR REPLACING USED END EFFECTORS ON ROBOTIC SURGICAL SYSTEMS, filed May 29, 2015, which issued on Nov. 20, 2018 as U.S. Pat. No. 10,130,366, which is a continuation application claiming priority under 35 U.S.C. § 120 to U.S. patent application Ser. No. 13/118,241, entitled SURGICAL STAPLING INSTRUMENTS WITH ROTATABLE STAPLE DEPLOYMENT ARRANGEMENTS, filed May 27, 2011, which issued on Jul. 7, 2015 as U.S. Pat. No. 9,072,535, the entire disclosures of which are hereby incorporated by reference herein.

BACKGROUND

Over the years a variety of minimally invasive robotic (or "telesurgical") systems have been developed to increase surgical dexterity as well as to permit a surgeon to operate on a patient in an intuitive manner. Many of such systems are disclosed in the following U.S. Patents which are each herein incorporated by reference in their respective entirety: U.S. Pat. No. 5,792,135, entitled ARTICULATED SURGICAL INSTRUMENT FOR PERFORMING MINIMALLY INVASIVE SURGERY WITH ENHANCED DEXTERITY AND SENSITIVITY, U.S. Pat. No. 6,231,565, entitled ROBOTIC ARM DLUS FOR PERFORMING SURGICAL TASKS, U.S. Pat. No. 6,783,524, entitled ROBOTIC SURGICAL TOOL WITH ULTRASOUND CAUTERIZING AND CUTTING INSTRUMENT, U.S. Pat. No. 6,364,888, entitled ALIGNMENT OF MASTER AND SLAVE IN A MINIMALLY INVASIVE SURGICAL APPARATUS, U.S. Pat. No. 7,524,320, entitled MECHANICAL ACTUATOR INTERFACE SYSTEM FOR ROBOTIC SURGICAL TOOLS, U.S. Pat. No. 7,691,098, entitled PLATFORM LINK WRIST MECHANISM, U.S. Pat. No. 7,806,891, entitled REPOSITIONING AND REORIENTATION OF MASTER/SLAVE RELATIONSHIP IN MINIMALLY INVASIVE TELESURGERY, and U.S. Pat. No. 7,824,401, entitled ROBOTIC TOOL WITH WRISTED MONOPOLAR ELECTROSURGICAL END EFFECTORS. Many of such systems, however, have in the past been unable to generate the magnitude of forces required to effectively cut and fasten tissue.

SUMMARY

According to general aspects of various embodiments of the present invention, there is provided a surgical stapling instrument that includes an actuation system for selectively generating a plurality of control motions. A surgical end effector is operably coupled to the actuation system. In various embodiments, the surgical end effector comprises a surgical staple cartridge that operably supports a plurality of surgical staples that are arranged in at least two spaced staple lines. An actuation member operably interfaces with the actuation system such that upon application of the control motions thereto, the actuation member is axially driven within the surgical staple cartridge between a starting position and an ending position. The actuation member has rotatable staple camming members thereon that correspond to each one of the at least two staple lines such that as the actuation member is driven from the starting to the ending position, each rotatable camming member is rotated into camming driving engagement with the surgical staples in the corresponding staple lines.

In accordance with other general aspects of various embodiments of the present invention, there is provided a surgical stapling instrument that includes an actuation system for selectively generating a plurality of control motions. A surgical end effector is operably coupled to the actuation system. In various embodiments, the surgical end effector comprises an anvil that is movable between an open position and a closed position in response to closure motions applied thereto by the actuation system. The instrument further includes a surgical staple cartridge that operably supports a plurality of linearly arranged pusher members therein. Each pusher member operably supports at least one unformed surgical staple thereon. The instrument also comprises a plurality of linearly arranged staple drivers that correspond to the plurality of linearly arranged pusher members. Each staple driver is rotatably supported within the end effector. An actuation member operably interfaces with the actuation system such that upon application of firing control motions thereto, the actuation member is axially driven within the surgical staple cartridge between a starting position and an ending position. In various embodiments, the actuation member is configured to move each staple driver into rotatable camming engagement with each corresponding pusher member to drive at least one surgical staple supported thereon into forming contact with the anvil as the actuator is driven from the starting position to the ending position.

In accordance with still other general aspects, various embodiments of the present invention are directed to a surgical stapling instrument that comprises an actuation system for selectively generating a plurality of control motions. A surgical end effector is operably coupled to the actuation system. In various embodiments, the surgical end effector comprises an anvil that is movable between an open position and a closed position in response to closure motions applied thereto by the actuation system. The instrument further comprises a surgical staple cartridge that operably supports a plurality of linearly arranged pusher members therein. Each pusher member operably supports at least one unformed surgical staple thereon. The instrument also comprises an actuation member that operably interfaces with the actuation system such that upon application of the control motions thereto, the actuation member is axially driven within the surgical staple cartridge between a starting position and an ending position. Camming means also interfaces with the actuation member such that as the actuation member is driven from the starting to ending position, the camming means are moved into rotatable camming engagement with each surgical pusher member to drive at least one surgical staple supported thereon into forming contact with the anvil when the anvil is in the closed position.

FIGURES

Various embodiments of the present invention are described herein by way of example in conjunction with the following Figures wherein.

Figure 94:
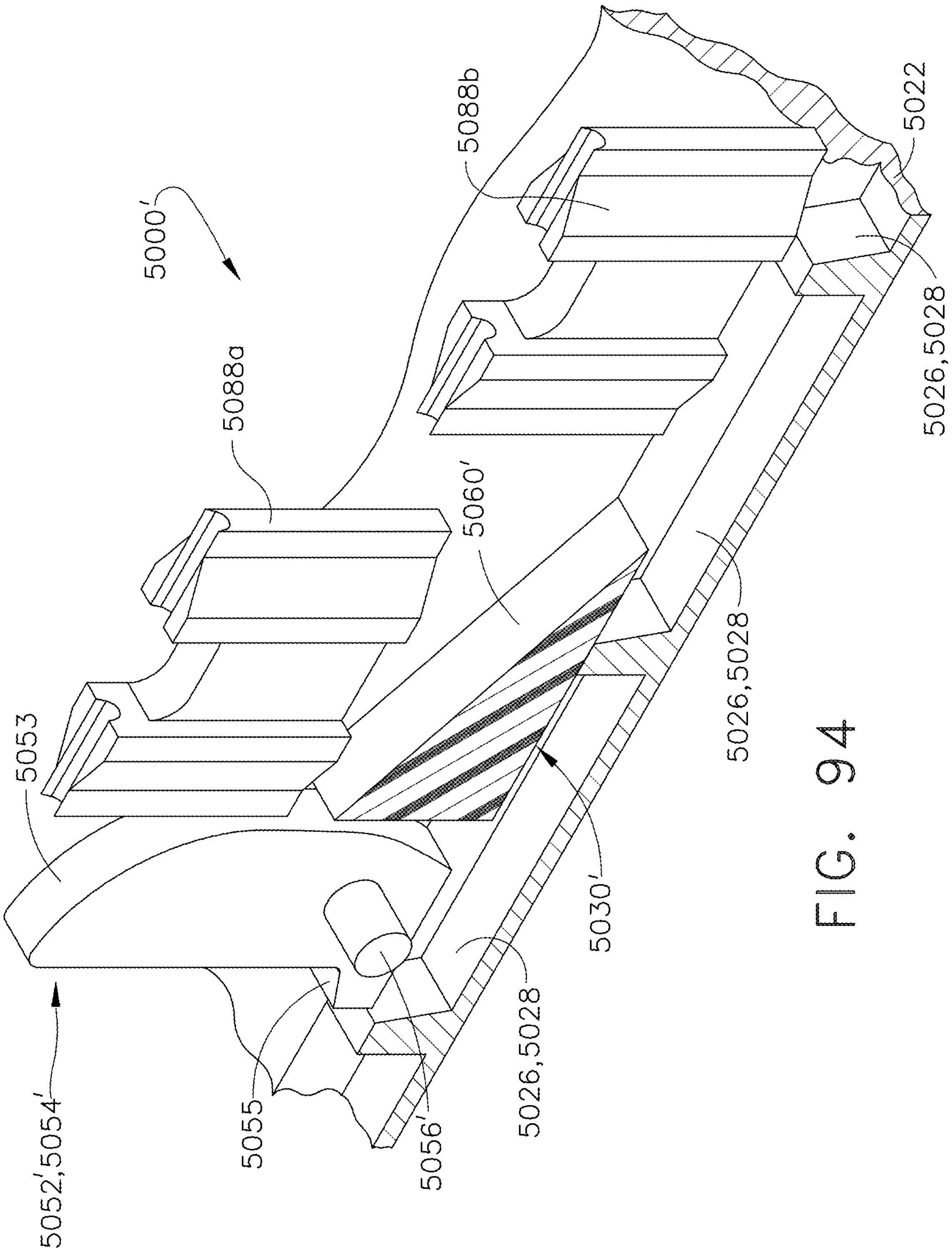
Figure 95:
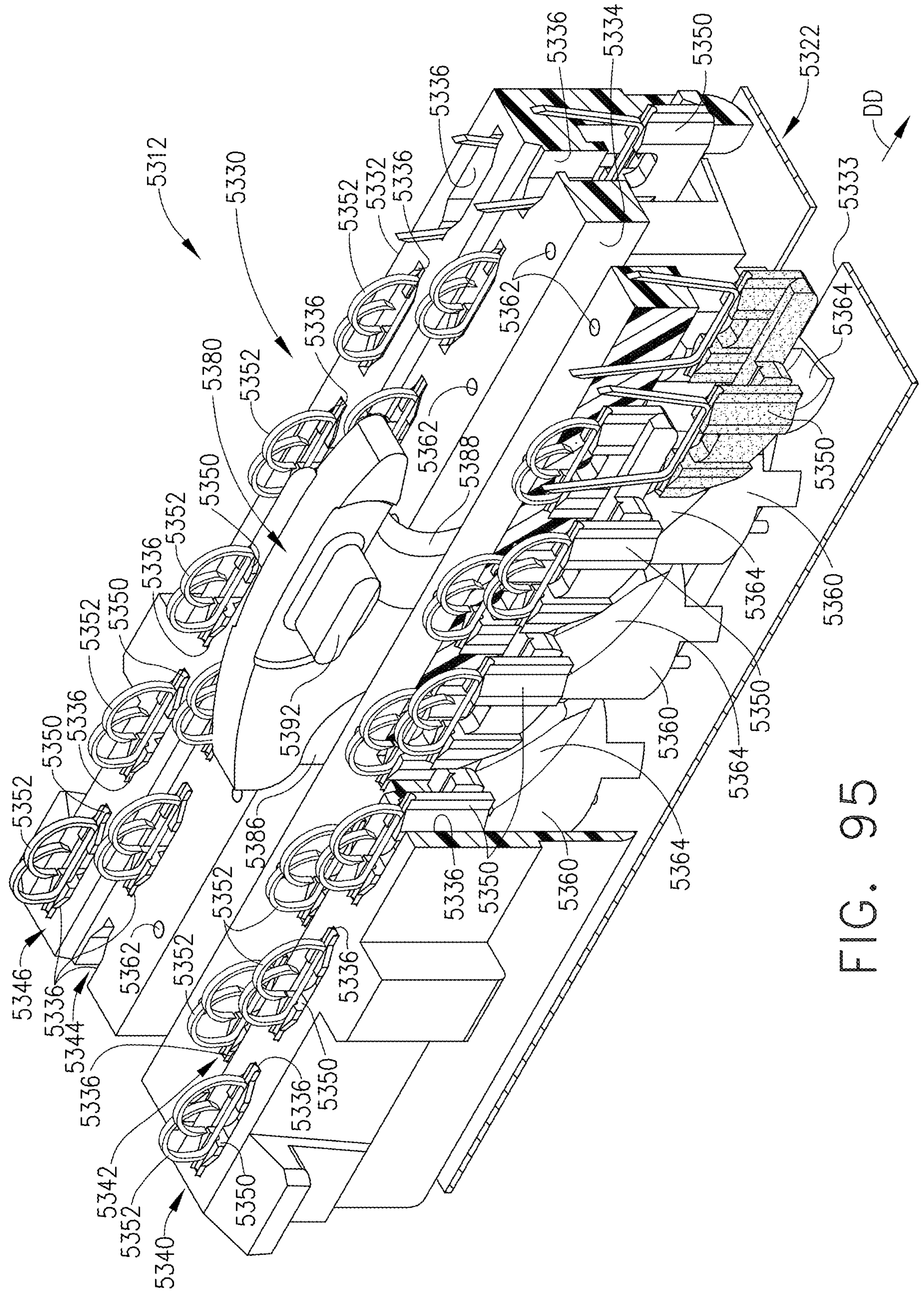
Figure 96:
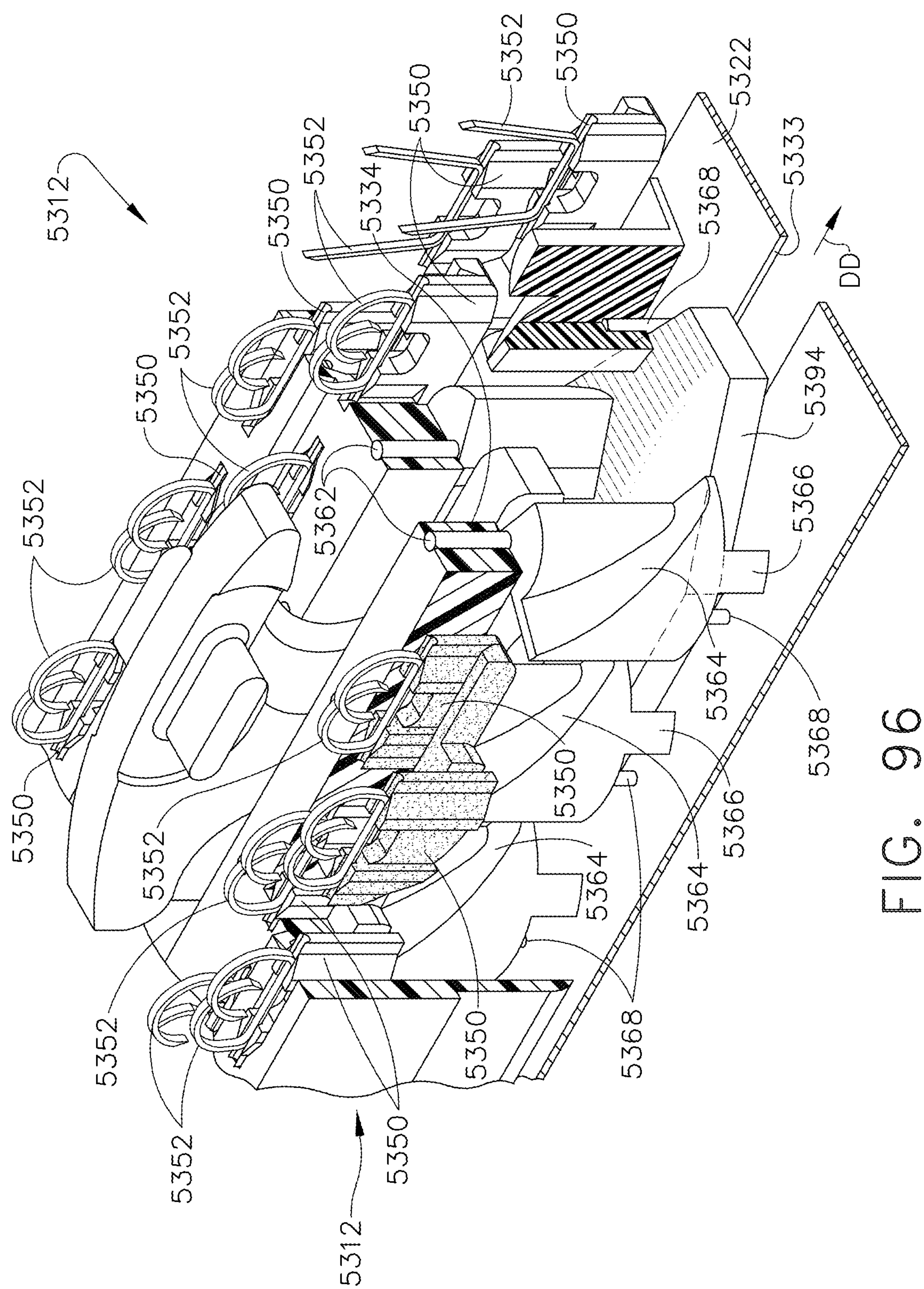
Figure 97:
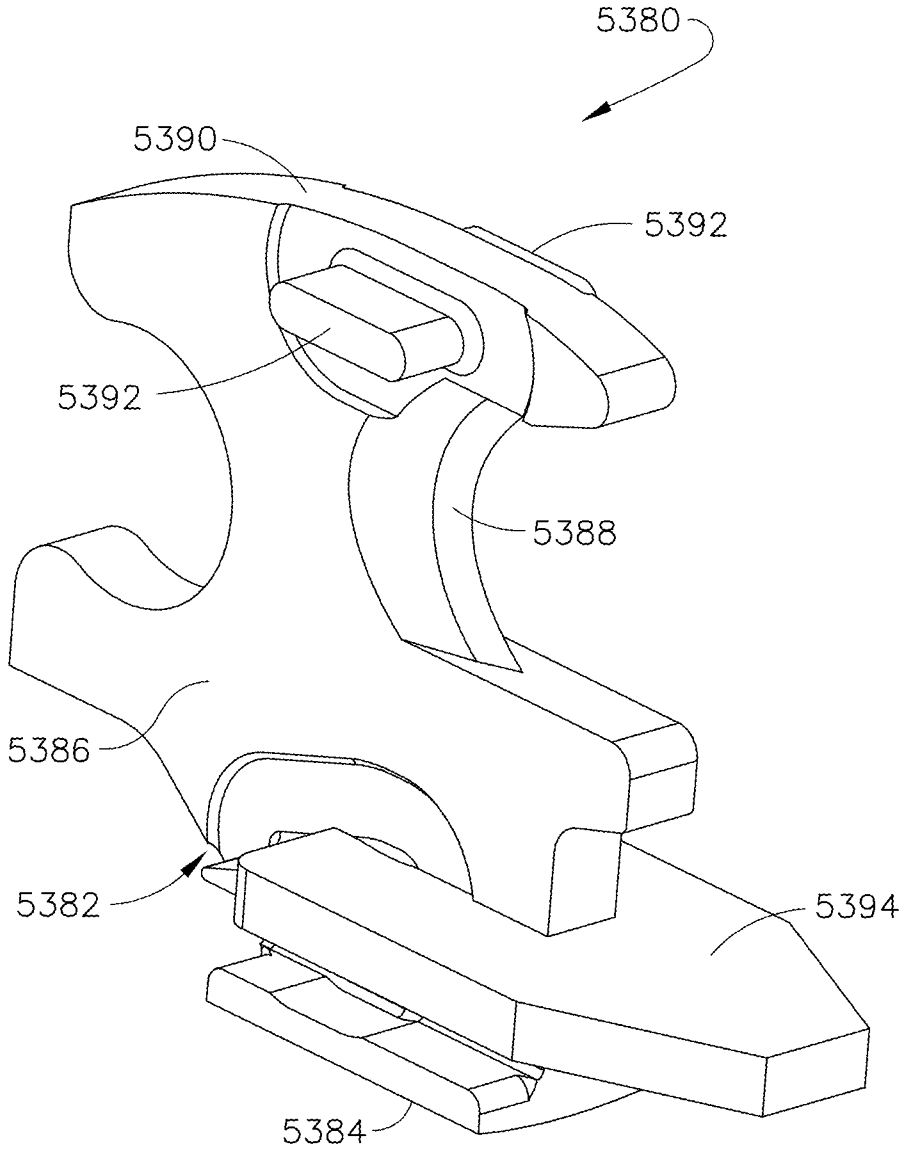
Figure 98:
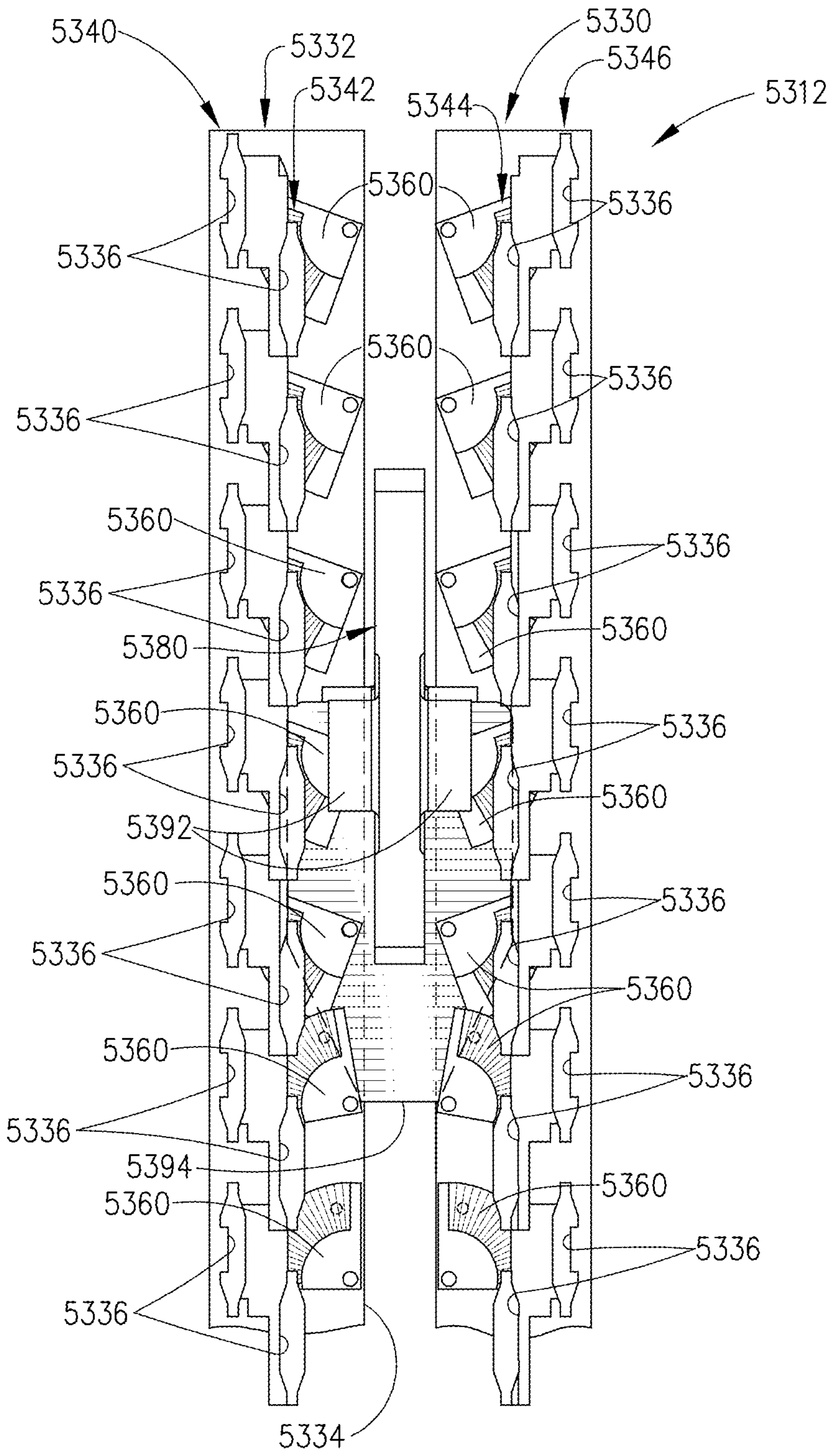
Figure 99:
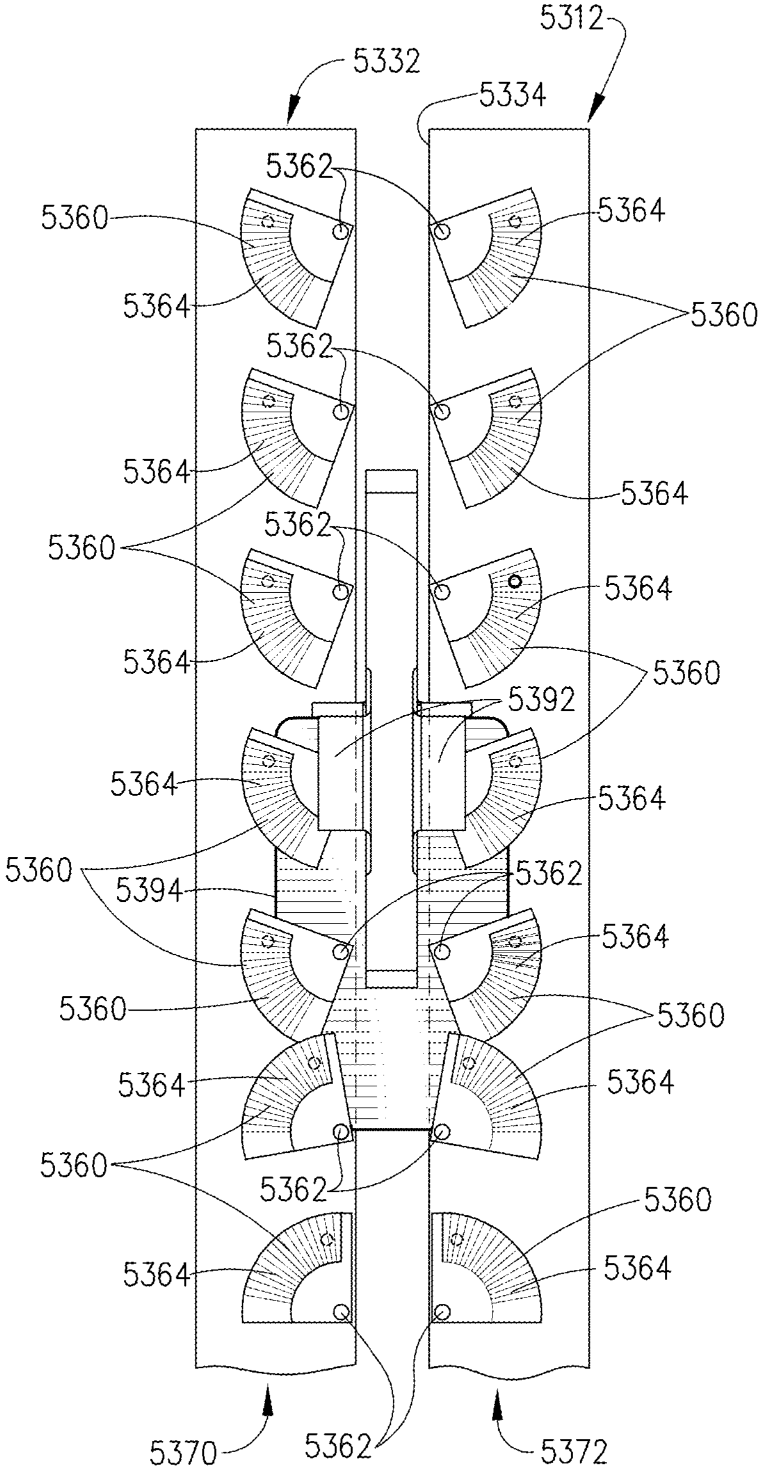
Figure 100:
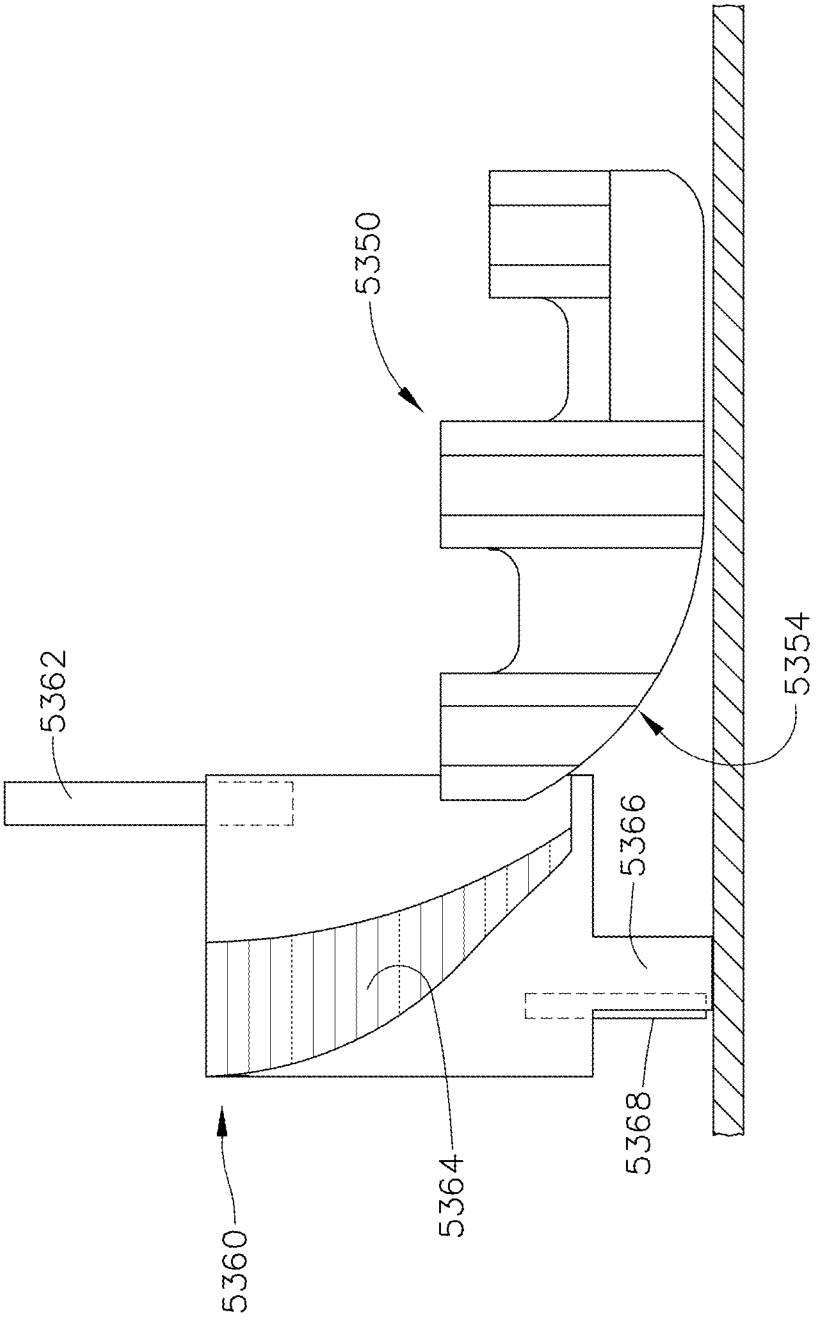
Figure 101:
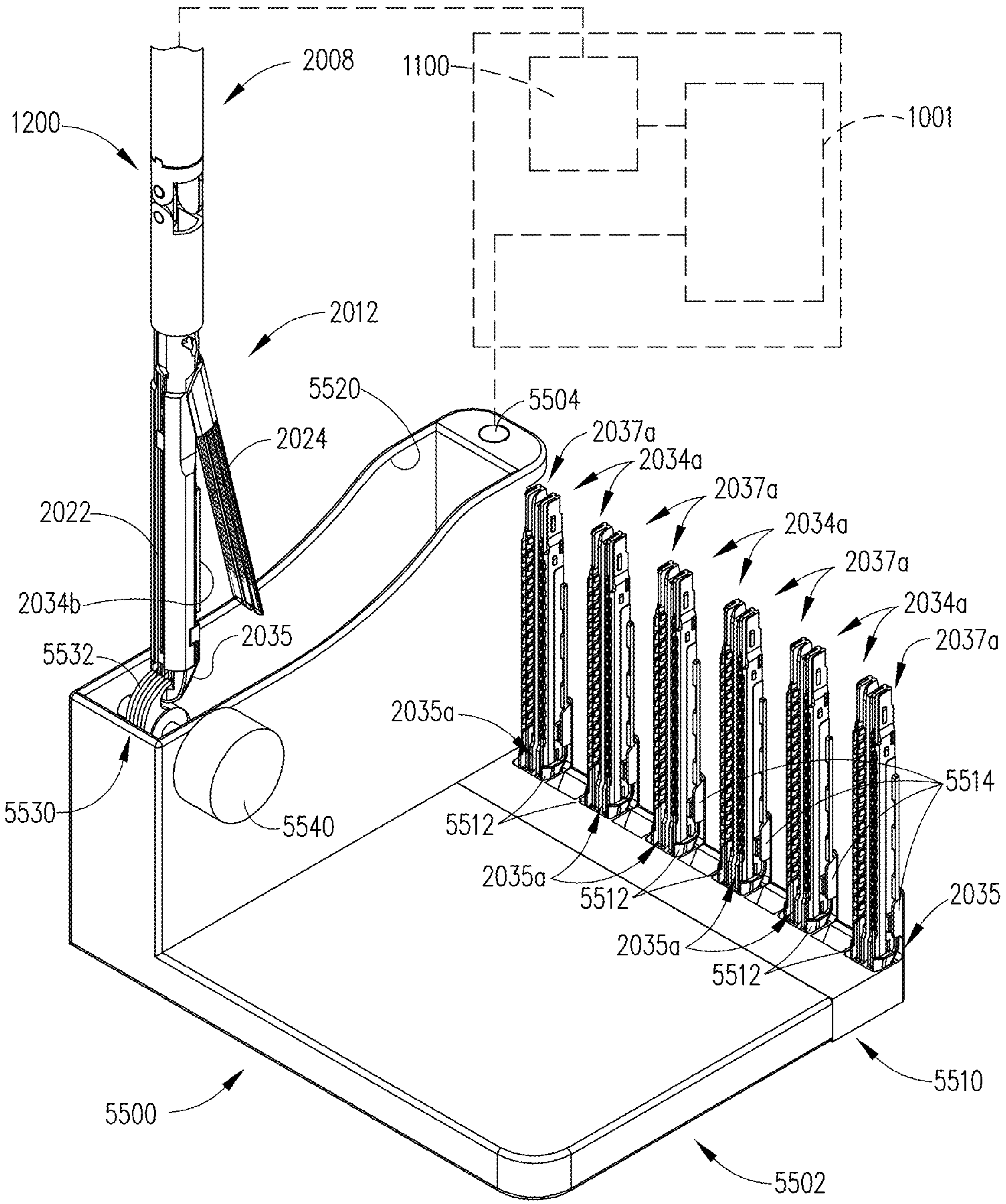
Figure 102:
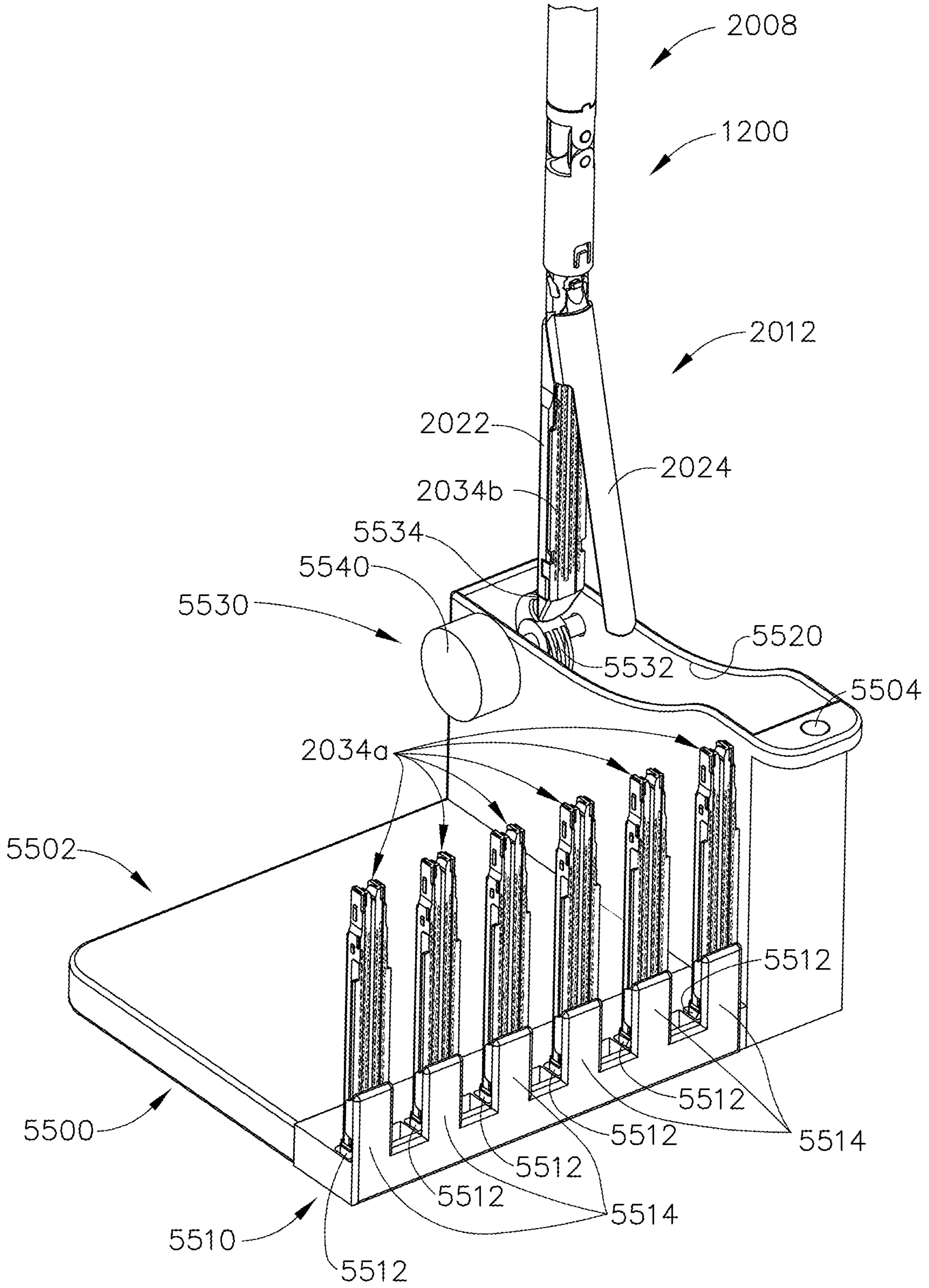
Figure 103:
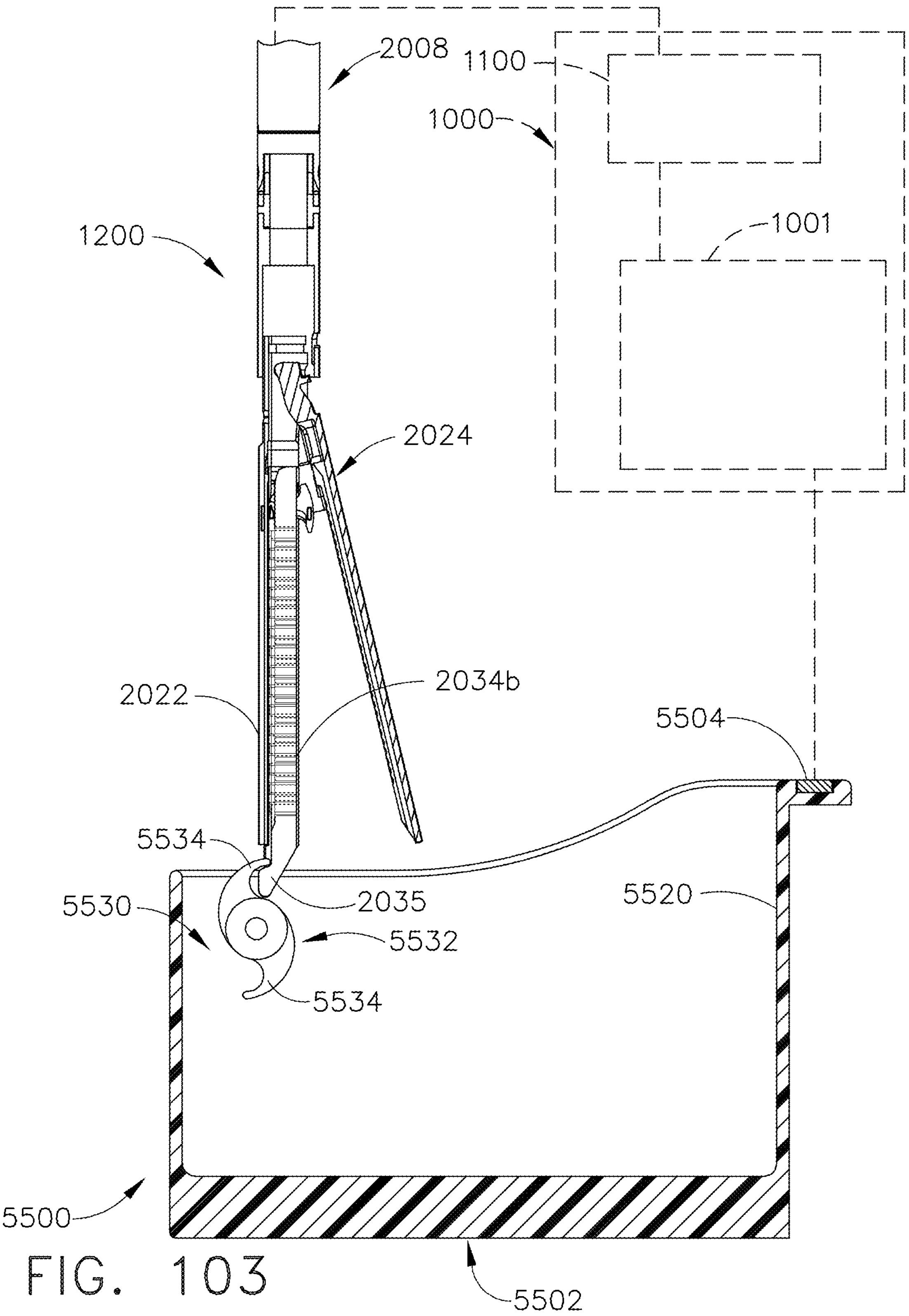
Figure 104:
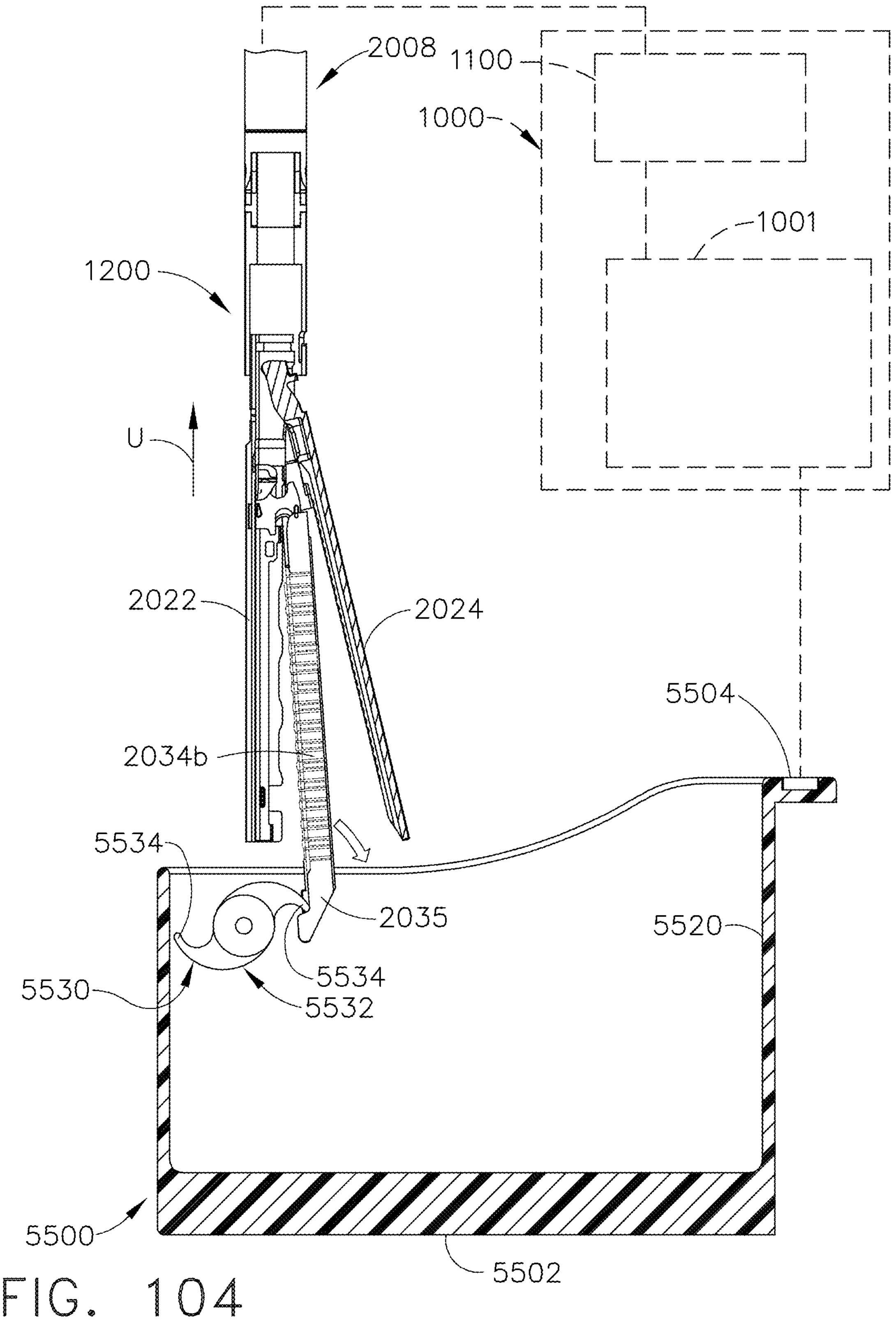
Figure 105:
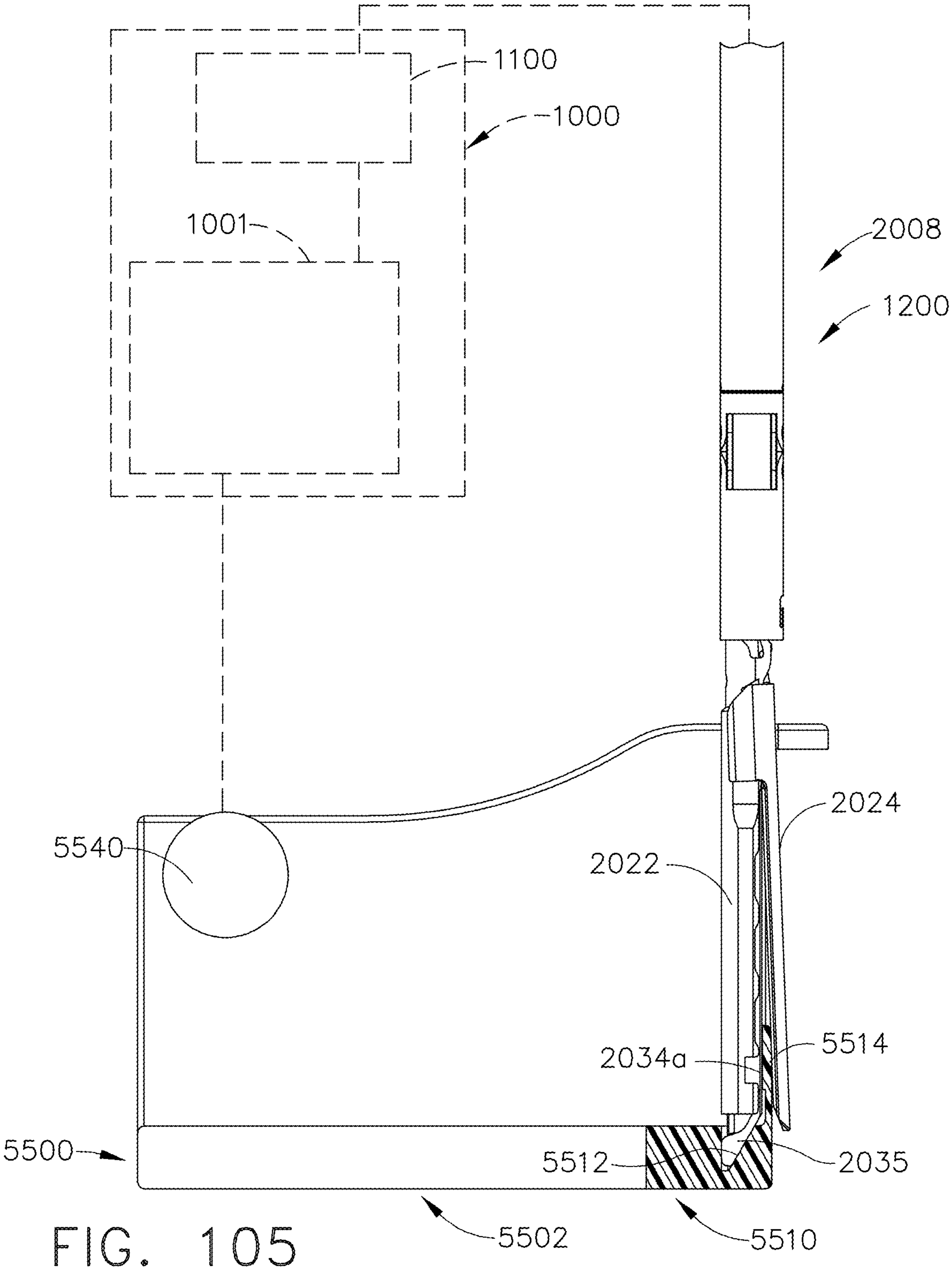
Figure 106:
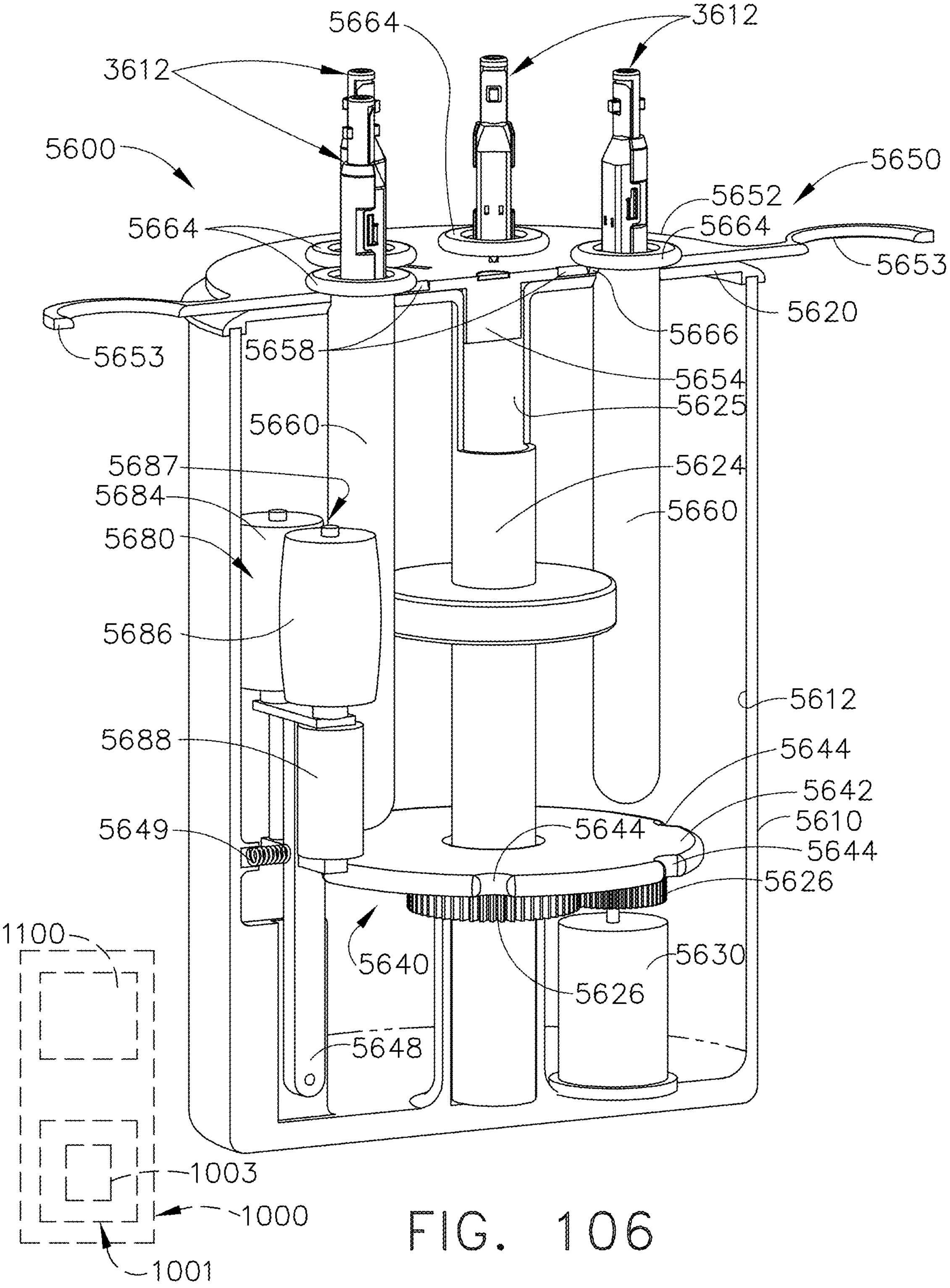
Figure 107:
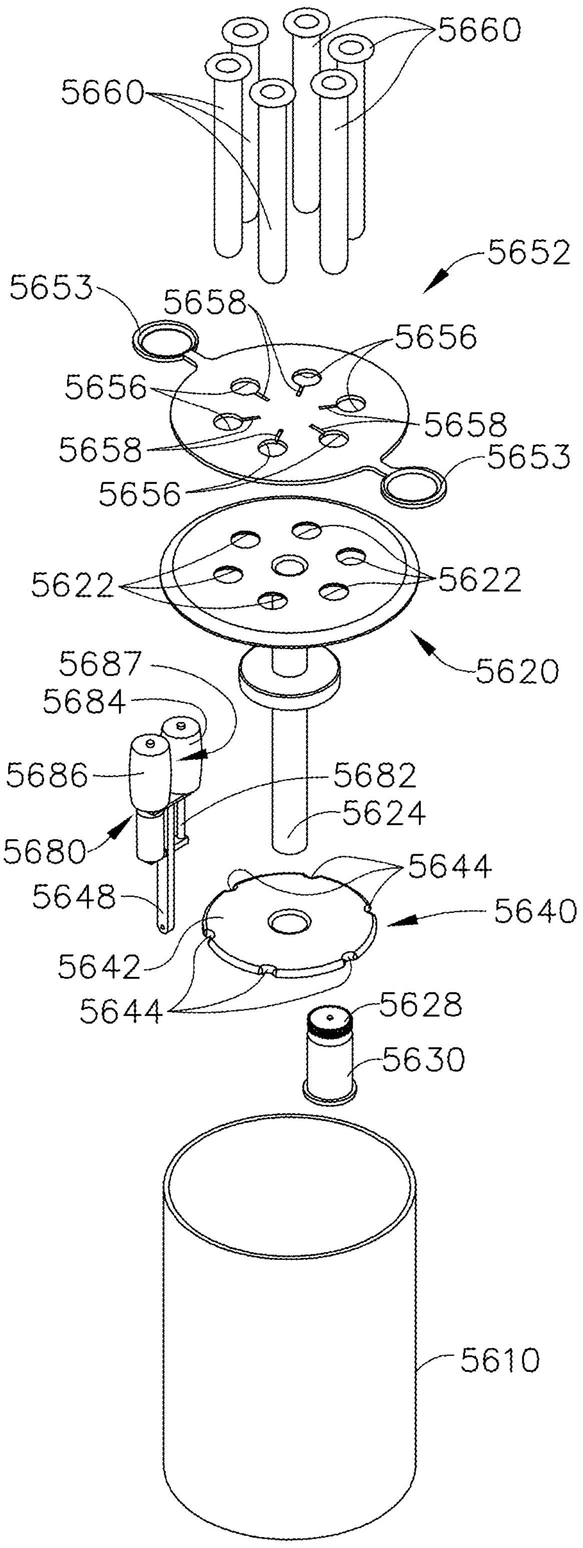
Figure 108:
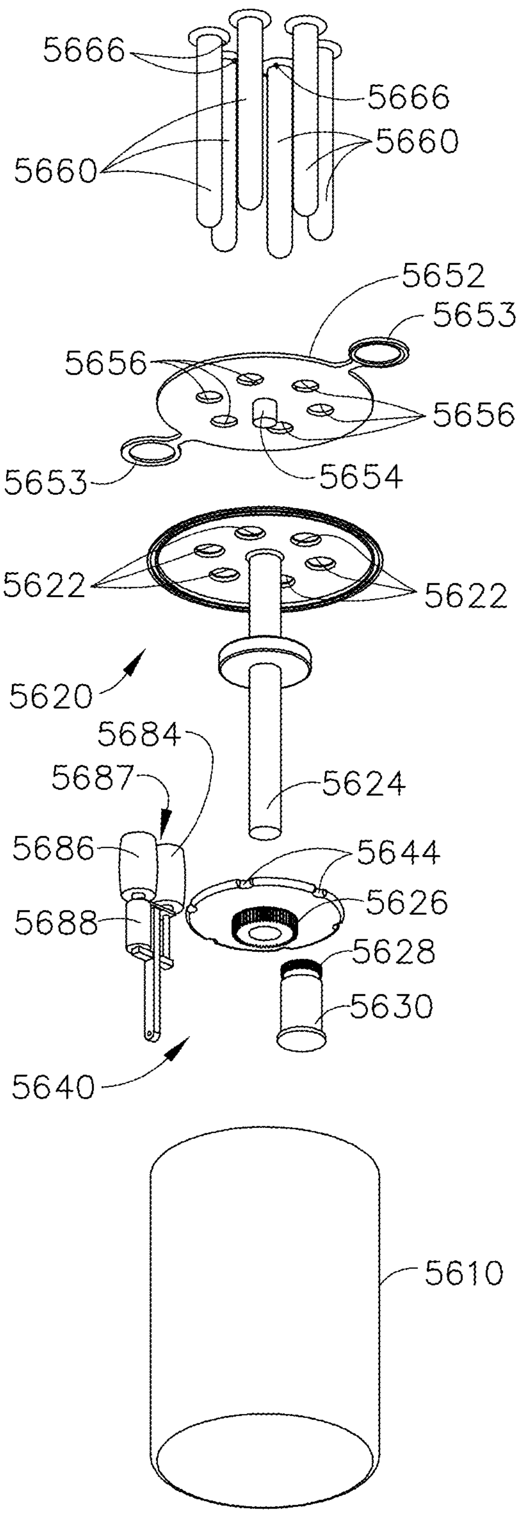
Figure 109:
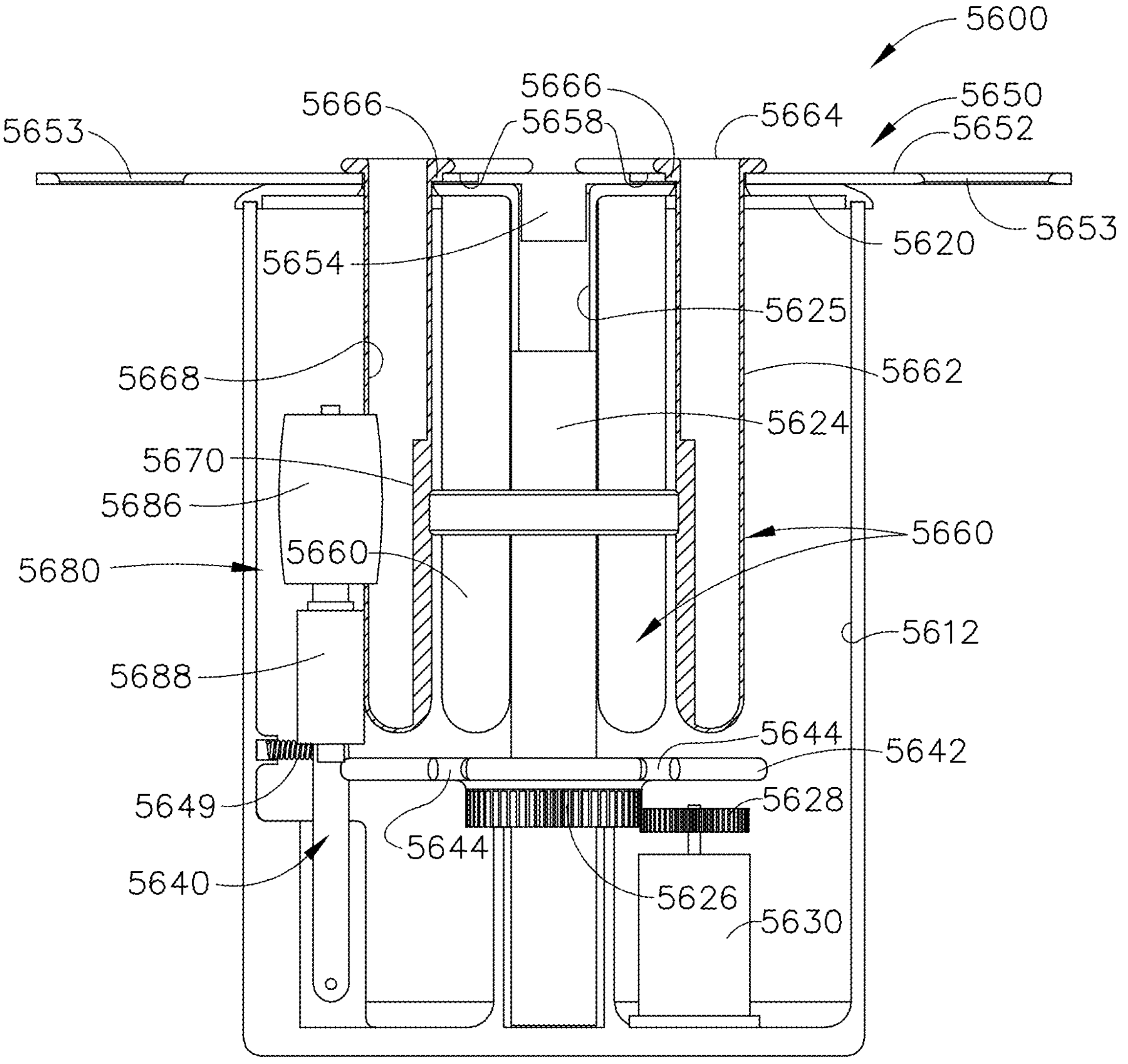
Figure 110:
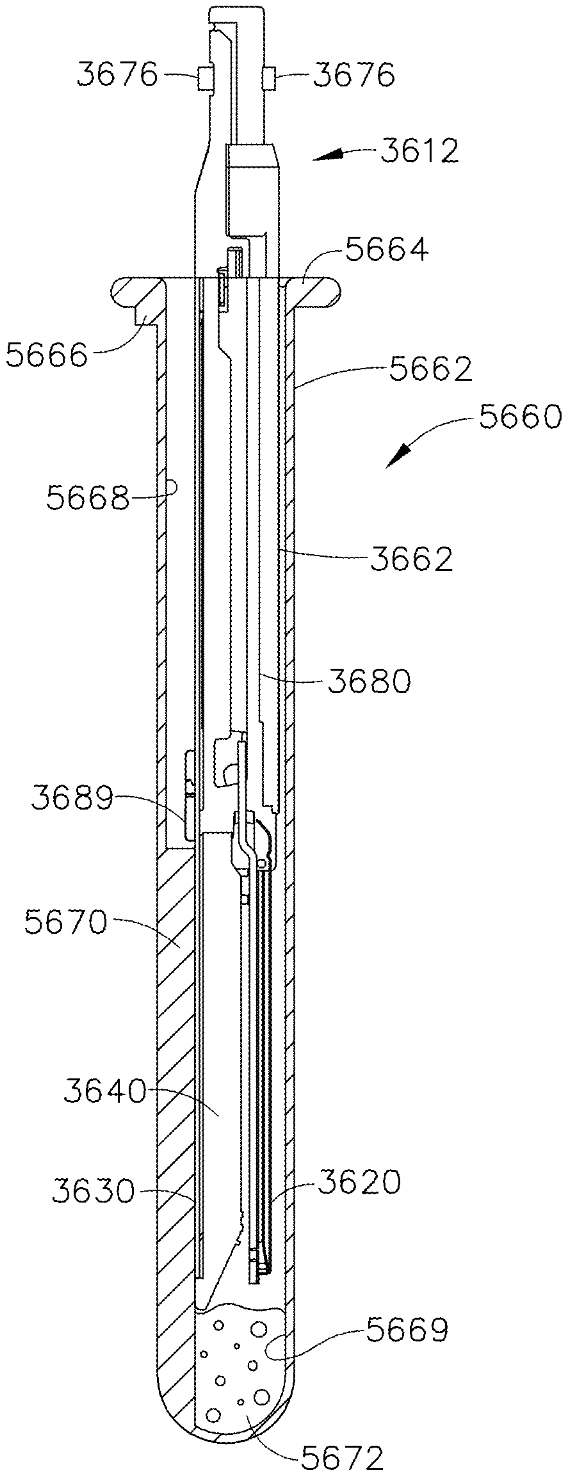
Figure 111:
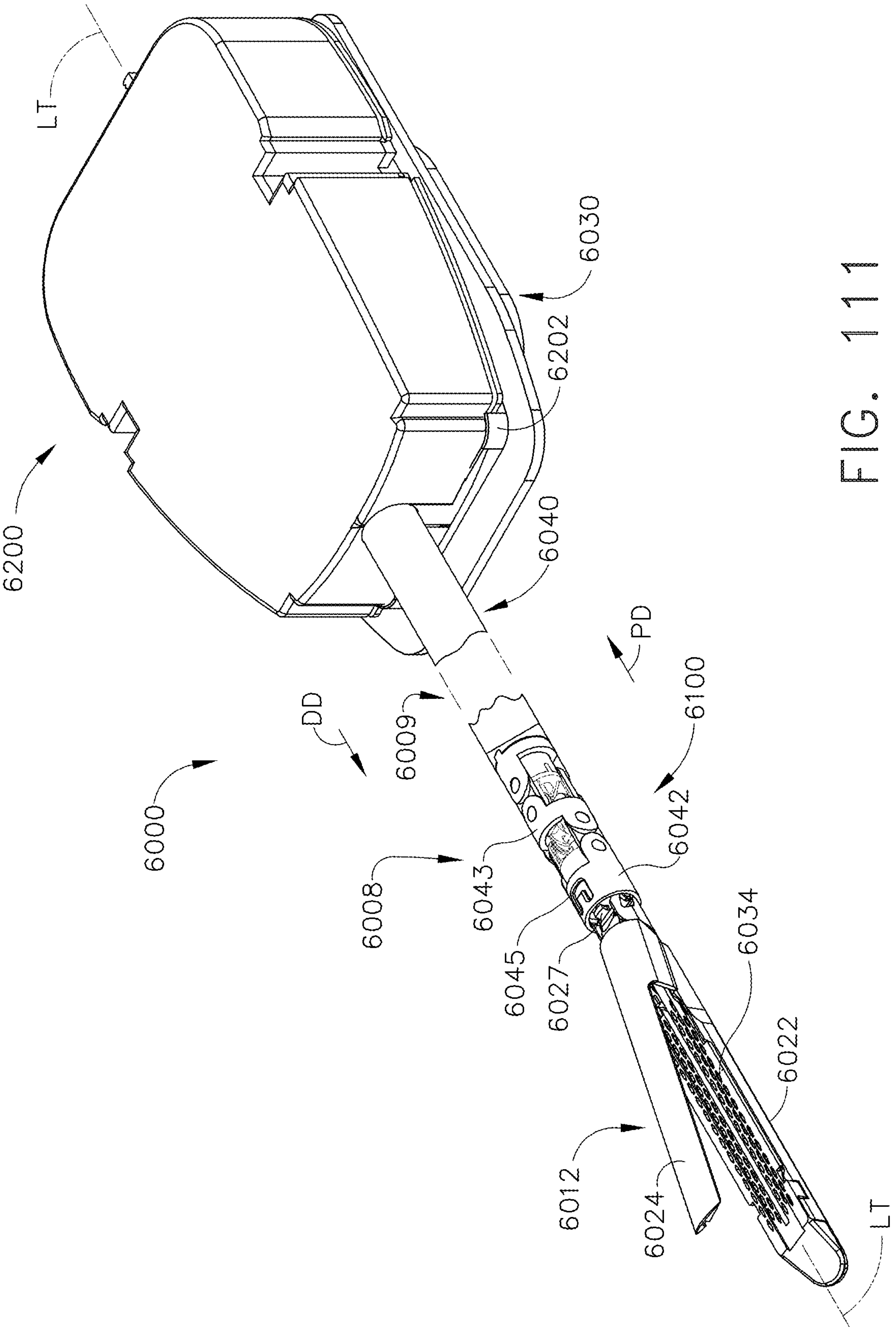
Figure 112:
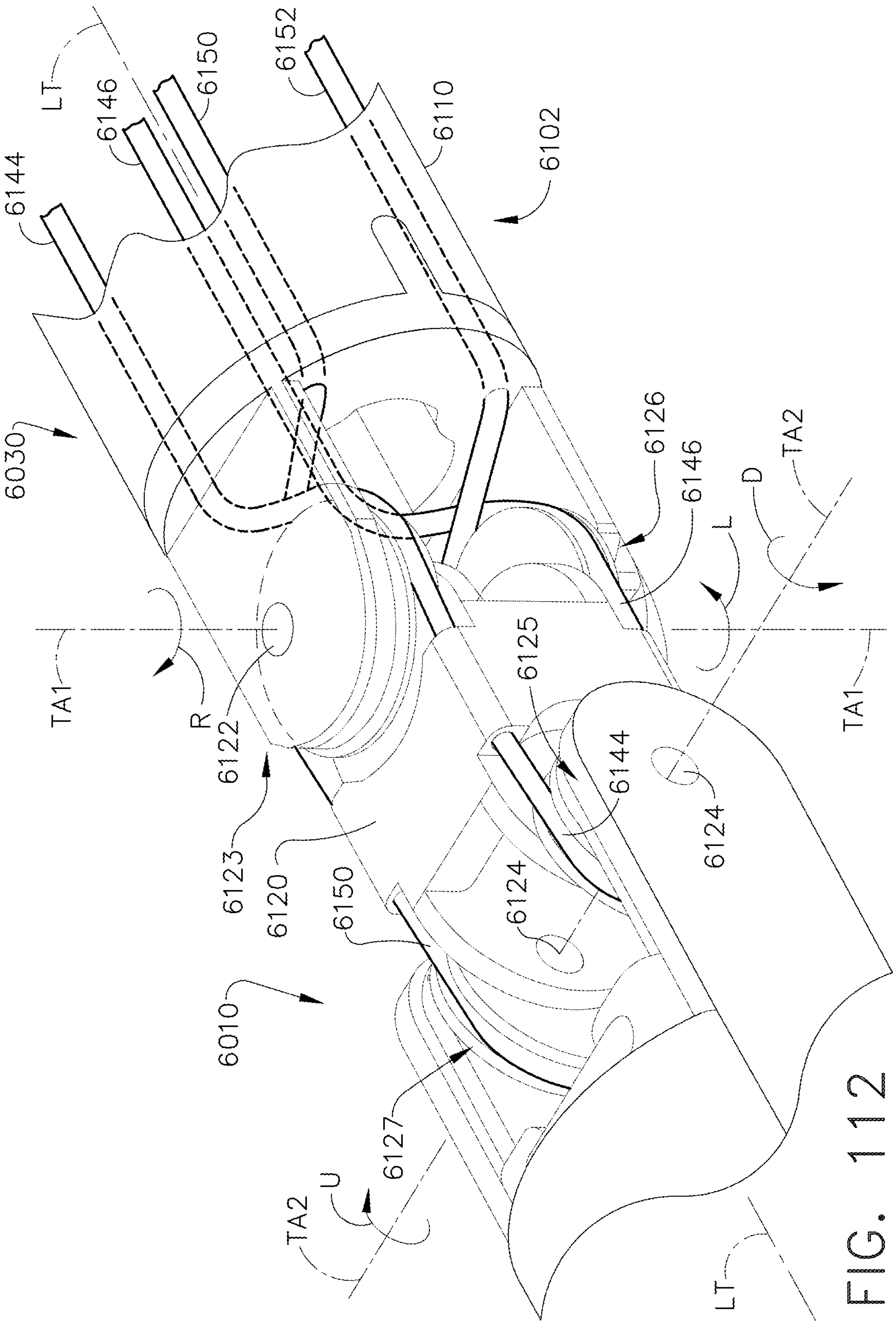
Figure 113:
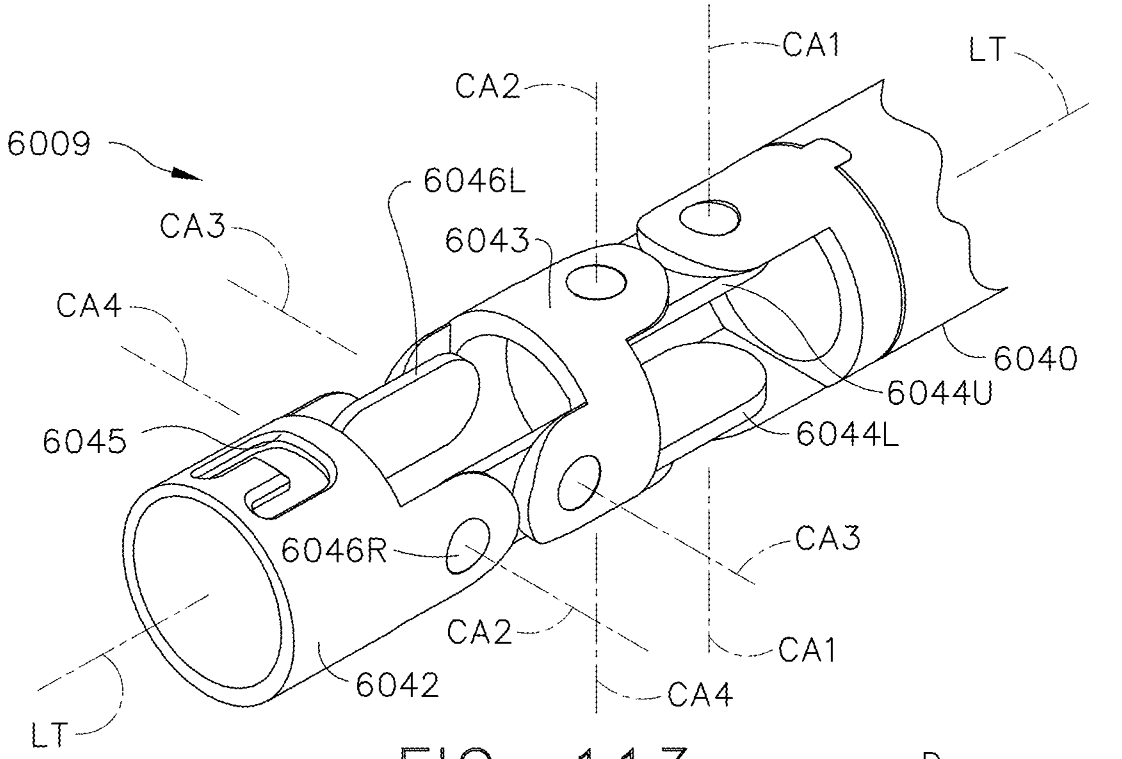
Figure 114:
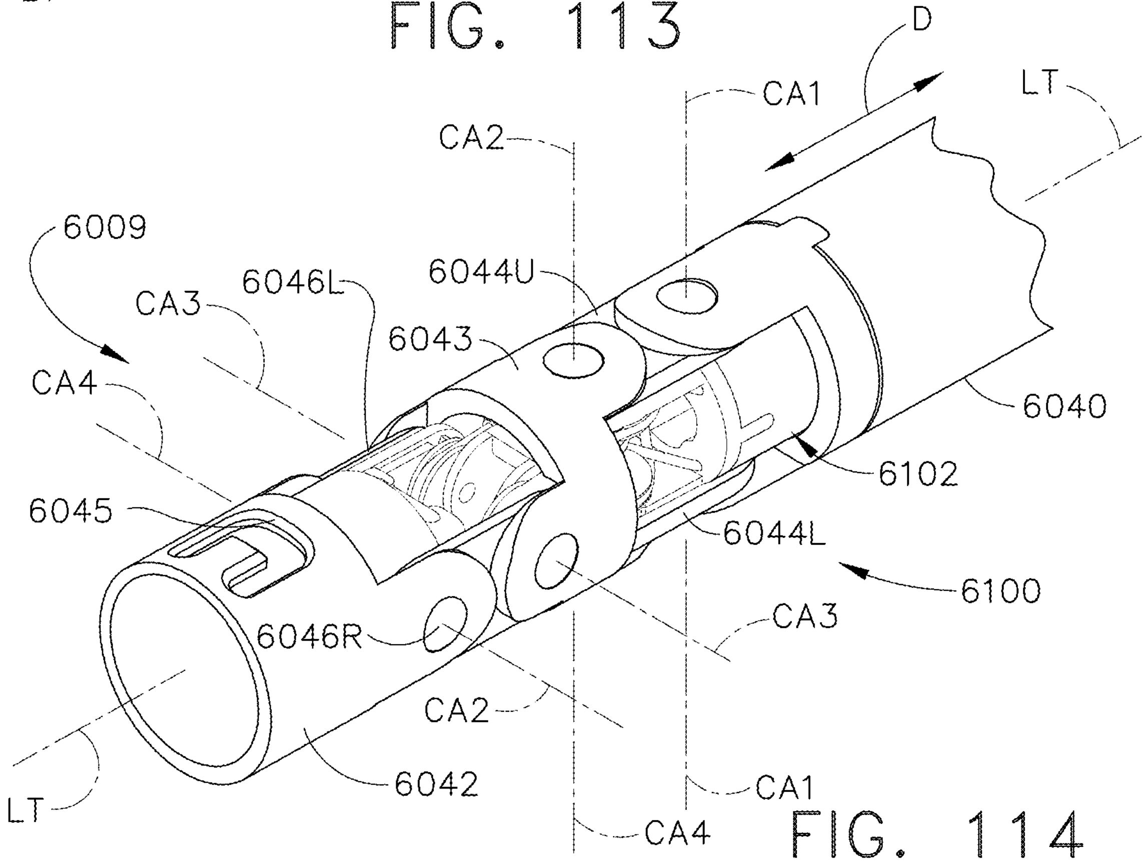
Figure 115:
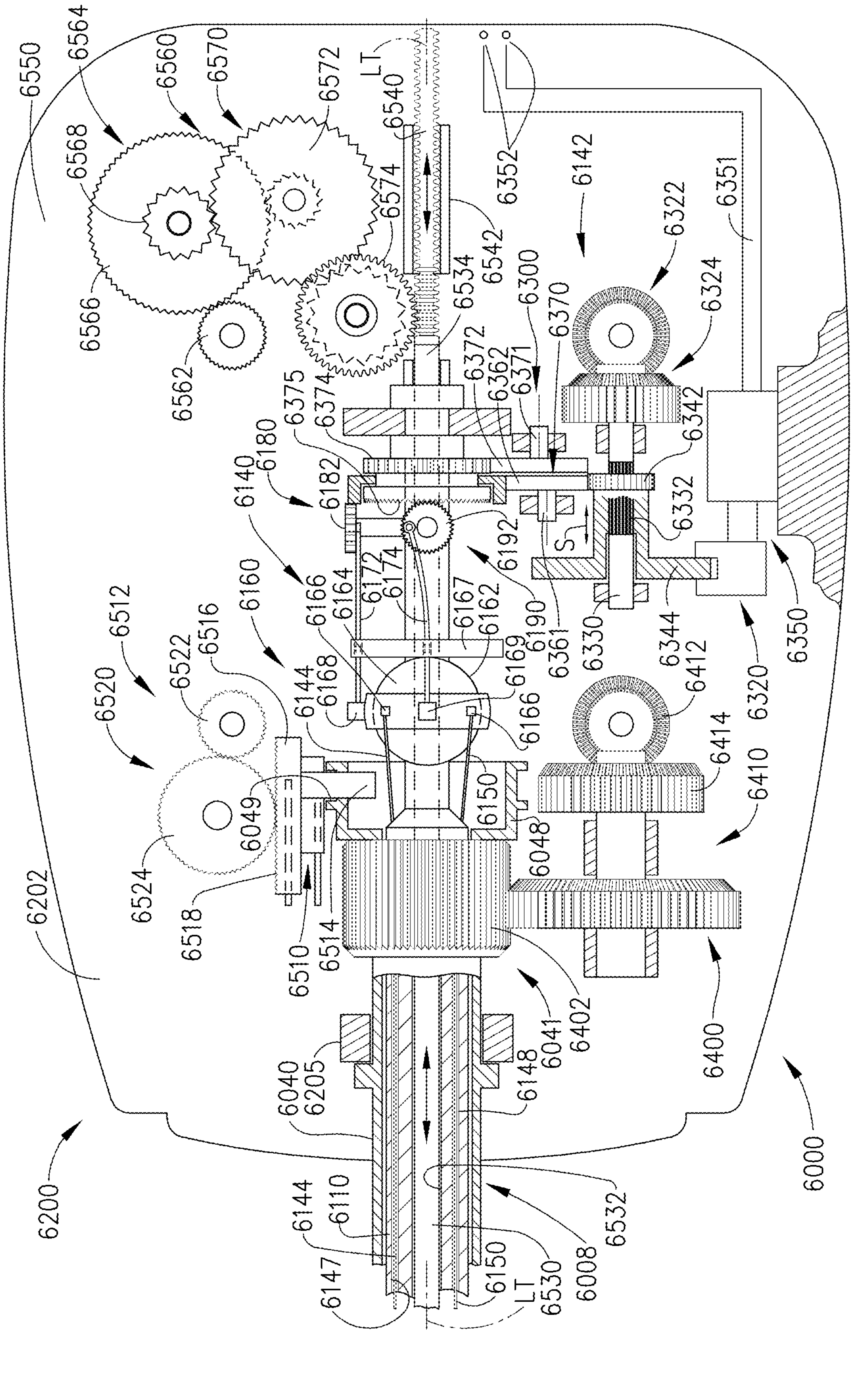
Figure 116:
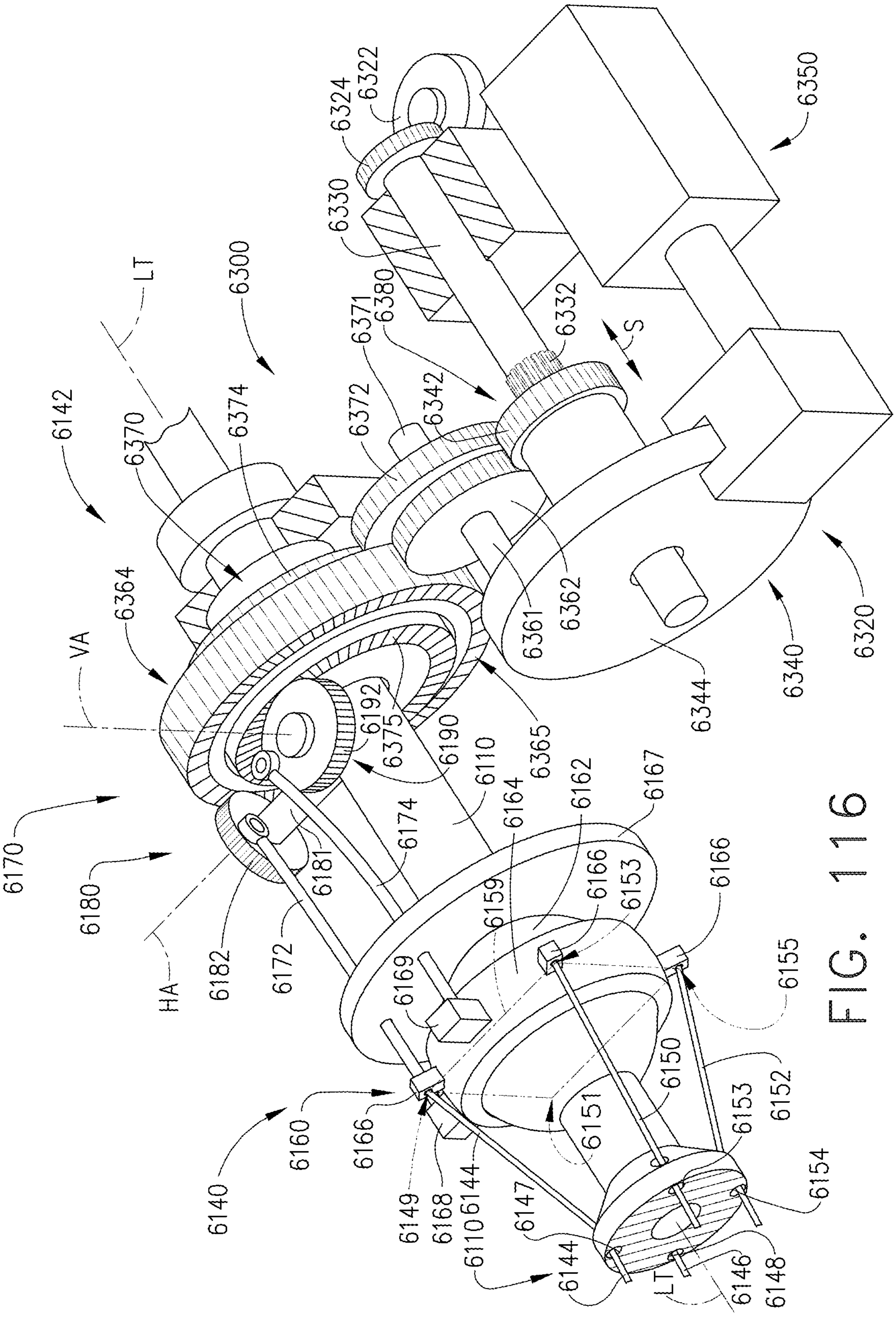
Figure 117:
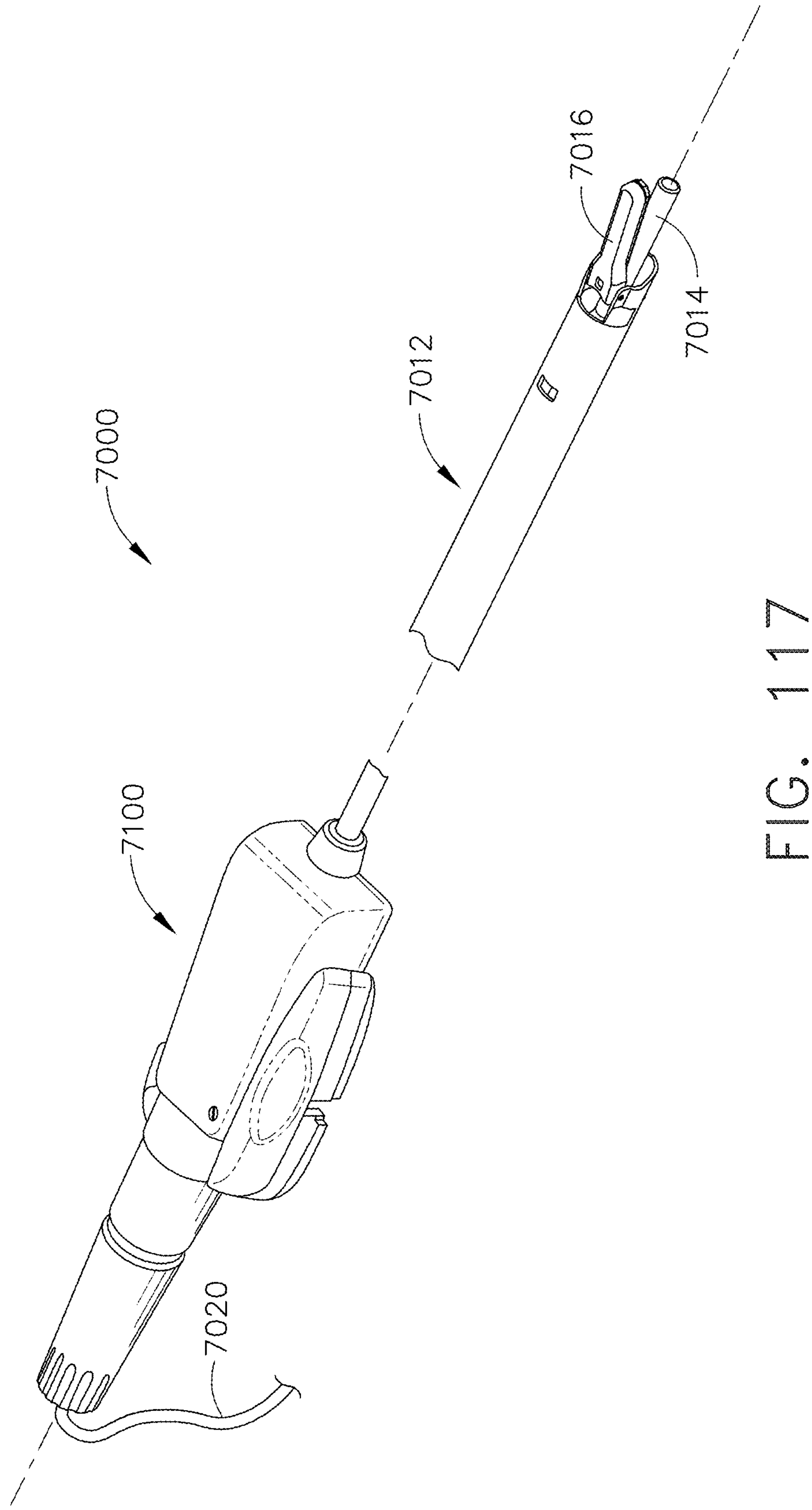
Figure 118:
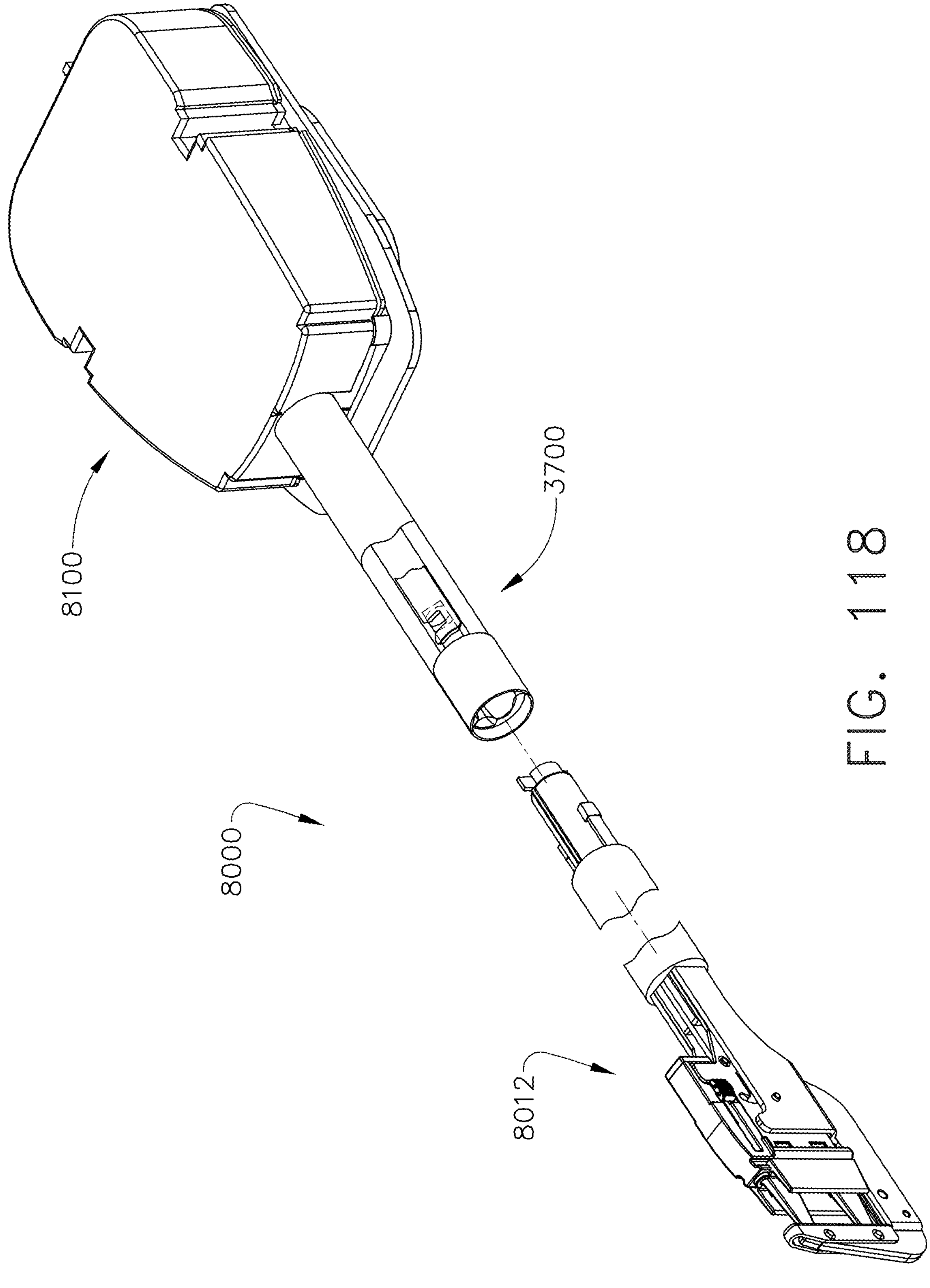

FIGS. 88-93 diagrammatically depict the sequential firing of staples in a surgical tool embodiment of the present invention;

FIG. 94 is a partial perspective view of a portion of a surgical end effector embodiment of the present invention;

FIG. 95 is a partial cross-sectional perspective view of a portion of a surgical end effector embodiment of a surgical tool embodiment of the present invention;

FIG. 96 is another partial cross-sectional perspective view of the surgical end effector embodiment of FIG. 95 with a sled assembly axially advancing therethrough;

FIG. 97 is a perspective view of another sled assembly embodiment of another surgical tool embodiment of the present invention;

FIG. 98 is a partial top view of a portion of the surgical end effector embodiment depicted in FIGS. 95 and 96 with the sled assembly axially advancing therethrough;

FIG. 99 is another partial top view of the surgical end effector embodiment of FIG. 98 with the top surface of the surgical staple cartridge omitted for clarity;

FIG. 100 is a partial cross-sectional side view of a rotary driver embodiment and staple pusher embodiment of the surgical end effector depicted in FIGS. 95 and 97;

FIG. 101 is a perspective view of an automated reloading system embodiment of the present invention with a surgical end effector in extractive engagement with the extraction system thereof;

FIG. 102 is another perspective view of the automated reloading system embodiment depicted in FIG. 101;

FIG. 103 is a cross-sectional elevational view of the automated reloading system embodiment depicted in FIGS. 101 and 102;

FIG. 104 is another cross-sectional elevational view of the automated reloading system embodiment depicted in FIGS. 101-103 with the extraction system thereof removing a spent surgical staple cartridge from the surgical end effector;

FIG. 105 is another cross-sectional elevational view of the automated reloading system embodiment depicted in FIGS. 101-104 illustrating the loading of a new surgical staple cartridge into a surgical end effector;

FIG. 106 is a perspective view of another automated reloading system embodiment of the present invention with some components shown in cross-section;

FIG. 107 is an exploded perspective view of a portion of the automated reloading system embodiment of FIG. 106;

FIG. 108 is another exploded perspective view of the portion of the automated reloading system embodiment depicted in FIG. 107;

FIG. 109 is a cross-sectional elevational view of the automated reloading system embodiment of FIGS. 106-108;

FIG. 110 is a cross-sectional view of an orientation tube embodiment supporting a disposable loading unit therein;

FIG. 111 is a perspective view of another surgical tool embodiment of the present invention;

FIG. 112 is a partial perspective view of an articulation joint embodiment of a surgical tool embodiment of the present invention;

FIG. 113 is a perspective view of a closure tube embodiment of a surgical tool embodiment of the present invention;

FIG. 114 is a perspective view of the closure tube embodiment of FIG. 113 assembled on the articulation joint embodiment of FIG. 112;

FIG. 115 is a top view of a portion of a tool mounting portion embodiment of a surgical tool embodiment of the present invention;

FIG. 116 is a perspective view of an articulation drive assembly embodiment employed in the tool mounting portion embodiment of FIG. 115;

FIG. 117 is a perspective view of another surgical tool embodiment of the present invention; and FIG. 118 is a perspective view of another surgical tool embodiment of the present invention.

DETAILED DESCRIPTION

Applicant of the present application also owns the following patent applications that have been filed on May 27, 2011 and which are each herein incorporated by reference in their respective entireties:

U.S. patent application Ser. No. 13/118,259, entitled SURGICAL INSTRUMENT WITH WIRELESS COMMUNICATION BETWEEN A CONTROL UNIT OF A ROBOTIC SYSTEM AND REMOTE SENSOR, now U.S. Pat. No. 8,684,253;

U.S. patent application Ser. No. 13/118,210, entitled ROBOTICALLY-CONTROLLED DISPOSABLE MOTOR DRIVEN LOADING UNIT, now U.S. Pat. No. 8,752,749;

U.S. patent application Ser. No. 13/118,194, entitled ROBOTICALLY-CONTROLLED ENDOSCOPIC ACCESSORY CHANNEL, now U.S. Pat. No. 8,992,422;

U.S. patent application Ser. No. 13/118,253, entitled ROBOTICALLY-CONTROLLED MOTORIZED SURGICAL INSTRUMENT, now U.S. Pat. No. 9,386,983;

U.S. patent application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Pat. No. 9,237,891;

U.S. patent application Ser. No. 13/118,190, entitled ROBOTICALLY-CONTROLLED MOTORIZED CUTTING AND FASTENING INSTRUMENT, now U.S. Pat. No. 9,179,912;

U.S. patent application Ser. No. 13/118,223, entitled ROBOTICALLY-CONTROLLED SHAFT BASED ROTARY DRIVE SYSTEMS FOR SURGICAL INSTRUMENTS, now U.S. Pat. No. 8,931,682;

U.S. patent application Ser. No. 13/118,263, entitled ROBOTICALLY-CONTROLLED SURGICAL INSTRUMENT HAVING RECORDING CAPABILITIES, now U.S. Patent Application Publication No. 2011/0295295;

U.S. patent application Ser. No. 13/118,272, entitled ROBOTICALLY-CONTROLLED SURGICAL INSTRUMENT WITH FORCE FEEDBACK CAPABILITIES, now U.S. Patent Application Publication No. 2011/0290856; and U.S. patent application Ser. No. 13/118,246, entitled ROBOTICALLY-DRIVEN SURGICAL INSTRUMENT WITH E-BEAM DRIVER, now U.S. Pat. No. 9,060,770.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Uses of the phrases "in various embodiments," "in some embodiments," "in one embodiment", or "in an embodiment", or the like, throughout the specification are not necessarily all referring to the same embodiment. Furthermore, the particular features, structures, or characteristics of one or more embodiments may be combined in any suitable manner in one or more other embodiments. Such modifications and variations are intended to be included within the scope of the present invention.

Figure 1:
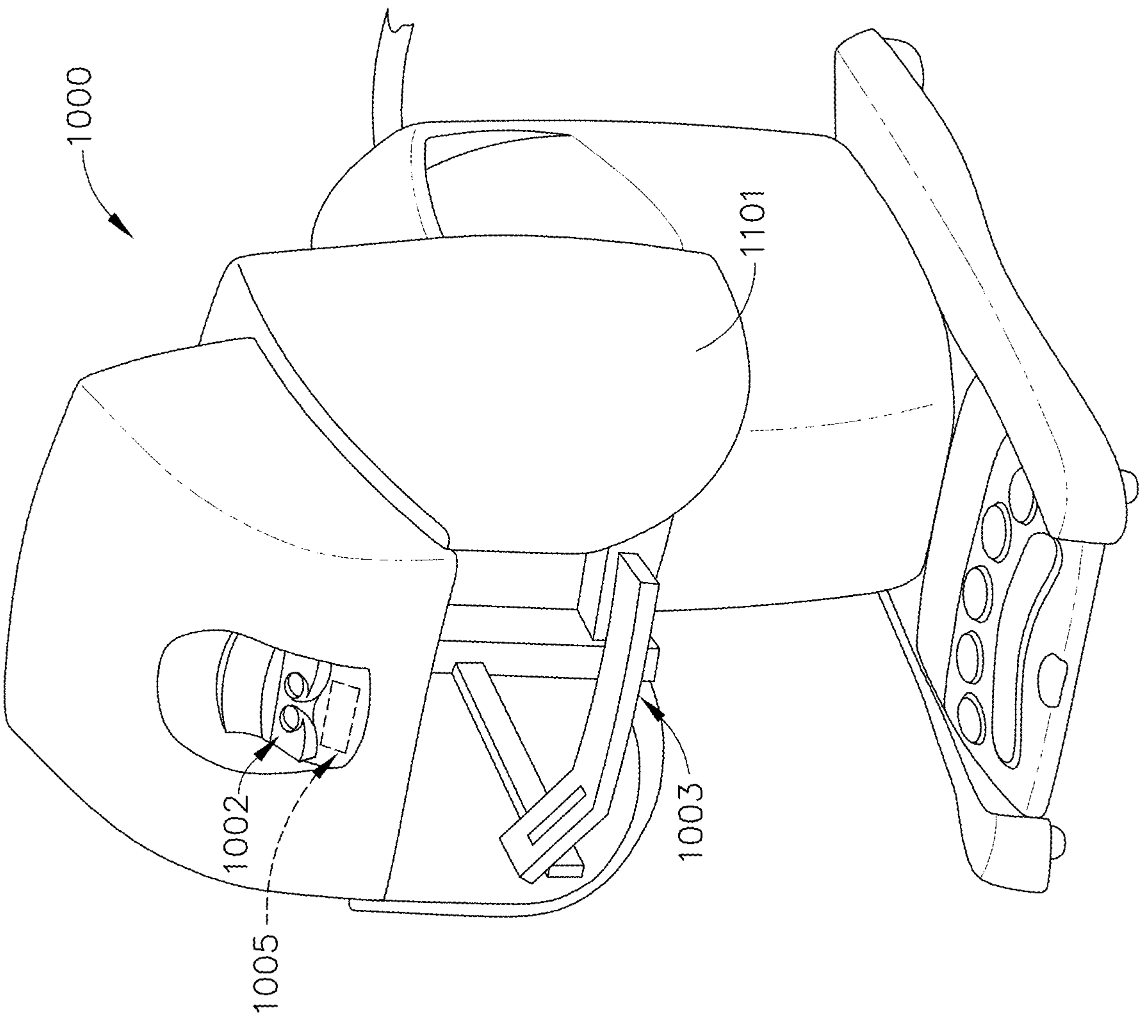
FIG. 1 is a perspective view of one robotic controller embodiment.
Figure 2:
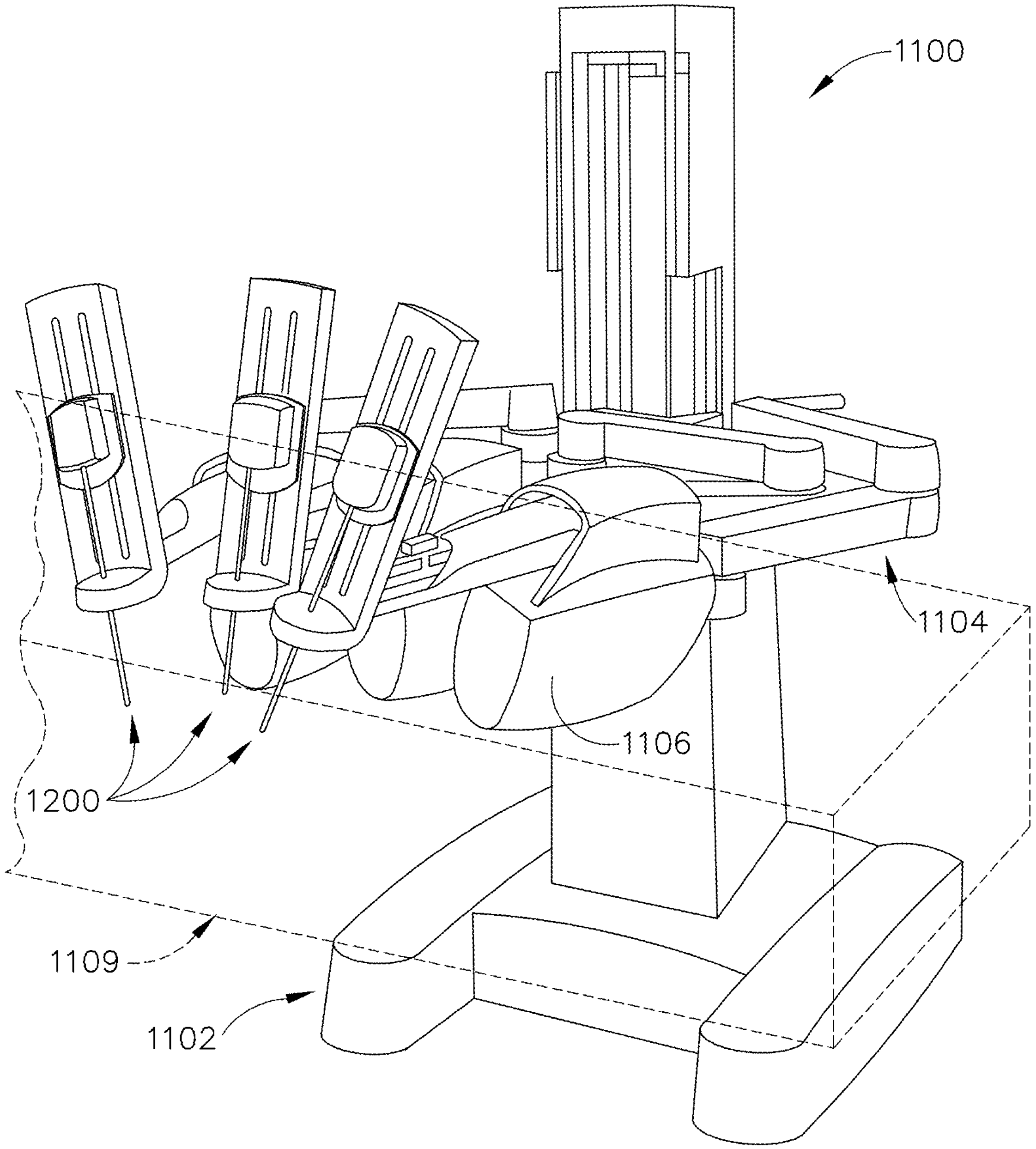
FIG. 2 is a perspective view of one robotic surgical arm cart/manipulator of a robotic system operably supporting a plurality of surgical tool embodiments of the present invention.

FIG. 1 depicts one version of a master controller 1001 that may be used in connection with a robotic arm slave cart 1100 of the type depicted in FIG. 2. Master controller 1001 and robotic arm slave cart 1100, as well as their respective components and control systems are collectively referred to herein as a robotic system 1000. Examples of such systems and devices are disclosed in U.S. Pat. No. 7,524,320 which has been herein incorporated by reference. Thus, various details of such devices will not be described in detail herein beyond that which may be necessary to understand various embodiments and forms of the present invention. As is known, the master controller 1001 generally includes master controllers (generally represented as 1003 in FIG. 1) which are grasped by the surgeon and manipulated in space while the surgeon views the procedure via a stereo display 1002. The master controllers 1001 generally comprise manual input devices which preferably move with multiple degrees of freedom, and which often further have an actuatable handle for actuating tools (for example, for closing grasping saws, applying an electrical potential to an electrode, or the like).

As can be seen in FIG. 2, in one form, the robotic arm cart 1100 is configured to actuate a plurality of surgical tools, generally designated as 1200. Various robotic surgery systems and methods employing master controller and robotic arm cart arrangements are disclosed in U.S. Pat. No. 6,132,368, entitled MULTI-COMPONENT TELEPRESENCE SYSTEM AND METHOD, the full disclosure of which is incorporated herein by reference. In various forms, the robotic arm cart 1100 includes a base 1002 from which, in the illustrated embodiment, three surgical tools 1200 are supported. In various forms, the surgical tools 1200 are each supported by a series of manually articulatable linkages, generally referred to as set-up joints 1104, and a robotic manipulator 1106. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 1100. Cart 1100 will generally have dimensions suitable for transporting the cart 1100 between operating rooms. The cart 1100 may be configured to typically fit through standard operating room doors and onto standard hospital elevators. In various forms, the cart 1100 would preferably have a weight and include a wheel (or other transportation) system that allows the cart 1100 to be positioned adjacent an operating table by a single attendant.

Figure 3:
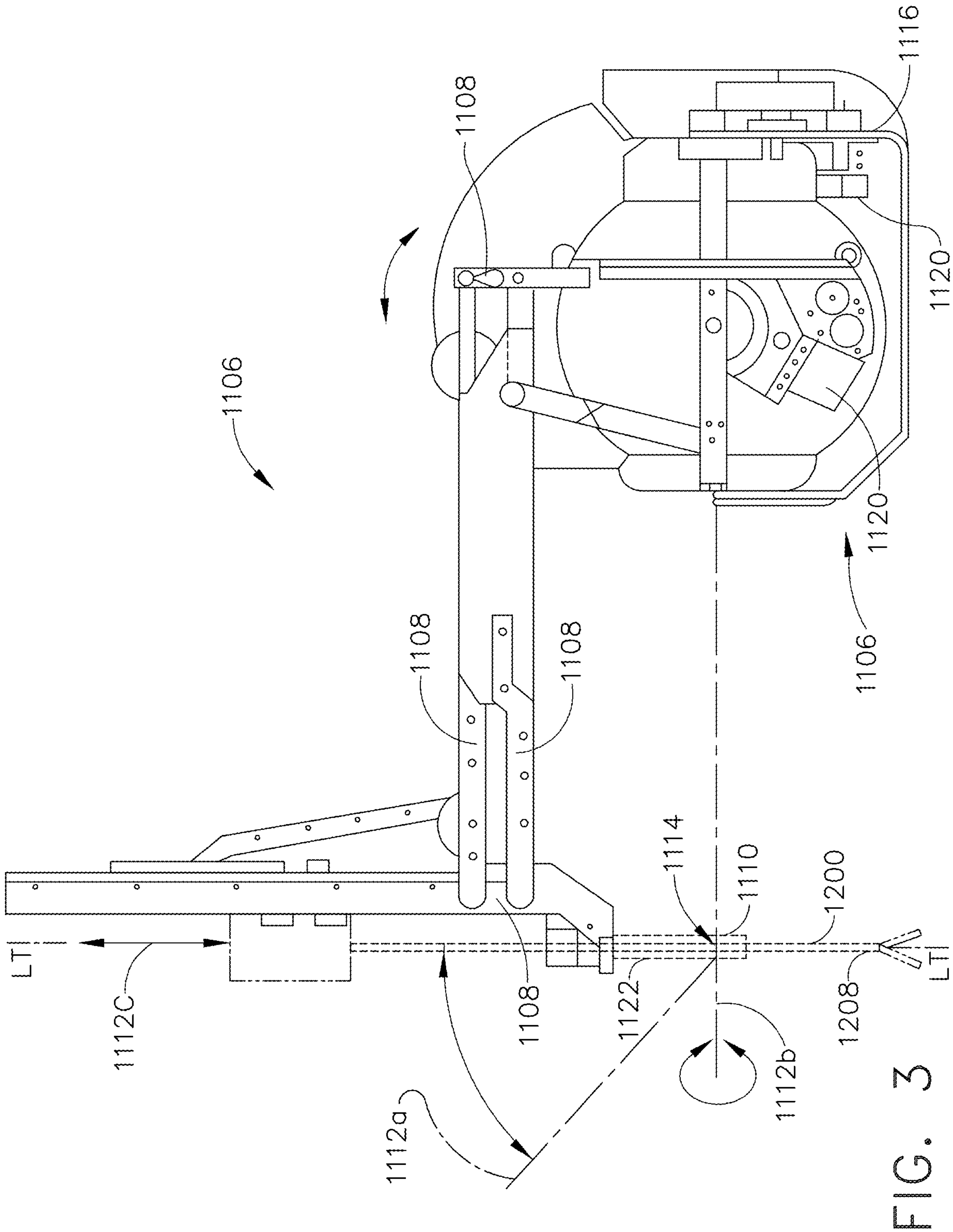
FIG. 3 is a side view of the robotic surgical arm cart/manipulator depicted in FIG. 2.

Referring now to FIG. 3, in at least one form, robotic manipulators 1106 may include a linkage 1108 that constrains movement of the surgical tool 1200. In various embodiments, linkage 1108 includes rigid links coupled together by rotational joints in a parallelogram arrangement so that the surgical tool 1200 rotates around a point in space 1110, as more fully described in issued U.S. Pat. No. 5,817,084, the full disclosure of which is herein incorporated by reference. The parallelogram arrangement constrains rotation to pivoting about an axis 1112*a*, sometimes called the pitch axis. The links supporting the parallelogram linkage are pivotally mounted to set-up joints 1104 (FIG. 2) so that the surgical tool 1200 further rotates about an axis 1112*b*, sometimes called the yaw axis. The pitch and yaw axes 1112*a*, 1112*b* intersect at the remote center 1114, which is aligned along a shaft 1208 of the surgical tool 1200. The surgical tool 1200 may have further degrees of driven freedom as supported by manipulator 1106, including sliding motion of the surgical tool 1200 along the longitudinal tool axis "LT-LT". As the surgical tool 1200 slides along the tool axis LT-LT relative to manipulator 1106 (arrow 1112*c*), remote center 1114 remains fixed relative to base 1116 of manipulator 1106. Hence, the entire manipulator is generally moved to re-position remote center 1114. Linkage 1108 of manipulator 1106 is driven by a series of motors 1120. These motors actively move linkage 1108 in response to commands from a processor of a control system. As will be discussed in further detail below, motors 1120 are also employed to manipulate the surgical tool 1200.

Figure 4:
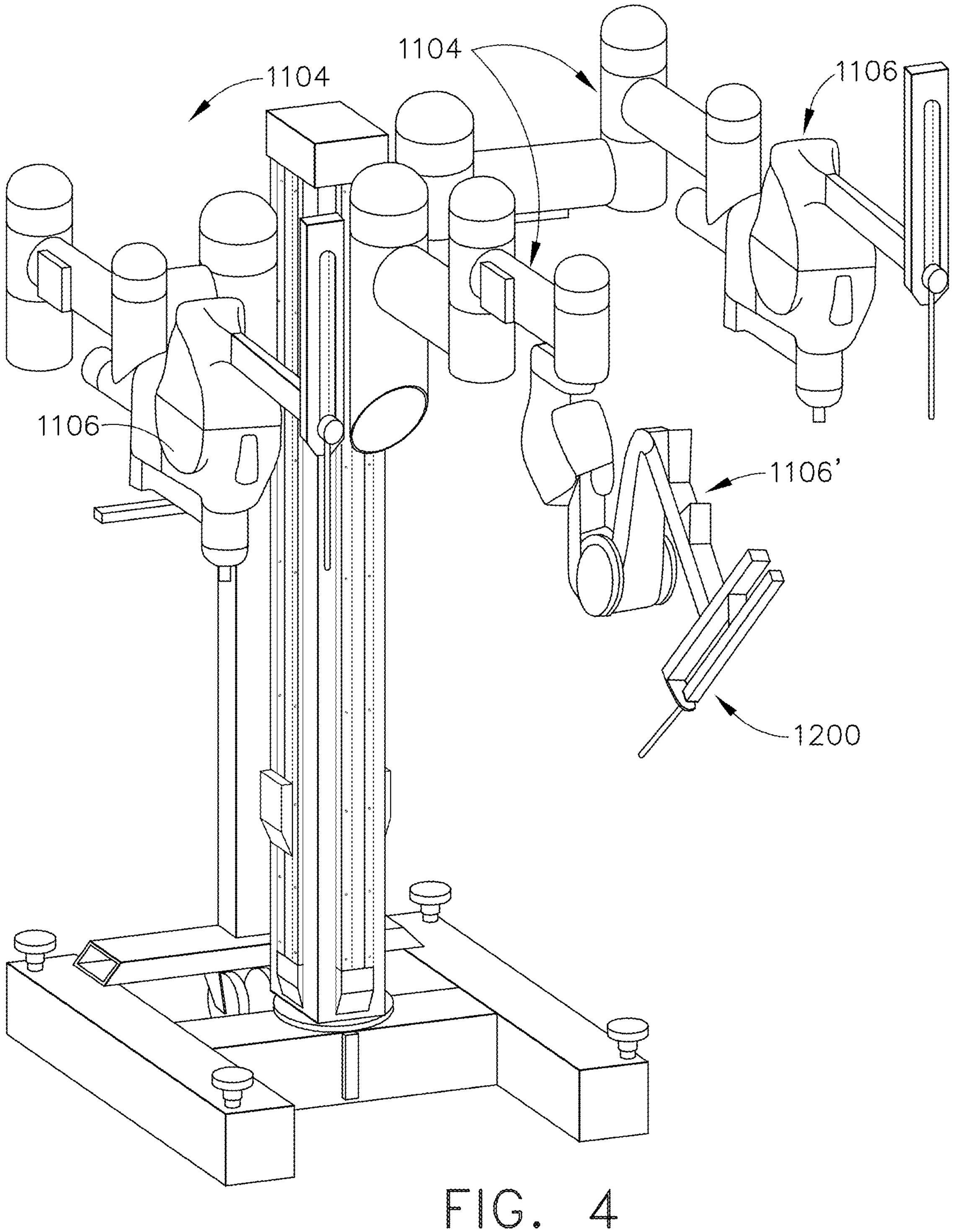
FIG. 4 is a perspective view of an exemplary cart structure with positioning linkages for operably supporting robotic manipulators that may be used with various surgical tool embodiments of the present invention.

An alternative set-up joint structure is illustrated in FIG. 4. In this embodiment, a surgical tool 1200 is supported by an alternative manipulator structure 1106' between two tissue manipulation tools. Those of ordinary skill in the art will appreciate that various embodiments of the present invention may incorporate a wide variety of alternative robotic structures, including those described in U.S. Pat. No. 5,878,193, entitled AUTOMATED ENDOSCOPE SYSTEM FOR OPTIMAL POSITIONING, the full disclosure of which is incorporated herein by reference. Additionally, while the data communication between a robotic component and the processor of the robotic surgical system is primarily described herein with reference to communication between the surgical tool 1200 and the master controller 1001, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 5:
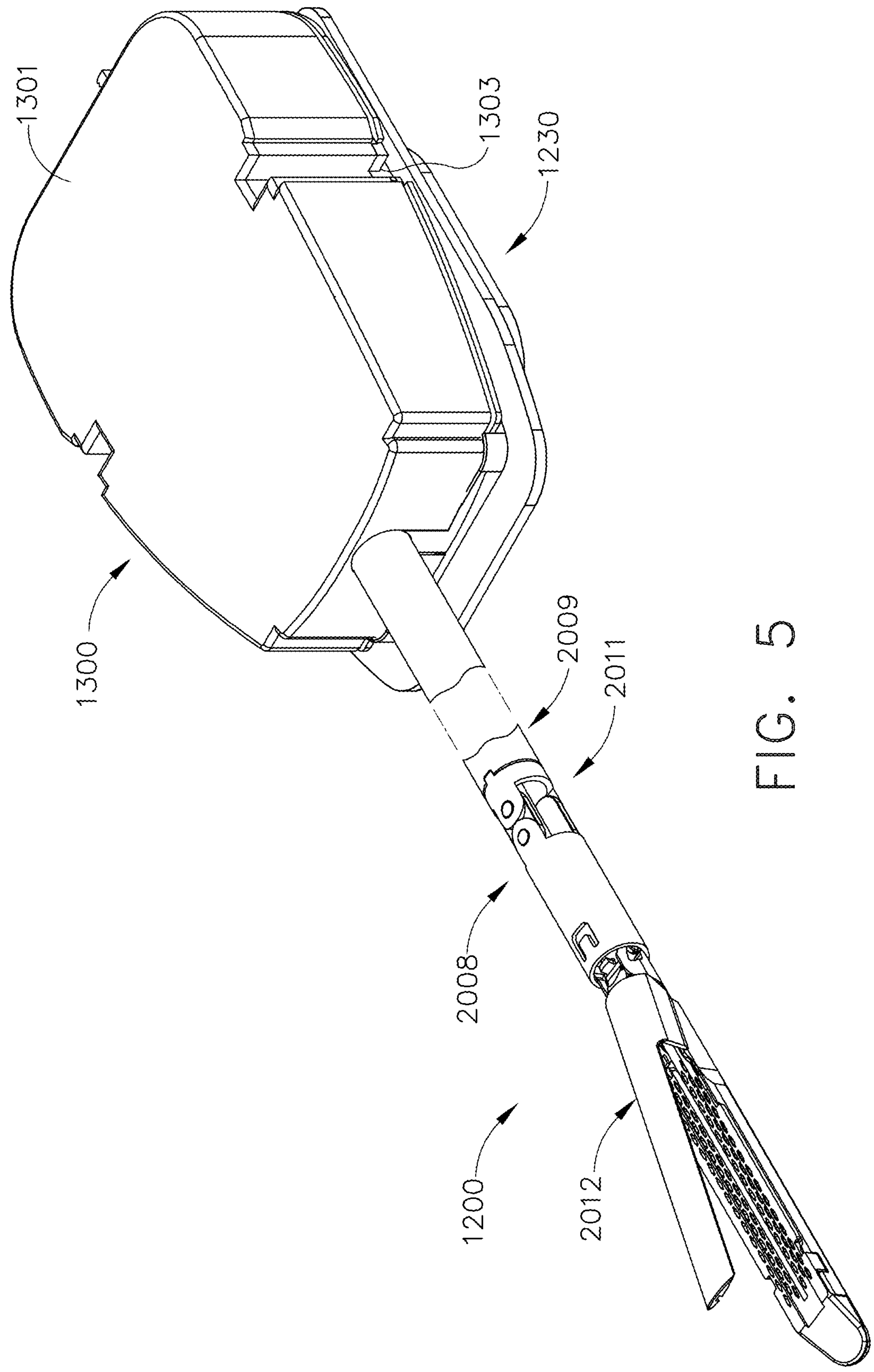
FIG. 5 is a perspective view of a surgical tool embodiment of the present invention.
Figure 10:
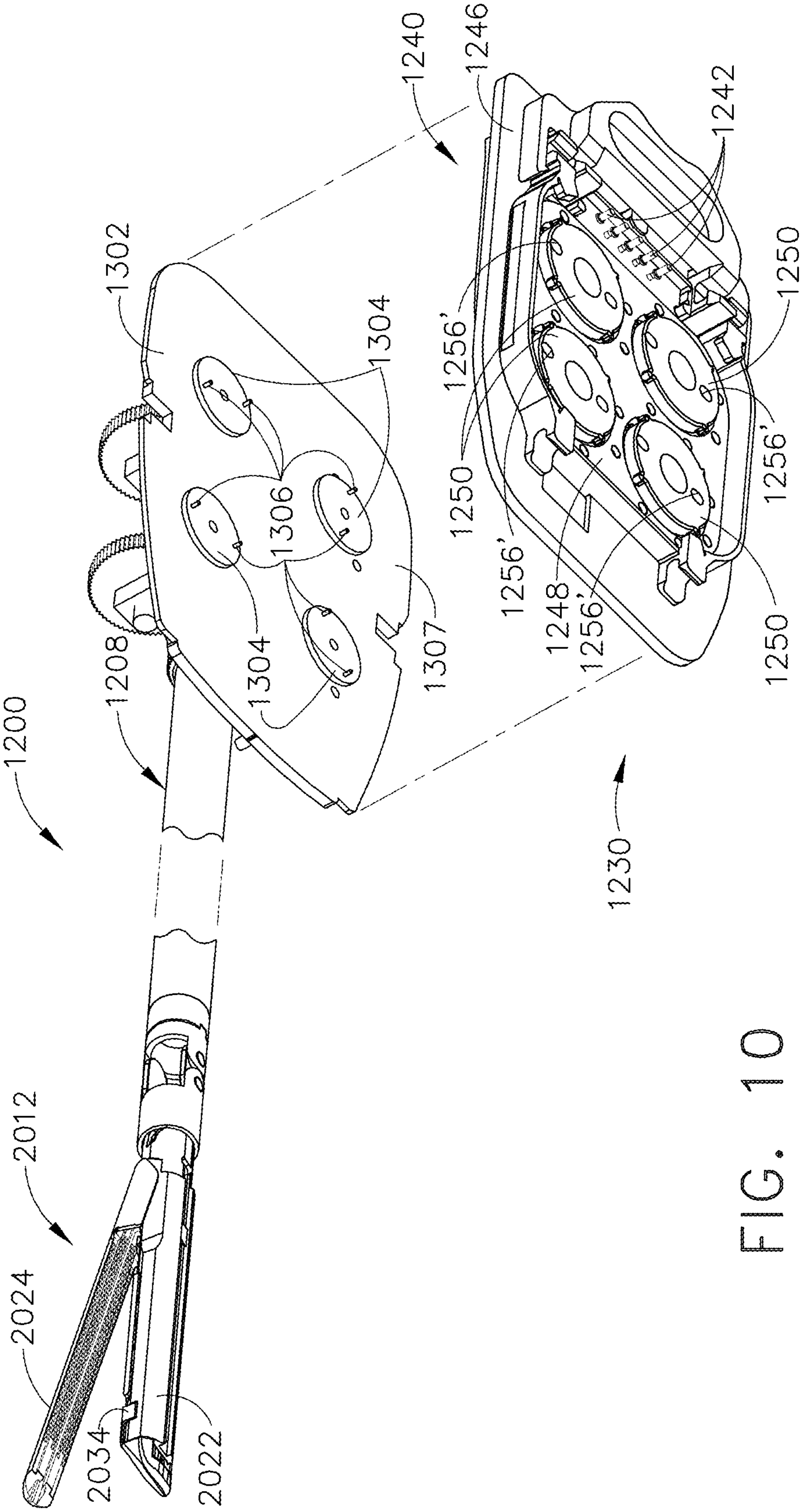
FIG. 10 is a partial bottom perspective view of the surgical tool embodiment of FIG. 5.
Figure 11:
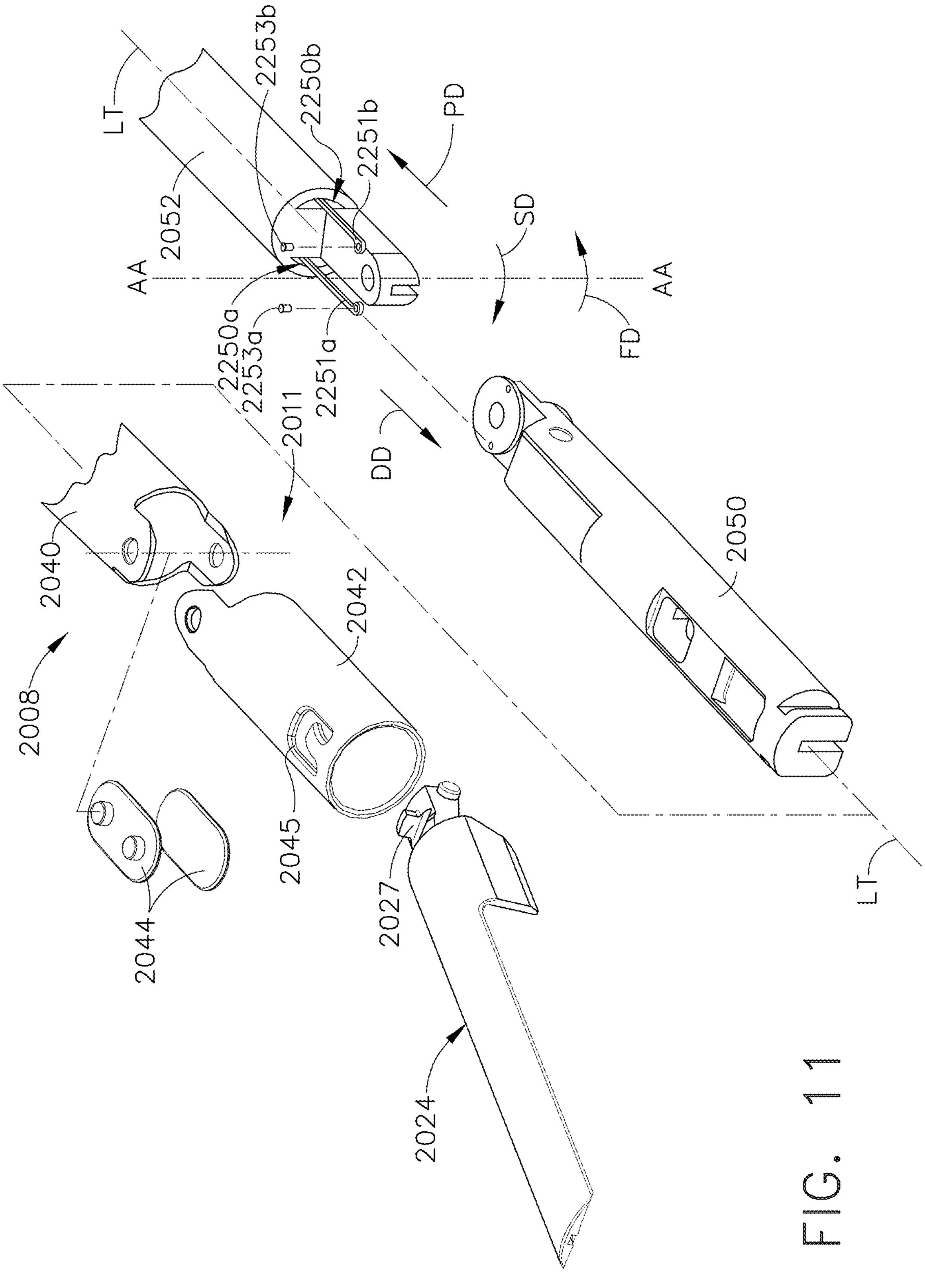
FIG. 11 is a partial exploded view of a portion of an articulatable surgical end effector embodiment of the present invention.
Figure 12:
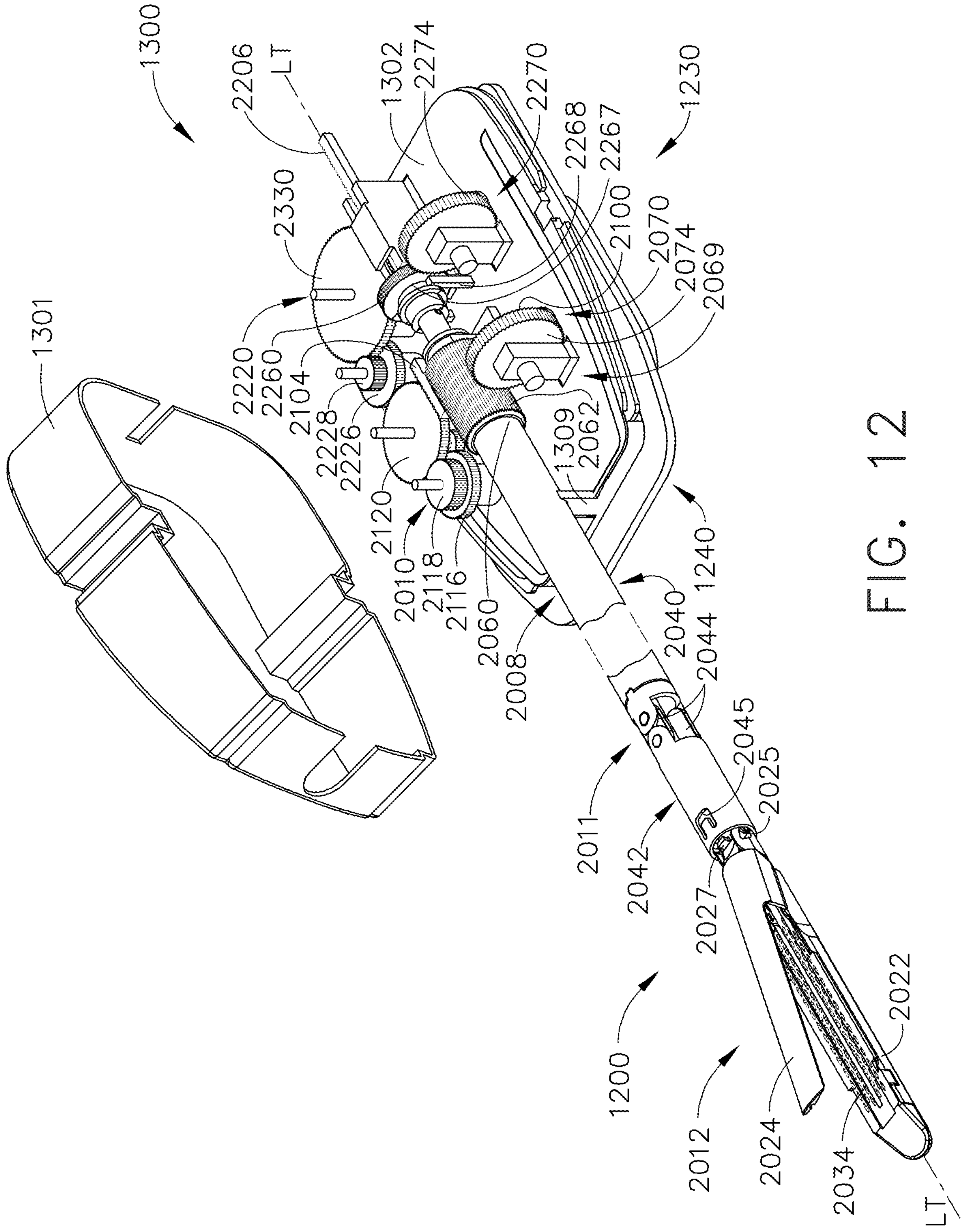
FIG. 12 is a perspective view of the surgical tool embodiment of FIG. 10 with the tool mounting housing removed.

An exemplary non-limiting surgical tool 1200 that is well-adapted for use with a robotic system 1000 that has a tool drive assembly 1010 (FIG. 6) that is operatively coupled to a master controller 1001 that is operable by inputs from an operator (i.e., a surgeon) is depicted in FIG. 5. As can be seen in that Figure, the surgical tool 1200 includes a surgical end effector 2012 that comprises an endocutter. In at least one form, the surgical tool 1200 generally includes an elongated shaft assembly 2008 that has a proximal closure tube 2040 and a distal closure tube 2042 that are coupled together by an articulation joint 2011. The surgical tool 1200 is operably coupled to the manipulator by a tool mounting portion, generally designated as 1300. The surgical tool 1200 further includes an interface 1230 which mechanically and electrically couples the tool mounting portion 1300 to the manipulator. One form of interface 1230 is illustrated in FIGS. 6-10. In various embodiments, the tool mounting portion 1300 includes a tool mounting plate 1302 that operably supports a plurality of (four are shown in FIG. 10) rotatable body portions, driven discs or elements 1304, that each include a pair of pins 1306 that extend from a surface of the driven element 1304. One pin 1306 is closer to an axis of rotation of each driven elements 1304 than the other pin 1306 on the same driven element 1304, which helps to ensure positive angular alignment of the driven element 1304. Interface 1230 includes an adaptor portion 1240 that is configured to mountingly engage the mounting plate 1302 as will be further discussed below. The adaptor portion 1240 may include an array of electrical connecting pins 1242 (FIG. 8) which may be coupled to a memory structure by a circuit board within the tool mounting portion 1300. While interface 1230 is described herein with reference to mechanical, electrical, and magnetic coupling elements, it should be understood that a wide variety of telemetry modalities might be used, including infrared, inductive coupling, or the like.

As can be seen in FIGS. 6-9, the adapter portion 1240 generally includes a tool side 1244 and a holder side 1246. In various forms, a plurality of rotatable bodies 1250 are mounted to a floating plate 1248 which has a limited range of movement relative to the surrounding adaptor structure normal to the major surfaces of the adaptor 1240. Axial movement of the floating plate 1248 helps decouple the rotatable bodies 1250 from the tool mounting portion 1300 when the levers 1303 along the sides of the tool mounting portion housing 1301 are actuated (Sec FIG. 5). Other mechanisms/arrangements may be employed for releasably coupling the tool mounting portion 1300 to the adaptor 1240. In at least one form, rotatable bodies 1250 are resiliently mounted to floating plate 1248 by resilient radial members which extend into a circumferential indentation about the rotatable bodies 1250. The rotatable bodies 1250 can move axially relative to plate 1248 by deflection of these resilient structures. When disposed in a first axial position (toward tool side 1244) the rotatable bodies 1250 are free to rotate without angular limitation. However, as the rotatable bodies 1250 move axially toward tool side 1244, tabs 1252 (extending radially from the rotatable bodies 1250) laterally engage detents on the floating plates so as to limit angular rotation of the rotatable bodies 1250 about their axes. This limited rotation can be used to help drivingly engage the rotatable bodies 1250 with drive pins 1272 of a corresponding tool holder portion 1270 of the robotic system 1000, as the drive pins 1272 will push the rotatable bodies 1250 into the limited rotation position until the pins 1234 are aligned with (and slide into) openings 1256'. Openings 1256 on the tool side 1244 and openings 1256' on the holder side 1246 of rotatable bodies 1250 are configured to accurately align the driven elements 1304 (FIG. 10) of the tool mounting portion 1300 with the drive elements 1271 of the tool holder 1270. As described above regarding inner and outer pins 1306 of driven elements 1304, the openings 1256, 1256' are at differing distances from the axis of rotation on their respective rotatable bodies 1250 so as to ensure that the alignment is not 180 degrees from its intended position. Additionally, each of the openings 1256 is slightly radially elongated so as to fittingly receive the pins 1306 in the circumferential orientation. This allows the pins 1306 to slide radially within the openings 1256, 1256' and accommodate some axial misalignment between the tool 1200 and tool holder 1270, while minimizing any angular misalignment and backlash between the drive and driven elements. Openings 1256 on the tool side 1244 are offset by about 90 degrees from the openings 1256' (shown in broken lines) on the holder side 1246, as can be seen most clearly in FIG. 9.

Various embodiments may further include an array of electrical connector pins 1242 located on holder side 1246 of adaptor 1240, and the tool side 1244 of the adaptor 1240 may include slots 1258 (FIG. 9) for receiving a pin array (not shown) from the tool mounting portion 1300. In addition to transmitting electrical signals between the surgical tool 1200 and the tool holder 1270, at least some of these electrical connections may be coupled to an adaptor memory device 1260 (FIG. 8) by a circuit board of the adaptor 1240.

Figure 6:
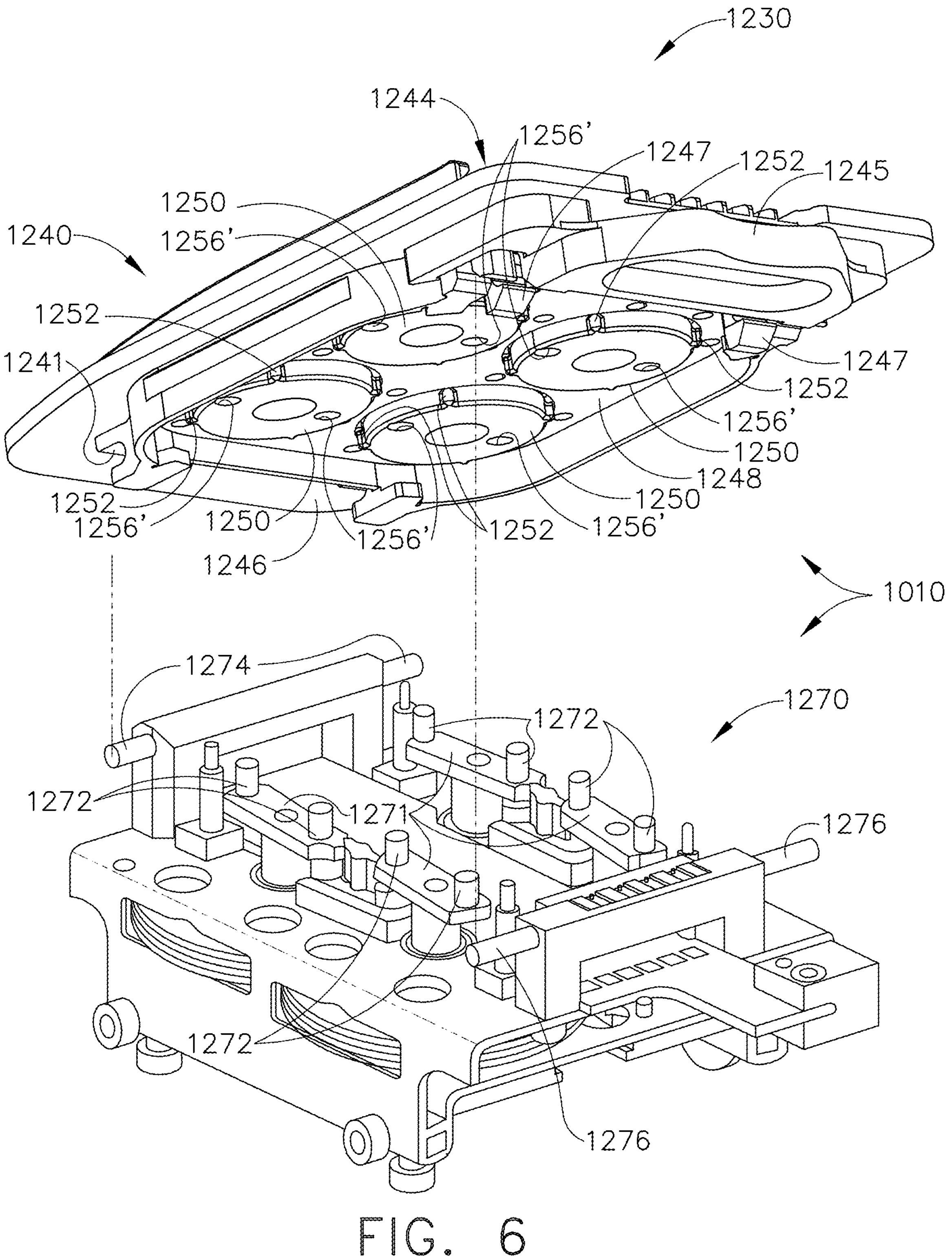
FIG. 6 is an exploded assembly view of an adapter and tool holder arrangement for attaching various surgical tool embodiments to a robotic system.
Figure 7:
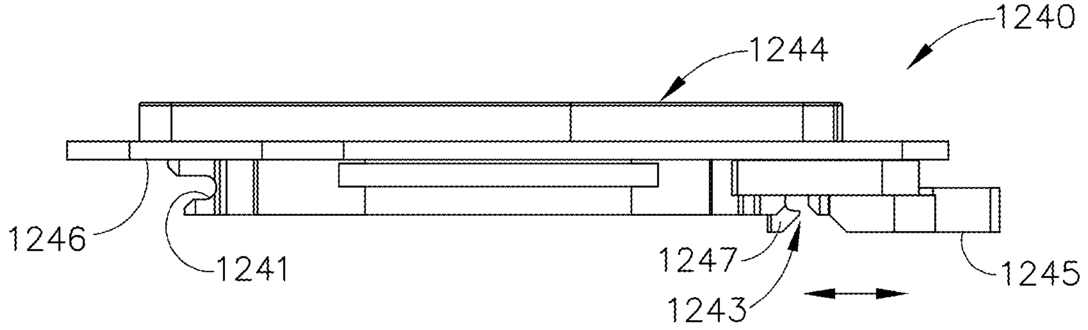
FIG. 7 is a side view of the adapter shown in FIG. 6.
Figure 8:
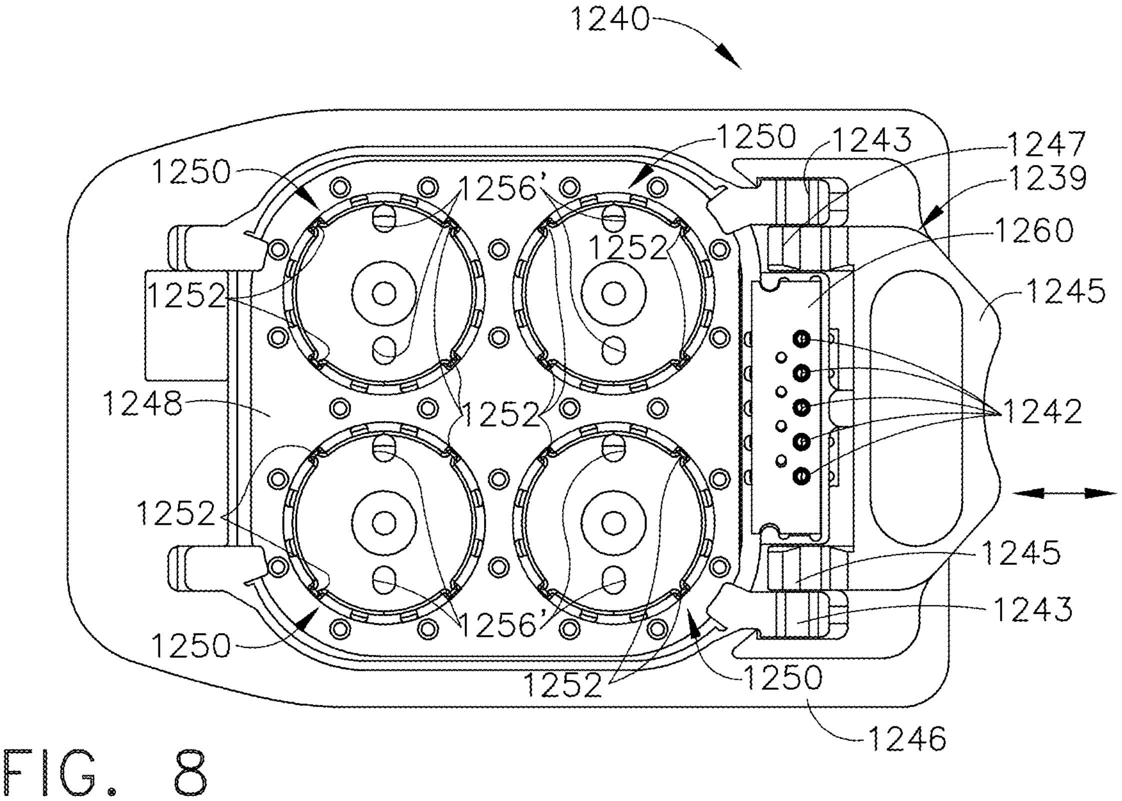
FIG. 8 is a bottom view of the adapter shown in FIG. 6.
Figure 9:
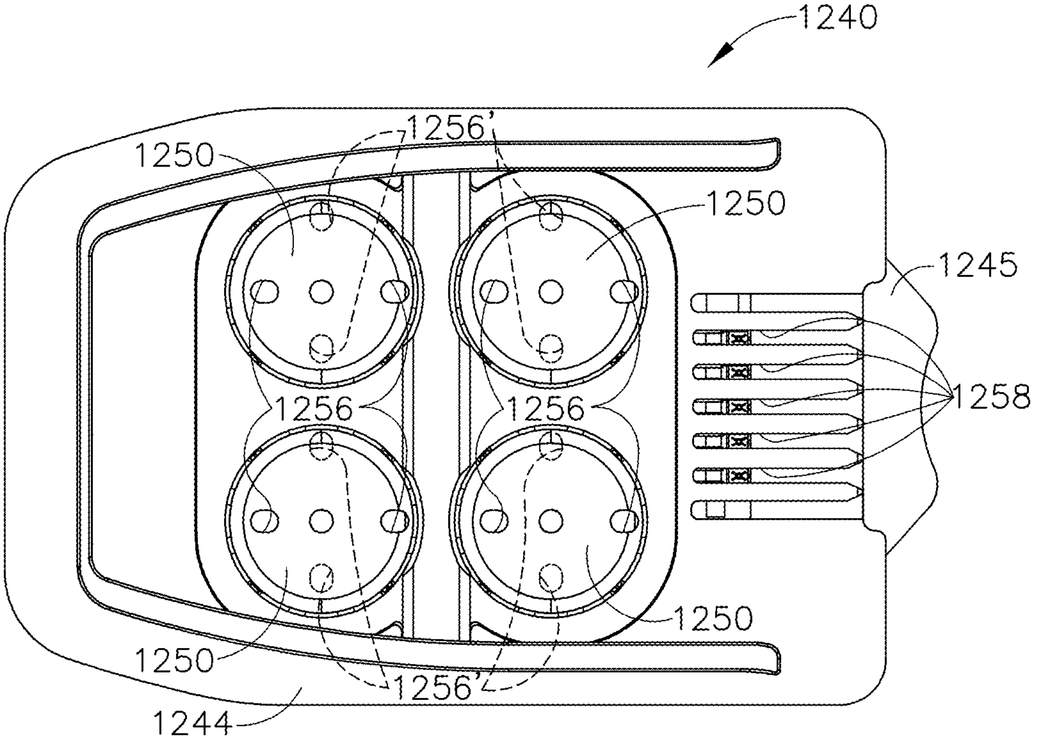
FIG. 9 is a top view of the adapter of FIGS. 6 and 7.

A detachable latch arrangement 1239 may be employed to releasably affix the adaptor 1240 to the tool holder 1270. As used herein, the term "tool drive assembly" when used in the context of the robotic system 1000, at least encompasses various embodiments of the adapter 1240 and tool holder 1270 and which has been generally designated as 1010 in FIG. 6. For example, as can be seen in FIG. 6, the tool holder 1270 may include a first latch pin arrangement 1274 that is sized to be received in corresponding clevis slots 1241 provided in the adaptor 1240. In addition, the tool holder 1270 may further have second latch pins 1276 that are sized to be retained in corresponding latch clevises 1243 in the adaptor 1240. See FIG. 29. In at least one form, a latch assembly 1245 is movably supported on the adapter 1240 and is biasable between a first latched position wherein the latch pins 1276 are retained within their respective latch clevis 1243 and an unlatched position wherein the second latch pins 1276 may be into or removed from the latch clevises 1243. A spring or springs (not shown) are employed to bias the latch assembly into the latched position. A lip on the tool side 1244 of adaptor 1240 may slidably receive laterally extending tabs of tool mounting housing 1301.

Figure 14:
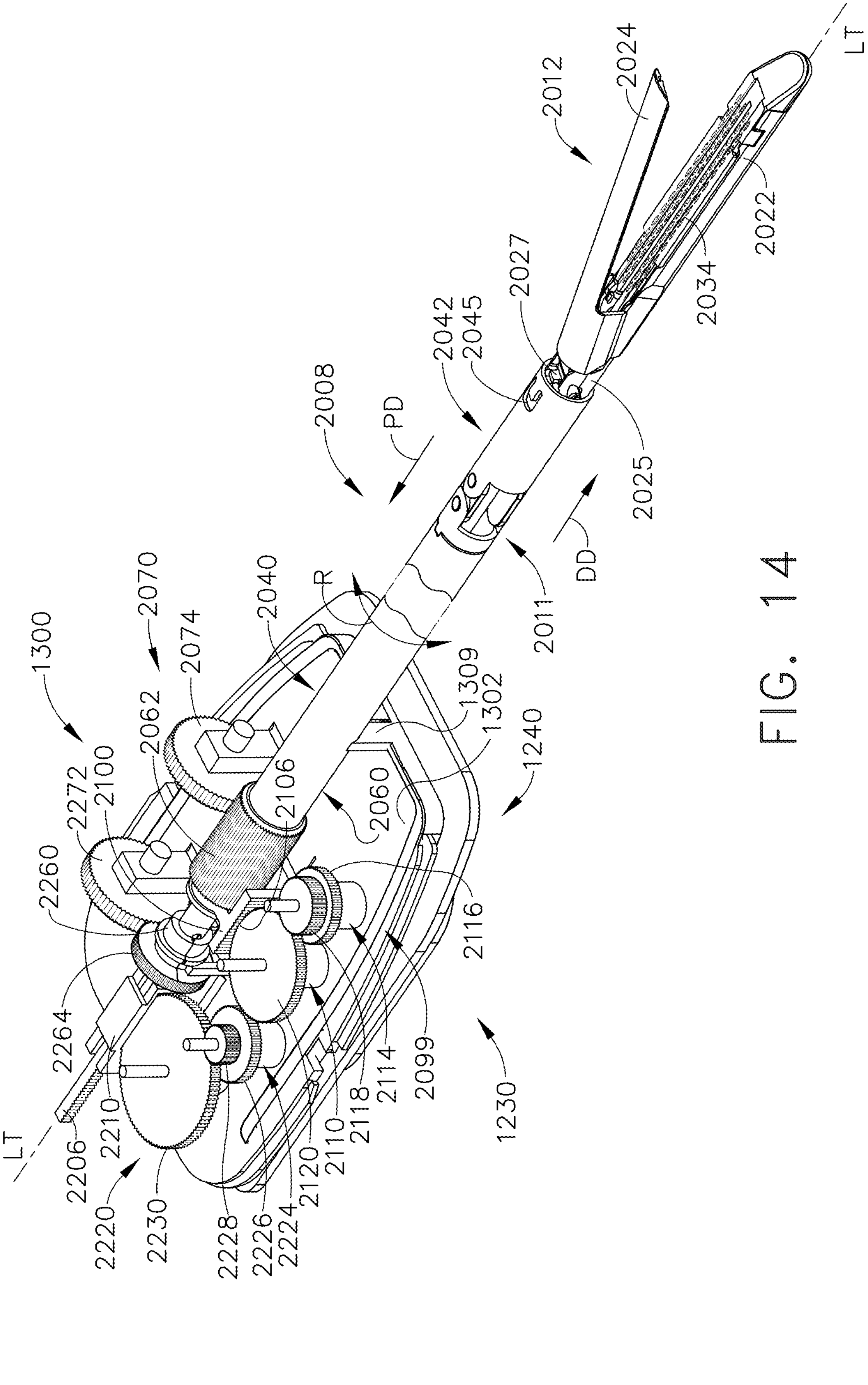
FIG. 14 is a front perspective view of the surgical tool embodiment of FIG. 10 with the tool mounting housing removed.
Figure 15:
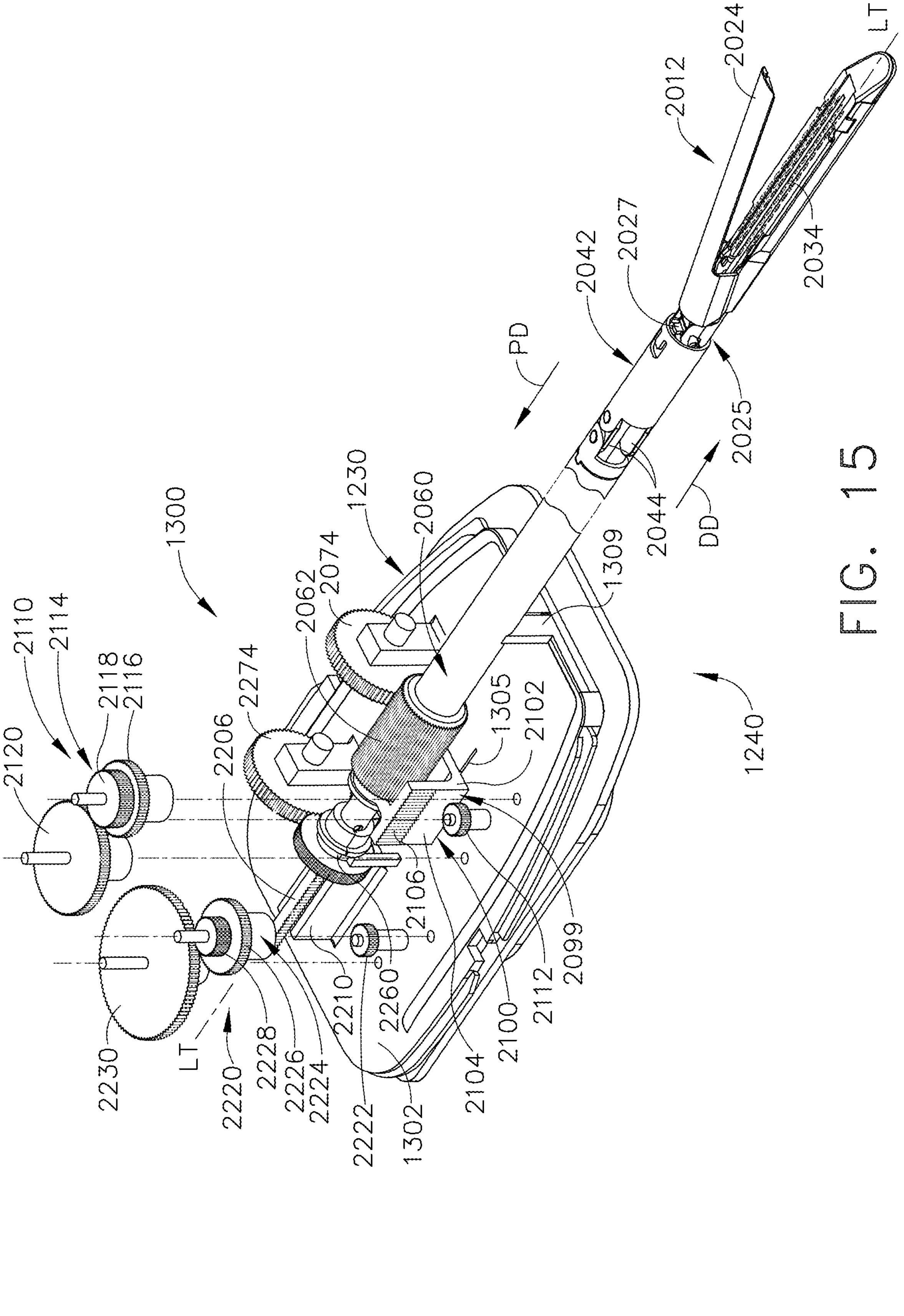
FIG. 15 is a partial exploded perspective view of the surgical tool embodiment of FIG. 14.
Figure 16:
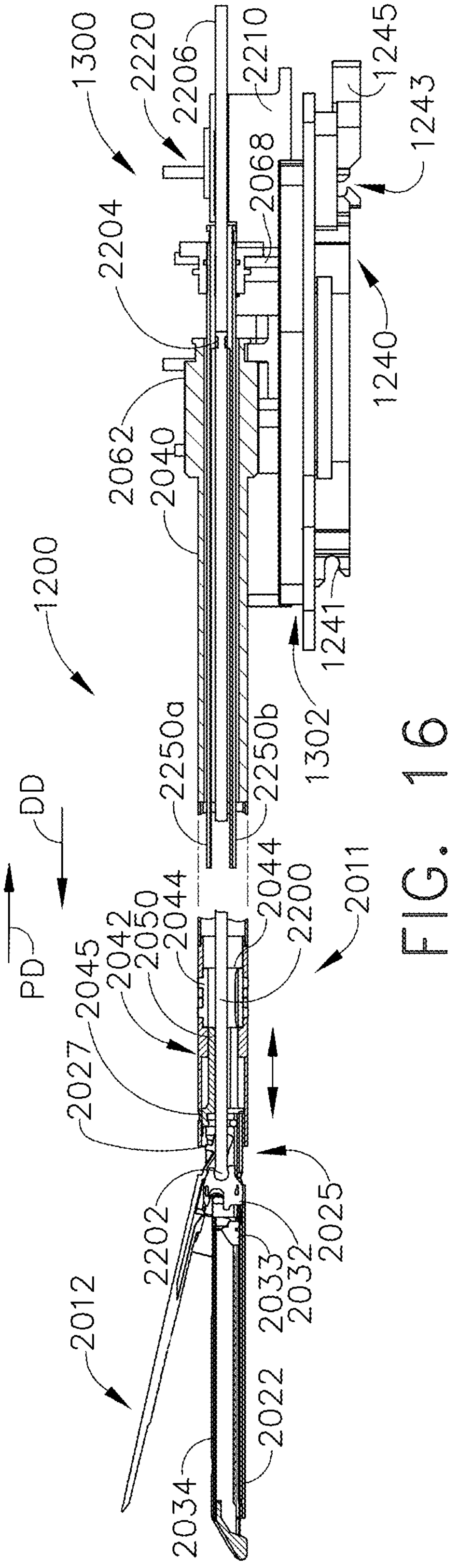
FIG. 16 is a partial cross-sectional side view of the surgical tool embodiment of FIG. 10.
Figure 17:
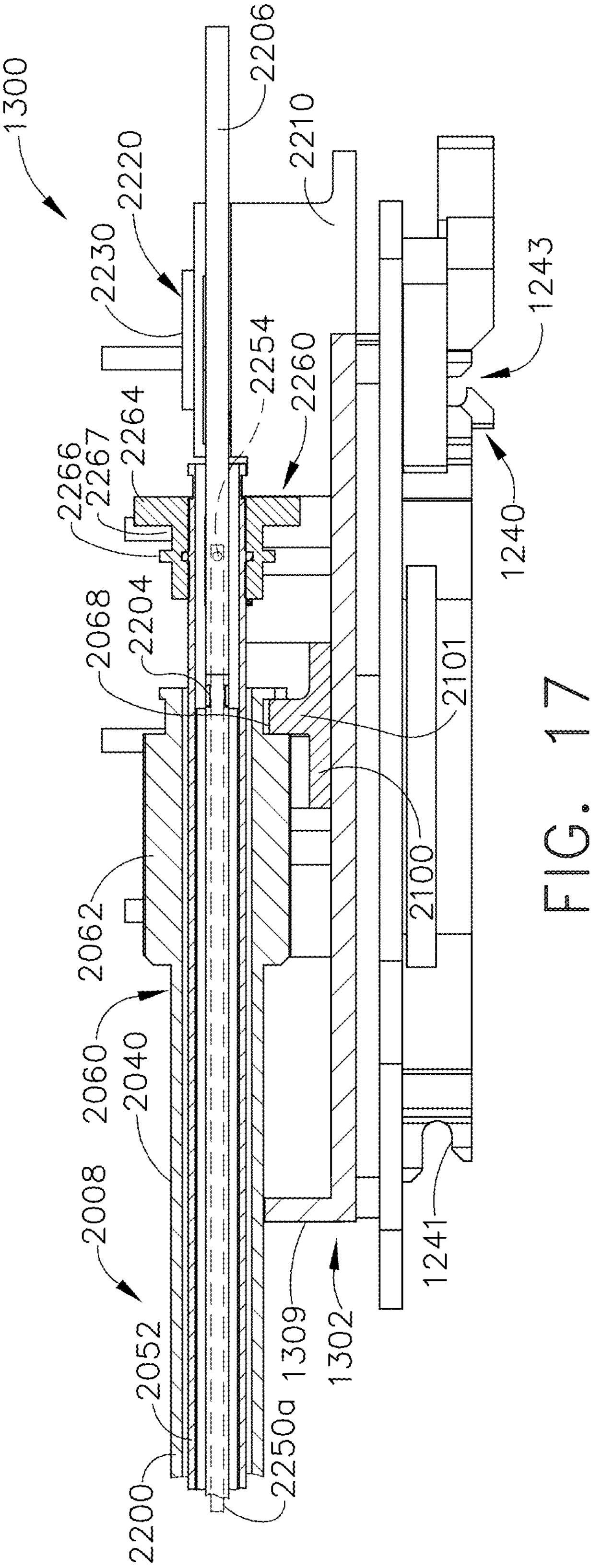
FIG. 17 is an enlarged cross-sectional view of a portion of the surgical tool depicted in FIG. 16.

Turning next to FIGS. 10-17, in at least one embodiment, the surgical tool 1200 includes a surgical end effector 2012 that comprises in this example, among other things, at least one component 2024 that is selectively movable between first and second positions relative to at least one other component 2022 in response to various control motions applied thereto as will be discussed in further detail below. In various embodiments, component 2022 comprises an elongated channel 2022 configured to operably support a surgical staple cartridge 2034 therein and component 2024 comprises a pivotally translatable clamping member, such as an anvil 2024. Various embodiments of the surgical end effector 2012 are configured to maintain the anvil 2024 and elongated channel 2022 at a spacing that assures effective stapling and severing of tissue clamped in the surgical end effector 2012. As can be seen in FIG. 16, the surgical end effector 2012 further includes a cutting instrument 2032 and a sled 2033. The cutting instrument 2032 may be, for example, a knife. The surgical staple cartridge 2034 operably houses a plurality of surgical staples (not show) therein that are supported on movable staple drivers (not shown). As the cutting instrument 2032 is driven distally through a centrally-disposed slot (not shown) in the surgical staple cartridge 2034, it forces the sled 2033 distally as well. As the sled 2033 is driven distally, its "wedge-shaped" configuration contacts the movable staple drivers and drives them vertically toward the closed anvil 2024. The surgical staples are formed as they are driven into the forming surface located on the underside of the anvil 2024. The sled 2033 may be part of the surgical staple cartridge 2034, such that when the cutting instrument 2032 is retracted following the cutting operation, the sled 2033 does not retract. The anvil 2024 may be pivotably opened and closed at a pivot point 2025 located at the proximal end of the elongated channel 2022. The anvil 2024 may also include a tab 2027 at its proximal end that interacts with a component of the mechanical closure system (described further below) to facilitate the opening of the anvil 2024. The elongated channel 2022 and the anvil 2024 may be made of an electrically conductive material (such as metal) so that they may serve as part of an antenna that communicates with sensor(s) in the end effector, as described above. The surgical staple cartridge 2034 could be made of a nonconductive material (such as plastic) and the sensor may be connected to or disposed in the surgical staple cartridge 2034, as was also described above.

As can be seen in FIGS. 10-17, the surgical end effector 2012 is attached to the tool mounting portion 1300 by an elongated shaft assembly 2008 according to various embodiments. As shown in the illustrated embodiment, the shaft assembly 2008 includes an articulation joint generally indicated as 2011 that enables the surgical end effector 2012 to be selectively articulated about an articulation axis AA-AA that is substantially transverse to a longitudinal tool axis LT-LT. See FIG. 11. In other embodiments, the articulation joint is omitted. In various embodiments, the shaft assembly 2008 may include a closure tube assembly 2009 that comprises a proximal closure tube 2040 and a distal closure tube 2042 that are pivotably linked by a pivot links 2044 and operably supported on a spine assembly generally depicted as 2049. In the illustrated embodiment, the spine assembly 2049 comprises a distal spine portion 2050 that is attached to the elongated channel 2022 and is pivotally coupled to the proximal spine portion 2052. The closure tube assembly 2009 is configured to axially slide on the spine assembly 2049 in response to actuation motions applied thereto. The distal closure tube 2042 includes an opening 2045 into which the tab 2027 on the anvil 2024 is inserted in order to facilitate opening of the anvil 2024 as the distal closure tube 2042 is moved axially in the proximal direction “PD”. The closure tubes 2040, 2042 may be made of electrically conductive material (such as metal) so that they may serve as part of the antenna, as described above. Components of the main drive shaft assembly (e.g., the drive shafts 2048, 2050) may be made of a nonconductive material (such as plastic).

Figure 13:
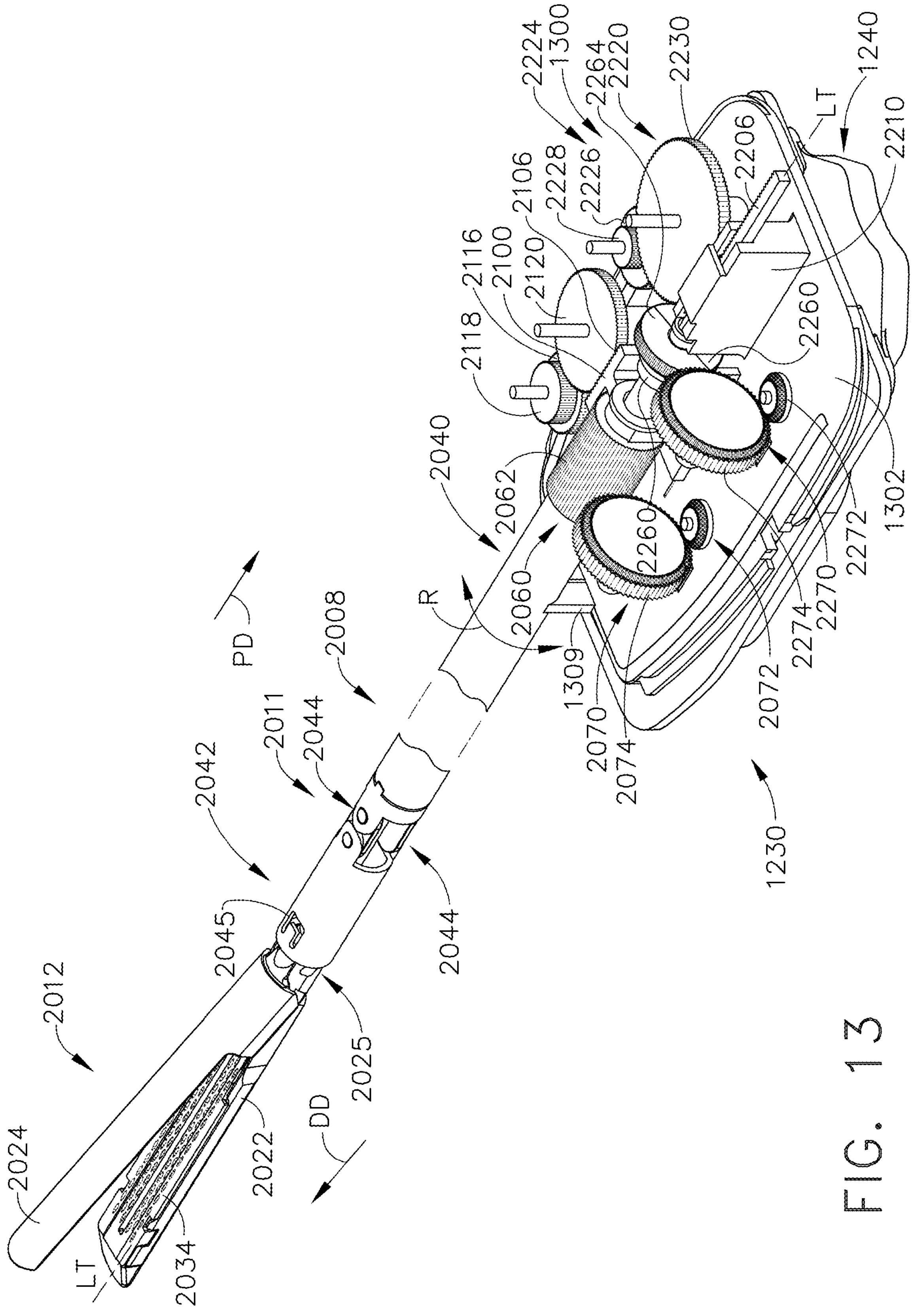
FIG. 13 is a rear perspective view of the surgical tool embodiment of FIG. 10 with the tool mounting housing removed.

In use, it may be desirable to rotate the surgical end effector 2012 about the longitudinal tool axis LT-LT. In at least one embodiment, the tool mounting portion 1300 includes a rotational transmission assembly 2069 that is configured to receive a corresponding rotary output motion from the tool drive assembly 1010 of the robotic system 1000 and convert that rotary output motion to a rotary control motion for rotating the elongated shaft assembly 2008 (and surgical end effector 2012) about the longitudinal tool axis LT-LT. In various embodiments, for example, the proximal end 2060 of the proximal closure tube 2040 is rotatably supported on the tool mounting plate 1302 of the tool mounting portion 1300 by a forward support cradle 1309 and a closure sled 2100 that is also movably supported on the tool mounting plate 1302. In at least one form, the rotational transmission assembly 2069 includes a tube gear segment 2062 that is formed on (or attached to) the proximal end 2060 of the proximal closure tube 2040 for operable engagement by a rotational gear assembly 2070 that is operably supported on the tool mounting plate 1302. As can be seen in FIG. 13, the rotational gear assembly 2070, in at least one embodiment, comprises a rotation drive gear 2072 that is coupled to a corresponding first one of the driven discs or elements 1304 on the adapter side 1307 of the tool mounting plate 1302 when the tool mounting portion 1300 is coupled to the tool drive assembly 1010. See FIG. 10. The rotational gear assembly 2070 further comprises a rotary driven gear 2074 that is rotatably supported on the tool mounting plate 1302 in meshing engagement with the tube gear segment 2062 and the rotation drive gear 2072. Application of a first rotary output motion from the tool drive assembly 1010 of the robotic system 1000 to the corresponding driven element 1304 will thereby cause rotation of the rotation drive gear 2072. Rotation of the rotation drive gear 2072 ultimately results in the rotation of the elongated shaft assembly 2008 (and the surgical end effector 2012) about the longitudinal tool axis LT-LT (represented by arrow “R” in FIG. 13). It will be appreciated that the application of a rotary output motion from the tool drive assembly 1010 in one direction will result in the rotation of the elongated shaft assembly 2008 and surgical end effector 2012 about the longitudinal tool axis LT-LT in a first direction and an application of the rotary output motion in an opposite direction will result in the rotation of the elongated shaft assembly 2008 and surgical end effector 2012 in a second direction that is opposite to the first direction.

Figure 18:
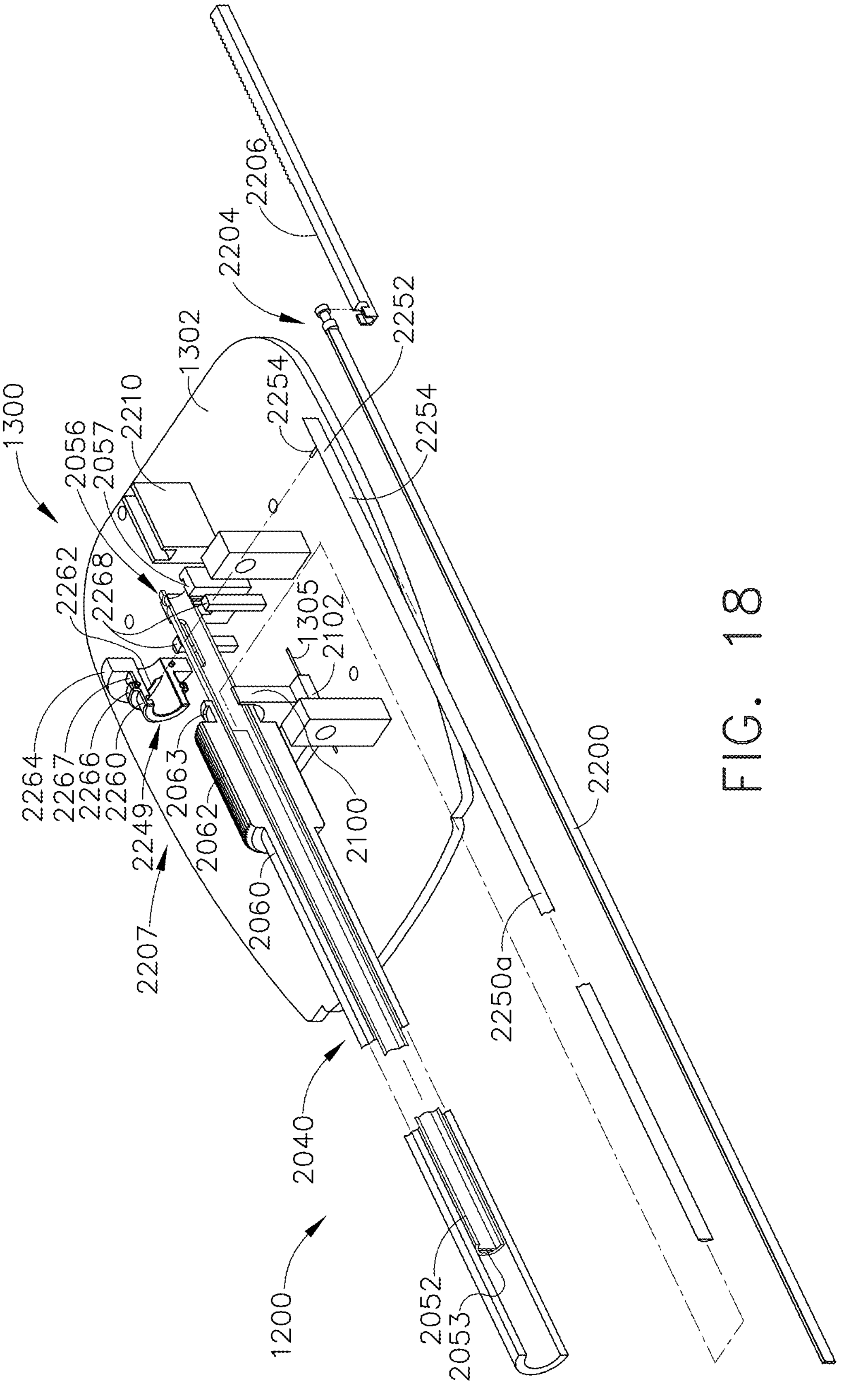
FIG. 18 is an exploded perspective view of a portion of the tool mounting portion of the surgical tool embodiment depicted in FIG. 10.

In at least one embodiment, the closure of the anvil 2024 relative to the staple cartridge 2034 is accomplished by axially moving the closure tube assembly 2009 in the distal direction “DD” on the spine assembly 2049. As indicated above, in various embodiments, the proximal end 2060 of the proximal closure tube 2040 is supported by the closure sled 2100 which comprises a portion of a closure transmission, generally depicted as 2099. In at least one form, the closure sled 2100 is configured to support the closure tube 2009 on the tool mounting plate 1320 such that the proximal closure tube 2040 can rotate relative to the closure sled 2100, yet travel axially with the closure sled 2100. In particular, as can be seen in FIG. 18, the closure sled 2100 has an upstanding tab 2101 that extends into a radial groove 2063 in the proximal end portion of the proximal closure tube 2040. In addition, as can be seen in FIGS. 15 and 18, the closure sled 2100 has a tab portion 2102 that extends through a slot 1305 in the tool mounting plate 1302. The tab portion 2102 is configured to retain the closure sled 2100 in sliding engagement with the tool mounting plate 1302. In various embodiments, the closure sled 2100 has an upstanding portion 2104 that has a closure rack gear 2106 formed thereon. The closure rack gear 2106 is configured for driving engagement with a closure gear assembly 2110. Sec FIG. 15.

In various forms, the closure gear assembly 2110 includes a closure spur gear 2112 that is coupled to a corresponding second one of the driven discs or elements 1304 on the adapter side 1307 of the tool mounting plate 1302. See FIG. 10. Thus, application of a second rotary output motion from the tool drive assembly 1010 of the robotic system 1000 to the corresponding second driven element 1304 will cause rotation of the closure spur gear 2112 when the tool mounting portion 1300 is coupled to the tool drive assembly 1010. The closure gear assembly 2110 further includes a closure reduction gear set 2114 that is supported in meshing engagement with the closure spur gear 2112. As can be seen in FIGS. 14 and 15, the closure reduction gear set 2114 includes a driven gear 2116 that is rotatably supported in meshing engagement with the closure spur gear 2112. The closure reduction gear set 2114 further includes a first closure drive gear 2118 that is in meshing engagement with a second closure drive gear 2120 that is rotatably supported on the tool mounting plate 1302 in meshing engagement with the closure rack gear 2106. Thus, application of a second rotary output motion from the tool drive assembly 1010 of the robotic system 1000 to the corresponding second driven element 1304 will cause rotation of the closure spur gear 2112 and the closure transmission 2110 and ultimately drive the closure sled 2100 and closure tube assembly 2009 axially. The axial direction in which the closure tube assembly 2009 moves ultimately depends upon the direction in which the second driven element 1304 is rotated. For example, in response to one rotary output motion received from the tool drive assembly 1010 of the robotic system 1000, the closure sled 2100 will be driven in the distal direction "DD" and ultimately drive the closure tube assembly 1009 in the distal direction. As the distal closure tube 2042 is driven distally, the end of the closure tube segment 2042 will engage a portion of the anvil 2024 and cause the anvil 2024 to pivot to a closed position. Upon application of an "opening" out put motion from the tool drive assembly 1010 of the robotic system 1000, the closure sled 2100 and shaft assembly 2008 will be driven in the proximal direction "PD". As the distal closure tube 2042 is driven in the proximal direction, the opening 2045 therein interacts with the tab 2027 on the anvil 2024 to facilitate the opening thereof. In various embodiments, a spring (not shown) may be employed to bias the anvil to the open position when the distal closure tube 2042 has been moved to its starting position. In various embodiments, the various gears of the closure gear assembly 2110 are sized to generate the necessary closure forces needed to satisfactorily close the anvil 2024 onto the tissue to be cut and stapled by the surgical end effector 2012. For example, the gears of the closure transmission 2110 may be sized to generate approximately 70-120 pounds.

Figure 19:
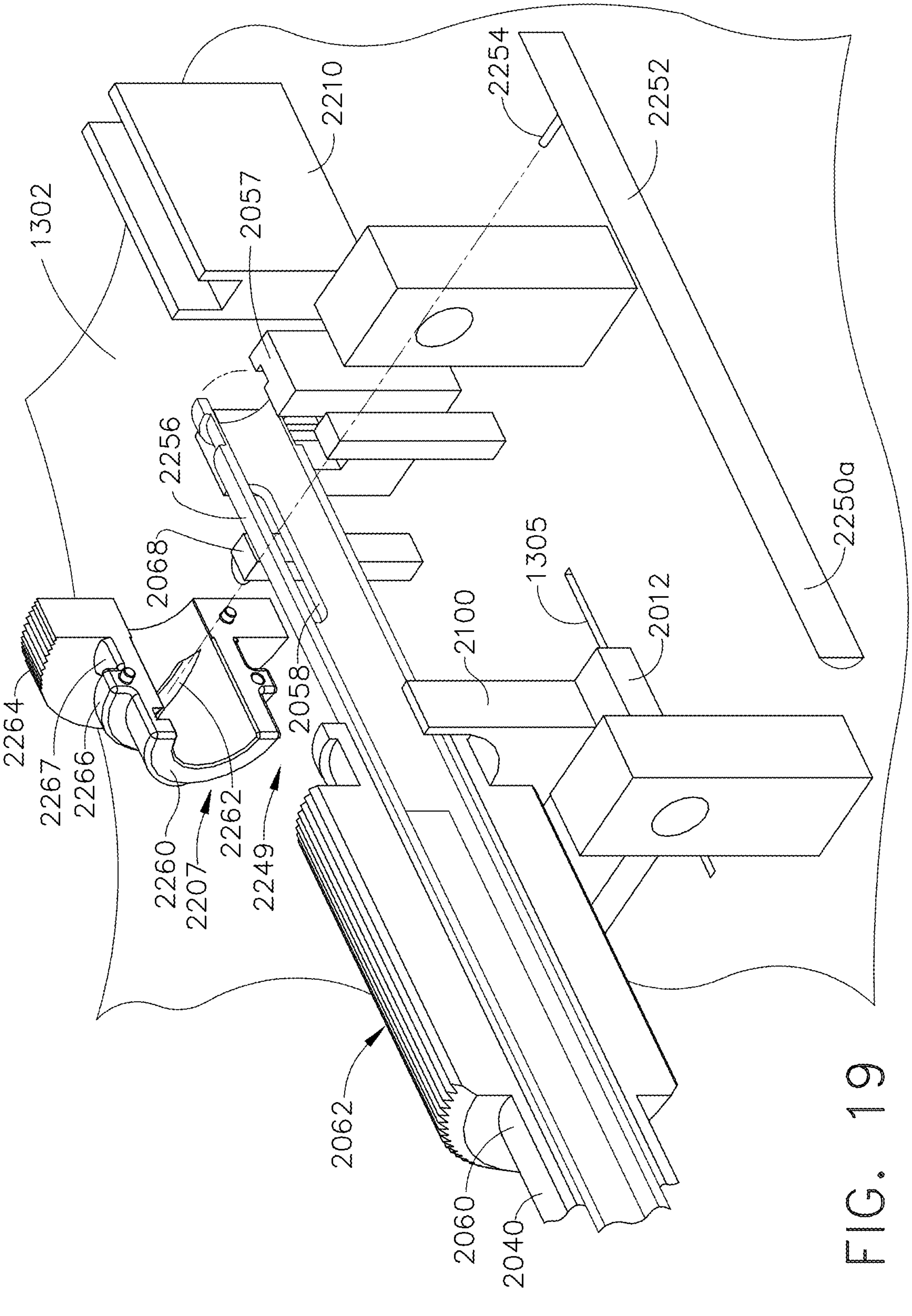
FIG. 19 is an enlarged exploded perspective view of a portion of the tool mounting portion of FIG. 18.
Figure 20:
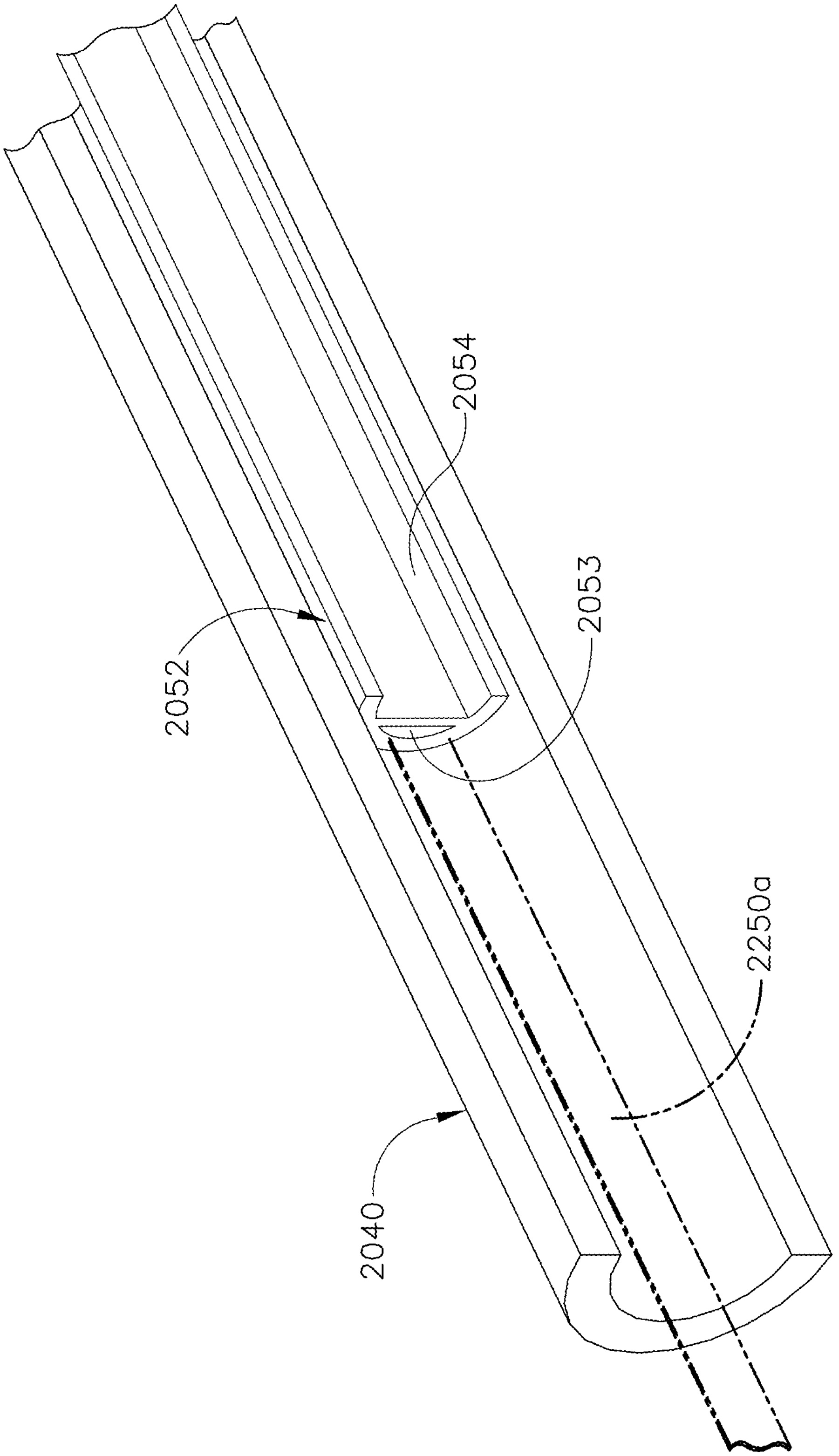
FIG. 20 is a partial cross-sectional view of a portion of the elongated shaft assembly of the surgical tool of FIG. 10.
Figure 21:
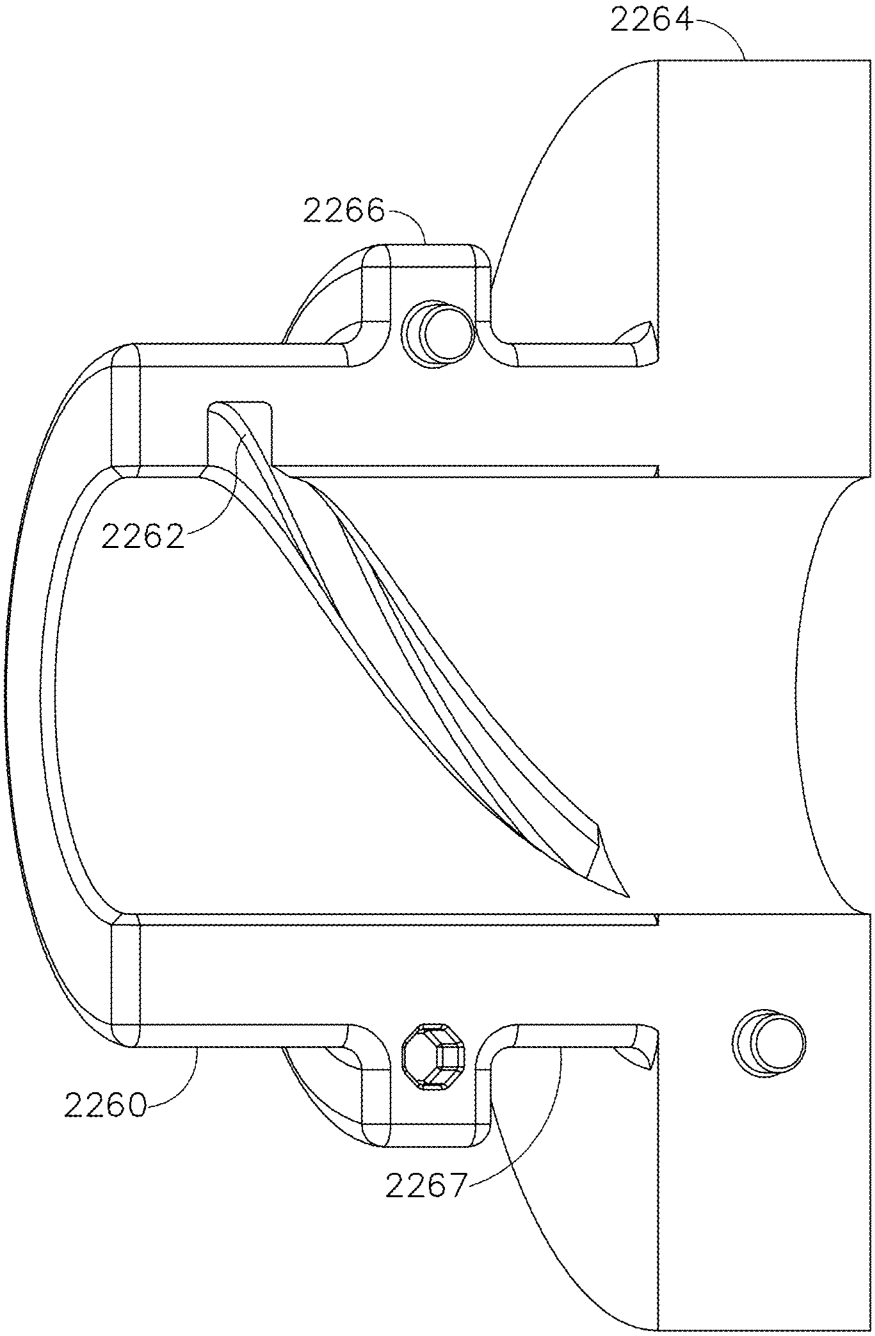
FIG. 21 is a side view of a half portion of a closure nut embodiment of a surgical tool embodiment of the present invention.
Figure 22:
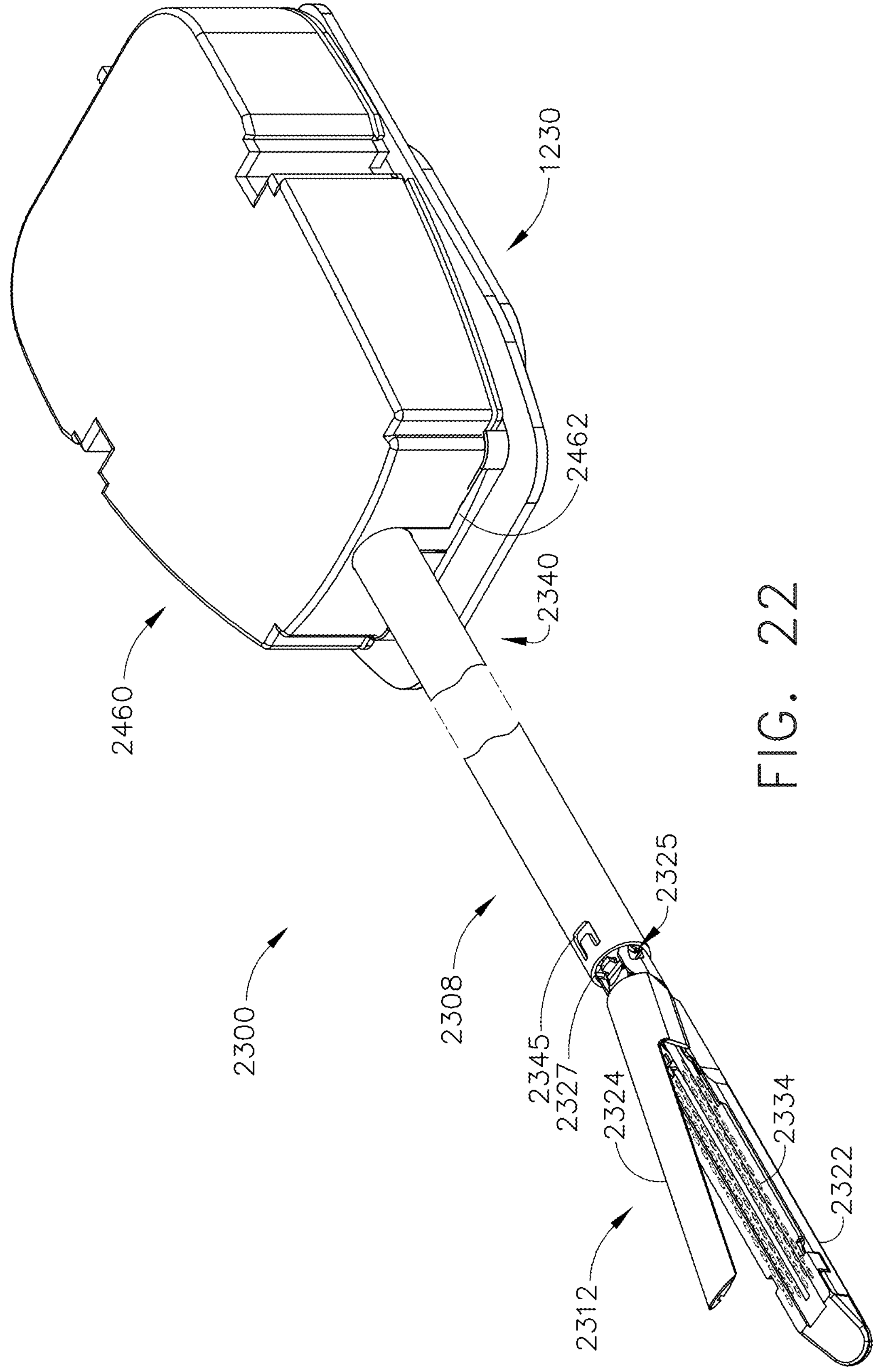
FIG. 22 is a perspective view of another surgical tool embodiment of the present invention.

In various embodiments, the cutting instrument 2032 is driven through the surgical end effector 2012 by a knife bar 2200. See FIGS. 16 and 18. In at least one form, the knife bar 2200 may be fabricated from, for example, stainless steel or other similar material and has a substantially rectangular cross-sectional shape. Such knife bar configuration is sufficiently rigid to push the cutting instrument 2032 through tissue clamped in the surgical end effector 2012, while still being flexible enough to enable the surgical end effector 2012 to articulate relative to the proximal closure tube 2040 and the proximal spine portion 2052 about the articulation axis AA-AA as will be discussed in further detail below. As can be seen in FIGS. 19 and 20, the proximal spine portion 2052 has a rectangular-shaped passage 2054 extending therethrough to provide support to the knife bar 2200 as it is axially pushed therethrough. The proximal spine portion 2052 has a proximal end 2056 that is rotatably mounted to a spine mounting bracket 2057 attached to the tool mounting plate 1032. See FIG. 18. Such arrangement permits the proximal spine portion 2052 to rotate, but not move axially, within the proximal closure tube 2040.

As shown in FIG. 16, the distal end 2202 of the knife bar 2200 is attached to the cutting instrument 2032. The proximal end 2204 of the knife bar 2200 is rotatably affixed to a knife rack gear 2206 such that the knife bar 2200 is free to rotate relative to the knife rack gear 2206. See FIG. 18. As can be seen in FIGS. 12-17, the knife rack gear 2206 is slidably supported within a rack housing 2210 that is attached to the tool mounting plate 1302 such that the knife rack gear 2206 is retained in meshing engagement with a knife gear assembly 2220. More specifically and with reference to FIG. 15, in at least one embodiment, the knife gear assembly 2220 includes a knife spur gear 2222 that is coupled to a corresponding third one of the driven discs or elements 1304 on the adapter side 1307 of the tool mounting plate 1302. See FIG. 10. Thus, application of another rotary output motion from the robotic system 1000 through the tool drive assembly 1010 to the corresponding third driven element 1304 will cause rotation of the knife spur gear 2222. The knife gear assembly 2220 further includes a knife gear reduction set 2224 that includes a first knife driven gear 2226 and a second knife drive gear 2228. The knife gear reduction set 2224 is rotatably mounted to the tool mounting plate 1302 such that the first knife driven gear 2226 is in meshing engagement with the knife spur gear 2222. Likewise, the second knife drive gear 2228 is in meshing engagement with a third knife drive gear 2230 that is rotatably supported on the tool mounting plate 1302 in meshing engagement with the knife rack gear 2206. In various embodiments, the gears of the knife gear assembly 2220 are sized to generate the forces needed to drive the cutting element 2032 through the tissue clamped in the surgical end effector 2012 and actuate the staples therein. For example, the gears of the knife drive assembly 2230 may be sized to generate approximately 40 to 100 pounds. It will be appreciated that the application of a rotary output motion from the tool drive assembly 1010 in one direction will result in the axial movement of the cutting instrument 2032 in a distal direction and application of the rotary output motion in an opposite direction will result in the axial travel of the cutting instrument 2032 in a proximal direction.

In various embodiments, the surgical tool 1200 employs and articulation system 2007 that includes an articulation joint 2011 that enables the surgical end effector 2012 to be articulated about an articulation axis AA-AA that is substantially transverse to the longitudinal tool axis LT-LT. In at least one embodiment, the surgical tool 1200 includes first and second articulation bars 2250*a*, 2250*b* that are slidably supported within corresponding passages 2053 provided through the proximal spine portion 2052. Sec FIGS. 18 and 20. In at least one form, the first and second articulation bars 2250*a*, 2250*b* are actuated by an articulation transmission generally designated as 2249 that is operably supported on the tool mounting plate 1032. Each of the articulation bars 2250*a*, 2250*b* has a proximal end 2252 that has a guide rod protruding therefrom which extend laterally through a corresponding slot in the proximal end portion of the proximal spine portion 2052 and into a corresponding arcuate slot in an articulation nut 2260 which comprises a portion of the articulation transmission. FIG. 19 illustrates articulation bar 2250*a*. It will be understood that articulation bar 2250*b* is similarly constructed. As can be seen in FIG. 19, for example, the articulation bar 2250*a* has a guide rod 2254 which extends laterally through a corresponding slot 2058 in the proximal end portion 2056 of the distal spine portion 2050 and into a corresponding arcuate slot 2262 in the articulation nut 2260. In addition, the articulation bar 2250*a* has a distal end 2251*a* that is pivotally coupled to the distal spine portion 2050 by, for example, a pin 2253*a* and articulation bar 2250*b* has a distal end 2251*b* that is pivotally coupled to the distal spine portion 2050 by, for example, a pin 2253*b*. In particular, the articulation bar 2250*a* is laterally offset in a first lateral direction from the longitudinal tool axis LT-LT and the articulation bar 2250*b* is laterally offset in a second lateral direction from the longitudinal tool axis LT-LT. Thus, axial movement of the articulation bars 2250*a* and 2250*b* in opposing directions will result in the articulation of the distal spine portion 2050 as well as the surgical end effector 2012 attached thereto about the articulation axis AA-AA as will be discussed in further detail below.

Articulation of the surgical end effector 2012 is controlled by rotating the articulation nut 2260 about the longitudinal tool axis LT-LT. The articulation nut 2260 is rotatably journaled on the proximal end portion 2056 of the distal spine portion 2050 and is rotatably driven thereon by an articulation gear assembly 2270. More specifically and with reference to FIG. 13, in at least one embodiment, the articulation gear assembly 2270 includes an articulation spur gear 2272 that is coupled to a corresponding fourth one of the driven discs or elements 1304 on the adapter side 1307 of the tool mounting plate 1302. See FIG. 10. Thus, application of another rotary input motion from the robotic system 1000 through the tool drive assembly 1010 to the corresponding fourth driven element 1304 will cause rotation of the articulation spur gear 2272 when the interface 1230 is coupled to the tool holder 1270. An articulation drive gear 2274 is rotatably supported on the tool mounting plate 1302 in meshing engagement with the articulation spur gear 2272 and a gear portion 2264 of the articulation nut 2260 as shown. As can be seen in FIGS. 18 and 19, the articulation nut 2260 has a shoulder 2266 formed thereon that defines an annular groove 2267 for receiving retaining posts 2268 therein. Retaining posts 2268 are attached to the tool mounting plate 1302 and serve to prevent the articulation nut 2260 from moving axially on the proximal spine portion 2052 while maintaining the ability to be rotated relative thereto. Thus, rotation of the articulation nut 2260 in a first direction, will result in the axial movement of the articulation bar 2250*a* in a distal direction "DD" and the axial movement of the articulation bar 2250*b* in a proximal direction "PD" because of the interaction of the guide rods 2254 with the spiral slots 2262 in the articulation gear 2260. Similarly, rotation of the articulation nut 2260 in a second direction that is opposite to the first direction will result in the axial movement of the articulation bar 2250*a* in the proximal direction "PD" as well as cause articulation bar 2250*b* to axially move in the distal direction "DD". Thus, the surgical end effector 2012 may be selectively articulated about articulation axis "AA-AA" in a first direction "FD" by simultaneously moving the articulation bar 2250*a* in the distal direction "DD" and the articulation bar 2250*b* in the proximal direction "PD". Likewise, the surgical end effector 2012 may be selectively articulated about the articulation axis "AA-AA" in a second direction "SD" by simultaneously moving the articulation bar 2250*a* in the proximal direction "PD" and the articulation bar 2250*b* in the distal direction "DD." See FIG. 11.

The tool embodiment described above employs an interface arrangement that is particularly well-suited for mounting the robotically controllable medical tool onto at least one form of robotic arm arrangement that generates at least four different rotary control motions. Those of ordinary skill in the art will appreciate that such rotary output motions may be selectively controlled through the programmable control systems employed by the robotic system/controller. For example, the tool arrangement described above may be well-suited for use with those robotic systems manufactured by Intuitive Surgical, Inc. of Sunnyvale, California, U.S.A., many of which may be described in detail in various patents incorporated herein by reference. The unique and novel aspects of various embodiments of the present invention serve to utilize the rotary output motions supplied by the robotic system to generate specific control motions having sufficient magnitudes that enable end effectors to cut and staple tissue. Thus, the unique arrangements and principles of various embodiments of the present invention may enable a variety of different forms of the tool systems disclosed and claimed herein to be effectively employed in connection with other types and forms of robotic systems that supply programmed rotary or other output motions. In addition, as will become further apparent as the present Detailed Description proceeds, various end effector embodiments of the present invention that require other forms of actuation motions may also be effectively actuated utilizing one or more of the control motions generated by the robotic system.

FIGS. 22-26 illustrate yet another surgical tool 2300 that may be effectively employed in connection with the robotic system 1000 that has a tool drive assembly that is operably coupled to a controller of the robotic system that is operable by inputs from an operator and which is configured to provide at least one rotary output motion to at least one rotatable body portion supported on the tool drive assembly. In various forms, the surgical tool 2300 includes a surgical end effector 2312 that includes an elongated channel 2322 and a pivotally translatable clamping member, such as an anvil 2324, which are maintained at a spacing that assures effective stapling and severing of tissue clamped in the surgical end effector 2312. As shown in the illustrated embodiment, the surgical end effector 2312 may include, in addition to the previously-mentioned elongated channel 2322 and anvil 2324, a cutting instrument 2332 that has a sled portion 2333 formed thereon, a surgical staple cartridge 2334 that is seated in the elongated channel 2322, and a rotary end effector drive shaft 2336 that has a helical screw thread formed thereon. The cutting instrument 2332 may be, for example, a knife. As will be discussed in further detail below, rotation of the end effector drive shaft 2336 will cause the cutting instrument 2332 and sled portion 2333 to axially travel through the surgical staple cartridge 2334 to move between a starting position and an ending position. The direction of axial travel of the cutting instrument 2332 depends upon the direction in which the end effector drive shaft 2336 is rotated. The anvil 2324 may be pivotably opened and closed at a pivot point 2325 connected to the proximate end of the elongated channel 2322. The anvil 2324 may also include a tab 2327 at its proximate end that operably interfaces with a component of the mechanical closure system (described further below) to open and close the anvil 2324. When the end effector drive shaft 2336 is rotated, the cutting instrument 2332 and sled 2333 will travel longitudinally through the surgical staple cartridge 2334 from the starting position to the ending position, thereby cutting tissue clamped within the surgical end effector 2312. The movement of the sled 2333 through the surgical staple cartridge 2334 causes the staples therein to be driven through the severed tissue and against the closed anvil 2324, which turns the staples to fasten the severed tissue. In one form, the elongated channel 2322 and the anvil 2324 may be made of an electrically conductive material (such as metal) so that they may serve as part of the antenna that communicates with sensor(s) in the end effector, as described above. The surgical staple cartridge 2334 could be made of a nonconductive material (such as plastic) and the sensor may be connected to or disposed in the surgical staple cartridge 2334, as described above.

It should be noted that although the embodiments of the surgical tool 2300 described herein employ a surgical end effector 2312 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled ELECTROSURGICAL HEMOSTATIC DEVICE, and U.S. Pat. No. 5,688,270, entitled ELECTROSURGICAL HEMOSTATIC DEVICE WITH RECESSED AND/OR OFFSET ELECTRODES, which are incorporated herein by reference, discloses cutting instruments that use RF energy to fasten the severed tissue. U.S. patent application Ser. No. 11/267,811, now U.S. Pat. No. 7,673,783 and U.S. patent application Ser. No. 11/267,383, now U.S. Pat. No. 7,607,557, which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

In the illustrated embodiment, the surgical end effector 2312 is coupled to an elongated shaft assembly 2308 that is coupled to a tool mounting portion 2460 and defines a longitudinal tool axis LT-LT. In this embodiment, the elongated shaft assembly 2308 does not include an articulation joint. Those of ordinary skill in the art will understand that other embodiments may have an articulation joint therein. In at least one embodiment, the elongated shaft assembly 2308 comprises a hollow outer tube 2340 that is rotatably supported on a tool mounting plate 2462 of a tool mounting portion 2460 as will be discussed in further detail below. In various embodiments, the elongated shaft assembly 2308 further includes a distal spine shaft 2350. Distal spine shaft 2350 has a distal end portion 2354 that is coupled to, or otherwise integrally formed with, a distal stationary base portion 2360 that is non-movably coupled to the channel 2322. Sec FIGS. 23-25.

Figure 23:
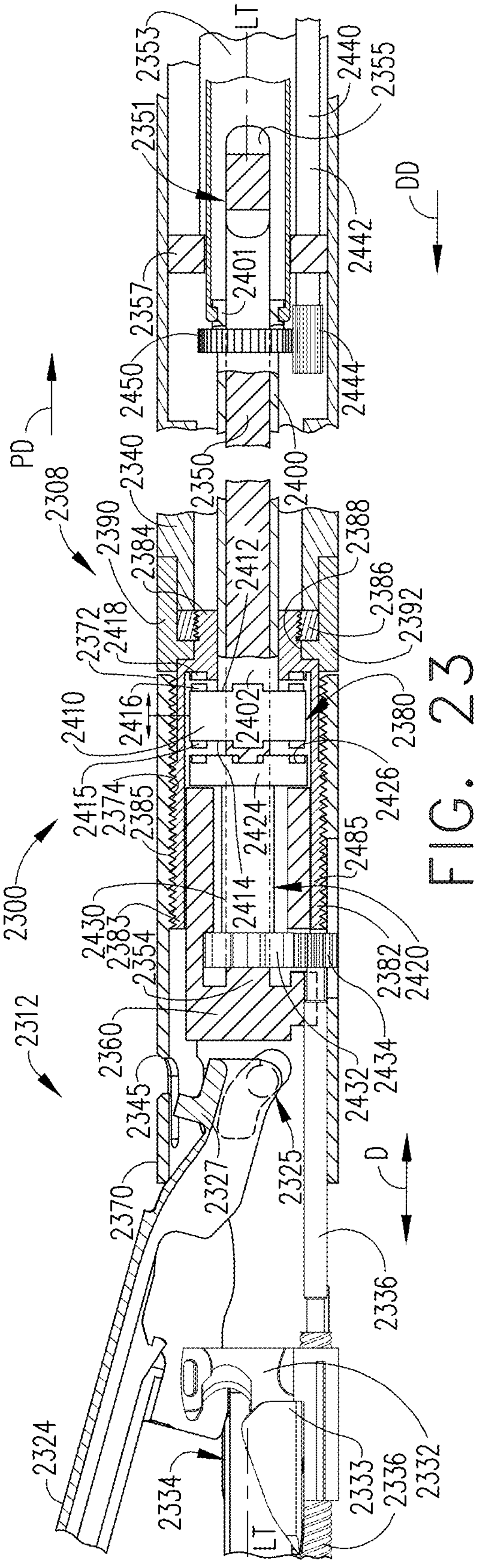
FIG. 23 is a cross-sectional side view of a portion of the surgical end effector and elongated shaft assembly of the surgical tool embodiment of FIG. 22 with the anvil in the open position and the closure clutch assembly in a neutral position.

As shown in FIG. 23, the distal spine shaft 2350 has a proximal end portion 2351 that is slidably received within a slot 2355 in a proximal spine shaft 2353 that is non-movably supported within the hollow outer tube 2340 by at least one support collar 2357. As can be further seen in FIGS. 23 and 24, the surgical tool 2300 includes a closure tube 2370 that is constrained to only move axially relative to the distal stationary base portion 2360. The closure tube 2370 has a proximal end 2372 that has an internal thread 2374 formed therein that is in threaded engagement with a transmission arrangement, generally depicted as 2375 that is operably supported on the tool mounting plate 2462. In various forms, the transmission arrangement 2375 includes a rotary drive shaft assembly, generally designated as 2381. When rotated, the rotary drive shaft assembly 2381 will cause the closure tube 2370 to move axially as will be describe in further detail below. In at least one form, the rotary drive shaft assembly 2381 includes a closure drive nut 2382 of a closure clutch assembly generally designated as 2380. More specifically, the closure drive nut 2382 has a proximal end portion 2384 that is rotatably supported relative to the outer tube 2340 and is in threaded engagement with the closure tube 2370. For assembly purposes, the proximal end portion 2384 may be threadably attached to a retention ring 2386. Retention ring 2386, in cooperation with an end 2387 of the closure drive nut 2382, defines an annular slot 2388 into which a shoulder 2392 of a locking collar 2390 extends. The locking collar 2390 is non-movably attached (e.g., welded, glued, etc.) to the end of the outer tube 2340. Such arrangement serves to affix the closure drive nut 2382 to the outer tube 2340 while enabling the closure drive nut 2382 to rotate relative to the outer tube 2340. The closure drive nut 2382 further has a distal end 2383 that has a threaded portion 2385 that threadably engages the internal thread 2374 of the closure tube 2370. Thus, rotation of the closure drive nut 2382 will cause the closure tube 2370 to move axially as represented by arrow "D" in FIG. 24.

Figure 24:
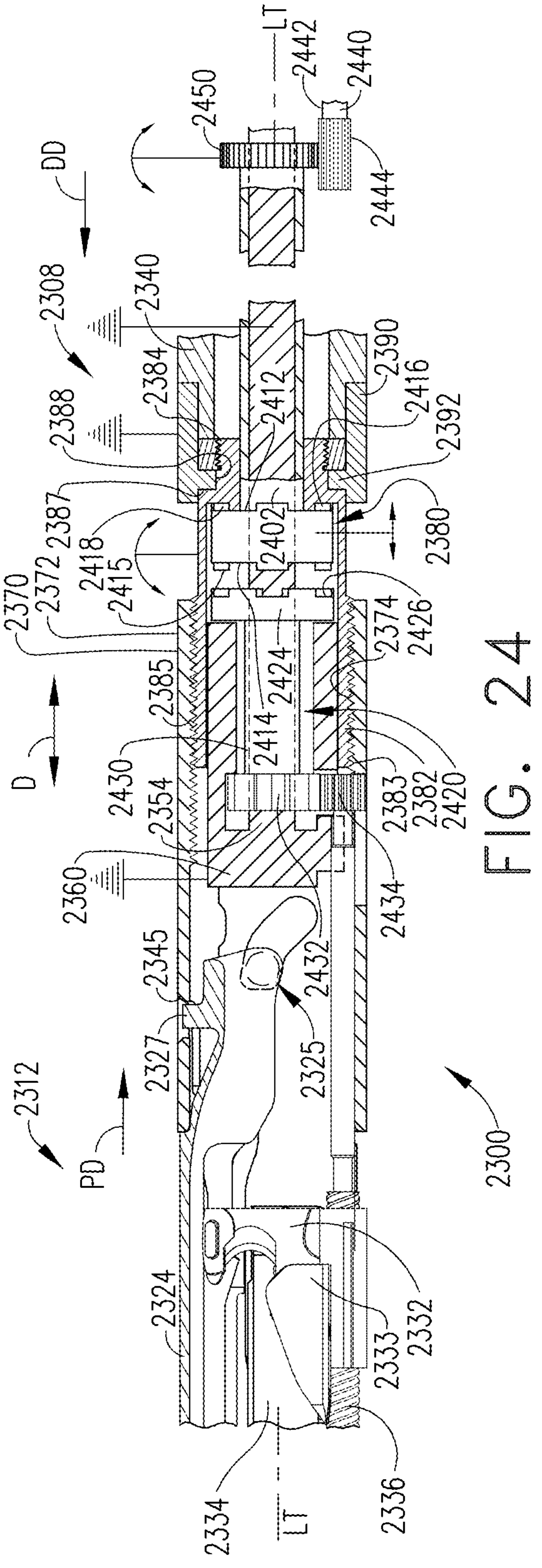
FIG. 24 is another cross-sectional side view of the surgical end effector and elongated shaft assembly shown in FIG. 23 with the clutch assembly engaged in a closure position.

Closure of the anvil 2324 and actuation of the cutting instrument 2332 are accomplished by control motions that are transmitted by a hollow drive sleeve 2400. As can be seen in FIGS. 23 and 24, the hollow drive sleeve 2400 is rotatably and slidably received on the distal spine shaft 2350. The drive sleeve 2400 has a proximal end portion 2401 that is rotatably mounted to the proximal spine shaft 2353 that protrudes from the tool mounting portion 2460 such that the drive sleeve 2400 may rotate relative thereto. See FIG. 23. As can also be seen in FIGS. 23-25, the drive sleeve 2400 is rotated about the longitudinal tool axis "LT-LT" by a drive shaft 2440. The drive shaft 2440 has a drive gear 2444 that is attached to its distal end 2442 and is in meshing engagement with a driven gear 2450 that is attached to the drive sleeve 2400.

The drive sleeve 2400 further has a distal end portion 2402 that is coupled to a closure clutch 2410 portion of the closure clutch assembly 2380 that has a proximal face 2412 and a distal face 2414. The proximal face 2412 has a series of proximal teeth 2416 formed thereon that are adapted for selective engagement with corresponding proximal teeth cavities 2418 formed in the proximal end portion 2384 of the closure drive nut 2382. Thus, when the proximal teeth 2416 are in meshing engagement with the proximal teeth cavities 2418 in the closure drive nut 2382, rotation of the drive sleeve 2400 will result in rotation of the closure drive nut 2382 and ultimately cause the closure tube 2370 to move axially as will be discussed in further detail below.

Figure 25:
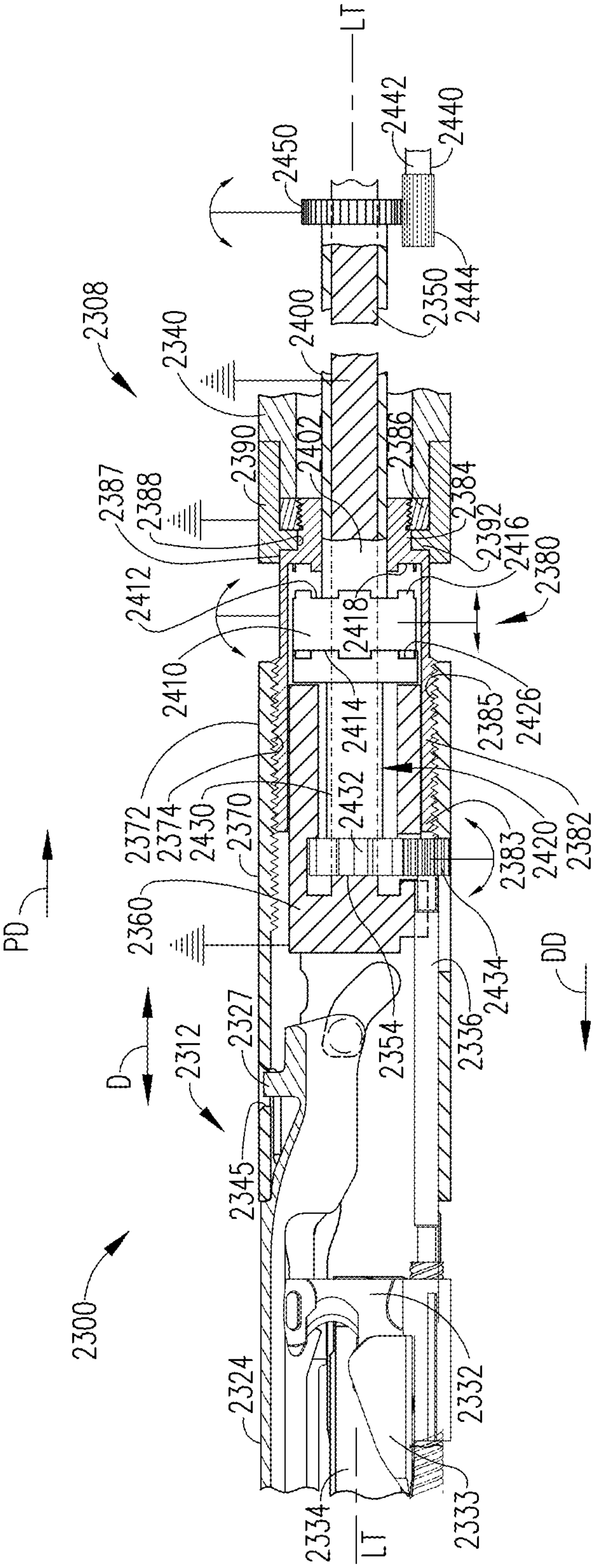
FIG. 25 is another cross-sectional side view of the surgical end effector and elongated shaft assembly shown in FIG. 23 with the clutch assembly engaged in a firing position.

As can be most particularly seen in FIGS. 23 and 24, the distal face 2414 of the drive clutch portion 2410 has a series of distal teeth 2415 formed thereon that are adapted for selective engagement with corresponding distal teeth cavities 2426 formed in a face plate portion 2424 of a knife drive shaft assembly 2420. In various embodiments, the knife drive shaft assembly 2420 comprises a hollow knife shaft segment 2430 that is rotatably received on a corresponding portion of the distal spine shaft 2350 that is attached to or protrudes from the stationary base 2360. When the distal teeth 2415 of the closure clutch portion 2410 are in meshing engagement with the distal teeth cavities 2426 in the face plate portion 2424, rotation of the drive sleeve 2400 will result in rotation of the drive shaft segment 2430 about the stationary shaft 2350. As can be seen in FIGS. 23-25, a knife drive gear 2432 is attached to the drive shaft segment 2430 and is meshing engagement with a drive knife gear 2434 that is attached to the end effector drive shaft 2336. Thus, rotation of the drive shaft segment 2430 will result in the rotation of the end effector drive shaft 2336 to drive the cutting instrument 2332 and sled 2333 distally through the surgical staple cartridge 2334 to cut and staple tissue clamped within the surgical end effector 2312. The sled 2333 may be made of, for example, plastic, and may have a sloped distal surface. As the sled 2333 traverses the elongated channel 2322, the sloped forward surface of the sled 2333 pushes up or "drive" the staples in the surgical staple cartridge 2334 through the clamped tissue and against the anvil 2324. The anvil 2324 turns or "forms" the staples, thereby stapling the severed tissue. As used herein, the term "fire" refers to the initiation of actions required to drive the cutting instrument and sled portion in a distal direction through the surgical staple cartridge to cut the tissue clamped in the surgical end effector and drive the staples through the severed tissue.

Figure 26:
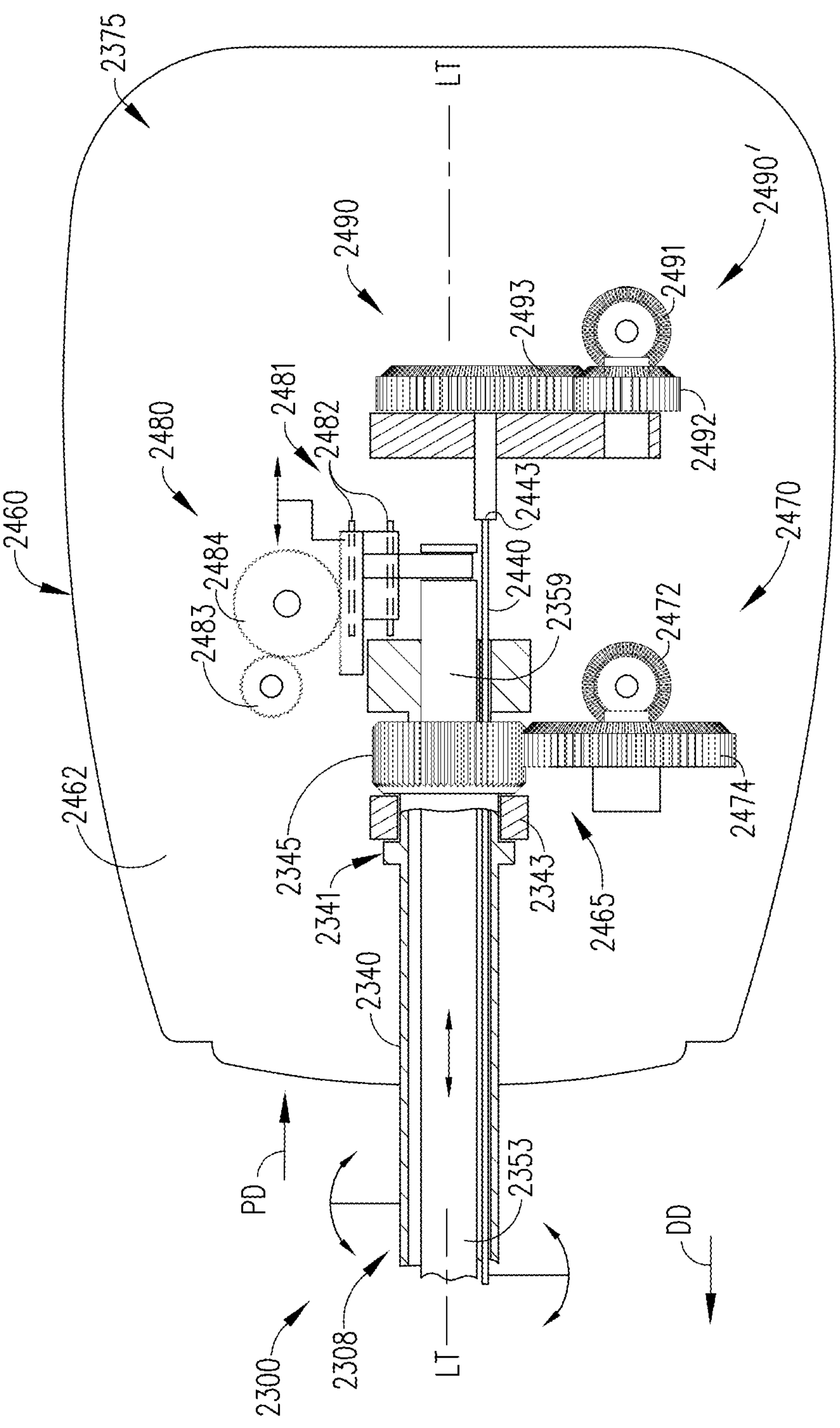
FIG. 26 is a top view of a portion of a tool mounting portion embodiment of the present invention.

In use, it may be desirable to rotate the surgical end effector 2312 about the longitudinal tool axis LT-LT. In at least one embodiment, the transmission arrangement 2375 includes a rotational transmission assembly 2465 that is configured to receive a corresponding rotary output motion from the tool drive assembly 1010 of the robotic system 1000 and convert that rotary output motion to a rotary control motion for rotating the elongated shaft assembly 2308 (and surgical end effector 2312) about the longitudinal tool axis LT-LT. As can be seen in FIG. 26, a proximal end 2341 of the outer tube 2340 is rotatably supported within a cradle arrangement 2343 attached to the tool mounting plate 2462 of the tool mounting portion 2460. A rotation gear 2345 is formed on or attached to the proximal end 2341 of the outer tube 2340 of the elongated shaft assembly 2308 for meshing engagement with a rotation gear assembly 2470 operably supported on the tool mounting plate 2462. In at least one embodiment, a rotation drive gear 2472 is coupled to a corresponding first one of the driven discs or elements 1304 on the adapter side of the tool mounting plate 2462 when the tool mounting portion 2460 is coupled to the tool drive assembly 1010. See FIGS. 10 and 26. The rotation drive assembly 2470 further comprises a rotary driven gear 2474 that is rotatably supported on the tool mounting plate 2462 in meshing engagement with the rotation gear 2345 and the rotation drive gear 2472. Application of a first rotary output motion from the robotic system 1000 through the tool drive assembly 1010 to the corresponding driven element 1304 will thereby cause rotation of the rotation drive gear 2472 by virtue of being operably coupled thereto. Rotation of the rotation drive gear 2472 ultimately results in the rotation of the elongated shaft assembly 2308 (and the end effector 2312) about the longitudinal tool axis LT-LT (primary rotary motion).

Closure of the anvil 2324 relative to the staple cartridge 2034 is accomplished by axially moving the closure tube 2370 in the distal direction "DD". Axial movement of the closure tube 2370 in the distal direction "DD" is accomplished by applying a rotary control motion to the closure drive nut 2382. To apply the rotary control motion to the closure drive nut 2382, the closure clutch 2410 must first be brought into meshing engagement with the proximal end portion 2384 of the closure drive nut 2382. In various embodiments, the transmission arrangement 2375 further includes a shifter drive assembly 2480 that is operably supported on the tool mounting plate 2462. More specifically and with reference to FIG. 26, it can be seen that a proximal end portion 2359 of the proximal spine portion 2353 extends through the rotation gear 2345 and is rotatably coupled to a shifter gear rack 2481 that is slidably affixed to the tool mounting plate 2462 through slots 2482. The shifter drive assembly 2480 further comprises a shifter drive gear 2483 that is coupled to a corresponding second one of the driven discs or elements 1304 on the adapter side of the tool mounting plate 2462 when the tool mounting portion 2460 is coupled to the tool holder 1270. See FIGS. 10 and 26. The shifter drive assembly 2480 further comprises a shifter driven gear 2478 that is rotatably supported on the tool mounting plate 2462 in meshing engagement with the shifter drive gear 2483 and the shifter rack gear 2482. Application of a second rotary output motion from the robotic system 1000 through the tool drive assembly 1010 to the corresponding driven element 1304 will thereby cause rotation of the shifter drive gear 2483 by virtue of being operably coupled thereto. Rotation of the shifter drive gear 2483 ultimately results in the axial movement of the shifter gear rack 2482 and the proximal spine portion 2353 as well as the drive sleeve 2400 and the closure clutch 2410 attached thereto. The direction of axial travel of the closure clutch 2410 depends upon the direction in which the shifter drive gear 2483 is rotated by the robotic system 1000. Thus, rotation of the shifter drive gear 2483 in a first rotary direction will result in the axial movement of the closure clutch 2410 in the proximal direction "PD" to bring the proximal teeth 2416 into meshing engagement with the proximal teeth cavities 2418 in the closure drive nut 2382. Conversely, rotation of the shifter drive gear 2483 in a second rotary direction (opposite to the first rotary direction) will result in the axial movement of the closure clutch 2410 in the distal direction "DD" to bring the distal teeth 2415 into meshing engagement with corresponding distal teeth cavities 2426 formed in the face plate portion 2424 of the knife drive shaft assembly 2420.

Once the closure clutch 2410 has been brought into meshing engagement with the closure drive nut 2382, the closure drive nut 2382 is rotated by rotating the closure clutch 2410. Rotation of the closure clutch 2410 is controlled by applying rotary output motions to a rotary drive transmission portion 2490 of transmission arrangement 2375 that is operably supported on the tool mounting plate 2462 as shown in FIG. 26. In at least one embodiment, the rotary drive transmission 2490 includes a rotary drive assembly 2490' that includes a gear 2491 that is coupled to a corresponding third one of the driven discs or elements 1304 on the adapter side of the tool mounting plate 2462 when the tool mounting portion 2460 is coupled to the tool holder 1270. See FIGS. 10 and 26. The rotary drive transmission 2490 further comprises a first rotary driven gear 2492 that is rotatably supported on the tool mounting plate 2462 in meshing engagement with a second rotary driven gear 2493 and the rotary drive gear 2491. The second rotary driven gear 2493 is coupled to a proximal end portion 2443 of the drive shaft 2440.

Rotation of the rotary drive gear 2491 in a first rotary direction will result in the rotation of the drive shaft 2440 in a first direction. Conversely, rotation of the rotary drive gear 2491 in a second rotary direction (opposite to the first rotary direction) will cause the drive shaft 2440 to rotate in a second direction. As indicated above, the drive shaft 2440 has a drive gear 2444 that is attached to its distal end 2442 and is in meshing engagement with a driven gear 2450 that is attached to the drive sleeve 2400. Thus, rotation of the drive shaft 2440 results in rotation of the drive sleeve 2400.

A method of operating the surgical tool 2300 will now be described. Once the tool mounting portion 2462 has been operably coupled to the tool holder 1270 of the robotic system 1000 and oriented into position adjacent the target tissue to be cut and stapled, if the anvil 2334 is not already in the open position (FIG. 23), the robotic system 1000 may apply the first rotary output motion to the shifter drive gear 2483 which results in the axial movement of the closure clutch 2410 into meshing engagement with the closure drive nut 2382 (if it is not already in meshing engagement therewith). See FIG. 24. Once the controller 1001 of the robotic system 1000 has confirmed that the closure clutch 2410 is meshing engagement with the closure drive nut 2382 (e.g., by means of sensor(s)) in the surgical end effector 2312 that are in communication with the robotic control system), the robotic controller 1001 may then apply a second rotary output motion to the rotary drive gear 2492 which, as was described above, ultimately results in the rotation of the rotary drive nut 2382 in the first direction which results in the axial travel of the closure tube 2370 in the distal direction "DD". As the closure tube 2370 moved in the distal direction, it contacts a portion of the anvil 2323 and causes the anvil 2324 to pivot to the closed position to clamp the target tissue between the anvil 2324 and the surgical staple cartridge 2334. Once the robotic controller 1001 determines that the anvil 2334 has been pivoted to the closed position by corresponding sensor(s) in the surgical end effector 2312 in communication therewith, the robotic system 1000 discontinues the application of the second rotary output motion to the rotary drive gear 2491. The robotic controller 1001 may also provide the surgeon with an indication that the anvil 2334 has been fully closed. The surgeon may then initiate the firing procedure. In alternative embodiments, the firing procedure may be automatically initiated by the robotic controller 1001. The robotic controller 1001 then applies the primary rotary control motion 2483 to the shifter drive gear 2483 which results in the axial movement of the closure clutch 2410 into meshing engagement with the face plate portion 2424 of the knife drive shaft assembly 2420. See FIG. 25. Once the controller 1001 of the robotic system 1000 has confirmed that the closure clutch 2410 is meshing engagement with the face plate portion 2424 (by means of sensor(s)) in the end effector 2312 that are in communication with the robotic controller 1001), the robotic controller 1001 may then apply the second rotary output motion to the rotary drive gear 2492 which, as was described above, ultimately results in the axial movement of the cutting instrument 2332 and sled portion 2333 in the distal direction “DD” through the surgical staple cartridge 2334. As the cutting instrument 2332 moves distally through the surgical staple cartridge 2334, the tissue clamped therein is severed. As the sled portion 2333 is driven distally, it causes the staples within the surgical staple cartridge to be driven through the severed tissue into forming contact with the anvil 2324. Once the robotic controller 1001 has determined that the cutting instrument 2324 has reached the end position within the surgical staple cartridge 2334 (by means of sensor(s)) in the end effector 2312 that are in communication with the robotic controller 1001), the robotic controller 1001 discontinues the application of the second rotary output motion to the rotary drive gear 2491. Thereafter, the robotic controller 1001 applies the secondary rotary output motion to the rotary drive gear 2491 which ultimately results in the axial travel of the cutting instrument 2332 and sled portion 2333 in the proximal direction “PD” to the starting position. Once the robotic controller 1001 has determined that the cutting instrument 2324 has reached the starting position by means of sensor(s) in the surgical end effector 2312 that are in communication with the robotic controller 1001, the robotic controller 1001 discontinues the application of the secondary rotary output motion to the rotary drive gear 2491. Thereafter, the robotic controller 1001 applies the primary rotary output motion to the shifter drive gear 2483 to cause the closure clutch 2410 to move into engagement with the rotary drive nut 2382. Once the closure clutch 2410 has been moved into meshing engagement with the rotary drive nut 2382, the robotic controller 1001 then applies the secondary output motion to the rotary drive gear 2491 which ultimately results in the rotation of the rotary drive nut 2382 in the second direction to cause the closure tube 2370 to move in the proximal direction “PD”. As can be seen in FIGS. 23-25, the closure tube 2370 has an opening 2345 therein that engages the tab 2327 on the anvil 2324 to cause the anvil 2324 to pivot to the open position. In alternative embodiments, a spring may also be employed to pivot the anvil 2324 to the open position when the closure tube 2370 has been returned to the starting position (FIG. 23).

FIGS. 27-31 illustrate yet another surgical tool 2500 that may be effectively employed in connection with the robotic system 1000. In various forms, the surgical tool 2500 includes a surgical end effector 2512 that includes a “first portion” in the form of an elongated channel 2522 and a “second movable portion” in the form of a pivotally translatable clamping member, such as an anvil 2524, which are maintained at a spacing that assures effective stapling and severing of tissue clamped in the surgical end effector 2512. As shown in the illustrated embodiment, the surgical end effector 2512 may include, in addition to the previously-mentioned elongated channel 2522 and anvil 2524, a “third movable portion” in the form of a cutting instrument 2532, a sled (not shown), and a surgical staple cartridge 2534 that is removably seated in the elongated channel 2522. The cutting instrument 2532 may be, for example, a knife. The anvil 2524 may be pivotably opened and closed at a pivot point 2525 connected to the proximate end of the elongated channel 2522. The anvil 2524 may also include a tab 2527 at its proximate end that is configured to operably interface with a component of the mechanical closure system (described further below) to open and close the anvil 2524. When actuated, the knife 2532 and sled travel longitudinally along the elongated channel 2522, thereby cutting tissue clamped within the surgical end effector 2512. The movement of the sled along the elongated channel 2522 causes the staples of the surgical staple cartridge 2534 to be driven through the severed tissue and against the closed anvil 2524, which turns the staples to fasten the severed tissue. In one form, the elongated channel 2522 and the anvil 2524 may be made of an electrically conductive material (such as metal) so that they may serve as part of the antenna that communicates with sensor(s) in the surgical end effector, as described above. The surgical staple cartridge 2534 could be made of a nonconductive material (such as plastic) and the sensor may be connected to or disposed in the surgical staple cartridge 2534, as described above.

It should be noted that although the embodiments of the surgical tool 2500 described herein employ a surgical end effector 2512 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled ELECTROSURGICAL HEMOSTATIC DEVICE, and U.S. Pat. No. 5,688,270, entitled ELECTROSURGICAL HEMOSTATIC DEVICE WITH RECESSED AND/OR OFFSET ELECTRODES, which are incorporated herein by reference, discloses cutting instruments that use RF energy to fasten the severed tissue. U.S. patent application Ser. No. 11/267,811, now U.S. Pat. No. 7,673,783 and U.S. patent application Ser. No. 11/267,383, now U.S. Pat. No. 7,607,557, which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 27:
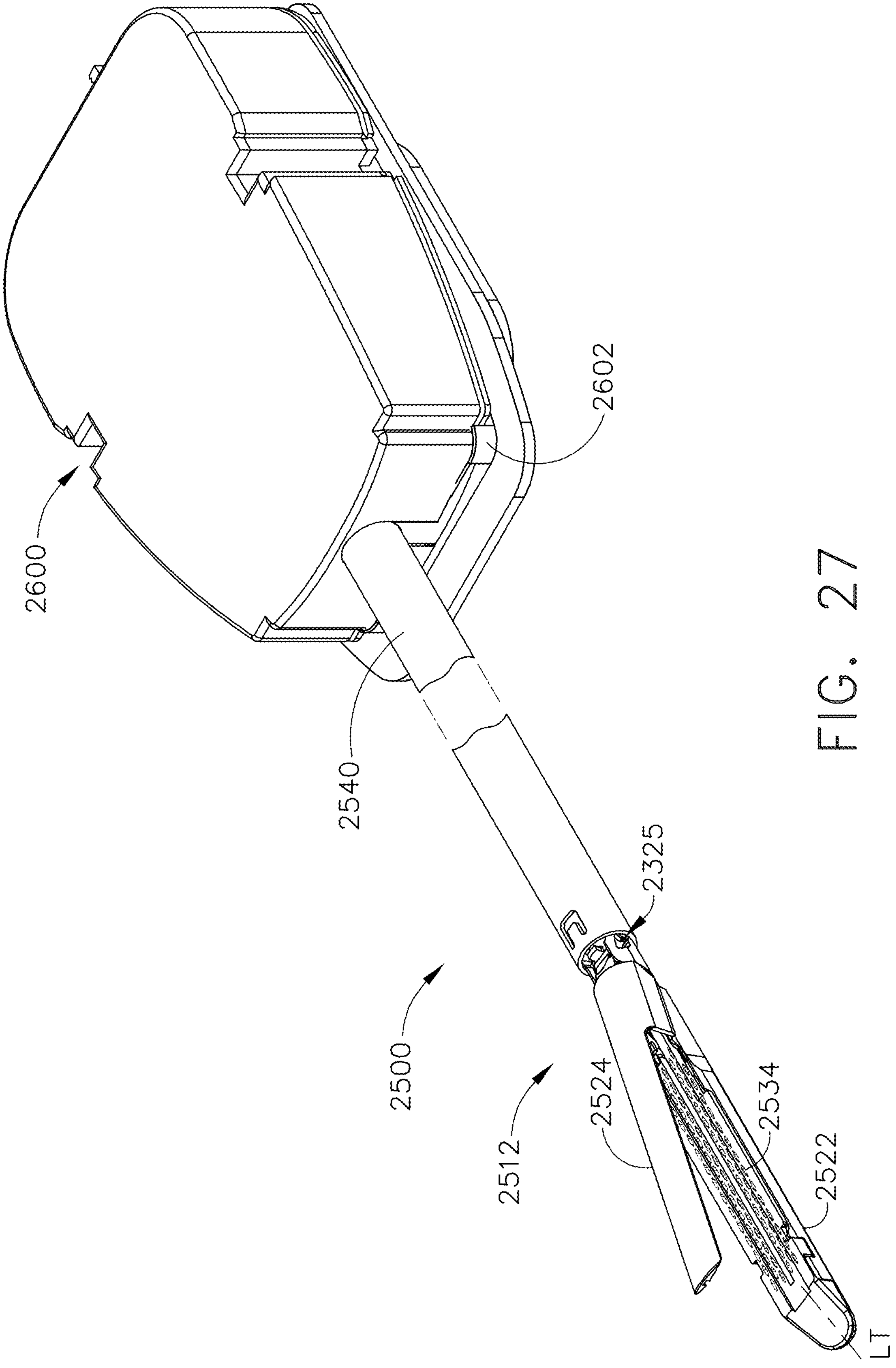
FIG. 27 is a perspective view of another surgical tool embodiment of the present invention.
Figure 28:
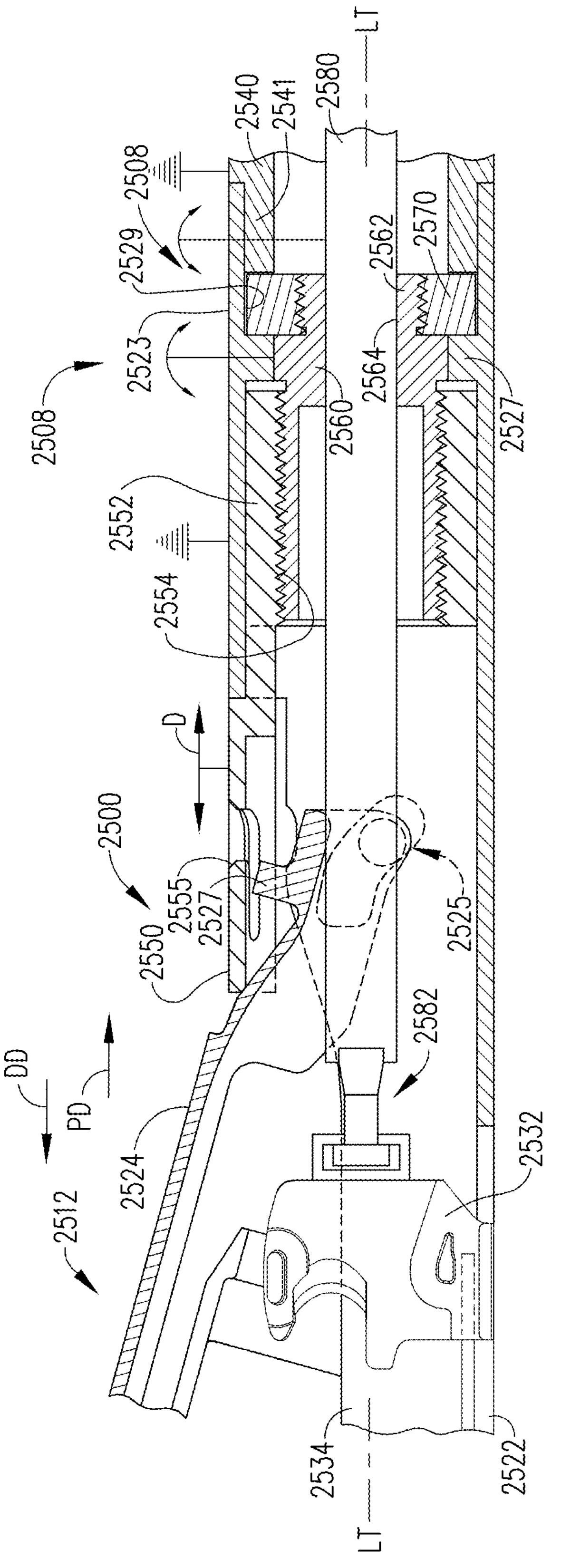
FIG. 28 is a cross-sectional side view of a portion of the surgical end effector and elongated shaft assembly of the surgical tool embodiment of FIG. 27 with the anvil in the open position.
Figure 29:
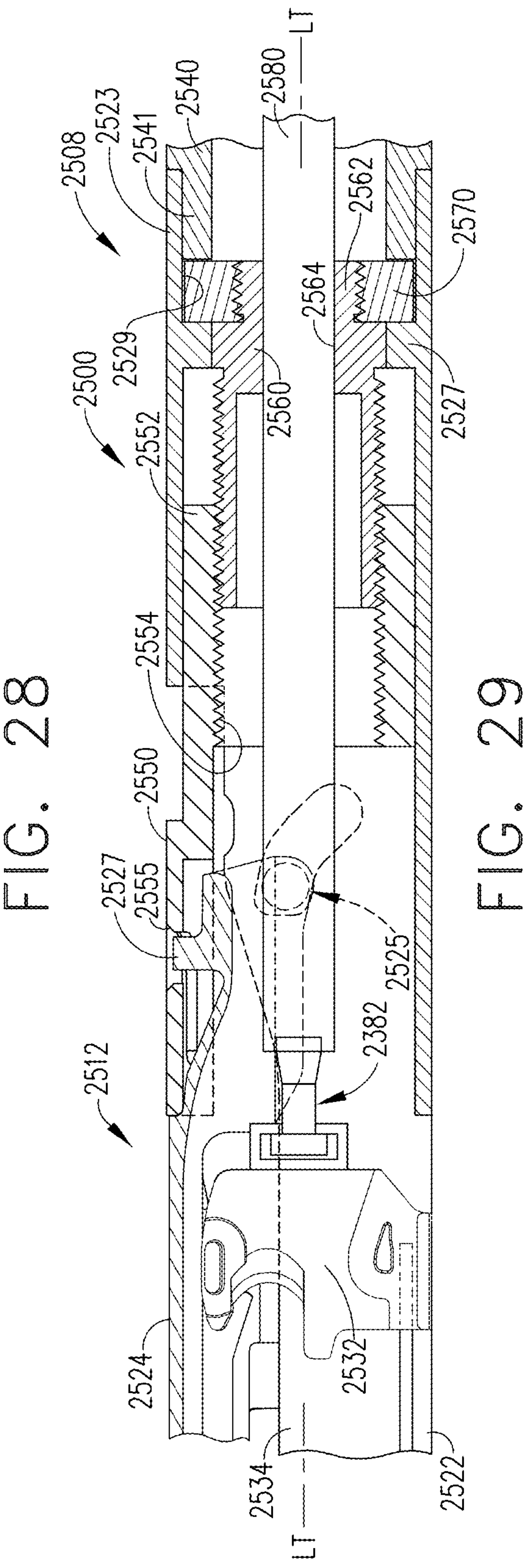
FIG. 29 is another cross-sectional side view of a portion of the surgical end effector and elongated shaft assembly of the surgical tool embodiment of FIG. 27 with the anvil in the closed position.
Figure 30:
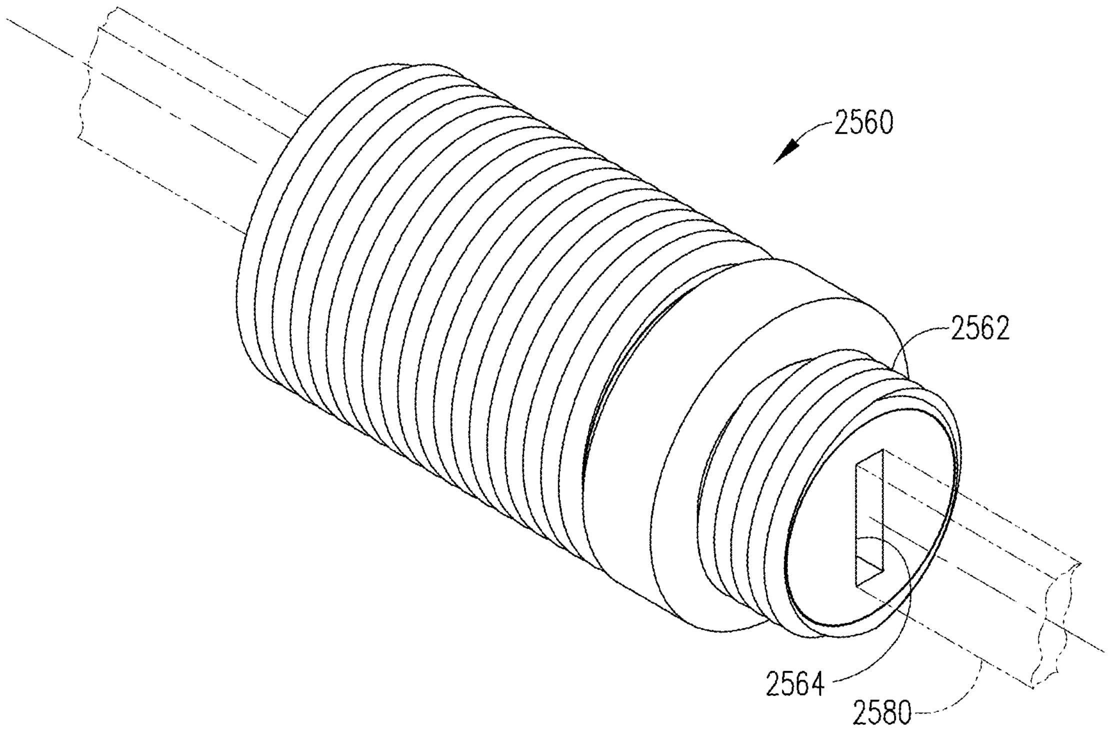
FIG. 30 is a perspective view of a closure drive nut and portion of a knife bar embodiment of the present invention.

In the illustrated embodiment, the elongated channel 2522 of the surgical end effector 2512 is coupled to an elongated shaft assembly 2508 that is coupled to a tool mounting portion 2600. As shown in FIG. 27, the elongated shaft assembly 2508 may include an articulation joint 2511 of the type and construction described herein to permit the surgical end effector 2512 to be selectively articulated about an axis that is substantially transverse to the tool axis LT-LT. Other embodiments, however, may lack an articulation joint arrangement. In at least one embodiment, the elongated shaft assembly 2508 comprises a hollow spine tube 2540 that is non-movably coupled to a tool mounting plate 2602 of the tool mounting portion 2600. As can be seen in FIGS. 28 and 29, the proximal end 2523 of the elongated channel 2522 comprises a hollow tubular structure configured to be attached to the distal end 2541 of the spine tube 2540. In one embodiment, for example, the proximal end 2523 of the elongated channel 2522 is welded or glued to the distal end of the spine tube 2540.

As can be further seen in FIGS. 28 and 29, in at least one non-limiting embodiment, the surgical tool 2500 further includes an axially movable actuation member in the form of a closure tube 2550 that is constrained to move axially relative to the elongated channel 2522 and the spine tube 1540. The closure tube 2550 has a proximal end 2552 that has an internal thread 2554 formed therein that is in threaded engagement with a rotatably movable portion in the form of a closure drive nut 2560. More specifically, the closure drive nut 2560 has a proximal end portion 2562 that is rotatably supported relative to the elongated channel 2522 and the spine tube 2540. For assembly purposes, the proximal end portion 2562 is threadably attached to a retention ring 2570. The retention ring 2570 is received in a groove 2529 formed between a shoulder 2527 on the proximal end 2523 of the elongated channel 2522 and the distal end 2541 of the spine tube 1540. Such arrangement serves to rotatably support the closure drive nut 2560 within the elongated channel 2522. Rotation of the closure drive nut 2560 will cause the closure tube 2550 to move axially as represented by arrow "D" in FIG. 28.

Figure 49:
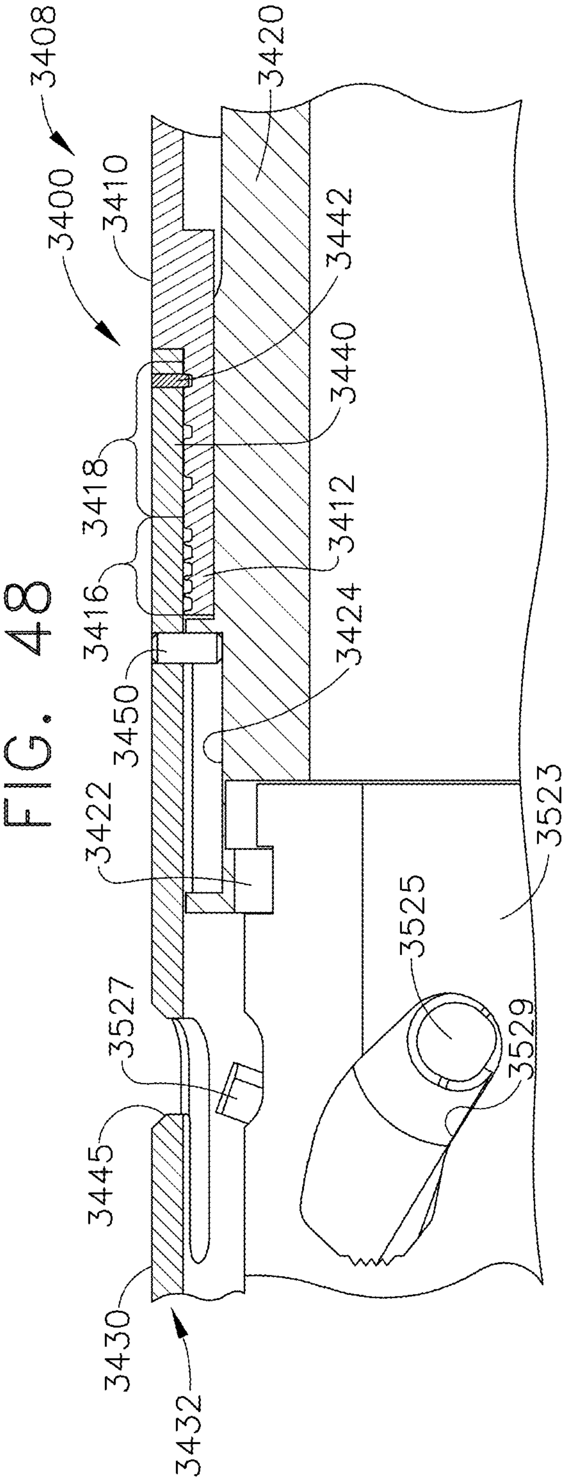
FIG. 49 is an enlarged cross-sectional side view of a portion of the surgical end effector and elongated shaft assembly of the surgical tool embodiment of FIG. 48.
Figure 50:
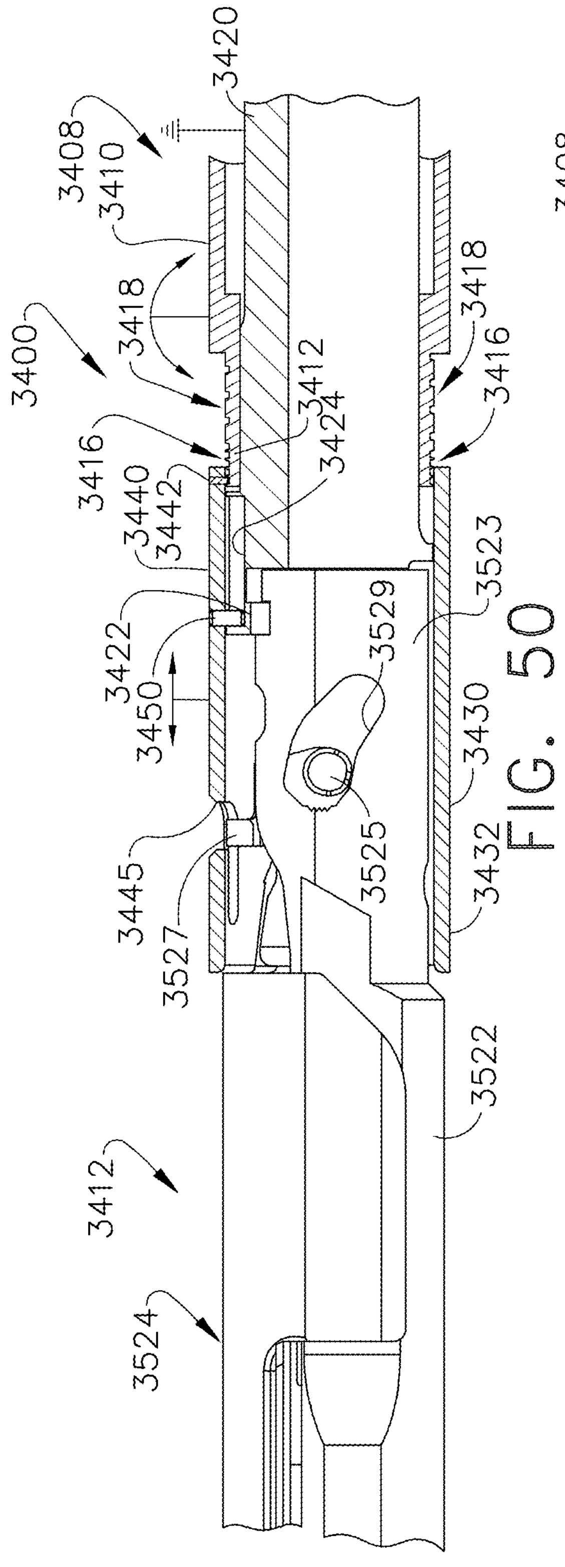
FIG. 50 is another cross-sectional side view of a portion of the surgical end effector and elongated shaft assembly of FIGS. 48 and 49 with the anvil thereof in the closed position.
Figure 51:
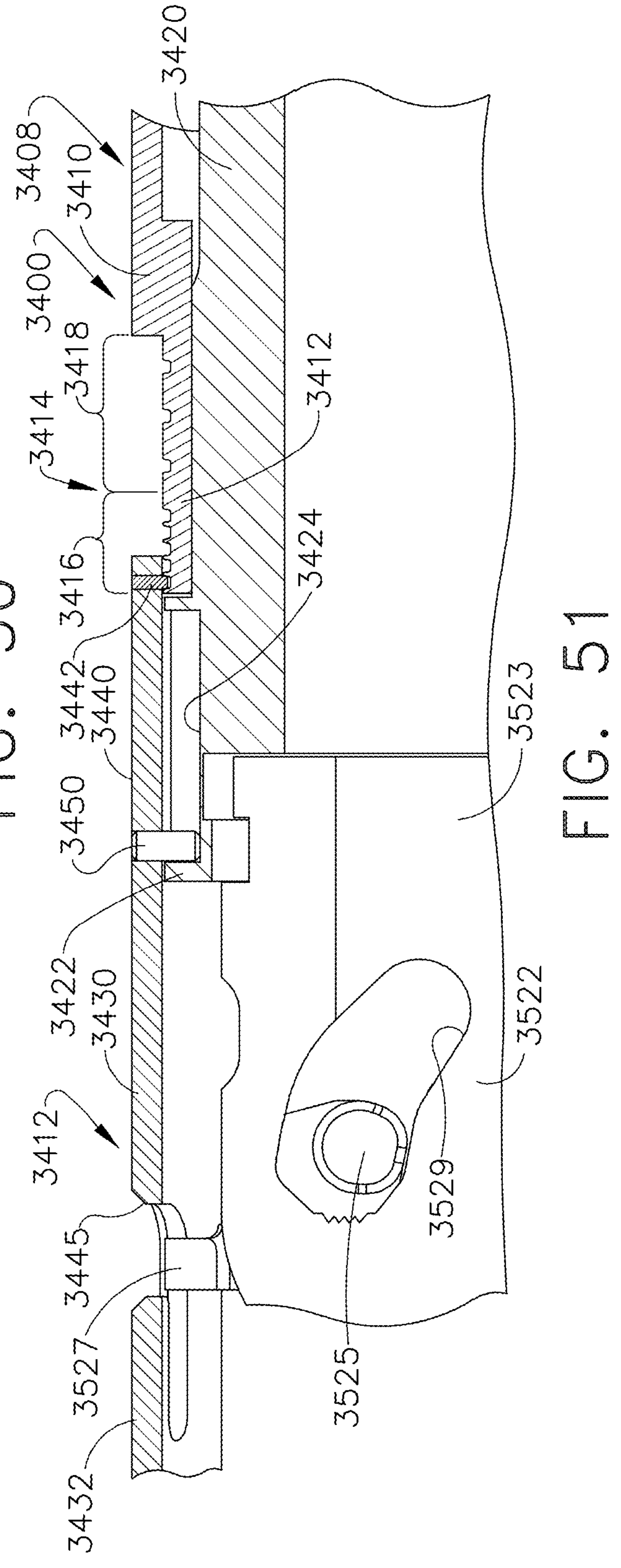
FIG. 51 is an enlarged cross-sectional side view of a portion of the surgical end effector and elongated shaft assembly of the surgical tool embodiment of FIGS. 48-50.

Extending through the spine tube 2540 and the closure drive nut 2560 is a drive member which, in at least one embodiment, comprises a knife bar 2580 that has a distal end portion 2582 that is rotatably coupled to the cutting instrument 2532 such that the knife bar 2580 may rotate relative to the cutting instrument 2582. As can be seen in FIG. 49-51, the closure drive nut 2560 has a slot 2564 therein through which the knife bar 2580 can slidably extend. Such arrangement permits the knife bar 2580 to move axially relative to the closure drive nut 2560. However, rotation of the knife bar 2580 about the longitudinal tool axis LT-LT will also result in the rotation of the closure drive nut 2560. The axial direction in which the closure tube 2550 moves ultimately depends upon the direction in which the knife bar 2580 and the closure drive nut 2560 are rotated. As the closure tube 2550 is driven distally, the distal end thereof will contact the anvil 2524 and cause the anvil 2524 to pivot to a closed position. Upon application of an opening rotary output motion from the robotic system 1000, the closure tube 2550 will be driven in the proximal direction "PD" and pivot the anvil 2524 to the open position by virtue of the engagement of the tab 2527 with the opening 2555 in the closure tube 2550.

In use, it may be desirable to rotate the surgical end effector 2512 about the longitudinal tool axis LT-LT. In at least one embodiment, the tool mounting portion 2600 is configured to receive a corresponding first rotary output motion from the robotic system 1000 and convert that first rotary output motion to a rotary control motion for rotating the elongated shaft assembly 2508 about the longitudinal tool axis LT-LT. As can be seen in FIG. 26, a proximal end 2542 of the hollow spine tube 2540 is rotatably supported within a cradle arrangement 2603 attached to a tool mounting plate 2602 of the tool mounting portion 2600. Various embodiments of the surgical tool 2500 further include a transmission arrangement, generally depicted as 2605, that is operably supported on the tool mounting plate 2602. In various forms the transmission arrangement 2605 include a rotation gear 2544 that is formed on or attached to the proximal end 2542 of the spine tube 2540 for meshing engagement with a rotation drive assembly 2610 that is operably supported on the tool mounting plate 2602. In at least one embodiment, a rotation drive gear 2612 is coupled to a corresponding first one of the rotational bodies, driven discs or elements 1304 on the adapter side of the tool mounting plate 2602 when the tool mounting portion 2600 is coupled to the tool holder 1270. See FIGS. 10 and 31. The rotation drive assembly 2610 further comprises a rotary driven gear 2614 that is rotatably supported on the tool mounting plate 2602 in meshing engagement with the rotation gear 2544 and the rotation drive gear 2612. Application of a first rotary output motion from the robotic system 1000 through the tool drive assembly 1010 to the corresponding driven rotational body 1304 will thereby cause rotation of the rotation drive gear 2612 by virtue of being operably coupled thereto. Rotation of the rotation drive gear 2612 ultimately results in the rotation of the elongated shaft assembly 2508 (and the end effector 2512) about the longitudinal tool axis LT-LT.

Figure 31:
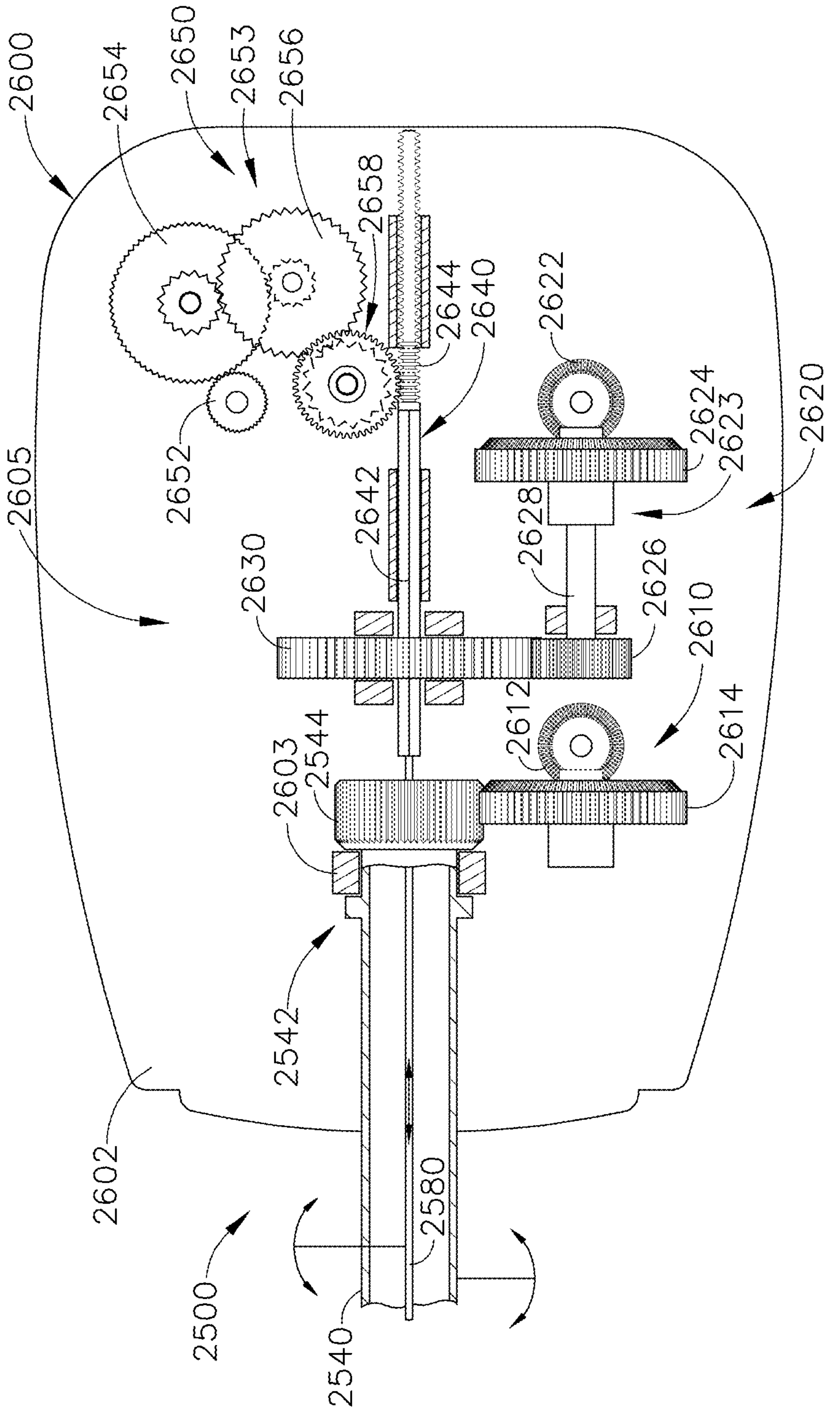
FIG. 31 is a top view of another tool mounting portion embodiment of the present invention.
Figure 32:
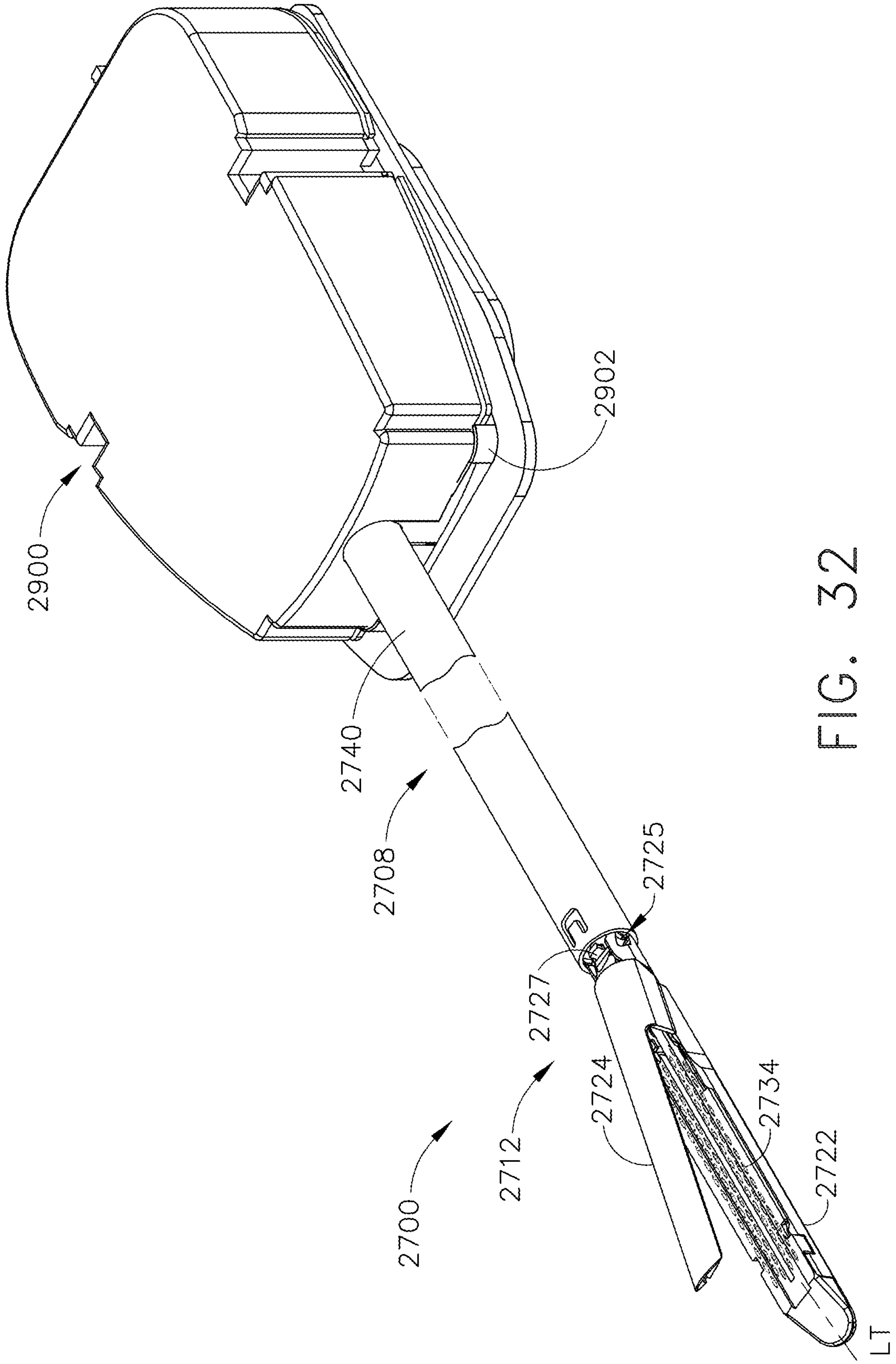
FIG. 32 is a perspective view of another surgical tool embodiment of the present invention.

Closure of the anvil 2524 relative to the surgical staple cartridge 2534 is accomplished by axially moving the closure tube 2550 in the distal direction "DD". Axial movement of the closure tube 2550 in the distal direction "DD" is accomplished by applying a rotary control motion to the closure drive nut 2382. In various embodiments, the closure drive nut 2560 is rotated by applying a rotary output motion to the knife bar 2580. Rotation of the knife bar 2580 is controlled by applying rotary output motions to a rotary closure system 2620 that is operably supported on the tool mounting plate 2602 as shown in FIG. 31. In at least one embodiment, the rotary closure system 2620 includes a closure drive gear 2622 that is coupled to a corresponding second one of the driven rotatable body portions discs or elements 1304 on the adapter side of the tool mounting plate 2462 when the tool mounting portion 2600 is coupled to the tool holder 1270. See FIGS. 10 and 31. The closure drive gear 2622, in at least one embodiment, is in meshing driving engagement with a closure gear train, generally depicted as 2623. The closure gear drive rain 2623 comprises a first driven closure gear 2624 that is rotatably supported on the tool mounting plate 2602. The first closure driven gear 2624 is attached to a second closure driven gear 2626 by a drive shaft 2628. The second closure driven gear 2626 is in meshing engagement with a third closure driven gear 2630 that is rotatably supported on the tool mounting plate 2602. Rotation of the closure drive gear 2622 in a second rotary direction will result in the rotation of the third closure driven gear 2630 in a second direction. Conversely, rotation of the closure drive gear 2483 in a secondary rotary direction (opposite to the second rotary direction) will cause the third closure driven gear 2630 to rotate in a secondary direction.

As can be seen in FIG. 31, a drive shaft assembly 2640 is coupled to a proximal end of the knife bar 2580. In various embodiments, the drive shaft assembly 2640 includes a proximal portion 2642 that has a square cross-sectional shape. The proximal portion 2642 is configured to slideably engage a correspondingly shaped aperture in the third driven gear 2630. Such arrangement results in the rotation of the drive shaft assembly 2640 (and knife bar 2580) when the third driven gear 2630 is rotated. The drive shaft assembly 2640 is axially advanced in the distal and proximal directions by a knife drive assembly 2650. One form of the knife drive assembly 2650 comprises a rotary drive gear 2652 that is coupled to a corresponding third one of the driven rotatable body portions, discs or elements 1304 on the adapter side of the tool mounting plate 2462 when the tool mounting portion 2600 is coupled to the tool holder 1270. See FIGS. 10 and 31. The rotary driven gear 2652 is in meshing driving engagement with a gear train, generally depicted as 2653. In at least one form, the gear train 2653 further comprises a first rotary driven gear assembly 2654 that is rotatably supported on the tool mounting plate 2602. The first rotary driven gear assembly 2654 is in meshing engagement with a third rotary driven gear assembly 2656 that is rotatably supported on the tool mounting plate 2602 and which is in meshing engagement with a fourth rotary driven gear assembly 2658 that is in meshing engagement with a threaded portion 2644 of the drive shaft assembly 2640. Rotation of the rotary drive gear 2652 in a third rotary direction will result in the axial advancement of the drive shaft assembly 2640 and knife bar 2580 in the distal direction "DD". Conversely, rotation of the rotary drive gear 2652 in a tertiary rotary direction (opposite to the third rotary direction) will cause the drive shaft assembly 2640 and the knife bar 2580 to move in the proximal direction.

A method of operating the surgical tool 2500 will now be described. Once the tool mounting portion 2600 has been operably coupled to the tool holder 1270 of the robotic system 1000, the robotic system 1000 can orient the surgical end effector 2512 in position adjacent the target tissue to be cut and stapled. If the anvil 2524 is not already in the open position (FIG. 49), the robotic system 1000 may apply the second rotary output motion to the closure drive gear 2622 which results in the rotation of the knife bar 2580 in a second direction. Rotation of the knife bar 2580 in the second direction results in the rotation of the closure drive nut 2560 in a second direction. As the closure drive nut 2560 rotates in the second direction, the closure tube 2550 moves in the proximal direction "PD". As the closure tube 2550 moves in the proximal direction "PD", the tab 2527 on the anvil 2524 interfaces with the opening 2555 in the closure tube 2550 and causes the anvil 2524 to pivot to the open position. In addition or in alternative embodiments, a spring (not shown) may be employed to pivot the anvil 2354 to the open position when the closure tube 2550 has been returned to the starting position (FIG. 28). The opened surgical end effector 2512 may then be manipulated by the robotic system 1000 to position the target tissue between the open anvil 2524 and the surgical staple cartridge 2534. Thereafter, the surgeon may initiate the closure process by activating the robotic control system 1000 to apply the second rotary output motion to the closure drive gear 2622 which, as was described above, ultimately results in the rotation of the closure drive nut 2382 in the second direction which results in the axial travel of the closure tube 2250 in the distal direction "DD". As the closure tube 2550 moves in the distal direction, it contacts a portion of the anvil 2524 and causes the anvil 2524 to pivot to the closed position to clamp the target tissue between the anvil 2524 and the staple cartridge 2534. Once the robotic controller 1001 determines that the anvil 2524 has been pivoted to the closed position by corresponding sensor(s) in the end effector 2512 that are in communication therewith, the robotic controller 1001 discontinues the application of the second rotary output motion to the closure drive gear 2622. The robotic controller 1001 may also provide the surgeon with an indication that the anvil 2524 has been fully closed. The surgeon may then initiate the firing procedure. In alternative embodiments, the firing procedure may be automatically initiated by the robotic controller 1001.

After the robotic controller 1001 has determined that the anvil 2524 is in the closed position, the robotic controller 1001 then applies the third rotary output motion to the rotary drive gear 2652 which results in the axial movement of the drive shaft assembly 2640 and knife bar 2580 in the distal direction "DD". As the cutting instrument 2532 moves distally through the surgical staple cartridge 2534, the tissue clamped therein is severed. As the sled portion (not shown) is driven distally, it causes the staples within the surgical staple cartridge 2534 to be driven through the severed tissue into forming contact with the anvil 2524. Once the robotic controller 1001 has determined that the cutting instrument 2532 has reached the end position within the surgical staple cartridge 2534 by means of sensor(s) in the surgical end effector 2512 that are in communication with the robotic controller 1001, the robotic controller 1001 discontinues the application of the second rotary output motion to the rotary drive gear 2652. Thereafter, the robotic controller 1001 applies the secondary rotary control motion to the rotary drive gear 2652 which ultimately results in the axial travel of the cutting instrument 2532 and sled portion in the proximal direction "PD" to the starting position. Once the robotic controller 1001 has determined that the cutting instrument 2524 has reached the starting position by means of sensor(s) in the end effector 2512 that are in communication with the robotic controller 1001, the robotic controller 1001 discontinues the application of the secondary rotary output motion to the rotary drive gear 2652. Thereafter, the robotic controller 1001 may apply the secondary rotary output motion to the closure drive gear 2622 which results in the rotation of the knife bar 2580 in a secondary direction. Rotation of the knife bar 2580 in the secondary direction results in the rotation of the closure drive nut 2560 in a secondary direction. As the closure drive nut 2560 rotates in the secondary direction, the closure tube 2550 moves in the proximal direction "PD" to the open position.

FIGS. 32-37B illustrate yet another surgical tool 2700 that may be effectively employed in connection with the robotic system 1000. In various forms, the surgical tool 2700 includes a surgical end effector 2712 that includes a "first portion" in the form of an elongated channel 2722 and a "second movable portion" in on form comprising a pivotally translatable clamping member, such as an anvil 2724, which are maintained at a spacing that assures effective stapling and severing of tissue clamped in the surgical end effector 2712. As shown in the illustrated embodiment, the surgical end effector 2712 may include, in addition to the previously-mentioned channel 2722 and anvil 2724, a "third movable portion" in the form of a cutting instrument 2732, a sled (not shown), and a surgical staple cartridge 2734 that is removably seated in the elongated channel 2722. The cutting instrument 2732 may be, for example, a knife. The anvil 2724 may be pivotably opened and closed at a pivot point 2725 connected to the proximal end of the elongated channel 2722. The anvil 2724 may also include a tab 2727 at its proximal end that interfaces with a component of the mechanical closure system (described further below) to open and close the anvil 2724. When actuated, the knife 2732 and sled to travel longitudinally along the elongated channel 2722, thereby cutting tissue clamped within the surgical end effector 2712. The movement of the sled along the elongated channel 2722 causes the staples of the surgical staple cartridge 2734 to be driven through the severed tissue and against the closed anvil 2724, which turns the staples to fasten the severed tissue. In one form, the elongated channel 2722 and the anvil 2724 may be made of an electrically conductive material (such as metal) so that they may serve as part of the antenna that communicates with sensor(s) in the surgical end effector, as described above. The surgical staple cartridge 2734 could be made of a nonconductive material (such as plastic) and the sensor may be connected to or disposed in the surgical staple cartridge 2734, as described above.

It should be noted that although the embodiments of the surgical tool 2500 described herein employ a surgical end effector 2712 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled ELECTROSURGICAL HEMOSTATIC DEVICE, and U.S. Pat.

No. 5,688,270, entitled ELECTROSURGICAL HEMOSTATIC DEVICE WITH RECESSED AND/OR OFFSET ELECTRODES, which are incorporated herein by reference, discloses cutting instruments that use RF energy to fasten the severed tissue. U.S. patent application Ser. No. 11/267,811, now U.S. Pat. No. 7,673,783, and U.S. patent application Ser. No. 11/267,383, now U.S. Pat. No. 7,607,557, which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 33:
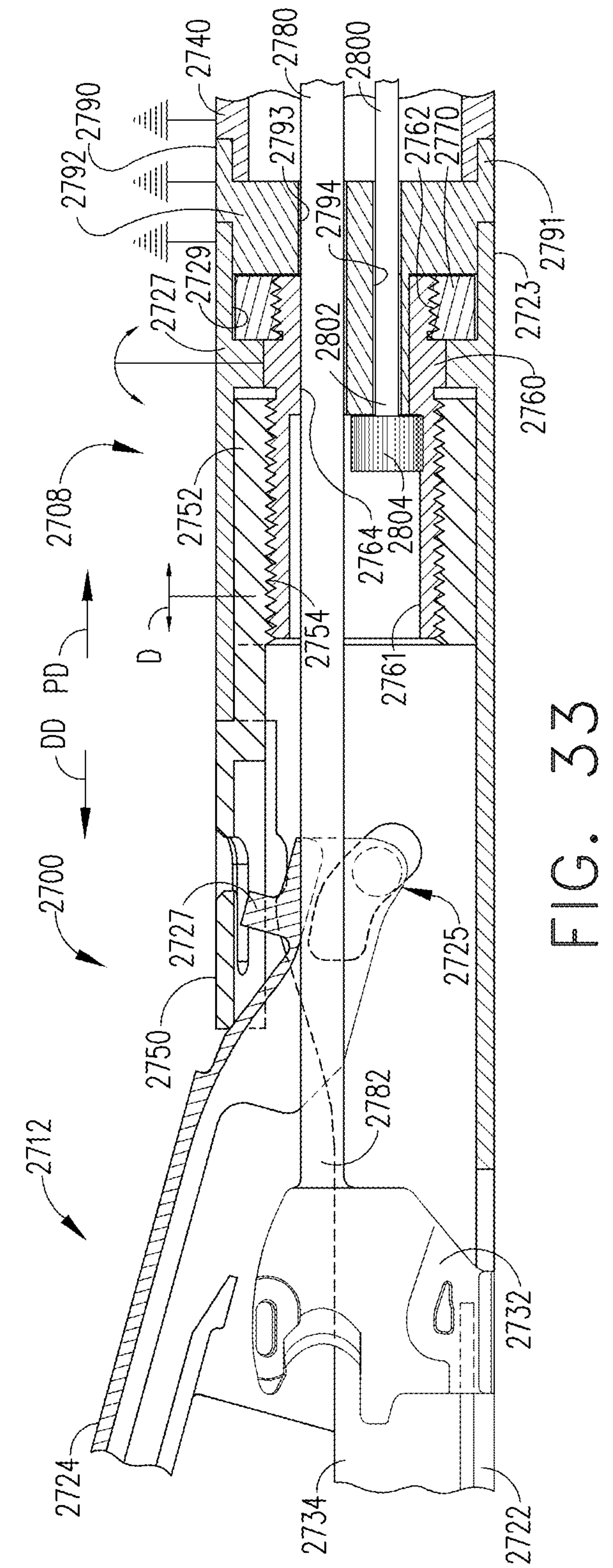
FIG. 33 is a cross-sectional side view of a portion of the surgical end effector and elongated shaft assembly of the surgical tool embodiment of FIG. 32 with the anvil in the open position.
Figure 34:
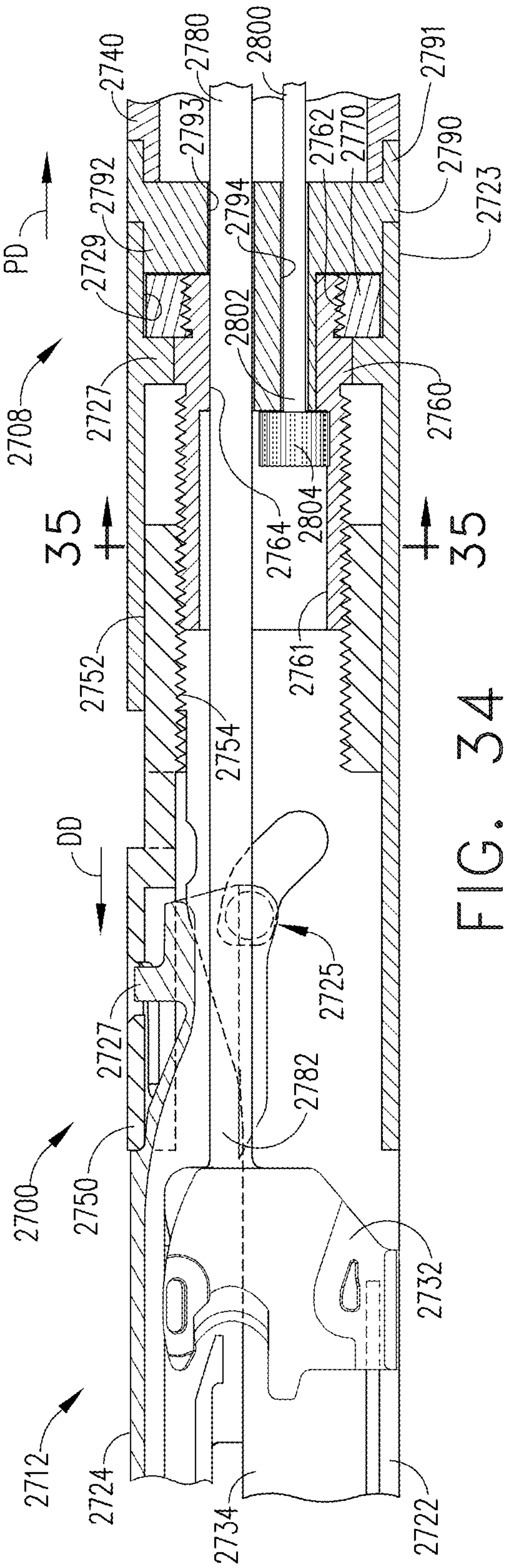
FIG. 34 is another cross-sectional side view of a portion of the surgical end effector and elongated shaft assembly of the surgical tool embodiment of FIG. 33 with the anvil in the closed position.
Figure 35:
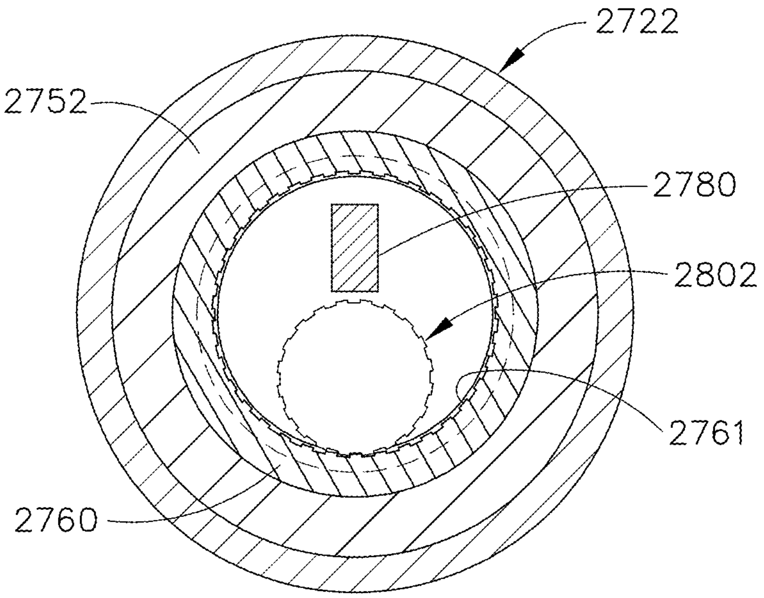
FIG. 35 is a cross-sectional view of a mounting collar embodiment of a surgical tool embodiment of the present invention showing the knife bar and distal end portion of the closure drive shaft.
Figure 36:
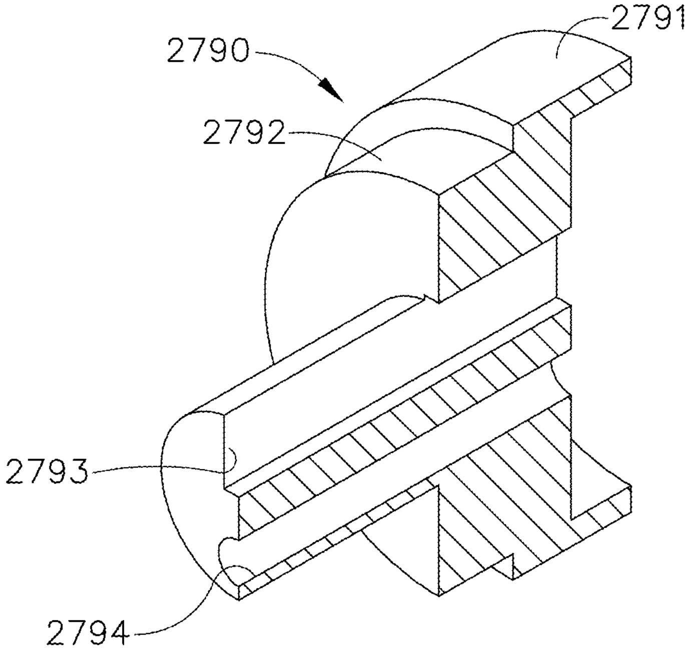
FIG. 36 is a cross-sectional view of the mounting collar embodiment of FIG. 35.

In the illustrated embodiment, the elongated channel 2722 of the surgical end effector 2712 is coupled to an elongated shaft assembly 2708 that is coupled to a tool mounting portion 2900. Although not shown, the elongated shaft assembly 2708 may include an articulation joint to permit the surgical end effector 2712 to be selectively articulated about an axis that is substantially transverse to the tool axis LT-LT. In at least one embodiment, the elongated shaft assembly 2708 comprises a hollow spine tube 2740 that is non-movably coupled to a tool mounting plate 2902 of the tool mounting portion 2900. As can be seen in FIGS. 33 and 34, the proximal end 2723 of the elongated channel 2722 comprises a hollow tubular structure that is attached to the spine tube 2740 by means of a mounting collar 2790. A cross-sectional view of the mounting collar 2790 is shown in FIG. 35. In various embodiments, the mounting collar 2790 has a proximal flanged end 2791 that is configured for attachment to the distal end of the spine tube 2740. In at least one embodiment, for example, the proximal flanged end 2791 of the mounting collar 2790 is welded or glued to the distal end of the spine tube 2740. As can be further seen in FIGS. 33 and 34, the mounting collar 2790 further has a mounting hub portion 2792 that is sized to receive the proximal end 2723 of the elongated channel 2722 thereon. The proximal end 2723 of the elongated channel 2722 is non-movably attached to the mounting hub portion 2792 by, for example, welding, adhesive, etc.

As can be further seen in FIGS. 33 and 34, the surgical tool 2700 further includes an axially movable actuation member in the form of a closure tube 2750 that is constrained to move axially relative to the elongated channel 2722. The closure tube 2750 has a proximal end 2752 that has an internal thread 2754 formed therein that is in threaded engagement with a rotatably movable portion in the form of a closure drive nut 2760. More specifically, the closure drive nut 2760 has a proximal end portion 2762 that is rotatably supported relative to the elongated channel 2722 and the spine tube 2740. For assembly purposes, the proximal end portion 2762 is threadably attached to a retention ring 2770. The retention ring 2770 is received in a groove 2729 formed between a shoulder 2727 on the proximal end 2723 of the channel 2722 and the mounting hub 2729 of the mounting collar 2790. Such arrangement serves to rotatably support the closure drive nut 2760 within the channel 2722. Rotation of the closure drive nut 2760 will cause the closure tube 2750 to move axially as represented by arrow "D" in FIG. 33.

Extending through the spine tube 2740, the mounting collar 2790, and the closure drive nut 2760 is a drive member, which in at least one embodiment, comprises a knife bar 2780 that has a distal end portion 2782 that is coupled to the cutting instrument 2732. As can be seen in FIGS. 33 and 34, the mounting collar 2790 has a passage 2793 therethrough for permitting the knife bar 2780 to slidably pass therethrough. Similarly, the closure drive nut 2760 has a slot 2764 therein through which the knife bar 2780 can slidably extend. Such arrangement permits the knife bar 2780 to move axially relative to the closure drive nut 2760.

Actuation of the anvil 2724 is controlled by a rotary driven closure shaft 2800. As can be seen in FIGS. 33 and 34, a distal end portion 2802 of the closure drive shaft 2800 extends through a passage 2794 in the mounting collar 2790 and a closure gear 2804 is attached thereto. The closure gear 2804 is configured for driving engagement with the inner surface 2761 of the closure drive nut 2760. Thus, rotation of the closure shaft 2800 will also result in the rotation of the closure drive nut 2760. The axial direction in which the closure tube 2750 moves ultimately depends upon the direction in which the closure shaft 2800 and the closure drive nut 2760 are rotated. For example, in response to one rotary closure motion received from the robotic system 1000, the closure tube 2750 will be driven in the distal direction "DD". As the closure tube 2750 is driven distally, the opening 2745 will engage the tab 2727 on the anvil 2724 and cause the anvil 2724 to pivot to a closed position. Upon application of an opening rotary motion from the robotic system 1000, the closure tube 2750 will be driven in the proximal direction "PD" and pivot the anvil 2724 to the open position. In various embodiments, a spring (not shown) may be employed to bias the anvil 2724 to the open position (FIG. 33).

Figure 37:
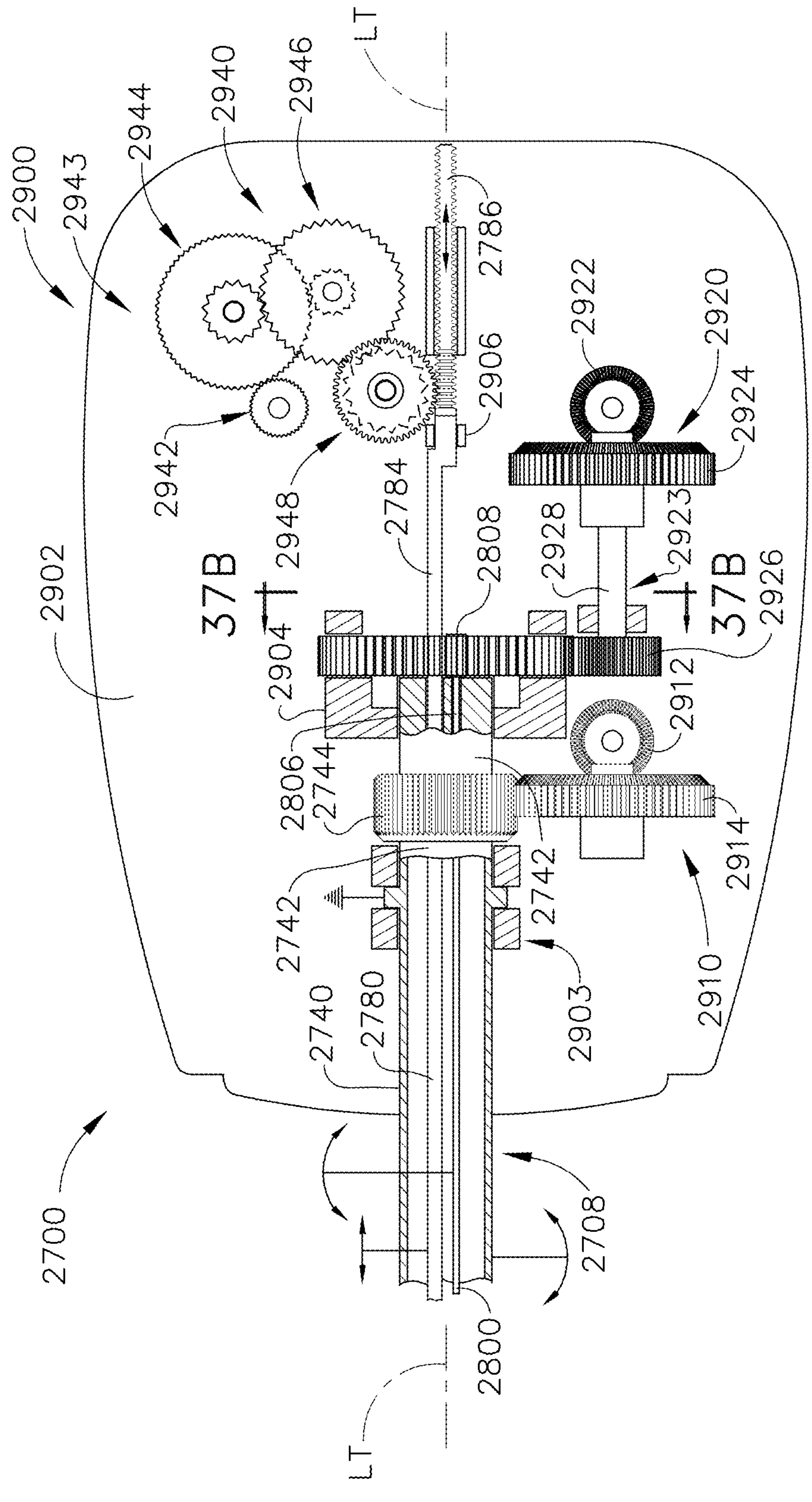
FIG. 37 is a top view of another tool mounting portion embodiment of another surgical tool embodiment of the present invention.

In use, it may be desirable to rotate the surgical end effector 2712 about the longitudinal tool axis LT-LT. In at least one embodiment, the tool mounting portion 2900 is configured to receive a corresponding first rotary output motion from the robotic system 1000 for rotating the elongated shaft assembly 2708 about the tool axis LT-LT. As can be seen in FIG. 37, a proximal end 2742 of the hollow spine tube 2740 is rotatably supported within a cradle arrangement 2903 and a bearing assembly 2904 that are attached to a tool mounting plate 2902 of the tool mounting portion 2900. A rotation gear 2744 is formed on or attached to the proximal end 2742 of the spine tube 2740 for meshing engagement with a rotation drive assembly 2910 that is operably supported on the tool mounting plate 2902. In at least one embodiment, a rotation drive gear 2912 is coupled to a corresponding first one of the driven discs or elements 1304 on the adapter side of the tool mounting plate 2602 when the tool mounting portion 2600 is coupled to the tool holder 1270. See FIGS. 10 and 37. The rotation drive assembly 2910 further comprises a rotary driven gear 2914 that is rotatably supported on the tool mounting plate 2902 in meshing engagement with the rotation gear 2744 and the rotation drive gear 2912. Application of a first rotary control motion from the robotic system 1000 through the tool holder 1270 and the adapter 1240 to the corresponding driven element 1304 will thereby cause rotation of the rotation drive gear 2912 by virtue of being operably coupled thereto. Rotation of the rotation drive gear 2912 ultimately results in the rotation of the elongated shaft assembly 2708 (and the end effector 2712) about the longitudinal tool axis LT-LT (primary rotary motion).

Figure 37A:
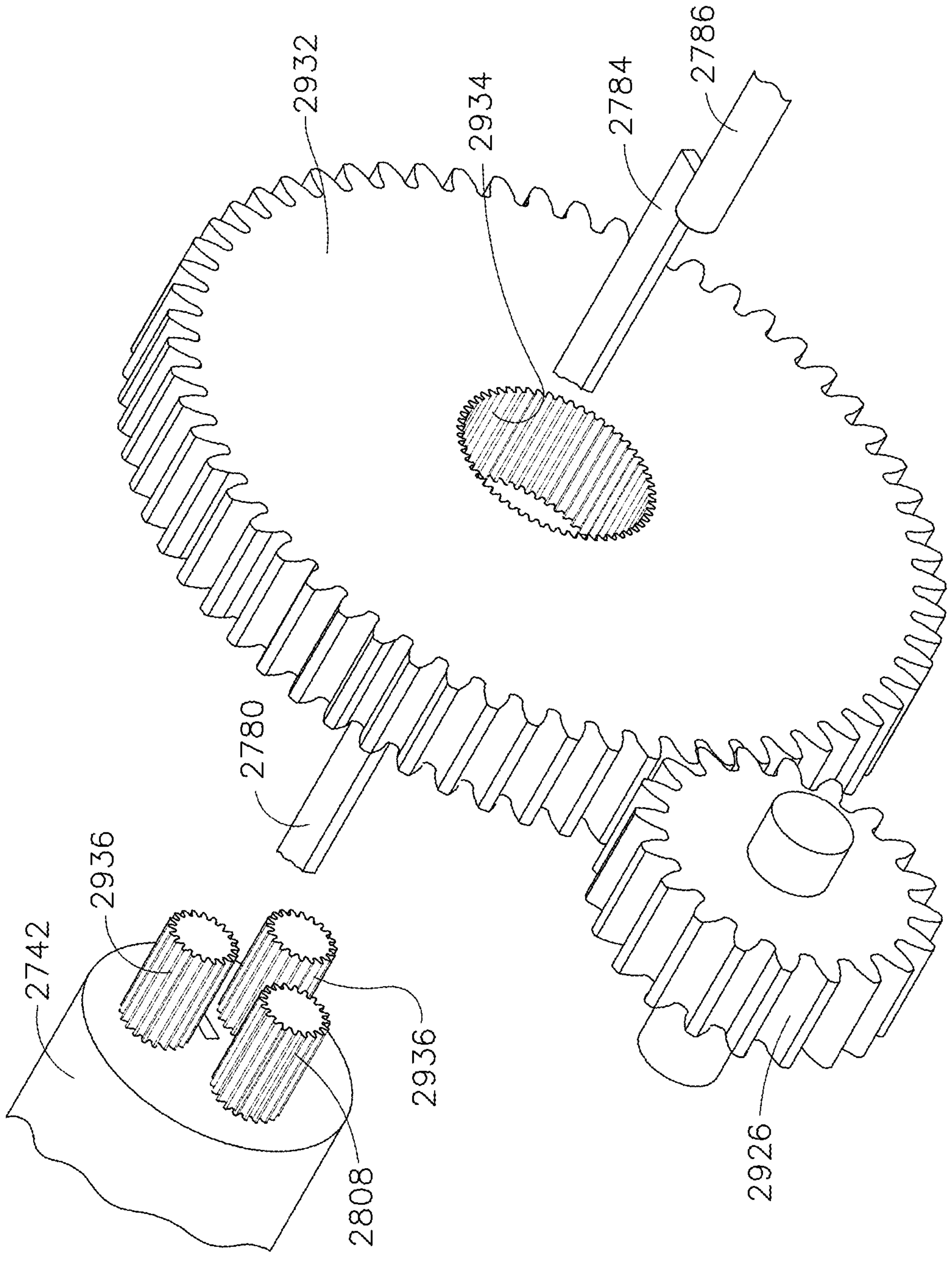
FIG. 37A is an exploded perspective view of a portion of a gear arrangement of another surgical tool embodiment of the present invention.
Figure 37B:
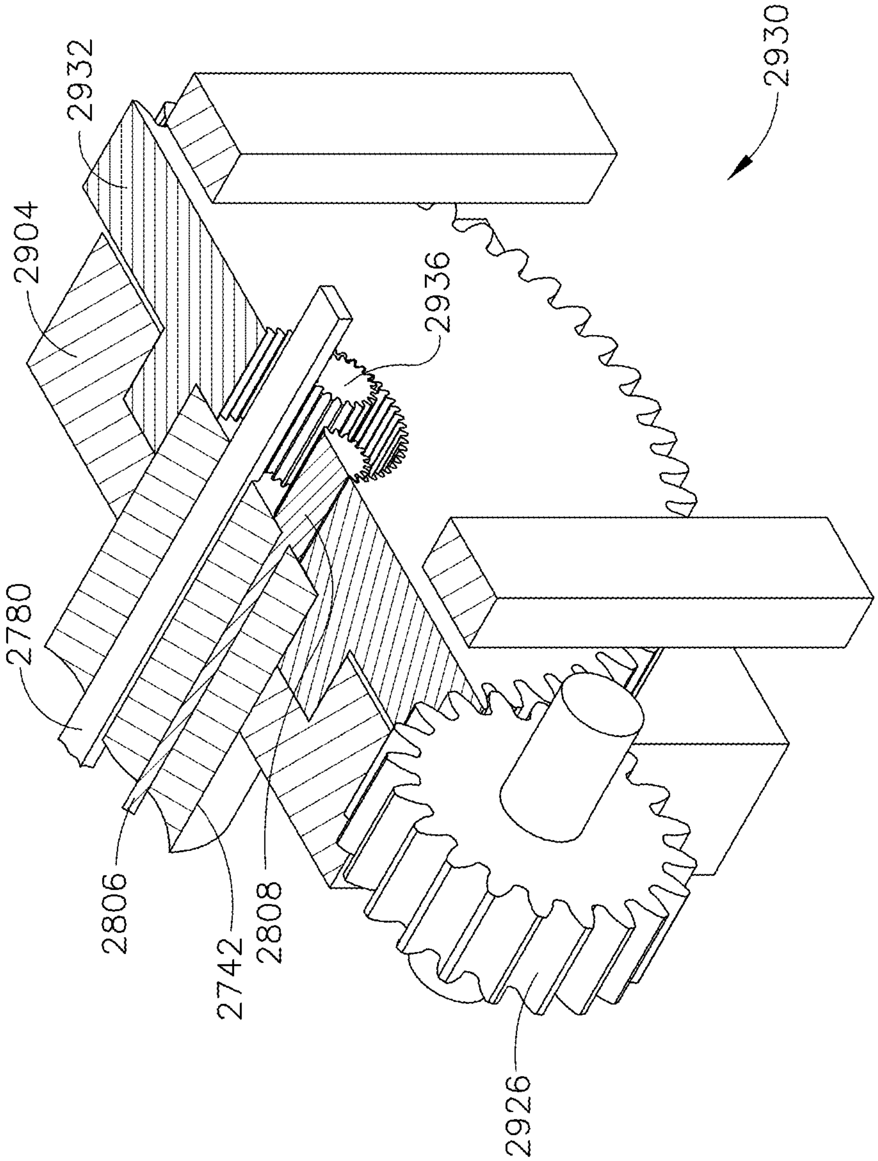
FIG. 37B is a cross-sectional perspective view of the gear arrangement shown in FIG. 37A.

Closure of the anvil 2724 relative to the staple cartridge 2734 is accomplished by axially moving the closure tube 2750 in the distal direction "DD". Axial movement of the closure tube 2750 in the distal direction "DD" is accomplished by applying a rotary control motion to the closure drive nut 2760. In various embodiments, the closure drive nut 2760 is rotated by applying a rotary output motion to the closure drive shaft 2800. As can be seen in FIG. 37, a proximal end portion 2806 of the closure drive shaft 2800 has a driven gear 2808 thereon that is in meshing engagement with a closure drive assembly 2920. In various embodiments, the closure drive system 2920 includes a closure drive gear 2922 that is coupled to a corresponding second one of the driven rotational bodies or elements 1304 on the adapter side of the tool mounting plate 2462 when the tool mounting portion 2900 is coupled to the tool holder 1270. See FIGS. 10 and 37. The closure drive gear 2922 is supported in meshing engagement with a closure gear train, generally depicted as 2923. In at least one form, the closure gear rain 2923 comprises a first driven closure gear 2924 that is rotatably supported on the tool mounting plate 2902. The first closure driven gear 2924 is attached to a second closure driven gear 2926 by a drive shaft 2928. The second closure driven gear 2926 is in meshing engagement with a planetary gear assembly 2930. In various embodiments, the planetary gear assembly 2930 includes a driven planetary closure gear 2932 that is rotatably supported within the bearing assembly 2904 that is mounted on tool mounting plate 2902. As can be seen in FIGS. 37 and 37B, the proximal end portion 2806 of the closure drive shaft 2800 is rotatably supported within the proximal end portion 2742 of the spine tube 2740 such that the driven gear 2808 is in meshing engagement with central gear teeth 2934 formed on the planetary gear 2932. As can also be seen in FIG. 37A, two additional support gears 2936 are attached to or rotatably supported relative to the proximal end portion 2742 of the spine tube 2740 to provide bearing support thereto. Such arrangement with the planetary gear assembly 2930 serves to accommodate rotation of the spine shaft 2740 by the rotation drive assembly 2910 while permitting the closure driven gear 2808 to remain in meshing engagement with the closure drive system 2920. In addition, rotation of the closure drive gear 2922 in a first direction will ultimately result in the rotation of the closure drive shaft 2800 and closure drive nut 2760 which will ultimately result in the closure of the anvil 2724 as described above. Conversely, rotation of the closure drive gear 2922 in a second opposite direction will ultimately result in the rotation of the closure drive nut 2760 in an opposite direction which results in the opening of the anvil 2724.

As can be seen in FIG. 31, the proximal end 2784 of the knife bar 2780 has a threaded shaft portion 2786 attached thereto which is in driving engagement with a knife drive assembly 2940. In various embodiments, the threaded shaft portion 2786 is rotatably supported by a bearing 2906 attached to the tool mounting plate 2902. Such arrangement permits the threaded shaft portion 2786 to rotate and move axially relative to the tool mounting plate 2902. The knife bar 2780 is axially advanced in the distal and proximal directions by the knife drive assembly 2940. One form of the knife drive assembly 2940 comprises a rotary drive gear 2942 that is coupled to a corresponding third one of the rotatable bodies, driven discs or elements 1304 on the adapter side of the tool mounting plate 2902 when the tool mounting portion 2900 is coupled to the tool holder 1270. See FIGS. 10 and 37. The rotary drive gear 2942 is in meshing engagement with a knife gear train, generally depicted as 2943. In various embodiments, the knife gear train 2943 comprises a first rotary driven gear assembly 2944 that is rotatably supported on the tool mounting plate 2902. The first rotary driven gear assembly 2944 is in meshing engagement with a third rotary driven gear assembly 2946 that is rotatably supported on the tool mounting plate 2902 and which is in meshing engagement with a fourth rotary driven gear assembly 2948 that is in meshing engagement with the threaded portion 2786 of the knife bar 2780. Rotation of the rotary drive gear 2942 in one direction will result in the axial advancement of the knife bar 2780 in the distal direction "DD". Conversely, rotation of the rotary drive gear 2942 in an opposite direction will cause the knife bar 2780 to move in the proximal direction. Tool 2700 may otherwise be used as described above.

Figure 38:
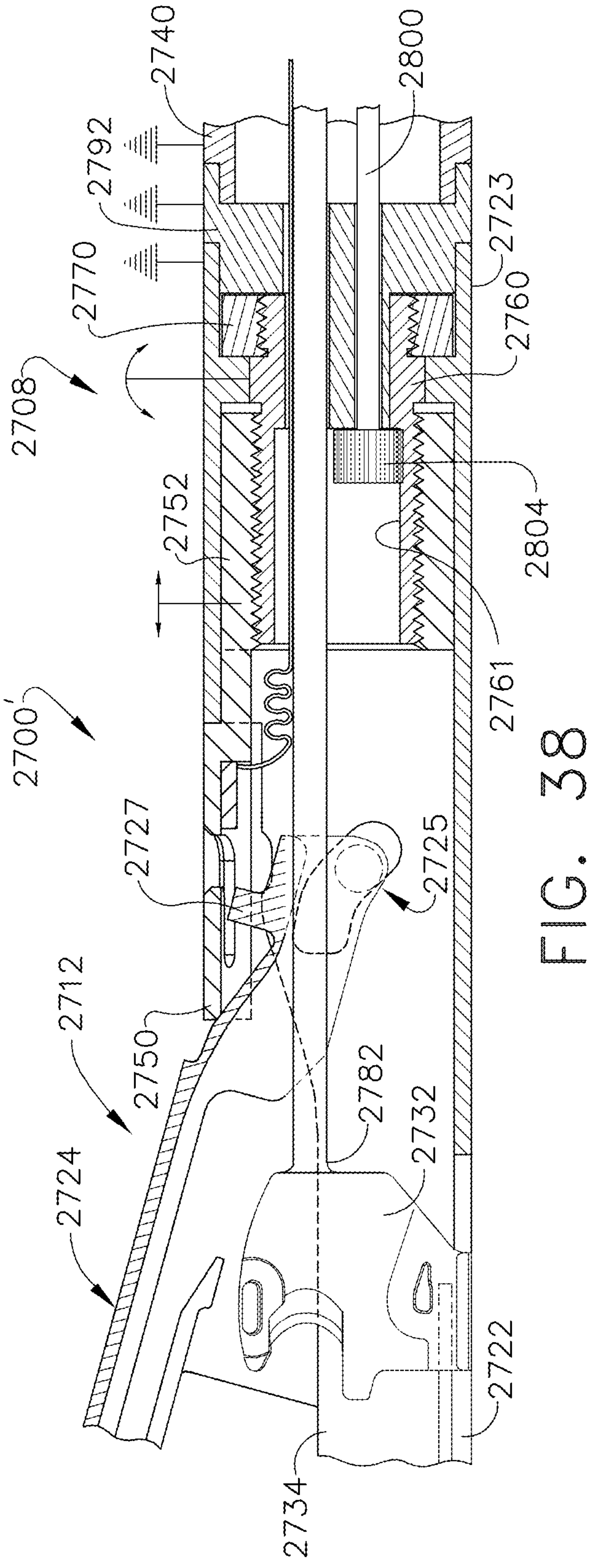
FIG. 38 is a cross-sectional side view of a portion of a surgical end effector and elongated shaft assembly of another surgical tool embodiment of the present invention employing a pressure sensor arrangement with the anvil in the open position.
Figure 39:
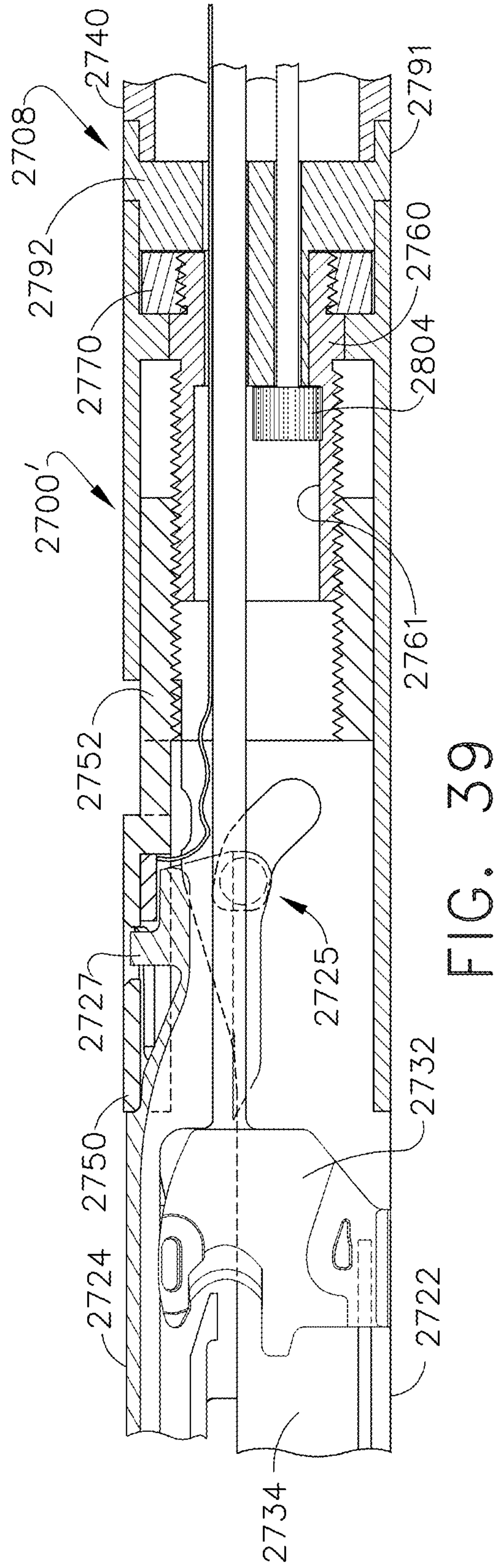
FIG. 39 is another cross-sectional side view of a portion of the surgical end effector and elongated shaft assembly of the surgical tool embodiment of FIG. 38 with the anvil in the closed position.

FIGS. 38 and 39 illustrate a surgical tool embodiment 2700 that is substantially identical to tool 2700 that was described in detail above. However tool 2700' includes a pressure sensor 2950 that is configured to provide feedback to the robotic controller 1001 concerning the amount of clamping pressure experienced by the anvil 2724. In various embodiments, for example, the pressure sensor may comprise a spring biased contact switch. For a continuous signal, it would use either a cantilever beam with a strain gage on it or a dome button top with a strain gage on the inside. Another version may comprise an off switch that contacts only at a known desired load. Such arrangement would include a dome on the based wherein the dome is one electrical pole and the base is the other electrical pole. Such arrangement permits the robotic controller 1001 to adjust the amount of clamping pressure being applied to the tissue within the surgical end effector 2712 by adjusting the amount of closing pressure applied to the anvil 2724. Those of ordinary skill in the art will understand that such pressure sensor arrangement may be effectively employed with several of the surgical tool embodiments described herein as well as their equivalent structures.

Figure 40:
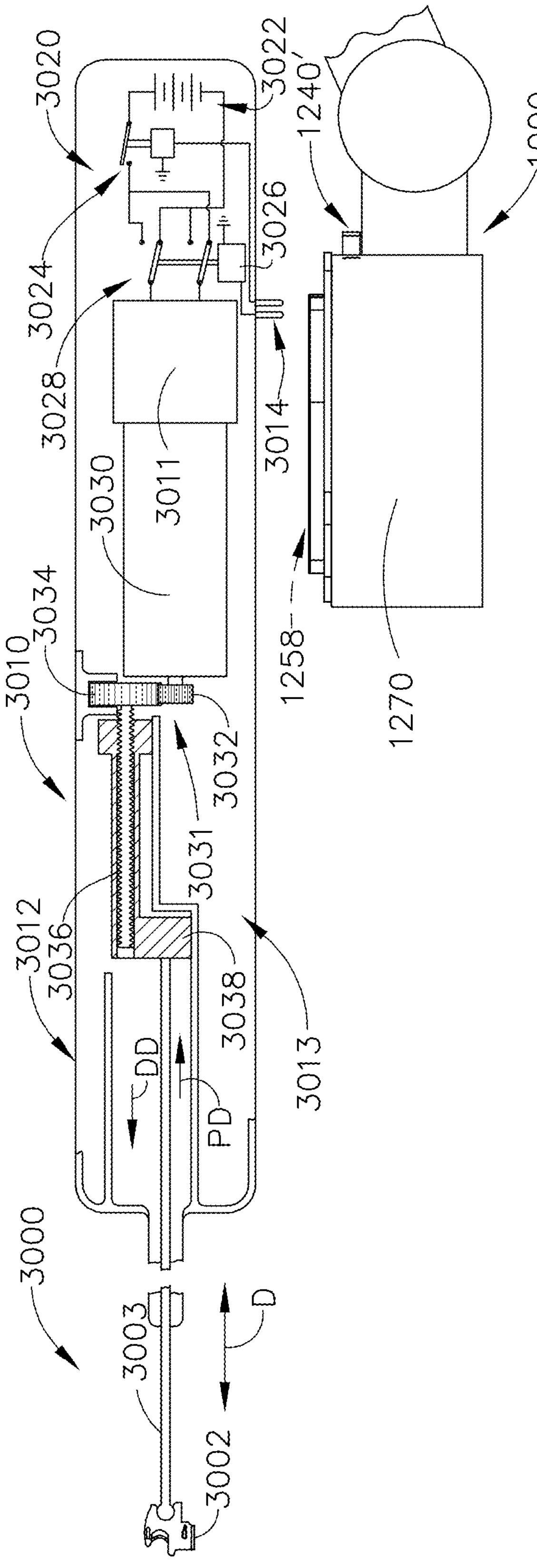
FIG. 40 is a side view of a portion of another surgical tool embodiment of the present invention in relation to a tool holder portion of a robotic system with some of the components thereof shown in cross-section.

FIG. 40 illustrates a portion of another surgical tool 3000 that may be effectively used in connection with a robotic system 1000. The surgical tool 3003 employs on-board motor(s) for powering various components of a surgical end effector cutting instrument. In at least one non-limiting embodiment for example, the surgical tool 3000 includes a surgical end effector in the form of an endocutter (not shown) that has an anvil (not shown) and surgical staple cartridge arrangement (not shown) of the types and constructions described above. The surgical tool 3000 also includes an elongated shaft (not shown) and anvil closure arrangement (not shown) of the types described above. Thus, this portion of the Detailed Description will not repeat the description of those components beyond that which is necessary to appreciate the unique and novel attributes of the various embodiments of surgical tool 3000.

In the depicted embodiment, the end effector includes a cutting instrument 3002 that is coupled to a knife bar 3003. As can be seen in FIG. 40, the surgical tool 3000 includes a tool mounting portion 3010 that includes a tool mounting plate 3012 that is configured to mountingly interface with the adaptor portion 1240' which is coupled to the robotic system 1000 in the various manners described above. The tool mounting portion 3010 is configured to operably support a transmission arrangement 3013 thereon. In at least one embodiment, the adaptor portion 1240' may be identical to the adaptor portion 1240 described in detail above without the powered rotation bodies and disc members employed by adapter 1240. In other embodiments, the adaptor portion 1240' may be identical to adaptor portion 1240. Still other modifications which are considered to be within the spirit and scope of the various forms of the present invention may employ one or more of the mechanical motions (i.e., rotary motion(s)) from the tool holder portion 1270 (as described hereinabove) to power/actuate the transmission arrangement 3013 while also employing one or more motors within the tool mounting portion 3010 to power one or more other components of the surgical end effector. In addition, while the end effector of the depicted embodiment comprises an endocutter, those of ordinary skill in the art will understand that the unique and novel attributes of the depicted embodiment may be effectively employed in connection with other types of surgical end effectors without departing from the spirit and scope of various forms of the present invention.

In various embodiments, the tool mounting plate 3012 is configured to at least house a first firing motor 3011 for supplying firing and retraction motions to the knife bar 3003 which is coupled to or otherwise operably interfaces with the cutting instrument 3002. The tool mounting plate 3012 has an array of electrical connecting pins 3014 which are configured to interface with the slots 1258 (FIG. 9) in the adapter 1240'. Such arrangement permits the controller 1001 of the robotic system 1000 to provide control signals to the electronic control circuit 3020 of the surgical tool 3000. While the interface is described herein with reference to mechanical, electrical, and magnetic coupling elements, it should be understood that a wide variety of telemetry modalities might be used, including infrared, inductive coupling, or the like.

Control circuit 3020 is shown in schematic form in FIG. 40. In one form or embodiment, the control circuit 3020 includes a power supply in the form of a battery 3022 that is coupled to an on-off solenoid powered switch 3024. Control circuit 3020 further includes an on/off firing solenoid 3026 that is coupled to a double pole switch 3028 for controlling the rotational direction of the motor 3011. Thus, when the controller 1001 of the robotic system 1000 supplies an appropriate control signal, switch 3024 will permit battery 3022 to supply power to the double pole switch 3028. The controller 1001 of the robotic system 1000 will also supply an appropriate signal to the double pole switch 3028 to supply power to the motor 3011. When it is desired to fire the surgical end effector (i.e., drive the cutting instrument 3002 distally through tissue clamped in the surgical end effector, the double pole switch 3028 will be in a first position. When it is desired to retract the cutting instrument 3002 to the starting position, the double pole switch 3028 will be moved to the second position by the controller 1001.

Various embodiments of the surgical tool 3000 also employ a gear box 3030 that is sized, in cooperation with a firing gear train 3031 that, in at least one non-limiting embodiment, comprises a firing drive gear 3032 that is in meshing engagement with a firing driven gear 3034 for generating a desired amount of driving force necessary to drive the cutting instrument 3002 through tissue and to drive and form staples in the various manners described herein. In the embodiment depicted in FIG. 40, the driven gear 3034 is coupled to a screw shaft 3036 that is in threaded engagement with a screw nut arrangement 3038 that is constrained to move axially (represented by arrow “D”). The screw nut arrangement 3038 is attached to the firing bar 3003. Thus, by rotating the screw shaft 3036 in a first direction, the cutting instrument 3002 is driven in the distal direction “DD” and rotating the screw shaft in an opposite second direction, the cutting instrument 3002 may be retracted in the proximal direction “PD”.

Figure 41:
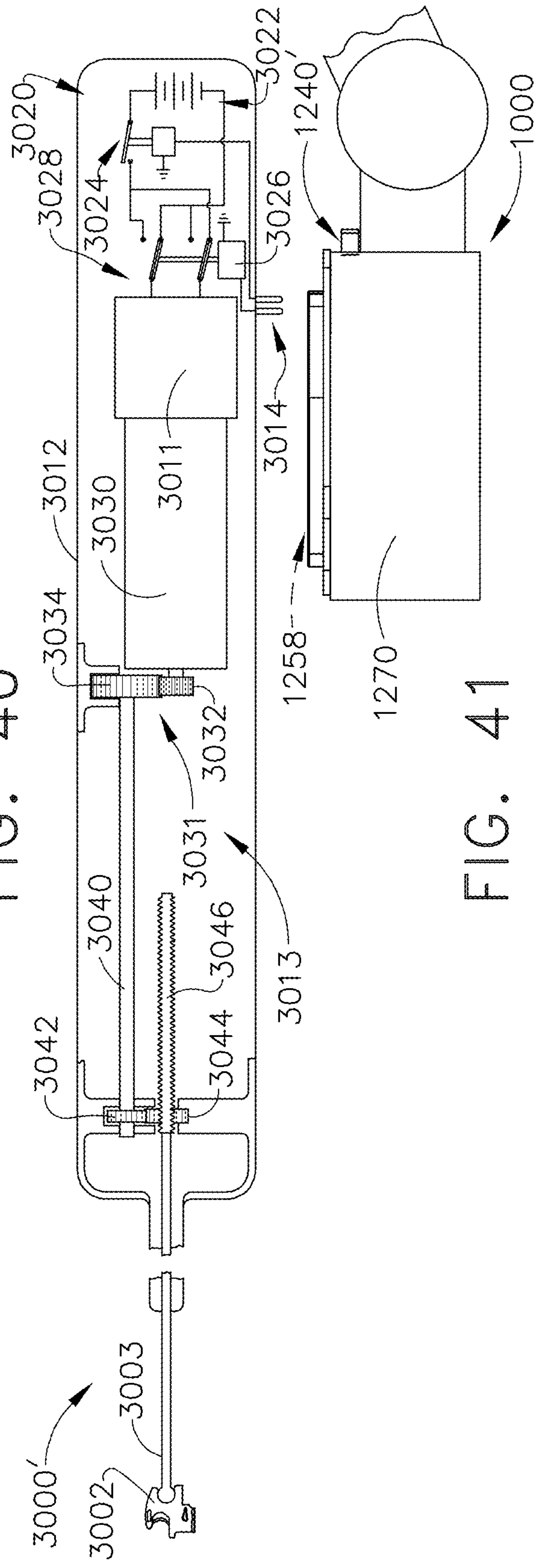
FIG. 41 is a side view of a portion of another surgical tool embodiment of the present invention in relation to a tool holder portion of a robotic system with some of the components thereof shown in cross-section.

FIG. 41 illustrates a portion of another surgical tool 3000' that is substantially identical to tool 3000 described above, except that the driven gear 3034 is attached to a drive shaft 3040. The drive shaft 3040 is attached to a second driver gear 3042 that is in meshing engagement with a third driven gear 3044 that is in meshing engagement with a screw 3046 coupled to the firing bar 3003.

Figure 42:
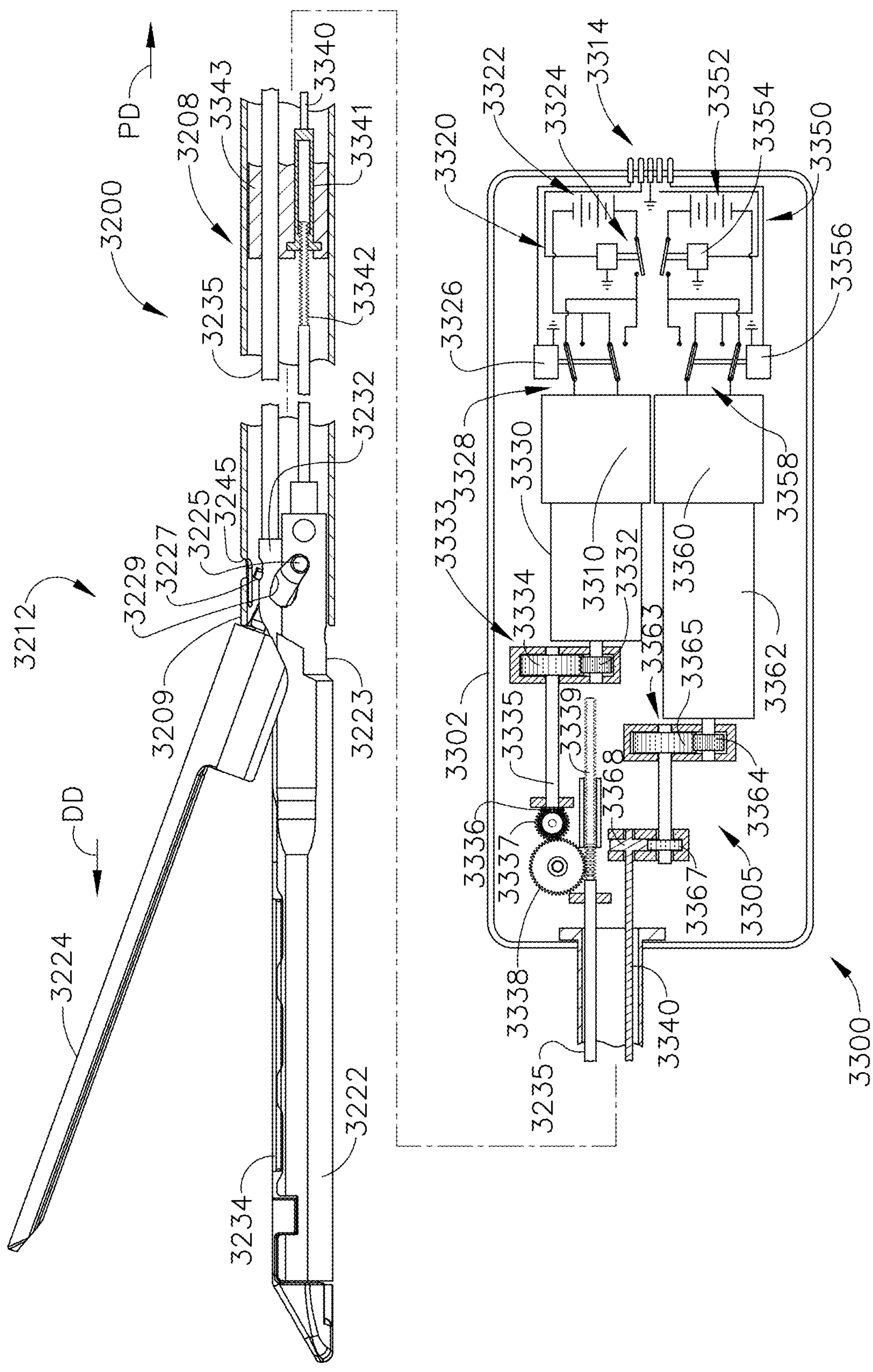
FIG. 42 is a side view of a portion of another surgical tool embodiment of the present invention with some of the components thereof shown in cross-section.
Figure 43:
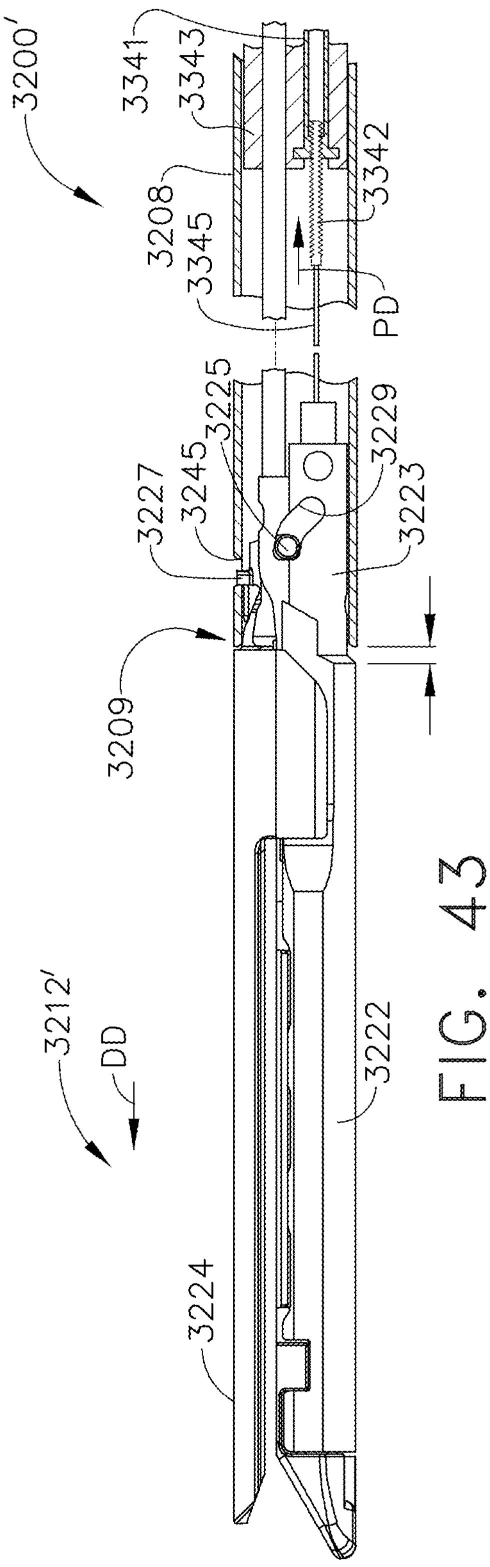
FIG. 43 is a side view of a portion of another surgical end effector embodiment of a portion of a surgical tool embodiment of the present invention with some components thereof shown in cross-section.

FIG. 42 illustrates another surgical tool 3200 that may be effectively used in connection with a robotic system 1000. In this embodiment, the surgical tool 3200 includes a surgical end effector 3212 that in one non-limiting form, comprises a component portion that is selectively movable between first and second positions relative to at least one other end effector component portion. As will be discussed in further detail below, the surgical tool 3200 employs on-board motors for powering various components of a transmission arrangement 3305. The surgical end effector 3212 includes an elongated channel 3222 that operably supports a surgical staple cartridge 3234. The elongated channel 3222 has a proximal end 3223 that slidably extends into a hollow elongated shaft assembly 3208 that is coupled to a tool mounting portion 3300. In addition, the surgical end effector 3212 includes an anvil 3224 that is pivotally coupled to the elongated channel 3222 by a pair of trunnions 3225 that are received within corresponding openings 3229 in the elongated channel 3222. A distal end portion 3209 of the shaft assembly 3208 includes an opening 3245 into which a tab 3227 on the anvil 3224 is inserted in order to open the anvil 3224 as the elongated channel 3222 is moved axially in the proximal direction “PD” relative to the distal end portion 3209 of the shaft assembly 3208. In various embodiments, a spring (not shown) may be employed to bias the anvil 3224 to the open position.

As indicated above, the surgical tool 3200 includes a tool mounting portion 3300 that includes a tool mounting plate 3302 that is configured to operably support the transmission arrangement 3305 and to mountingly interface with the adaptor portion 1240' which is coupled to the robotic system 1000 in the various manners described above. In at least one embodiment, the adaptor portion 1240' may be identical to the adaptor portion 1240 described in detail above without the powered disc members employed by adapter 1240. In other embodiments, the adaptor portion 1240' may be identical to adaptor portion 1240. However, in such embodiments, because the various components of the surgical end effector 3212 are all powered by motor(s) in the tool mounting portion 3300, the surgical tool 3200 will not employ or require any of the mechanical (i.e., non-electrical) actuation motions from the tool holder portion 1270 to power the surgical end effector 3200 components. Still other modifications which are considered to be within the spirit and scope of the various forms of the present invention may employ one or more of the mechanical motions from the tool holder portion 1270 (as described hereinabove) to power/actuate one or more of the surgical end effector components while also employing one or more motors within the tool mounting portion to power one or more other components of the surgical end effector.

In various embodiments, the tool mounting plate 3302 is configured to support a first firing motor 3310 for supplying firing and retraction motions to the transmission arrangement 3305 to drive a knife bar 3335 that is coupled to a cutting instrument 3332 of the type described above. As can be seen in FIG. 42, the tool mounting plate 3212 has an array of electrical connecting pins 3014 which are configured to interface with the slots 1258 (FIG. 9) in the adapter 1240'. Such arrangement permits the controller 1001 of the robotic system 1000 to provide control signals to the electronic control circuits 3320, 3340 of the surgical tool 3200. While the interface is described herein with reference to mechanical, electrical, and magnetic coupling elements, it should be understood that a wide variety of telemetry modalities might be used, including infrared, inductive coupling, or the like.

In one form or embodiment, the first control circuit 3320 includes a first power supply in the form of a first battery 3322 that is coupled to a first on-off solenoid powered switch 3324. The first firing control circuit 3320 further includes a first on/off firing solenoid 3326 that is coupled to a first double pole switch 3328 for controlling the rotational direction of the first firing motor 3310. Thus, when the robotic controller 1001 supplies an appropriate control signal, the first switch 3324 will permit the first battery 3322 to supply power to the first double pole switch 3328. The robotic controller 1001 will also supply an appropriate signal to the first double pole switch 3328 to supply power to the first firing motor 3310. When it is desired to fire the surgical end effector (i.e., drive the cutting instrument 3232 distally through tissue clamped in the surgical end effector 3212, the first switch 3328 will be positioned in a first position by the robotic controller 1001. When it is desired to retract the cutting instrument 3232 to the starting position, the robotic controller 1001 will send the appropriate control signal to move the first switch 3328 to the second position.

Various embodiments of the surgical tool 3200 also employ a first gear box 3330 that is sized, in cooperation with a firing drive gear 3332 coupled thereto that operably interfaces with a firing gear train 3333. In at least one non-limiting embodiment, the firing gear train 333 comprises a firing driven gear 3334 that is in meshing engagement with drive gear 3332, for generating a desired amount of driving force necessary to drive the cutting instrument 3232 through tissue and to drive and form staples in the various manners described herein. In the embodiment depicted in FIG. 41, the driven gear 3334 is coupled to a drive shaft 3335 that has a second driven gear 3336 coupled thereto. The second driven gear 3336 is supported in meshing engagement with a third driven gear 3337 that is in meshing engagement with a fourth driven gear 3338. The fourth driven gear 3338 is in meshing engagement with a threaded proximal portion 3339 of the knife bar 3235 that is constrained to move axially. Thus, by rotating the drive shaft 3335 in a first direction, the cutting instrument 3232 is driven in the distal direction "DD" and rotating the drive shaft 3335 in an opposite second direction, the cutting instrument 3232 may be retracted in the proximal direction "PD".

As indicated above, the opening and closing of the anvil 3224 is controlled by axially moving the elongated channel 3222 relative to the elongated shaft assembly 3208. The axial movement of the elongated channel 3222 is controlled by a closure control system 3339. In various embodiments, the closure control system 3339 includes a closure shaft 3340 which has a hollow threaded end portion 3341 that threadably engages a threaded closure rod 3342. The threaded end portion 3341 is rotatably supported in a spine shaft 3343 that operably interfaces with the tool mounting portion 3300 and extends through a portion of the shaft assembly 3208 as shown. The closure system 3339 further comprises a closure control circuit 3350 that includes a second power supply in the form of a second battery 3352 that is coupled to a second on-off solenoid powered switch 3354. Closure control circuit 3350 further includes a second on/off firing solenoid 3356 that is coupled to a second double pole switch 3358 for controlling the rotation of a second closure motor 3360. Thus, when the robotic controller 1001 supplies an appropriate control signal, the second switch 3354 will permit the second battery 3352 to supply power to the second double pole switch 3354. The robotic controller 1001 will also supply an appropriate signal to the second double pole switch 3358 to supply power to the second motor 3360. When it is desired to close the anvil 3224, the second switch 3348 will be in a first position. When it is desired to open the anvil 3224, the second switch 3348 will be moved to a second position.

Various embodiments of tool mounting portion 3300 also employ a second gear box 3362 that is coupled to a closure drive gear 3364. The closure drive gear 3364 is in meshing engagement with a closure gear train 3363. In various non-limiting forms, the closure gear train 3363 includes a closure driven gear 3365 that is attached to a closure drive shaft 3366. Also attached to the closure drive shaft 3366 is a closure drive gear 3367 that is in meshing engagement with a closure shaft gear 3360 attached to the closure shaft 3340. FIG. 42 depicts the end effector 3212 in the open position. As indicated above, when the threaded closure rod 3342 is in the position depicted in FIG. 42, a spring (not shown) biases the anvil 3224 to the open position. When it is desired to close the anvil 3224, the robotic controller 1001 will activate the second motor 3360 to rotate the closure shaft 3340 to draw the threaded closure rod 3342 and the channel 3222 in the proximal direction 'PD'. As the anvil 3224 contacts the distal end portion 3209 of the shaft 3208, the anvil 3224 is pivoted to the closed position.

A method of operating the surgical tool 3200 will now be described. Once the tool mounting portion 3302 has be operably coupled to the tool holder 1270 of the robotic system 1000, the robotic system 1000 can orient the end effector 3212 in position adjacent the target tissue to be cut and stapled. If the anvil 3224 is not already in the open position, the robotic controller 1001 may activate the second closure motor 3360 to drive the channel 3222 in the distal direction to the position depicted in FIG. 42. Once the robotic controller 1001 determines that the surgical end effector 3212 is in the open position by sensor(s) in the and effector and/or the tool mounting portion 3300, the robotic controller 1001 may provide the surgeon with a signal to inform the surgeon that the anvil 3224 may then be closed. Once the target tissue is positioned between the open anvil 3224 and the surgical staple cartridge 3234, the surgeon may then commence the closure process by activating the robotic controller 1001 to apply a closure control signal to the second closure motor 3360. The second closure motor 3360 applies a rotary motion to the closure shaft 3340 to draw the channel 3222 in the proximal direction "PD" until the anvil 3224 has been pivoted to the closed position. Once the robotic controller 1001 determines that the anvil 3224 has been moved to the closed position by sensor(s) in the surgical end effector 3212 and/or in the tool mounting portion 3300 that are in communication with the robotic control system, the motor 3360 may be deactivated. Thereafter, the firing process may be commenced either manually by the surgeon activating a trigger, button, etc. on the controller 1001 or the controller 1001 may automatically commence the firing process.

To commence the firing process, the robotic controller 1001 activates the firing motor 3310 to drive the firing bar 3235 and the cutting instrument 3232 in the distal direction "DD". Once robotic controller 1001 has determined that the cutting instrument 3232 has moved to the ending position within the surgical staple cartridge 3234 by means of sensors in the surgical end effector 3212 and/or the motor drive portion 3300, the robotic controller 1001 may provide the surgeon with an indication signal. Thereafter the surgeon may manually activate the first motor 3310 to retract the cutting instrument 3232 to the starting position or the robotic controller 1001 may automatically activate the first motor 3310 to retract the cutting element 3232.

Figure 44:
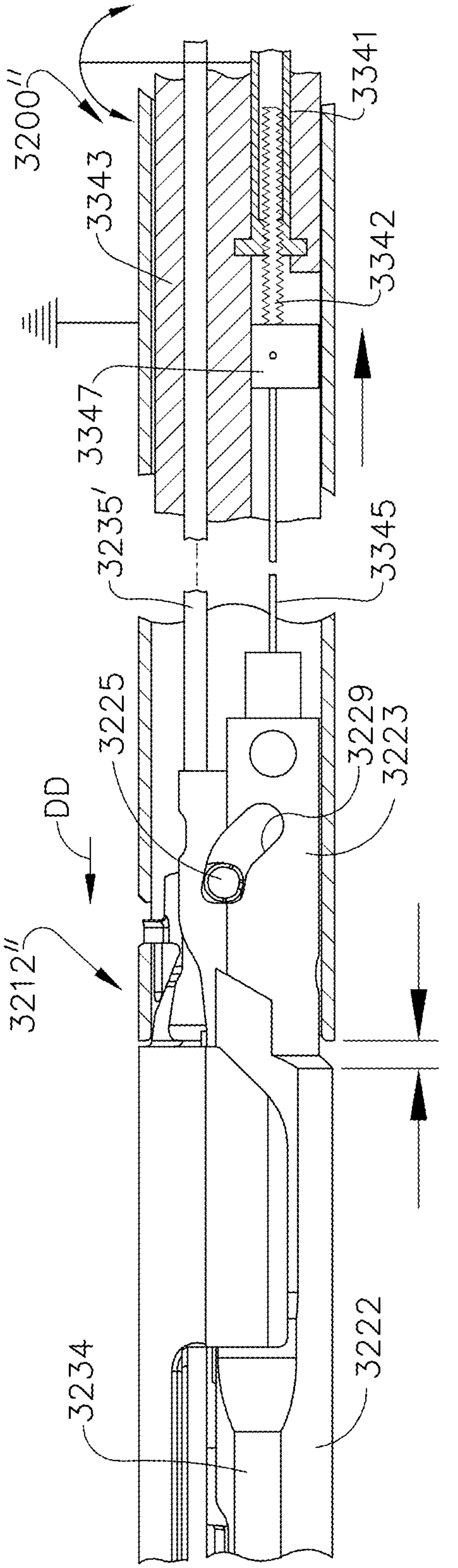
FIG. 44 is a side view of a portion of another surgical end effector embodiment of a portion of a surgical tool embodiment of the present invention with some components thereof shown in cross-section.
Figure 64:
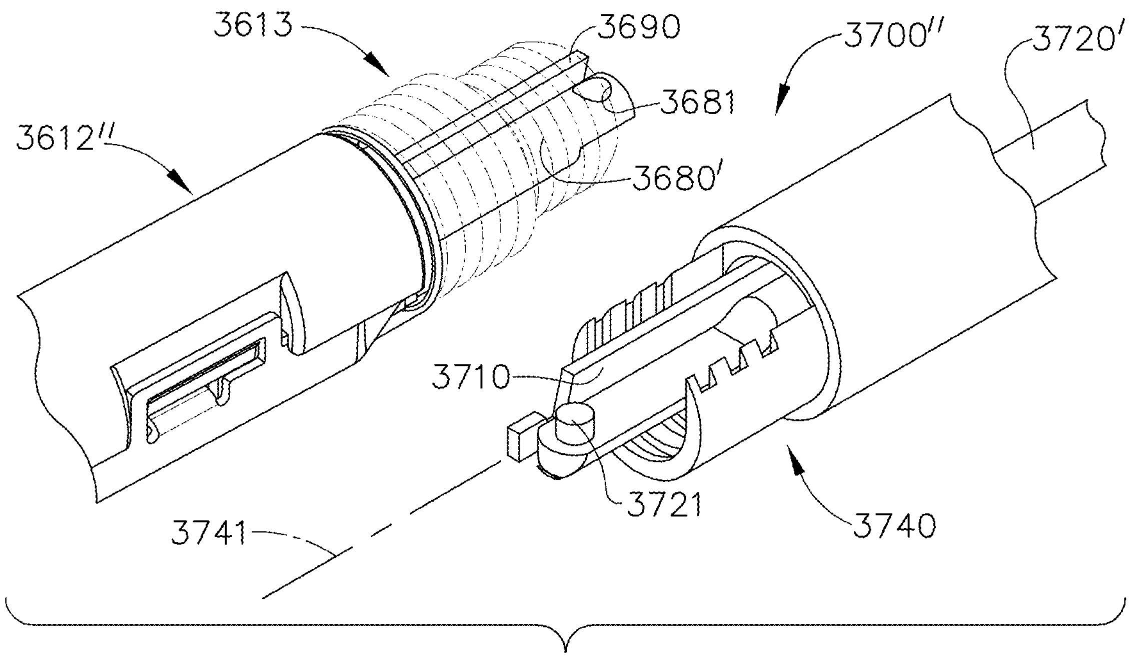
FIG. 64 is a partial exploded perspective view of a portion of another disposable loading unit embodiment and an elongated shaft assembly embodiment of a surgical tool embodiment of the present invention.
Figure 65:
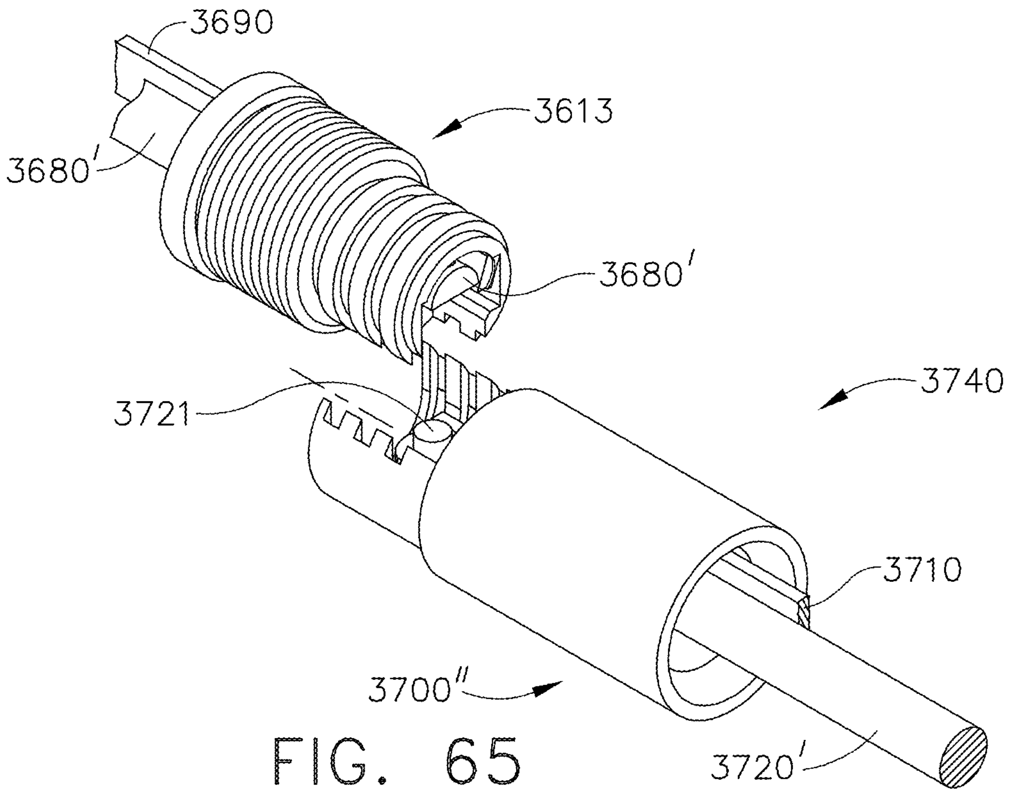
FIG. 65 is another partial exploded perspective view of the disposable loading unit embodiment and an elongated shaft assembly embodiment of FIG. 64.

The embodiment depicted in FIG. 42 does not include an articulation joint. FIGS. 64 and 65 illustrate surgical tools 3200' and 3200" that have end effectors 3212', 3212", respectively that may be employed with an elongated shaft embodiment that has an articulation joint of the various types disclosed herein. For example, as can be seen in FIG. 64, a threaded closure shaft 3342 is coupled to the proximal end 3223 of the elongated channel 3222 by a flexible cable or other flexible member 3345. The location of an articulation joint (not shown) within the elongated shaft assembly 3208 will coincide with the flexible member 3345 to enable the flexible member 3345 to accommodate such articulation. In addition, in the above-described embodiment, the flexible member 33345 is rotatably affixed to the proximal end portion 3223 of the elongated channel 3222 to enable the flexible member 3345 to rotate relative thereto to prevent the flexible member 3229 from "winding up" relative to the channel 3222. Although not shown, the cutting element may be driven in one of the above described manners by a knife bar that can also accommodate articulation of the elongated shaft assembly. FIG. 44 depicts a surgical end effector 3212" that is substantially identical to the surgical end effector 3212 described above, except that the threaded closure rod 3342 is attached to a closure nut 3347 that is constrained to only move axially within the elongated shaft assembly 3208. The flexible member 3345 is attached to the closure nut 3347. Such arrangement also prevents the threaded closure rod 3342 from winding-up the flexible member 3345. A flexible knife bar 3235' may be employed to facilitate articulation of the surgical end effector 3212".

The surgical tools 3200, 3200', and 3200" described above may also employ anyone of the cutting instrument embodiments described herein. As described above, the anvil of each of the end effectors of these tools is closed by drawing the elongated channel into contact with the distal end of the elongated shaft assembly. Thus, once the target tissue has been located between the staple cartridge 3234 and the anvil 3224, the robotic controller 1001 can start to draw the channel 3222 inward into the shaft assembly 3208. In various embodiments, however, to prevent the end effector 3212, 3212', 3212" from moving the target tissue with the end effector during this closing process, the controller 1001 may simultaneously move the tool holder and ultimately the tool such to compensate for the movement of the elongated channel 3222 so that, in effect, the target tissue is clamped between the anvil and the elongated channel without being otherwise moved.

Figure 45:
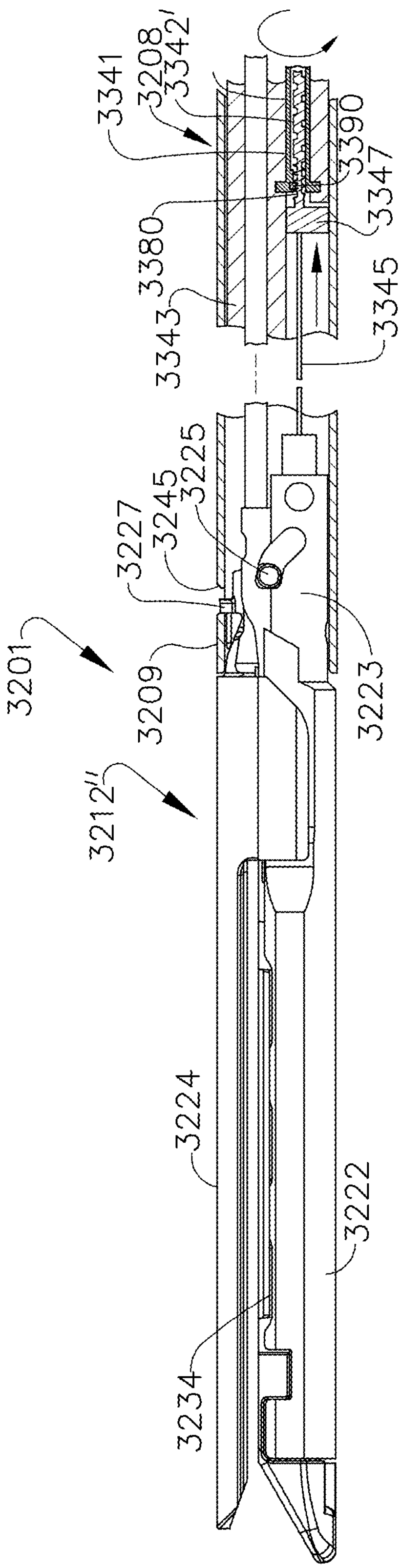
FIG. 45 is a side view of a portion of another surgical end effector embodiment of a portion of a surgical tool embodiment of the present invention with some components thereof shown in cross-section.
Figure 46:
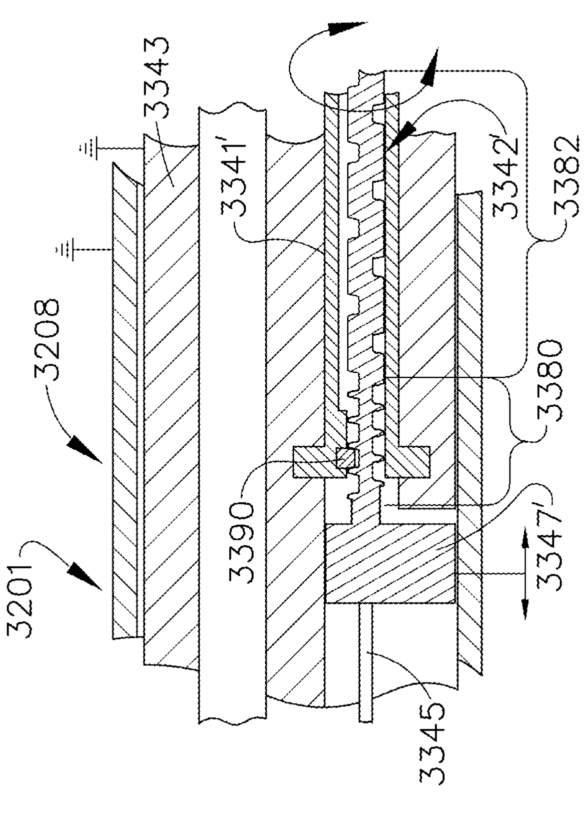
FIG. 46 is an enlarged cross-sectional view of a portion of the end effector of FIG. 45.
Figure 47:
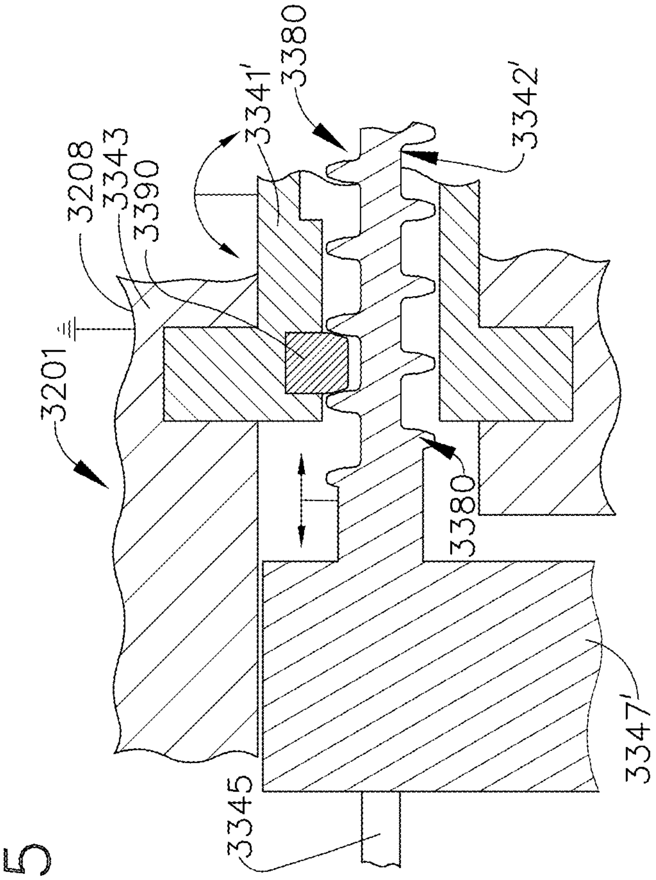
FIG. 47 is another cross-sectional view of a portion of the end effector of FIGS. 45 and 46.
Figure 48:
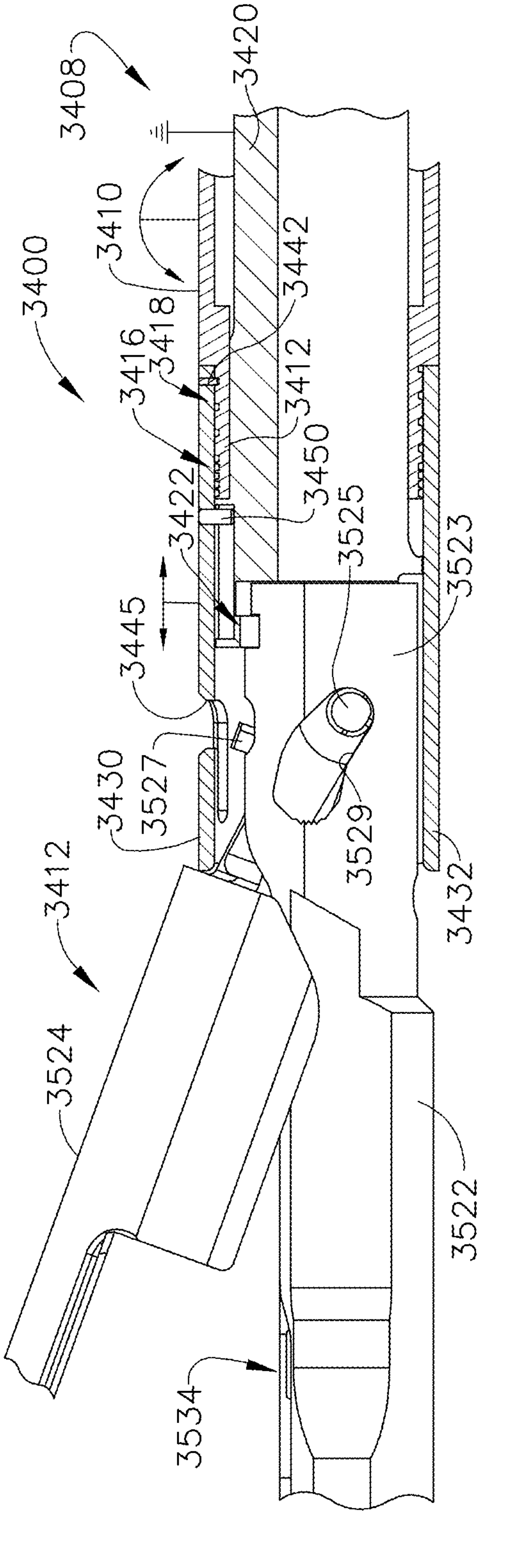
FIG. 48 is a cross-sectional side view of a portion of a surgical end effector and elongated shaft assembly of another surgical tool embodiment of the present invention with the anvil in the open position.

FIGS. 45-47 depict another surgical tool embodiment 3201 that is substantially identical to surgical tool 3200" described above, except for the differences discussed below. In this embodiment, the threaded closure rod 3342' has variable pitched grooves. More specifically, as can be seen in FIG. 46, the closure rod 3342' has a distal groove section 3380 and a proximal groove section 3382. The distal and proximal groove sections 3380, 3382 are configured for engagement with a lug 3390 supported within the hollow threaded end portion 3341'. As can be seen in FIG. 46, the distal groove section 3380 has a finer pitch than the groove section 3382. Thus, such variable pitch arrangement permits the elongated channel 3222 to be drawn into the shaft 3208 at a first speed or rate by virtue of the engagement between the lug 3390 and the proximal groove segment 3382. When the lug 3390 engages the distal groove segment, the channel 3222 will be drawn into the shaft 3208 at a second speed or rate. Because the proximal groove segment 3382 is coarser than the distal groove segment 3380, the first speed will be greater than the second speed. Such arrangement serves to speed up the initial closing of the end effector for tissue manipulation and then after the tissue has been properly positioned therein, generate the amount of closure forces to properly clamp the tissue for cutting and scaling. Thus, the anvil 3234 initially closes fast with a lower force and then applies a higher closing force as the anvil closes more slowly.

The surgical end effector opening and closing motions are employed to enable the user to use the end effector to grasp and manipulate tissue prior to fully clamping it in the desired location for cutting and sealing. The user may, for example, open and close the surgical end effector numerous times during this process to orient the end effector in a proper position which enables the tissue to be held in a desired location. Thus, in at least some embodiments, to produce the high loading for firing, the fine thread may require as many as 5-10 full rotations to generate the necessary load. In some cases, for example, this action could take as long as 2-5 seconds. If it also took an equally long time to open and close the end effector each time during the positioning/tissue manipulation process, just positioning the end effector may take an undesirably long time. If that happens, it is possible that a user may abandon such use of the end effector for use of a conventional grasper device. Use of graspers, etc. may undesirably increase the costs associated with completing the surgical procedure.

The above-described embodiments employ a battery or batteries to power the motors used to drive the end effector components. Activation of the motors is controlled by the robotic system 1000. In alternative embodiments, the power supply may comprise alternating current "AC" that is supplied to the motors by the robotic system 1000. That is, the AC power would be supplied from the system powering the robotic system 1000 through the tool holder and adapter. In still other embodiments, a power cord or tether may be attached to the tool mounting portion 3300 to supply the requisite power from a separate source of alternating or direct current.

In use, the controller 1001 may apply an initial rotary motion to the closure shaft 3340 (FIG. 42) to draw the elongated channel 3222 axially inwardly into the elongated shaft assembly 3208 and move the anvil from a first position to an intermediate position at a first rate that corresponds with the point wherein the distal groove section 3380 transitions to the proximal groove section 3382. Further application of rotary motion to the closure shaft 3340 will cause the anvil to move from the intermediate position to the closed position relative to the surgical staple cartridge. When in the closed position, the tissue to be cut and stapled is properly clamped between the anvil and the surgical staple cartridge.

FIGS. 48-52 illustrate another surgical tool embodiment 3400 of the present invention. This embodiment includes an elongated shaft assembly 3408 that extends from a tool mounting portion 3500. The elongated shaft assembly 3408 includes a rotatable proximal closure tube segment 3410 that is rotatably journaled on a proximal spine member 3420 that is rigidly coupled to a tool mounting plate 3502 of the tool mounting portion 3500. The proximal spine member 3420 has a distal end 3422 that is coupled to an elongated channel portion 3522 of a surgical end effector 3412. For example, in at least one embodiment, the elongated channel portion 3522 has a distal end portion 3523 that "hookingly engages" the distal end 3422 of the spine member 3420. The elongated channel 3522 is configured to support a surgical staple cartridge 3534 therein. This embodiment may employ one of the various cutting instrument embodiments disclosed herein to sever tissue that is clamped in the surgical end effector 3412 and fire the staples in the staple cartridge 3534 into the severed tissue.

Surgical end effector 3412 has an anvil 3524 that is pivotally coupled to the elongated channel 3522 by a pair of trunnions 3525 that are received in corresponding openings 3529 in the elongated channel 3522. The anvil 3524 is moved between the open (FIG. 48) and closed positions (FIGS. 49-51) by a distal closure tube segment 3430. A distal end portion 3432 of the distal closure tube segment 3430 includes an opening 3445 into which a tab 3527 on the anvil 3524 is inserted in order to open and close the anvil 3524 as the distal closure tube segment 3430 moves axially relative thereto. In various embodiments, the opening 3445 is shaped such that as the closure tube segment 3430 is moved in the proximal direction, the closure tube segment 3430 causes the anvil 3524 to pivot to an open position. In addition or in the alternative, a spring (not shown) may be employed to bias the anvil 3524 to the open position.

As can be seen in FIGS. 48-51, the distal closure tube segment 3430 includes a lug 3442 that extends from its distal end 3440 into threaded engagement with a variable pitch groove/thread 3414 formed in the distal end 3412 of the rotatable proximal closure tube segment 3410. The variable pitch groove/thread 3414 has a distal section 3416 and a proximal section 3418. The pitch of the distal groove/thread section 3416 is finer than the pitch of the proximal groove/thread section 3418. As can also be seen in FIGS. 48-51, the distal closure tube segment 3430 is constrained for axial movement relative to the spine member 3420 by an axial retainer pin 3450 that is received in an axial slot 3424 in the distal end of the spine member 3420.

As indicated above, the anvil 2524 is open and closed by rotating the proximal closure tube segment 3410. The variable pitch thread arrangement permits the distal closure tube segment 3430 to be driven in the distal direction "DD" at a first speed or rate by virtue of the engagement between the lug 3442 and the proximal groove/thread section 3418. When the lug 3442 engages the distal groove/thread section 3416, the distal closure tube segment 3430 will be driven in the distal direction at a second speed or rate. Because the proximal groove/thread section 3418 is coarser than the distal groove/thread segment 3416, the first speed will be greater than the second speed.

Figure 52:
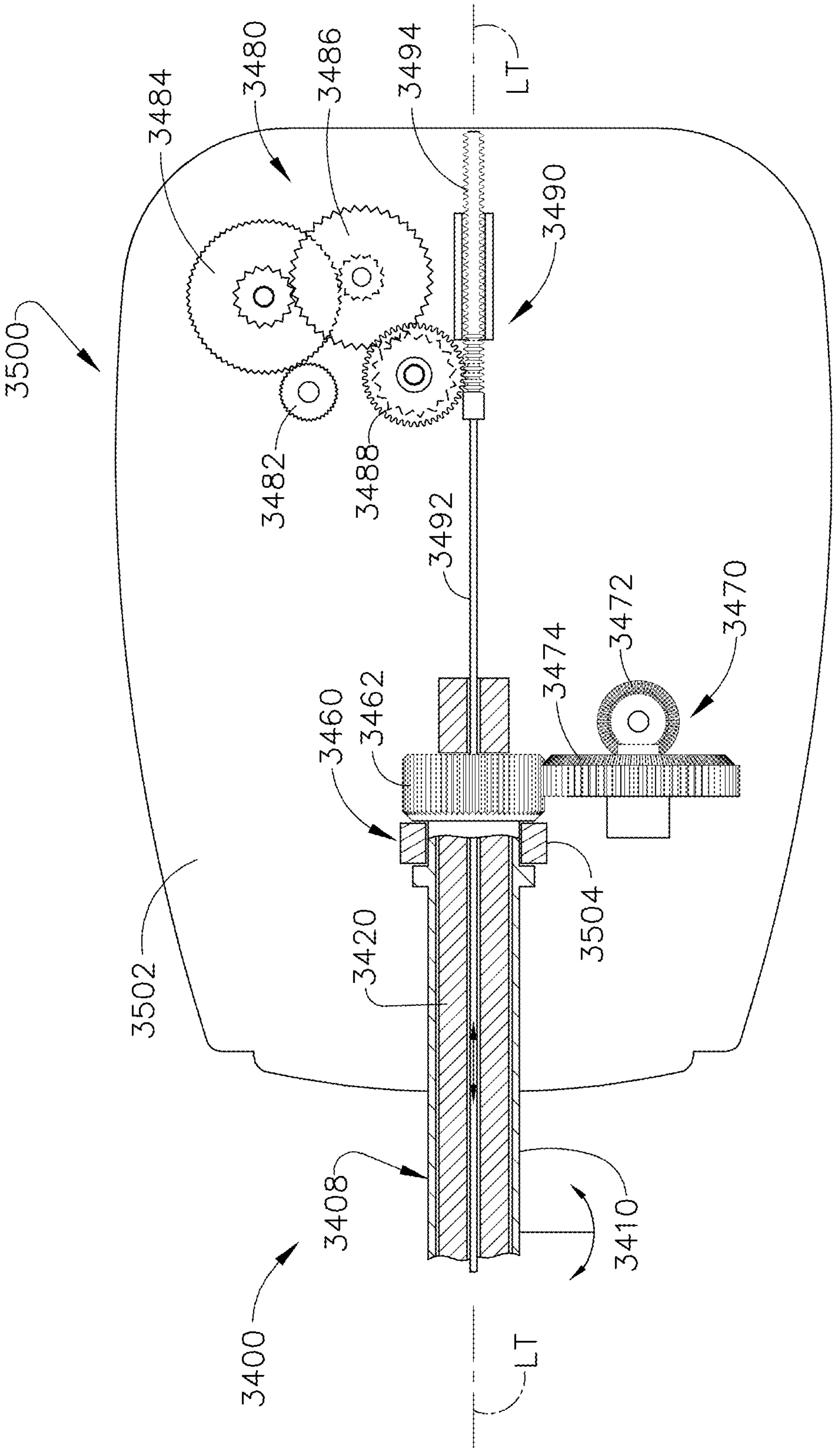
FIG. 52 is a top view of a tool mounting portion embodiment of a surgical tool embodiment of the present invention.

In at least one embodiment, the tool mounting portion 3500 is configured to receive a corresponding first rotary motion from the robotic controller 1001 and convert that first rotary motion to a primary rotary motion for rotating the rotatable proximal closure tube segment 3410 about a longitudinal tool axis LT-LT. As can be seen in FIG. 52, a proximal end 3460 of the proximal closure tube segment 3410 is rotatably supported within a cradle arrangement 3504 attached to a tool mounting plate 3502 of the tool mounting portion 3500. A rotation gear 3462 is formed on or attached to the proximal end 3460 of the closure tube segment 3410 for meshing engagement with a rotation drive assembly 3470 that is operably supported on the tool mounting plate 3502. In at least one embodiment, a rotation drive gear 3472 is coupled to a corresponding first one of the driven discs or elements 1304 on the adapter side of the tool mounting plate 3502 when the tool mounting portion 3500 is coupled to the tool holder 1270. See FIGS. 10 and 52. The rotation drive assembly 3470 further comprises a rotary driven gear 3474 that is rotatably supported on the tool mounting plate 3502 in meshing engagement with the rotation gear 3462 and the rotation drive gear 3472. Application of a first rotary control motion from the robotic controller 1001 through the tool holder 1270 and the adapter 1240 to the corresponding driven element 1304 will thereby cause rotation of the rotation drive gear 3472 by virtue of being operably coupled thereto. Rotation of the rotation drive gear 3472 ultimately results in the rotation of the closure tube segment 3410 to open and close the anvil 3524 as described above.

As indicated above, the surgical end effector 3412 employs a cutting instrument of the type and constructions described above. FIG. 52 illustrates one form of knife drive assembly 3480 for axially advancing a knife bar 3492 that is attached to such cutting instrument. One form of the knife drive assembly 3480 comprises a rotary drive gear 3482 that is coupled to a corresponding third one of the driven discs or elements 1304 on the adapter side of the tool mounting plate 3502 when the tool drive portion 3500 is coupled to the tool holder 1270. Sec FIGS. 10 and 52. The knife drive assembly 3480 further comprises a first rotary driven gear assembly 3484 that is rotatably supported on the tool mounting plate 5200. The first rotary driven gear assembly 3484 is in meshing engagement with a third rotary driven gear assembly 3486 that is rotatably supported on the tool mounting plate 3502 and which is in meshing engagement with a fourth rotary driven gear assembly 3488 that is in meshing engagement with a threaded portion 3494 of drive shaft assembly 3490 that is coupled to the knife bar 3492. Rotation of the rotary drive gear 3482 in a second rotary direction will result in the axial advancement of the drive shaft assembly 3490 and knife bar 3492 in the distal direction "DD". Conversely, rotation of the rotary drive gear 3482 in a secondary rotary direction (opposite to the second rotary direction) will cause the drive shaft assembly 3490 and the knife bar 3492 to move in the proximal direction.

Figure 53:
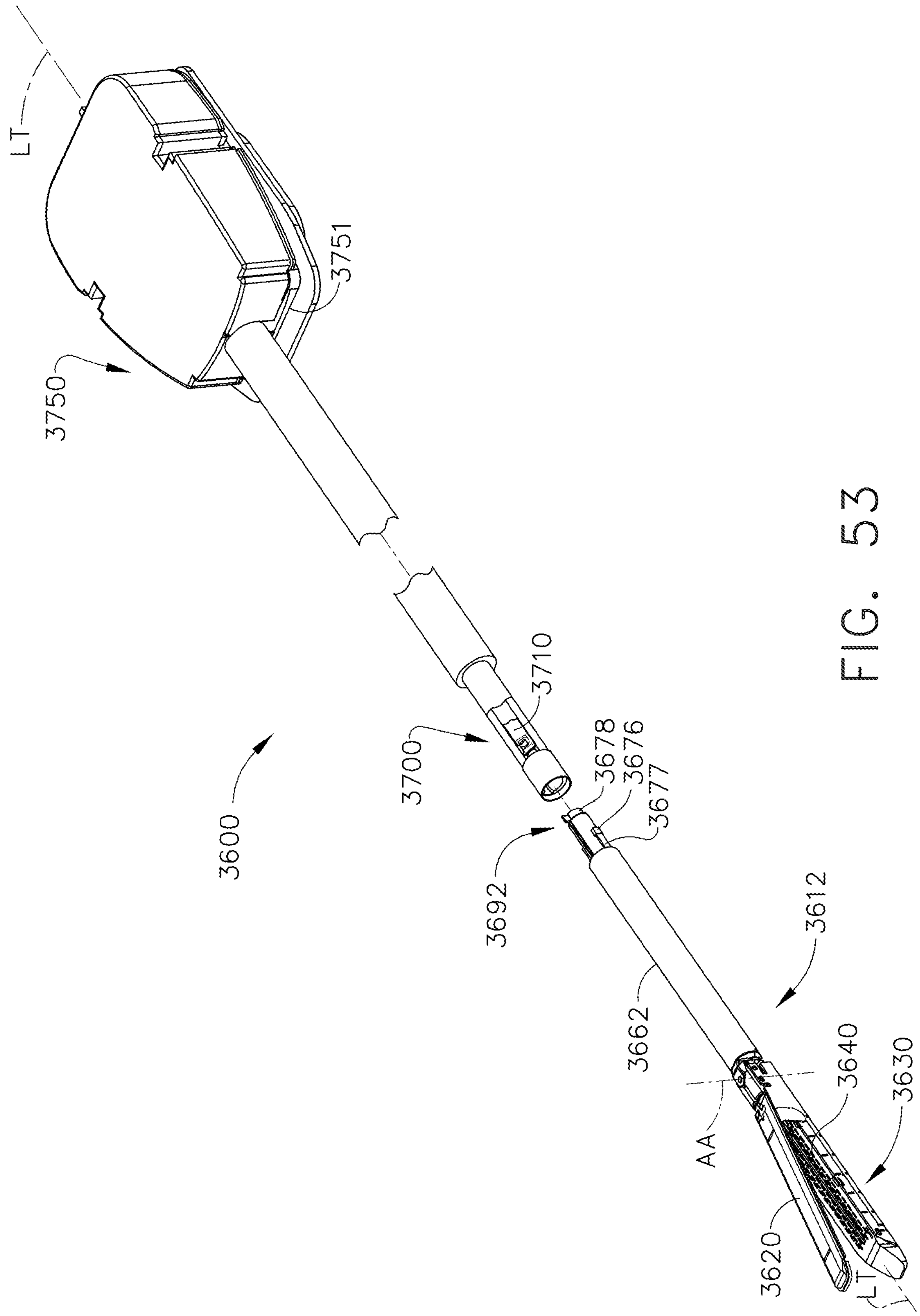
FIG. 53 is a perspective assembly view of another surgical tool embodiment of the present invention.
Figure 54:
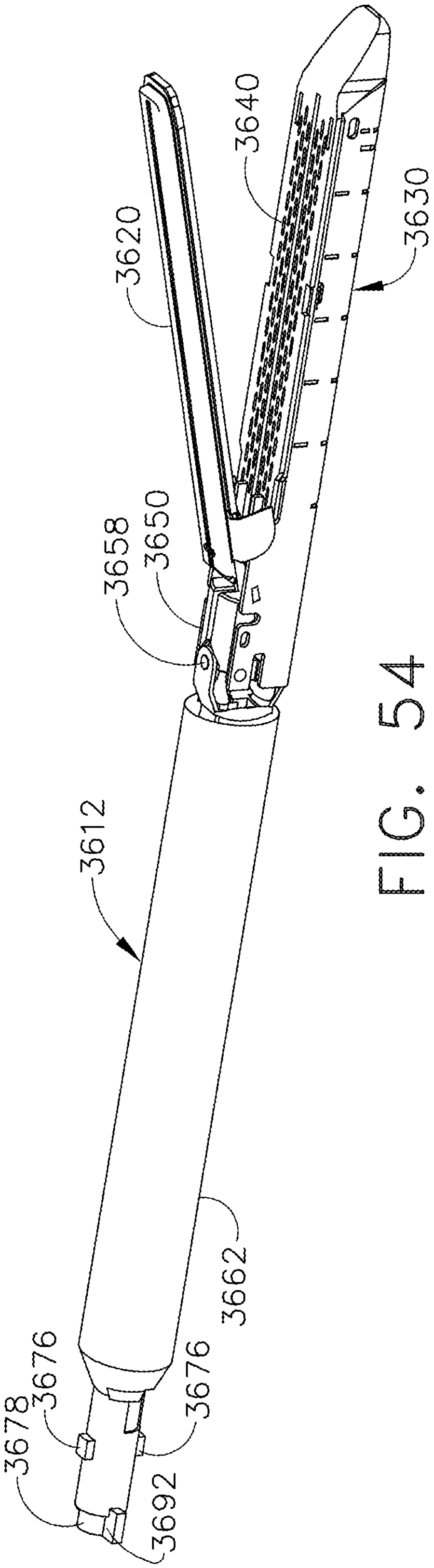
FIG. 54 is a front perspective view of a disposable loading unit arrangement that may be employed with various surgical tool embodiments of the present invention.
Figure 55:
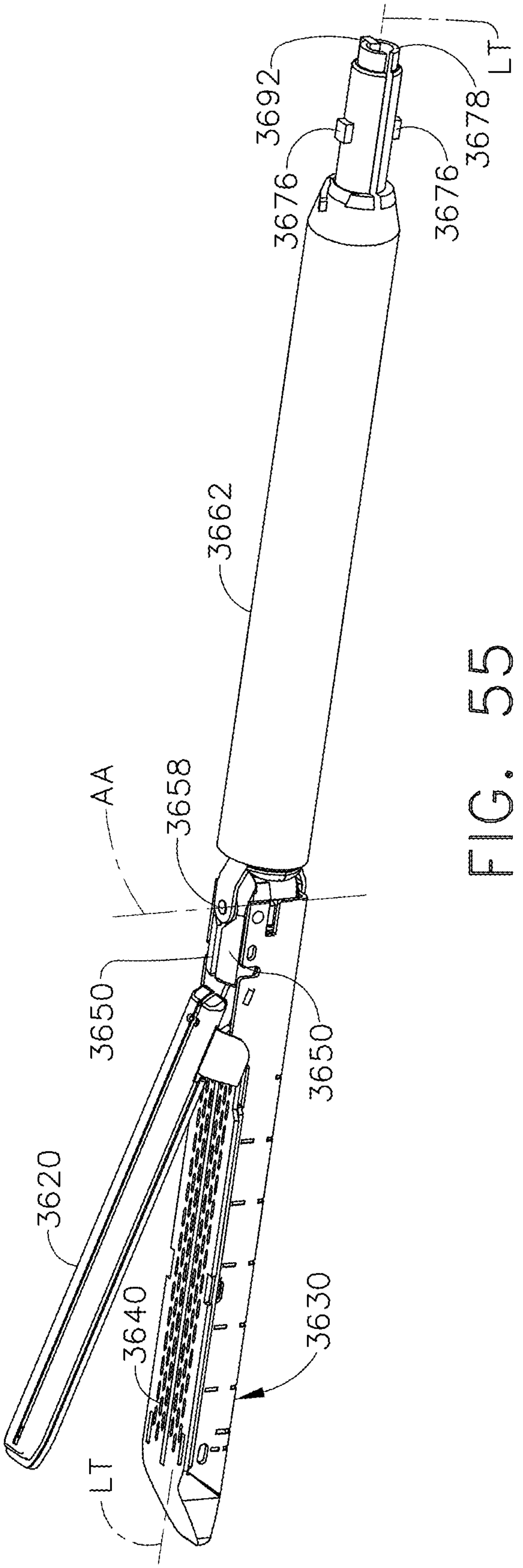
FIG. 55 is a rear perspective view of the disposable loading unit of FIG. 54.
Figure 56:
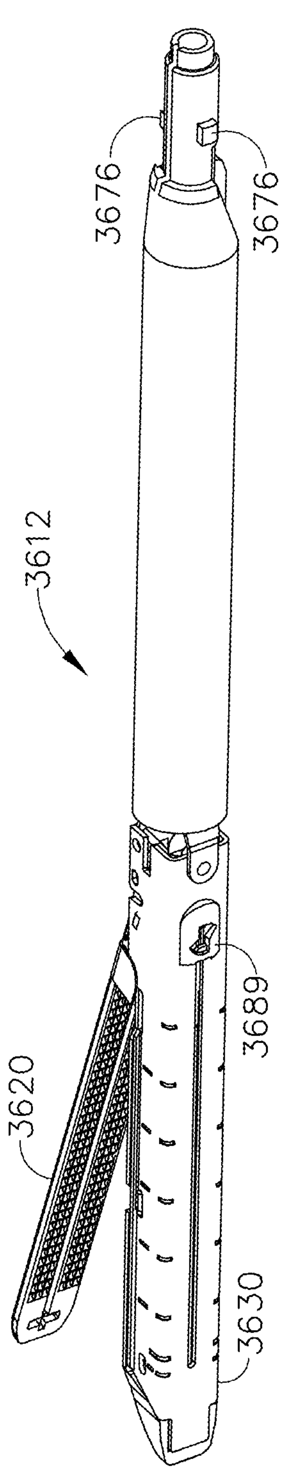
FIG. 56 is a bottom perspective view of the disposable loading unit of FIGS. 54 and 55.
Figure 57:
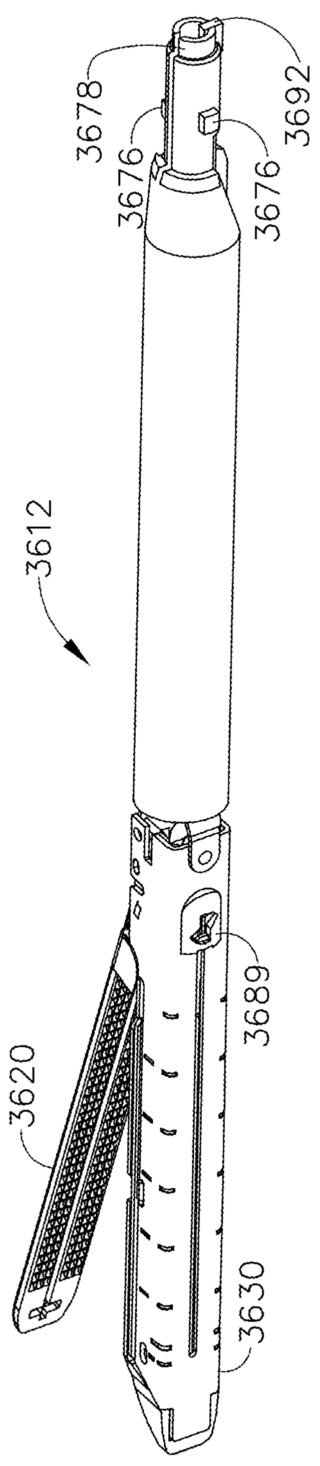
FIG. 57 is a bottom perspective view of another disposable loading unit embodiment that may be employed with various surgical tool embodiments of the present invention.

FIGS. 53-62 illustrate another surgical tool 3600 embodiment of the present invention that may be employed in connection with a robotic system 1000. As can be seen in FIG. 53, the tool 3600 includes an end effector in the form of a disposable loading unit 3612. Various forms of disposable loading units that may be employed in connection with tool 3600 are disclosed, for example, in U.S. Patent Application Publication No. 2009/0206131, entitled END EFFECTOR ARRANGEMENTS FOR A SURGICAL CUTTING AND STAPLING INSTRUMENT, the disclosure of which is herein incorporated by reference in its entirety.

Figure 58:
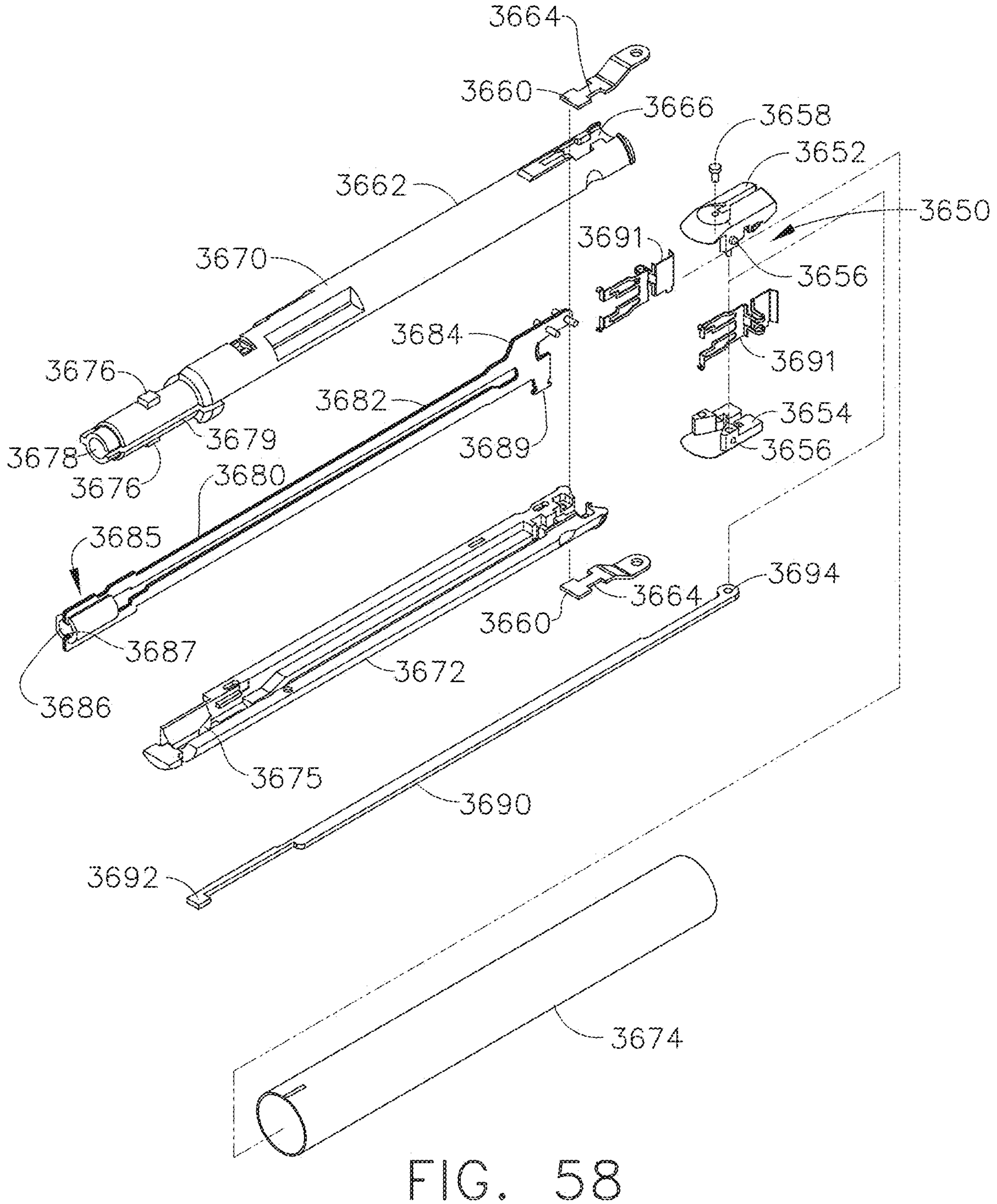
FIG. 58 is an exploded perspective view of a mounting portion of a disposable loading unit depicted in FIGS. 54-56.
Figure 59:
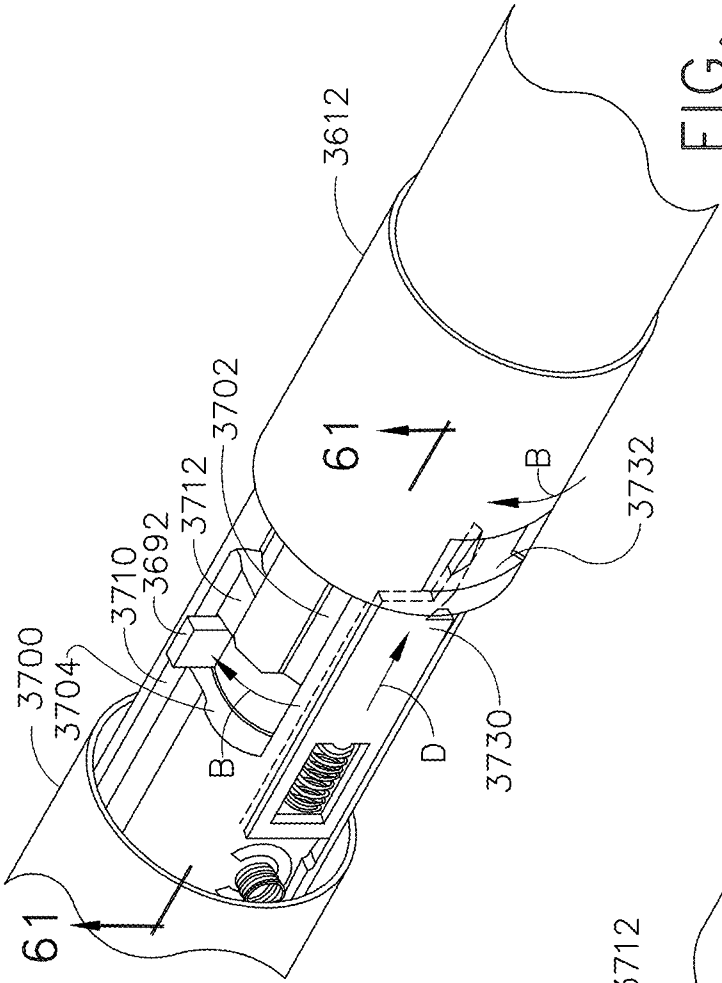
FIG. 59 is a perspective view of a portion of a disposable loading unit and an elongated shaft assembly embodiment of a surgical tool embodiment of the present invention with the disposable loading unit in a first position.
Figure 60:
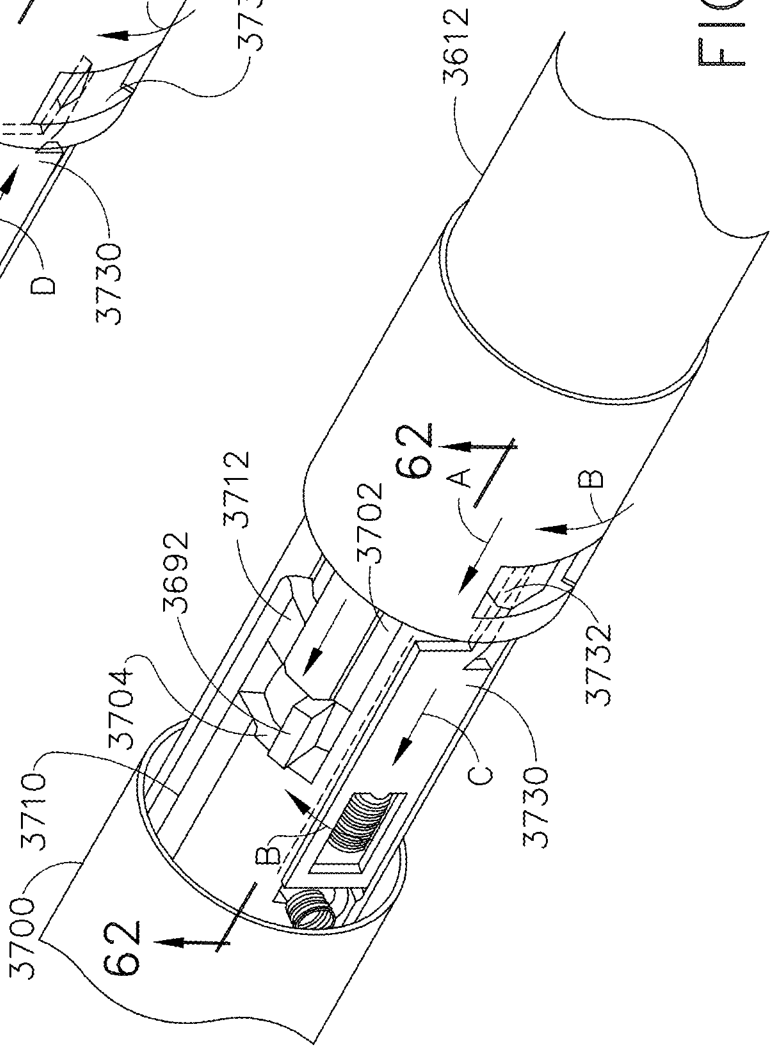
FIG. 60 is another perspective view of a portion of the disposable loading unit and elongated shaft assembly of FIG. 59 with the disposable loading unit in a second position.
Figure 61:
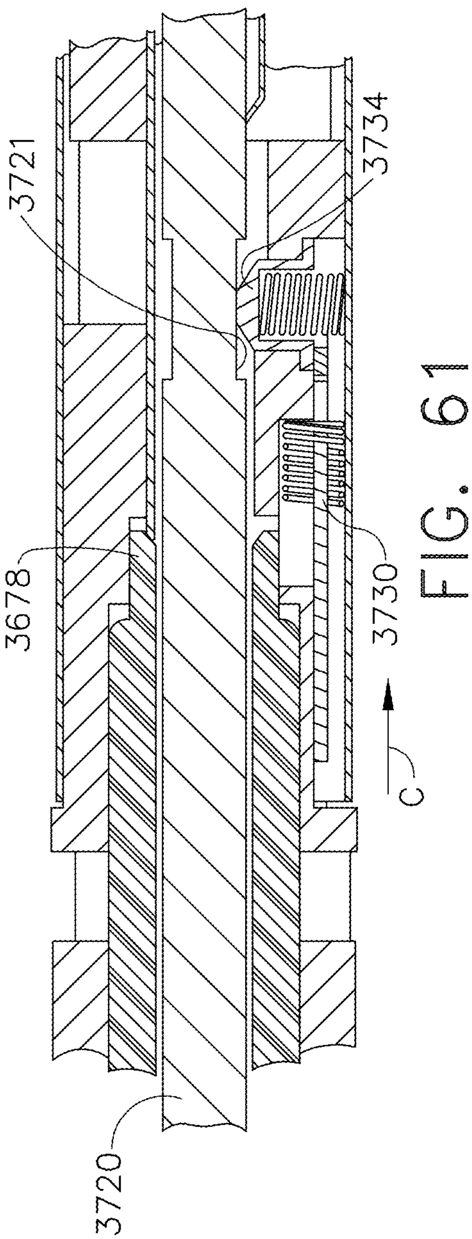
FIG. 61 is a cross-sectional view of a portion of the disposable loading unit and elongated shaft assembly embodiment depicted in FIGS. 59 and 60.
Figure 62:
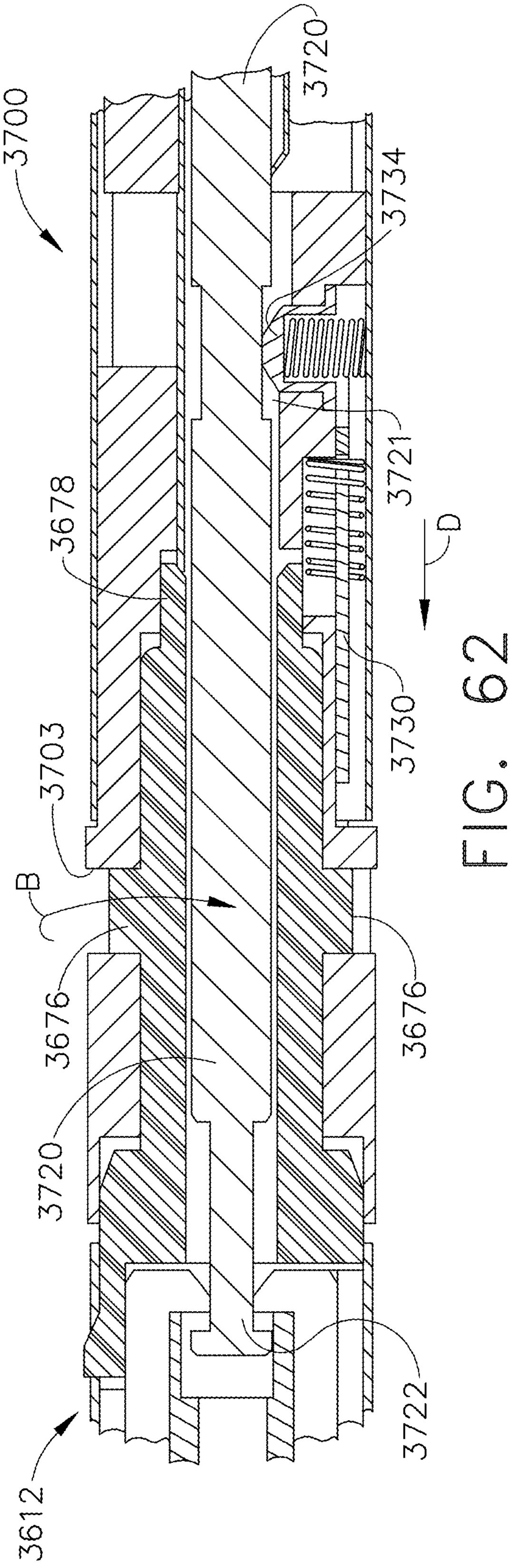
FIG. 62 is another cross-sectional view of the disposable loading unit and elongated shaft assembly embodiment depicted in FIGS. 59-61.

In at least one form, the disposable loading unit 3612 includes an anvil assembly 3620 that is supported for pivotal travel relative to a carrier 3630 that operably supports a staple cartridge 3640 therein. A mounting assembly 3650 is pivotally coupled to the cartridge carrier 3630 to enable the carrier 3630 to pivot about an articulation axis AA-AA relative to a longitudinal tool axis LT-LT. Referring to FIG. 58, mounting assembly 3650 includes upper and lower mounting portions 3652 and 3654. Each mounting portion includes a threaded bore 3656 on each side thereof dimensioned to receive threaded bolts (not shown) for securing the proximal end of carrier 3630 thereto. A pair of centrally located pivot members 3658 extends between upper and lower mounting portions via a pair of coupling members 3660 which engage a distal end of a housing portion 3662. Coupling members 3660 each include an interlocking proximal portion 3664 configured to be received in grooves 3666 formed in the proximal end of housing portion 3662 to retain mounting assembly 3650 and housing portion 3662 in a longitudinally fixed position in relation thereto.

In various forms, housing portion 3662 of disposable loading unit 3614 includes an upper housing half 3670 and a lower housing half 3672 contained within an outer casing 3674. The proximal end of housing half 3670 includes engagement nubs 3676 for releasably engaging an elongated shaft 3700 and an insertion tip 3678. Nubs 3676 form a bayonet-type coupling with the distal end of the elongated shaft 3700 which will be discussed in further detail below. Housing halves 3670, 3672 define a channel 3675 for slidably receiving axial drive assembly 3680. A second articulation link 3690 is dimensioned to be slidably positioned within a slot 3679 formed between housing halves 3670, 3672. A pair of blow out plates 3691 are positioned adjacent the distal end of housing portion 3662 adjacent the distal end of axial drive assembly 3680 to prevent outward bulging of drive assembly 3680 during articulation of carrier 3630.

In various embodiments, the second articulation link 3690 includes at least one elongated metallic plate. Preferably, two or more metallic plates are stacked to form link 3690. The proximal end of articulation link 3690 includes a hook portion 3692 configured to engage first articulation link 3710 extending through the elongated shaft 3700. The distal end of the second articulation link 3690 includes a loop 3694 dimensioned to engage a projection formed on mounting assembly 3650. The projection is laterally offset from pivot pin 3658 such that linear movement of second articulation link 3690 causes mounting assembly 3650 to pivot about pivot pins 3658 to articulate the carrier 3630.

In various forms, axial drive assembly 3680 includes an elongated drive beam 3682 including a distal working head 3684 and a proximal engagement section 3685. Drive beam 3682 may be constructed from a single sheet of material or, preferably, multiple stacked sheets. Engagement section 3685 includes a pair of engagement fingers which are dimensioned and configured to mountingly engage a pair of corresponding retention slots formed in drive member 3686. Drive member 3686 includes a proximal porthole 3687 configured to receive the distal end 3722 of control rod 3720 (See FIG. 62) when the proximal end of disposable loading unit 3614 is engaged with elongated shaft 3700 of surgical tool 3600.

Referring to FIGS. 53 and 60-62, to use the surgical tool 3600, a disposable loading unit 3612 is first secured to the distal end of elongated shaft 3700. It will be appreciated that the surgical tool 3600 may include an articulating or a non-articulating disposable loading unit. To secure the disposable loading unit 3612 to the elongated shaft 3700, the distal end 3722 of control rod 3720 is inserted into insertion tip 3678 of disposable loading unit 3612, and insertion tip 3678 is slid longitudinally into the distal end of the elongated shaft 3700 in the direction indicated by arrow "A" in FIG. 60 such that hook portion 3692 of second articulation link 3690 slides within a channel 3702 in the elongated shaft 3700. Nubs 3676 will each be aligned in a respective channel (not shown) in elongated shaft 3700. When hook portion 3692 engages the proximal wall 3704 of channel 3702, disposable loading unit 3612 is rotated in the direction indicated by arrow "B" in FIGS. 59 and 62 to move hook portion 3692 of second articulation link 3690 into engagement with finger 3712 of first articulation link 3710. Nubs 3676 also form a "bayonet-type" coupling within annular channel 3703 in the elongated shaft 3700. During rotation of loading unit 3612, nubs 3676 engage cam surface 3732 (FIG. 60) of block plate 3730 to initially move plate 3730 in the direction indicated by arrow "C" in FIG. 60 to lock engagement member 3734 in recess 3721 of control rod 3720 to prevent longitudinal movement of control rod 3720 during attachment of disposable loading unit 3612. During the final degree of rotation, nubs 3676 disengage from cam surface 3732 to allow blocking plate 3730 to move in the direction indicated by arrow "D" in FIGS. 59 and 62 from behind engagement member 3734 to once again permit longitudinal movement of control rod 3720. While the above-described attachment method reflects that the disposable loading unit 3612 is manipulated relative to the elongated shaft 3700, the person of ordinary skill in the art will appreciate that the disposable loading unit 3612 may be supported in a stationary position and the robotic system 1000 may manipulate the elongated shaft portion 3700 relative to the disposable loading unit 3612 to accomplish the above-described coupling procedure.

Figure 63:
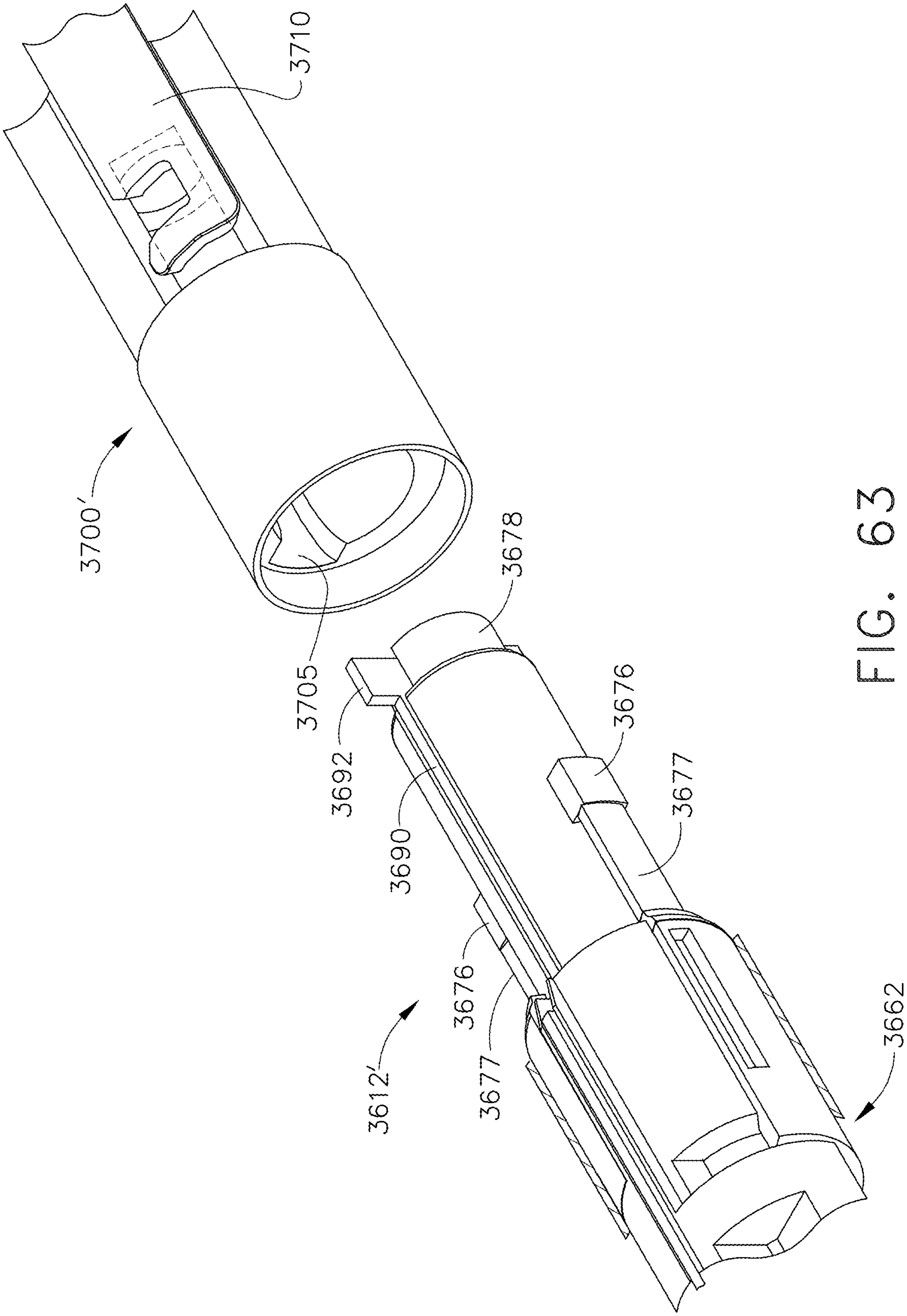
FIG. 63 is a partial exploded perspective view of a portion of another disposable loading unit embodiment and an elongated shaft assembly embodiment of a surgical tool embodiment of the present invention.

FIG. 63 illustrates another disposable loading unit 3612' that is attachable in a bayonet-type arrangement with the elongated shaft 3700' that is substantially identical to shaft 3700 except for the differences discussed below. As can be seen in FIG. 63, the elongated shaft 3700' has slots 3705 that extend for at least a portion thereof and which are configured to receive nubs 3676 therein. In various embodiments, the disposable loading unit 3612' includes arms 3677 extending therefrom which, prior to the rotation of disposable loading unit 3612', can be aligned, or at least substantially aligned, with nubs 3676 extending from housing portion 3662. In at least one embodiment, arms 3677 and nubs 3676 can be inserted into slots 3705 in elongated shaft 3700', for example, when disposable loading unit 3612' is inserted into elongated shaft 3700'. When disposable loading unit 3612' is rotated, arms 3677 can be sufficiently confined within slots 3705 such that slots 3705 can hold them in position, whereas nubs 3676 can be positioned such that they are not confined within slots 3705 and can be rotated relative to arms 3677. When rotated, the hook portion 3692 of the articulation link 3690 is engaged with the first articulation link 3710 extending through the elongated shaft 3700'.

Other methods of coupling the disposable loading units to the end of the elongated shaft may be employed. For example, as shown in FIGS. 64 and 65, disposable loading unit 3612" can include connector portion 3613 which can be configured to be engaged with connector portion 3740 of the elongated shaft 3700". In at least one embodiment, connector portion 3613 can include at least one projection and/or groove which can be mated with at least one projection and/or groove of connector portion 3740. In at least one such embodiment, the connector portions can include co-operating dovetail portions. In various embodiments, the connector portions can be configured to interlock with one another and prevent, or at least inhibit, distal and/or proximal movement of disposable loading unit 3612" along axis 3741. In at least one embodiment, the distal end of the axial drive assembly 3680' can include aperture 3681 which can be configured to receive projection 3721 extending from control rod 3720'. In various embodiments, such an arrangement can allow disposable loading unit 3612" to be assembled to elongated shaft 3700 in a direction which is not collinear with or parallel to axis 3741. Although not illustrated, axial drive assembly 3680' and control rod 3720 can include any other suitable arrangement of projections and apertures to operably connect them to each other. Also in this embodiment, the first articulation link 3710 which can be operably engaged with second articulation link 3690.

Figure 66:
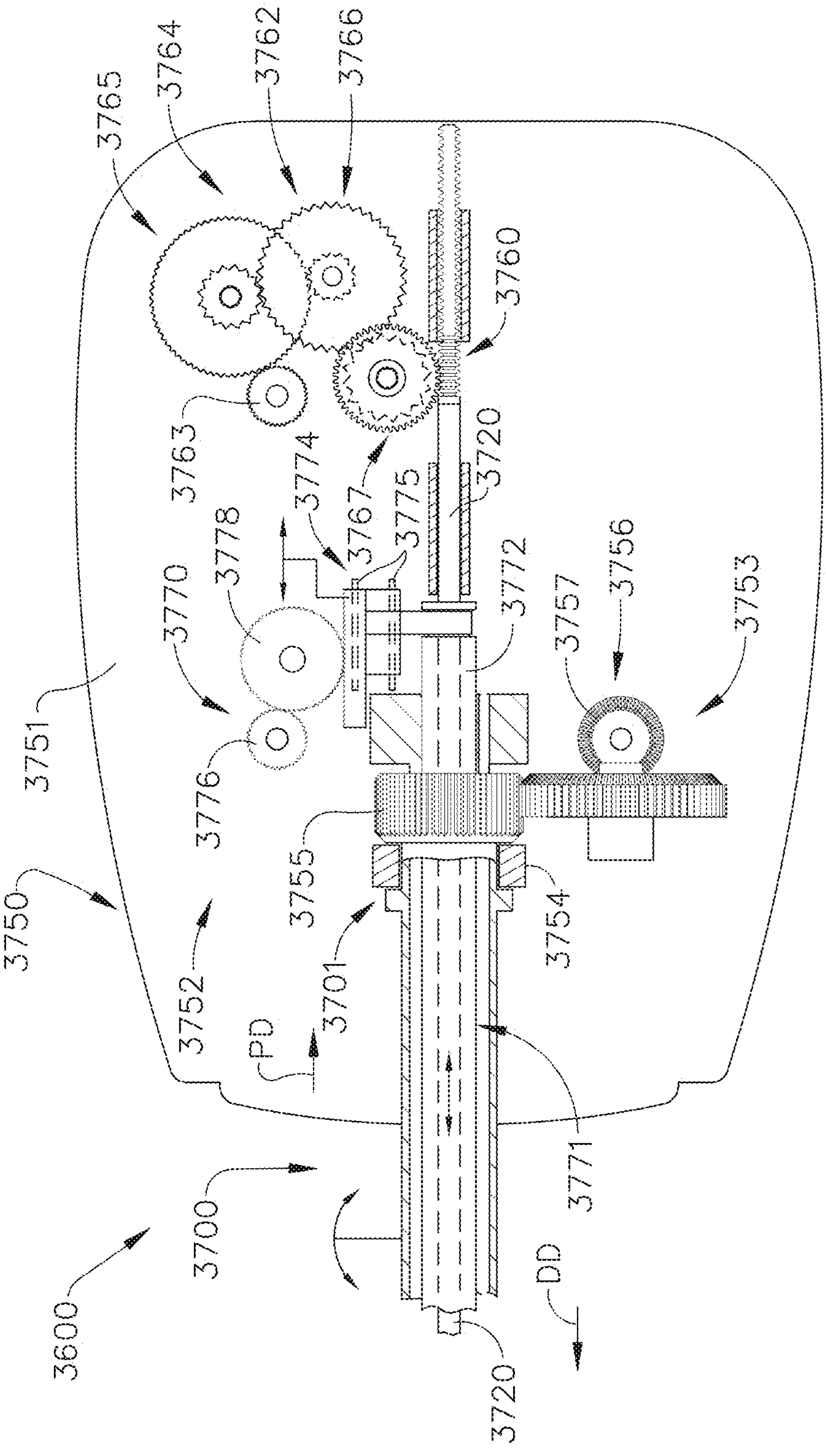
FIG. 66 is a top view of another tool mounting portion embodiment of a surgical tool embodiment of the present invention.

As can be seen in FIGS. 53 and 66, the surgical tool 3600 includes a tool mounting portion 3750. The tool mounting portion 3750 includes a tool mounting plate 3751 that is configured for attachment to the tool drive assembly 1010. The tool mounting portion operably supported a transmission arrangement 3752 thereon. In use, it may be desirable to rotate the disposable loading unit 3612 about the longitudinal tool axis defined by the elongated shaft 3700. In at least one embodiment, the transmission arrangement 3752 includes a rotational transmission assembly 3753 that is configured to receive a corresponding rotary output motion from the tool drive assembly 1010 of the robotic system 1000 and convert that rotary output motion to a rotary control motion for rotating the elongated shaft 3700 (and the disposable loading unit 3612) about the longitudinal tool axis LT-LT. As can be seen in FIG. 66, a proximal end 3701 of the elongated shaft 3700 is rotatably supported within a cradle arrangement 3754 that is attached to the tool mounting plate 3751 of the tool mounting portion 3750. A rotation gear 3755 is formed on or attached to the proximal end 3701 of the elongated shaft 3700 for meshing engagement with a rotation gear assembly 3756 operably supported on the tool mounting plate 3751. In at least one embodiment, a rotation drive gear 3757 drivingly coupled to a corresponding first one of the driven discs or elements 1304 on the adapter side of the tool mounting plate 3751 when the tool mounting portion 3750 is coupled to the tool drive assembly 1010. The rotation transmission assembly 3753 further comprises a rotary driven gear 3758 that is rotatably supported on the tool mounting plate 3751 in meshing engagement with the rotation gear 3755 and the rotation drive gear 3757. Application of a first rotary output motion from the robotic system 1000 through the tool drive assembly 1010 to the corresponding driven element 1304 will thereby cause rotation of the rotation drive gear 3757 by virtue of being operably coupled thereto. Rotation of the rotation drive gear 3757 ultimately results in the rotation of the elongated shaft 3700 (and the disposable loading unit 3612) about the longitudinal tool axis LT-LT (primary rotary motion).

As can be seen in FIG. 66, a drive shaft assembly 3760 is coupled to a proximal end of the control rod 3720. In various embodiments, the control rod 3720 is axially advanced in the distal and proximal directions by a knife/closure drive transmission 3762. One form of the knife/closure drive assembly 3762 comprises a rotary drive gear 3763 that is coupled to a corresponding second one of the driven rotatable body portions, discs or elements 1304 on the adapter side of the tool mounting plate 3751 when the tool mounting portion 3750 is coupled to the tool holder 1270. The rotary driven gear 3763 is in meshing driving engagement with a gear train, generally depicted as 3764. In at least one form, the gear train 3764 further comprises a first rotary driven gear assembly 3765 that is rotatably supported on the tool mounting plate 3751. The first rotary driven gear assembly 3765 is in meshing engagement with a second rotary driven gear assembly 3766 that is rotatably supported on the tool mounting plate 3751 and which is in meshing engagement with a third rotary driven gear assembly 3767 that is in meshing engagement with a threaded portion 3768 of the drive shaft assembly 3760. Rotation of the rotary drive gear 3763 in a second rotary direction will result in the axial advancement of the drive shaft assembly 3760 and control rod 3720 in the distal direction "DD". Conversely, rotation of the rotary drive gear 3763 in a secondary rotary direction which is opposite to the second rotary direction will cause the drive shaft assembly 3760 and the control rod 3720 to move in the proximal direction. When the control rod 3720 moves in the distal direction, it drives the drive beam 3682 and the working head 3684 thereof distally through the surgical staple cartridge 3640. As the working head 3684 is driven distally, it operably engages the anvil 3620 to pivot it to a closed position.

The cartridge carrier 3630 may be selectively articulated about articulation axis AA-AA by applying axial articulation control motions to the first and second articulation links 3710 and 3690. In various embodiments, the transmission arrangement 3752 further includes an articulation drive 3770 that is operably supported on the tool mounting plate 3751. More specifically and with reference to FIG. 66, it can be seen that a proximal end portion 3772 of an articulation drive shaft 3771 configured to operably engage with the first articulation link 3710 extends through the rotation gear 3755 and is rotatably coupled to a shifter rack gear 3774 that is slidably affixed to the tool mounting plate 3751 through slots 3775. The articulation drive 3770 further comprises a shifter drive gear 3776 that is coupled to a corresponding third one of the driven discs or elements 1304 on the adapter side of the tool mounting plate 3751 when the tool mounting portion 3750 is coupled to the tool holder 1270. The articulation drive assembly 3770 further comprises a shifter driven gear 3778 that is rotatably supported on the tool mounting plate 3751 in meshing engagement with the shifter drive gear 3776 and the shifter rack gear 3774. Application of a third rotary output motion from the robotic system 1000 through the tool drive assembly 1010 to the corresponding driven element 1304 will thereby cause rotation of the shifter drive gear 3776 by virtue of being operably coupled thereto. Rotation of the shifter drive gear 3776 ultimately results in the axial movement of the shifter gear rack 3774 and the articulation drive shaft 3771. The direction of axial travel of the articulation drive shaft 3771 depends upon the direction in which the shifter drive gear 3776 is rotated by the robotic system 1000. Thus, rotation of the shifter drive gear 3776 in a first rotary direction will result in the axial movement of the articulation drive shaft 3771 in the proximal direction "PD" and cause the cartridge carrier 3630 to pivot in a first direction about articulation axis AA-AA. Conversely, rotation of the shifter drive gear 3776 in a second rotary direction (opposite to the first rotary direction) will result in the axial movement of the articulation drive shaft 3771 in the distal direction "DD" to thereby cause the cartridge carrier 3630 to pivot about articulation axis AA-AA in an opposite direction.

Figure 67:
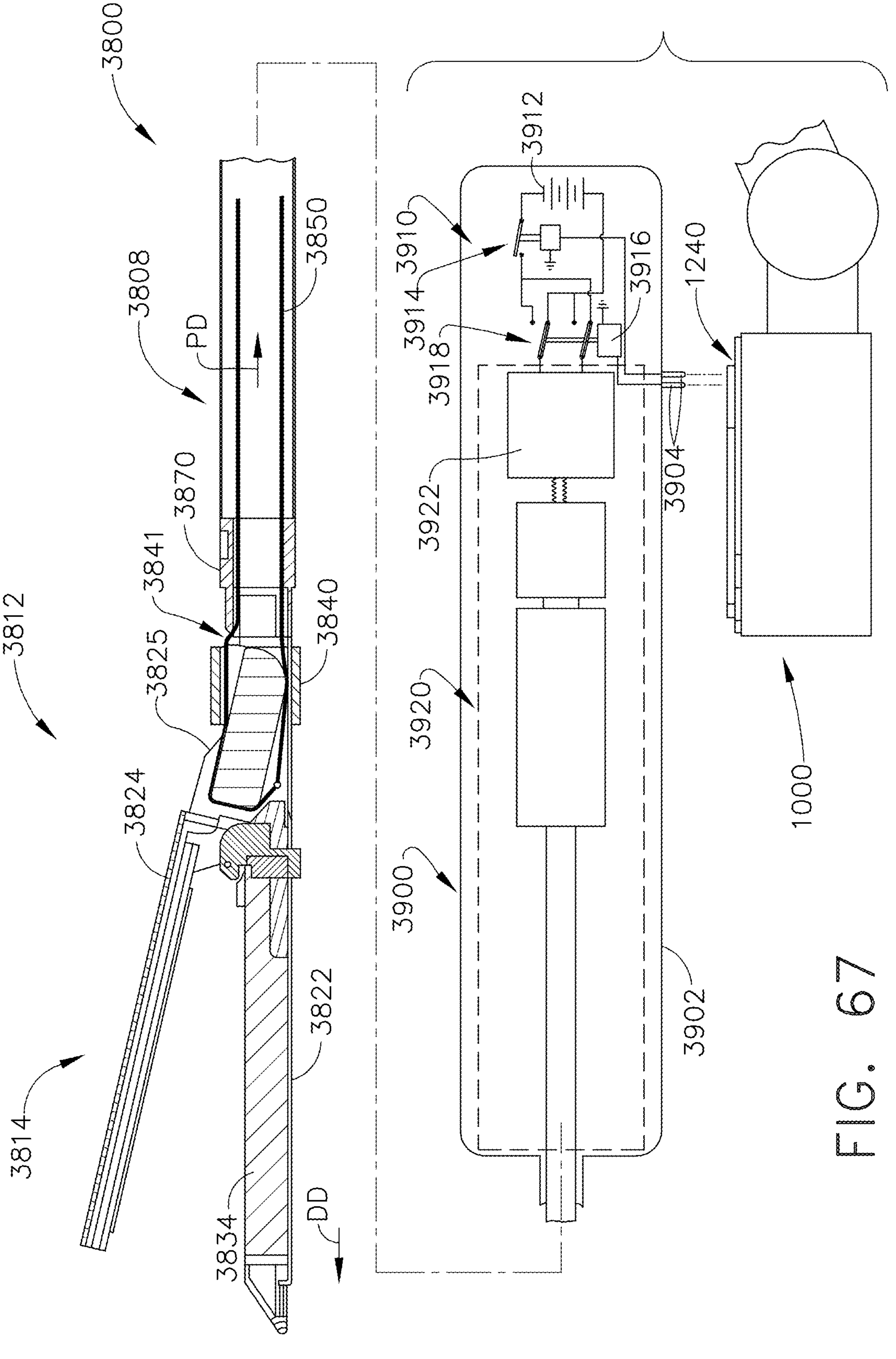
FIG. 67 is a side view of another surgical tool embodiment of the present invention with some of the components thereof shown in cross-section and in relation to a robotic tool holder of a robotic system.

FIG. 67 illustrates yet another surgical tool 3800 embodiment of the present invention that may be employed with a robotic system 1000. As can be seen in FIG. 67, the surgical tool 3800 includes a surgical end effector 3812 in the form of an endocutter 3814 that employs various cable-driven components. Various forms of cable driven endocutters are disclosed, for example, in U.S. Pat. No. 7,726,537, entitled SURGICAL STAPLER WITH UNIVERSAL ARTICULATION AND TISSUE PRE-CLAMP and U.S. Patent Application Publication No. 2008/0308603, entitled CABLE DRIVEN SURGICAL STAPLING AND CUTTING INSTRUMENT WITH IMPROVED CABLE ATTACHMENT ARRANGEMENTS, the disclosures of each are herein incorporated by reference in their respective entireties. Such endocutters 3814 may be referred to as a "disposable loading unit" because they are designed to be disposed of after a single use. However, the various unique and novel arrangements of various embodiments of the present invention may also be employed in connection with cable driven end effectors that are reusable.

As can be seen in FIG. 67, in at least one form, the endocutter 3814 includes an elongated channel 3822 that operably supports a surgical staple cartridge 3834 therein. An anvil 3824 is pivotally supported for movement relative to the surgical staple cartridge 3834. The anvil 3824 has a cam surface 3825 that is configured for interaction with a preclamping collar 3840 that is supported for axial movement relative thereto. The end effector 3814 is coupled to an elongated shaft assembly 3808 that is attached to a tool mounting portion 3900. In various embodiments, a closure cable 3850 is employed to move pre-clamping collar 3840 distally onto and over cam surface 3825 to close the anvil 3824 relative to the surgical staple cartridge 3834 and compress the tissue therebetween. Preferably, closure cable 3850 attaches to the pre-clamping collar 3840 at or near point 3841 and is fed through a passageway in anvil 3824 (or under a proximal portion of anvil 3824) and fed proximally through shaft 3808. Actuation of closure cable 3850 in the proximal direction "PD" forces pre-clamping collar 3840 distally against cam surface 3825 to close anvil 3824 relative to staple cartridge assembly 3834. A return mechanism, e.g., a spring, cable system or the like, may be employed to return pre-clamping collar 3840 to a pre-clamping orientation which re-opens the anvil 3824.

Figure 68:
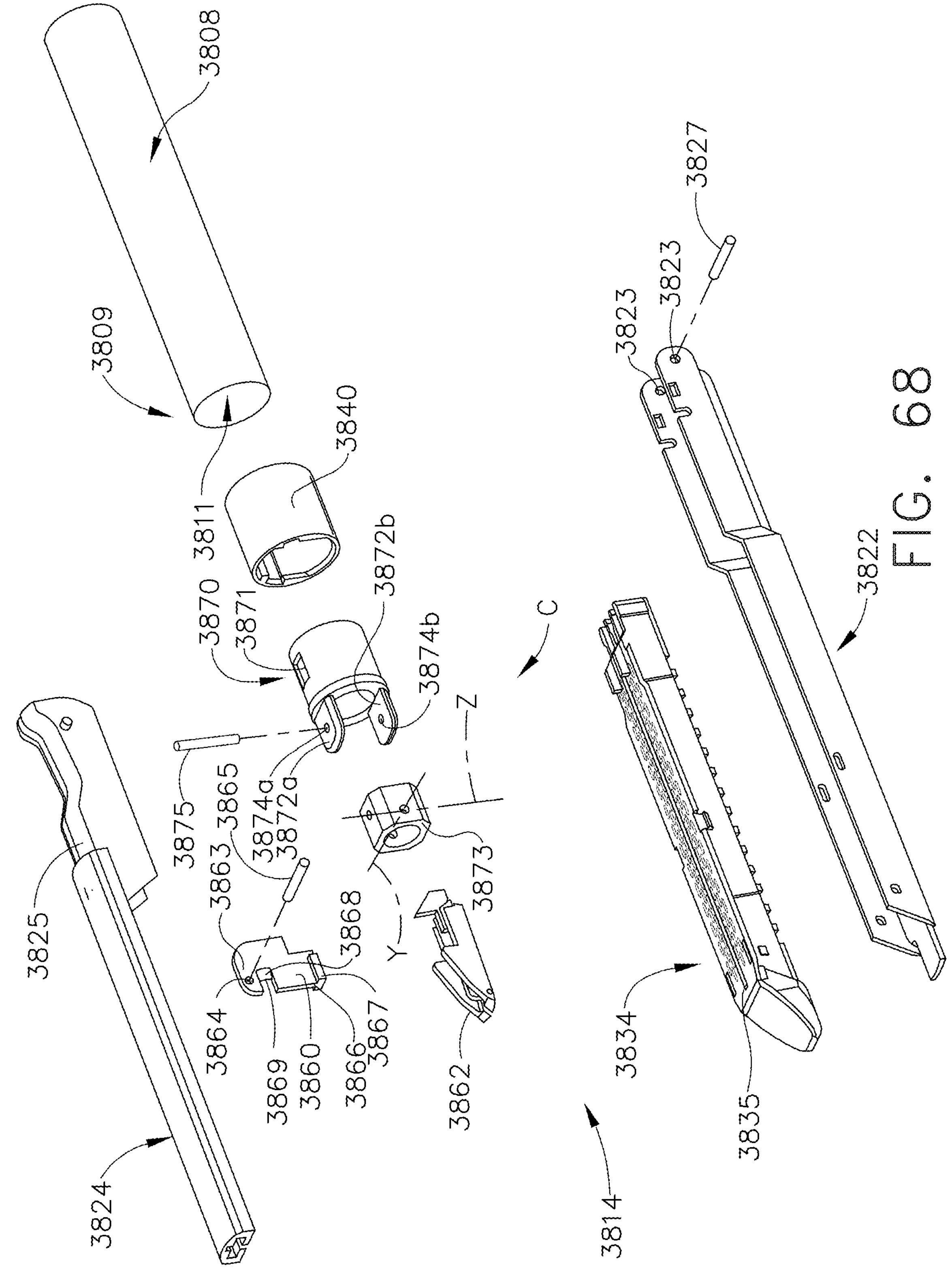
FIG. 68 is an exploded assembly view of a surgical end effector embodiment that may be used in connection with various surgical tool embodiments of the present invention.
Figure 69:
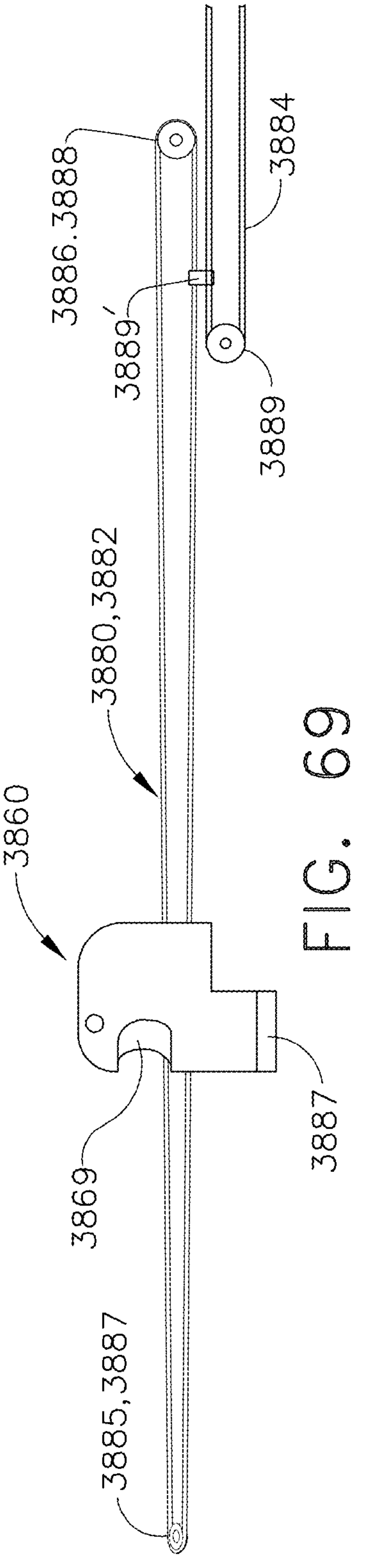
FIG. 69 is a side view of a portion of a cable-driven system for driving a cutting instrument employed in various surgical end effector embodiments of the present invention.
Figure 70:
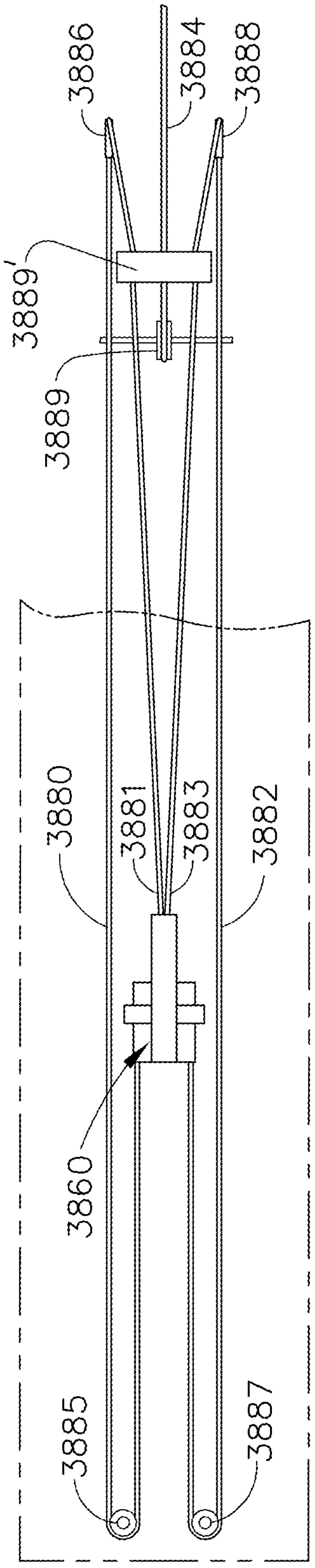
FIG. 70 is a top view of the cable-driven system and cutting instrument of FIG. 69.

The elongated shaft assembly 3808 may be cylindrical in shape and define a channel 3811 which may be dimensioned to receive a tube adapter 3870. See FIG. 68. In various embodiments, the tube adapter 3870 may be slidingly received in friction-fit engagement with the internal channel of elongated shaft 3808. The outer surface of the tube adapter 3870 may further include at least one mechanical interface, e.g., a cutout or notch 3871, oriented to mate with a corresponding mechanical interface, e.g., a radially inwardly extending protrusion or detent (not shown), disposed on the inner periphery of internal channel 3811 to lock the tube adapter 3870 to the elongated shaft 3808. In various embodiments, the distal end of tube adapter 3870 may include a pair of opposing flanges 3872*a* and 3872*b* which define a cavity for pivotably receiving a pivot block 3873 therein. Each flange 3872*a* and 3872*b* may include an aperture 3874*a* and 3874*b* that is oriented to receive a pivot pin 3875 that extends through an aperture in pivot block 3873 to allow pivotable movement of pivot block 3873 about an axis that is perpendicular to longitudinal tool axis "LT-LT". The channel 3822 may be formed with two upwardly extending flanges 3823*a*, 3823*b* that have apertures therein, which are dimensioned to receive a pivot pin 3827. In turn, pivot pin 3875 mounts through apertures in pivot block 3873 to permit rotation of the surgical end effector 3814 about the "Y" axis as needed during a given surgical procedure. Rotation of pivot block 3873 about pin 3875 along "Z" axis rotates the surgical end effector 3814 about the "Z" axis. See FIG. 68. Other methods of fastening the elongated channel 3822 to the pivot block 3873 may be effectively employed without departing from the spirit and scope of the present invention.

The surgical staple cartridge 3834 can be assembled and mounted within the elongated channel 3822 during the manufacturing or assembly process and sold as part of the surgical end effector 3812, or the surgical staple cartridge 3834 may be designed for selective mounting within the elongated channel 3822 as needed and sold separately, e.g., as a single use replacement, replaceable or disposable staple cartridge assembly. It is within the scope of this disclosure that the surgical end effector 3812 may be pivotally, operatively, or integrally attached, for example, to distal end 3809 of the elongated shaft assembly 3808 of a disposable surgical stapler. As is known, a used or spent disposable loading unit 3814 can be removed from the elongated shaft assembly 3808 and replaced with an unused disposable unit. The endocutter 3814 may also preferably include an actuator, preferably a dynamic clamping member 3860, a sled 3862, as well as staple pushers (not shown) and staples (not shown) once an unspent or unused cartridge 3834 is mounted in the elongated channel 3822. See FIG. 68.

In various embodiments, the dynamic clamping member 3860 is associated with, e.g., mounted on and rides on, or with or is connected to or integral with and/or rides behind sled 3862. It is envisioned that dynamic clamping member 3860 can have cam wedges or cam surfaces attached or integrally formed or be pushed by a leading distal surface thereof. In various embodiments, dynamic clamping member 3860 may include an upper portion 3863 having a transverse aperture 3864 with a pin 3865 mountable or mounted therein, a central support or upward extension 3866 and substantially T-shaped bottom flange 3867 which cooperate to slidingly retain dynamic clamping member 3860 along an ideal cutting path during longitudinal, distal movement of sled 3862. The leading cutting edge 3868, here, knife blade 3869, is dimensioned to ride within slot 3835 of staple cartridge assembly 3834 and separate tissue once stapled. As used herein, the term "knife assembly" may include the aforementioned dynamic clamping member 3860, knife 3869, and sled 3862 or other knife/beam/sled drive arrangements and cutting instrument arrangements. In addition, the various embodiments of the present invention may be employed with knife assembly/cutting instrument arrangements that may be entirely supported in the staple cartridge 3834 or partially supported in the staple cartridge 3834 and elongated channel 3822 or entirely supported within the elongated channel 3822.

Figure 90:
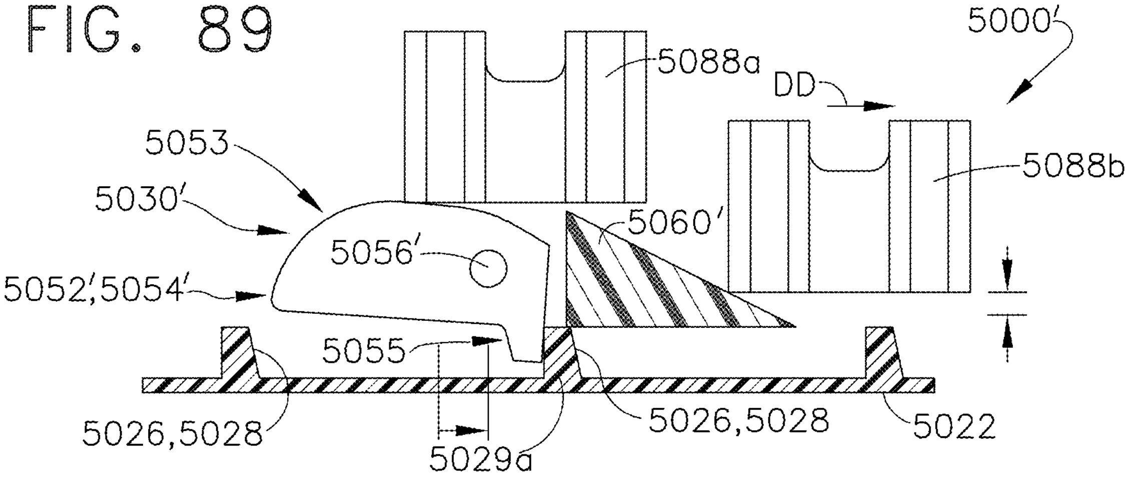
Figure 91:
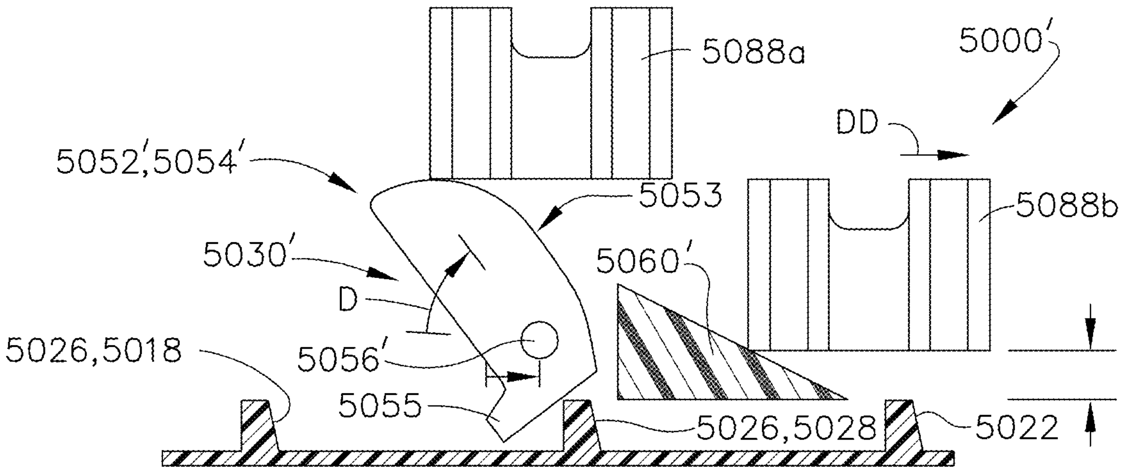
Figure 92:
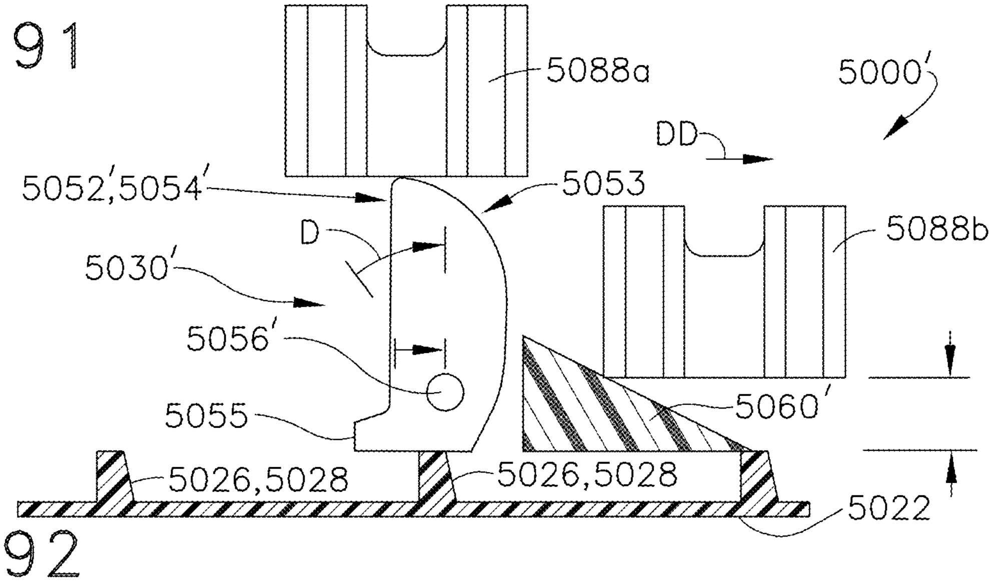
Figure 93:
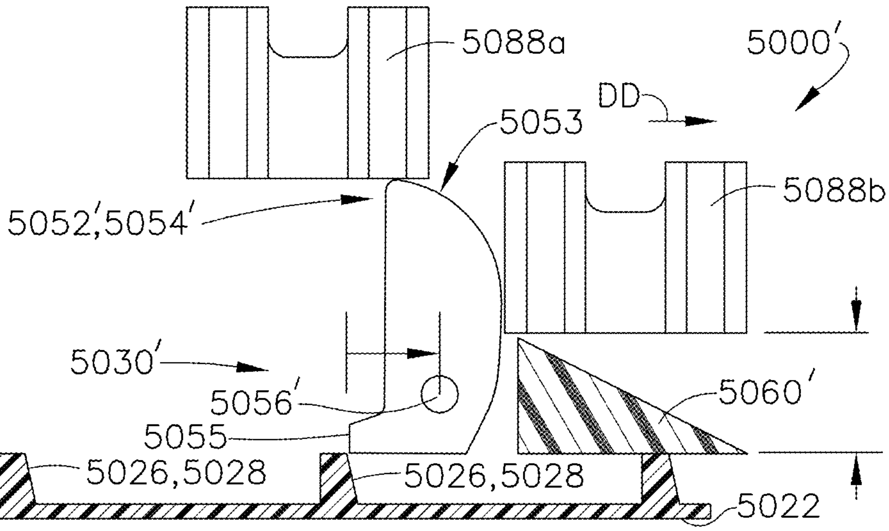

In various embodiments, the dynamic clamping member 3860 may be driven in the proximal and distal directions by a cable drive assembly 3870. In one non-limiting form, the cable drive assembly comprises a pair of advance cables 3880, 3882 and a firing cable 3884. FIGS. 90 and 91 illustrate the cables 3880, 3882, 3884 in diagrammatic form. As can be seen in those Figures, a first advance cable 3880 is operably supported on a first distal cable transition support 3885 which may comprise, for example, a pulley, rod, capstan, etc. that is attached to the distal end of the elongated channel 3822 and a first proximal cable transition support 3886 which may comprise, for example, a pulley, rod, capstan, etc. that is operably supported by the elongated channel 3822. A distal end 3881 of the first advance cable 3880 is affixed to the dynamic clamping assembly 3860. The second advance cable 3882 is operably supported on a second distal cable transition support 3887 which may, for example, comprise a pulley, rod, capstan etc. that is mounted to the distal end of the elongated channel 3822 and a second proximal cable transition support 3888 which may, for example, comprise a pulley, rod, capstan, etc. mounted to the proximal end of the elongated channel 3822. The proximal end 3883 of the second advance cable 3882 may be attached to the dynamic clamping assembly 3860. Also in these embodiments, an endless firing cable 3884 is employed and journaled on a support 3889 that may comprise a pulley, rod, capstan, etc. mounted within the elongated shaft 3808. In one embodiment, the retract cable 3884 may be formed in a loop and coupled to a connector 3889' that is fixedly attached to the first and second advance cables 3880, 3882.

Various non-limiting embodiments of the present invention include a cable drive transmission 3920 that is operably supported on a tool mounting plate 3902 of the tool mounting portion 3900. The tool mounting portion 3900 has an array of electrical connecting pins 3904 which are configured to interface with the slots 1258 (FIG. 9) in the adapter 1240'. Such arrangement permits the robotic system 1000 to provide control signals to a control circuit 3910 of the tool 3800. While the interface is described herein with reference to mechanical, electrical, and magnetic coupling elements, it should be understood that a wide variety of telemetry modalities might be used, including infrared, inductive coupling, or the like.

Control circuit 3910 is shown in schematic form in FIG. 67. In one form or embodiment, the control circuit 3910 includes a power supply in the form of a battery 3912 that is coupled to an on-off solenoid powered switch 3914. In other embodiments, however, the power supply may comprise a source of alternating current. Control circuit 3910 further includes an on/off solenoid 3916 that is coupled to a double pole switch 3918 for controlling motor rotation direction. Thus, when the robotic system 1000 supplies an appropriate control signal, switch 3914 will permit battery 3912 to supply power to the double pole switch 3918. The robotic system 1000 will also supply an appropriate signal to the double pole switch 3918 to supply power to a shifter motor 3922.

Turning to FIGS. 71-76, at least one embodiment of the cable drive transmission 3920 comprises a drive pulley 3930 that is operably mounted to a drive shaft 3932 that is attached to a driven element 1304 of the type and construction described above that is designed to interface with a corresponding drive element 1250 of the adapter 1240. See FIGS. 9 and 74. Thus, when the tool mounting portion 3900 is operably coupled to the tool holder 1270, the robot system 1000 can apply rotary motion to the drive pulley 3930 in a desired direction. A first drive member or belt 3934 drivingly engages the drive pulley 3930 and a second drive shaft 3936 that is rotatably supported on a shifter yoke 3940. The shifter yoke 3940 is operably coupled to the shifter motor 3922 such that rotation of the shaft 3923 of the shifter motor 3922 in a first direction will shift the shifter yoke in a first direction “FD” and rotation of the shifter motor shaft 3923 in a second direction will shift the shifter yoke 3940 in a second direction “SD”. Other embodiments of the present invention may employ a shifter solenoid arrangement for shifting the shifter yoke in said first and second directions.

As can be seen in FIGS. 71-74, a closure drive gear 3950 mounted to a second drive shaft 3936 and is configured to selectively mesh with a closure drive assembly, generally designated as 3951. Likewise a firing drive gear 3960 is also mounted to the second drive shaft 3936 and is configured to selectively mesh with a firing drive assembly generally designated as 3961. Rotation of the second drive shaft 3936 causes the closure drive gear 3950 and the firing drive gear 3960 to rotate. In one non-limiting embodiment, the closure drive assembly 3951 comprises a closure driven gear 3952 that is coupled to a first closure pulley 3954 that is rotatably supported on a third drive shaft 3956. The closure cable 3850 is drivingly received on the first closure pulley 3954 such that rotation of the closure driven gear 3952 will drive the closure cable 3850. Likewise, the firing drive assembly 3961 comprises a firing driven gear 3962 that is coupled to a first firing pulley 3964 that is rotatably supported on the third drive shaft 3956. The first and second driving pulleys 3954 and 3964 are independently rotatable on the third drive shaft 3956. The firing cable 3884 is drivingly received on the first firing pulley 3964 such that rotation of the firing driven gear 3962 will drive the firing cable 3884.

Also in various embodiments, the cable drive transmission 3920 further includes a braking assembly 3970. In at least one embodiment, for example, the braking assembly 3970 includes a closure brake 3972 that comprises a spring arm 3973 that is attached to a portion of the transmission housing 3971. The closure brake 3972 has a gear lug 3974 that is sized to engage the teeth of the closure driven gear 3952 as will be discussed in further detail below. The braking assembly 3970 further includes a firing brake 3976 that comprises a spring arm 3977 that is attached to another portion of the transmission housing 3971. The firing brake 3976 has a gear lug 3978 that is sized to engage the teeth of the firing driven gear 3962.

Figure 71:
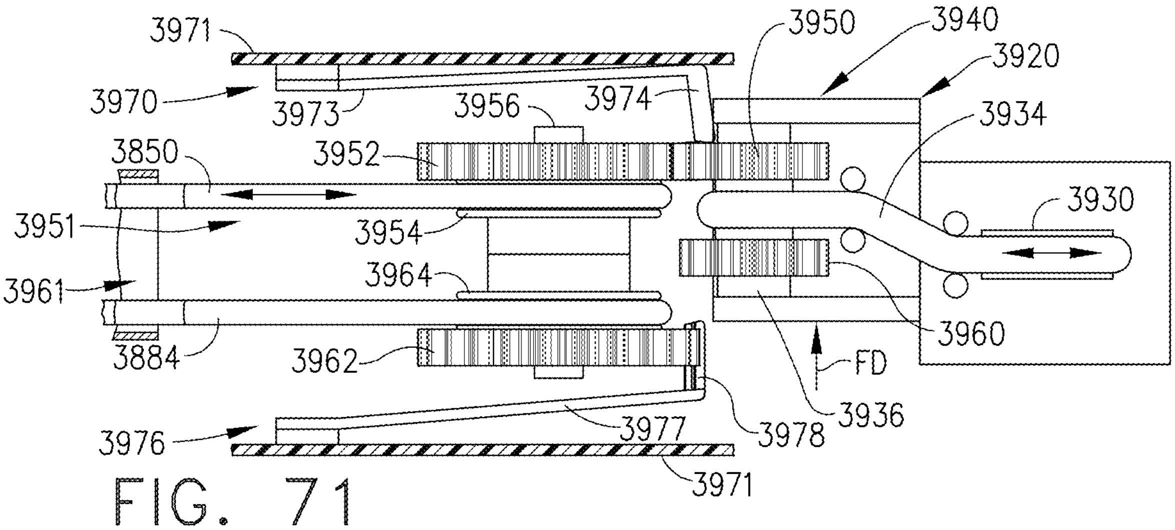
FIG. 71 is a top view of a cable drive transmission embodiment of the present invention in a closure position.
Figure 72:
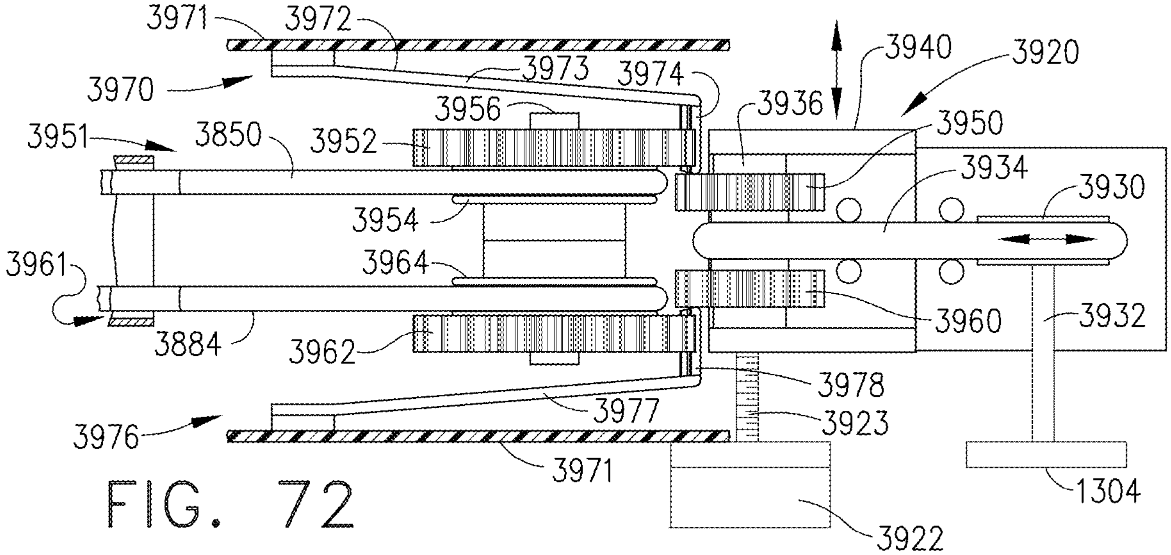
FIG. 72 is another top view of the cable drive transmission embodiment of FIG. 71 in a neutral position.
Figure 73:
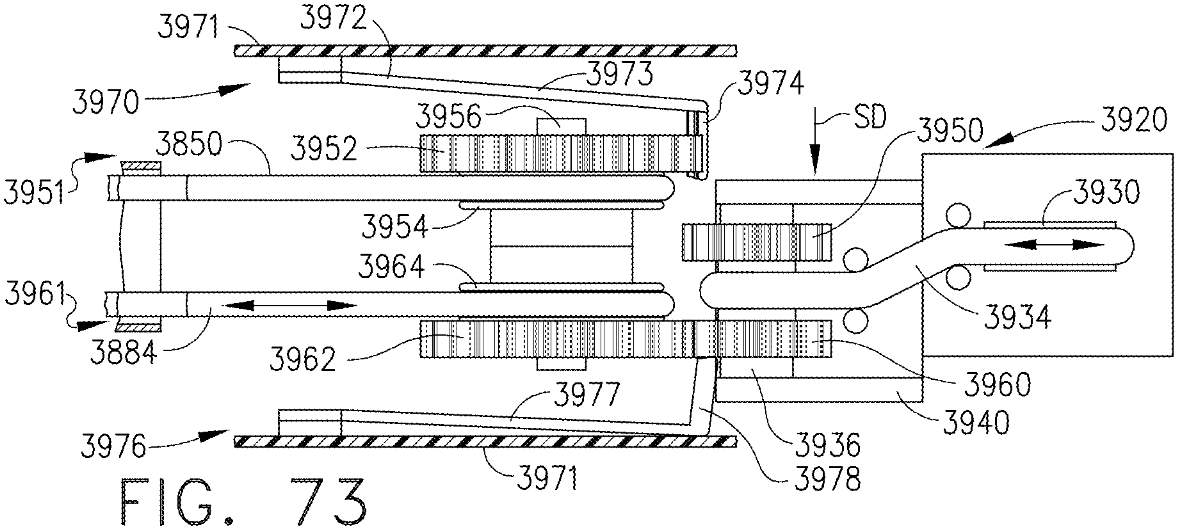
FIG. 73 is another top view of the cable drive transmission embodiment of FIGS. 71 and 72 in a firing position.
Figure 74:
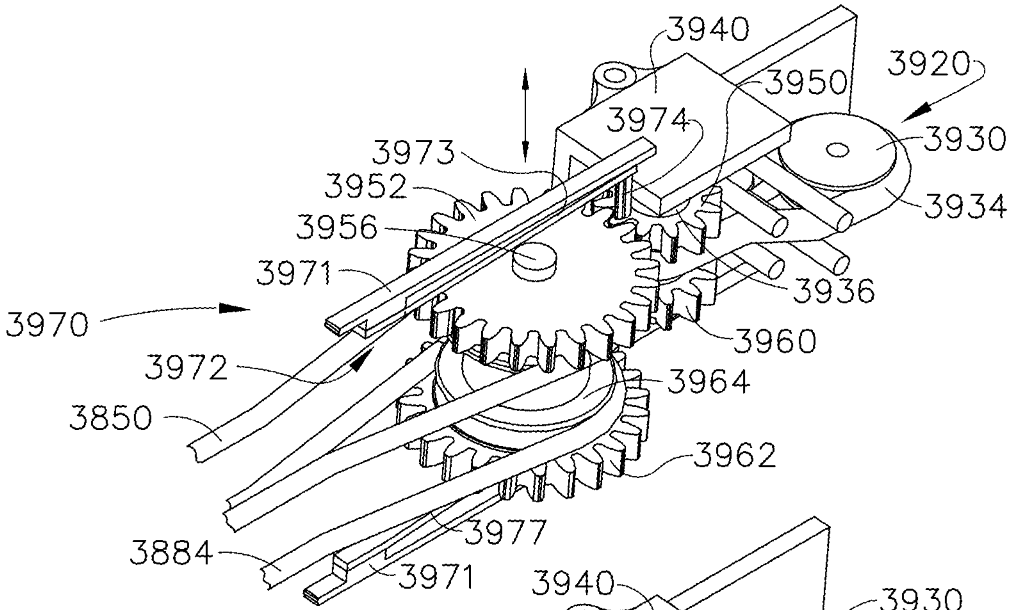
FIG. 74 is a perspective view of the cable drive transmission embodiment in the position depicted in FIG. 71.
Figure 75:
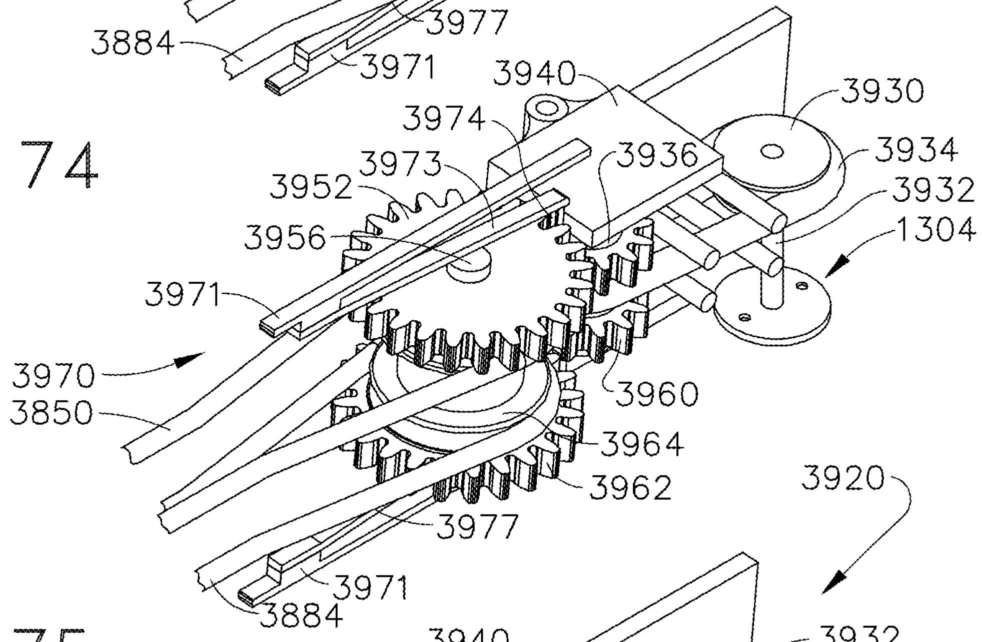
FIG. 75 is a perspective view of the cable drive transmission embodiment in the position depicted in FIG. 72.
Figure 76:
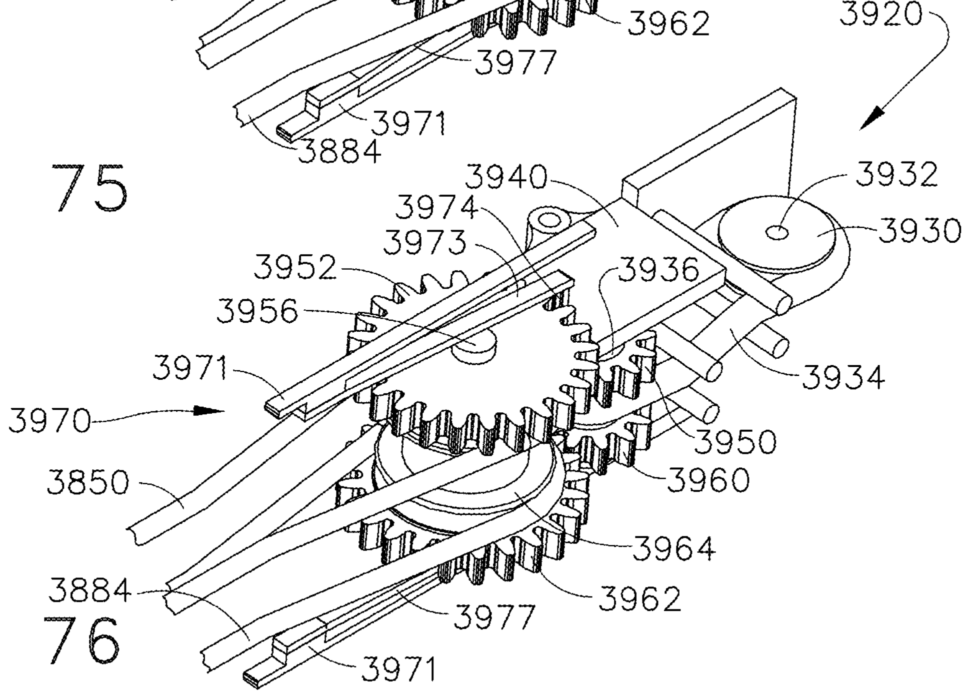
FIG. 76 is a perspective view of the cable drive transmission embodiment in the position depicted in FIG. 73.

At least one embodiment of the surgical tool 3800 may be used as follows. The tool mounting portion 3900 is operably coupled to the interface 1240 of the robotic system 1000. The controller or control unit of the robotic system is operated to locate the tissue to be cut and stapled between the open anvil 3824 and the staple cartridge 3834. When in that initial position, the braking assembly 3970 has locked the closure driven gear 3952 and the firing driven gear 3962 such that they cannot rotate. That is, as shown in FIG. 72, the gear lug 3974 is in locking engagement with the closure driven gear 3952 and the gear lug 3978 is in locking engagement with the firing driven gear 3962. Once the surgical end effector 3814 has been properly located, the controller 1001 of the robotic system 1000 will provide a control signal to the shifter motor 3922 (or shifter solenoid) to move the shifter yoke 3940 in the first direction. As the shifter yoke 3940 is moved in the first direction, the closure drive gear 3950 moves the gear lug 3974 out of engagement with the closure driven gear 3952 as it moves into meshing engagement with the closure driven gear 3952. As can be seen in FIG. 71, when in that position, the gear lug 3978 remains in locking engagement with the firing driven gear 3962 to prevent actuation of the firing system. Thereafter, the robotic controller 1001 provides a first rotary actuation motion to the drive pulley 3930 through the interface between the driven element 1304 and the corresponding components of the tool holder 1240. As the drive pulley 3930 is rotated in the first direction, the closure cable 3850 is rotated to drive the preclamping collar 3840 into closing engagement with the cam surface 3825 of the anvil 3824 to move it to the closed position thereby clamping the target tissue between the anvil 3824 and the staple cartridge 3834. See FIG. 67. Once the anvil 3824 has been moved to the closed position, the robotic controller 1001 stops the application of the first rotary motion to the drive pulley 3930. Thereafter, the robotic controller 1001 may commence the firing process by sending another control signal to the shifter motor 3922 (or shifter solenoid) to cause the shifter yoke to move in the second direction “SD” as shown in FIG. 94. As the shifter yoke 3940 is moved in the second direction, the firing drive gear 3960 moves the gear lug 3978 out of engagement with the firing driven gear 3962 as it moves into meshing engagement with the firing driven gear 3962. As can be seen in FIG. 73, when in that position, the gear lug 3974 remains in locking engagement with the closure driven gear 3952 to prevent actuation of the closure system. Thereafter, the robotic controller 1001 is activated to provide the first rotary actuation motion to the drive pulley 3930 through the interface between the driven element 1304 and the corresponding components of the tool holder 1240. As the drive pulley 3930 is rotated in the first direction, the firing cable 3884 is rotated to drive the dynamic clamping member 3860 in the distal direction “DD” thereby firing the stapes and cutting the tissue clamped in the end effector 3814. Once the robotic system 1000 determines that the dynamic clamping member 3860 has reached its distal most position-either through sensors or through monitoring the amount of rotary input applied to the drive pulley 3930, the controller 1001 may then apply a second rotary motion to the drive pulley 3930 to rotate the closure cable 3850 in an opposite direction to cause the dynamic clamping member 3860 to be retracted in the proximal direction “PD”. Once the dynamic clamping member has been retracted to the starting position, the application of the second rotary motion to the drive pulley 3930 is discontinued. Thereafter, the shifter motor 3922 (or shifter solenoid) is powered to move the shifter yoke 3940 to the closure position (FIG. 71). Once the closure drive gear 3950 is in meshing engagement with the closure driven gear 3952, the robotic controller 1001 may once again apply the second rotary motion to the drive pulley 3930. Rotation of the drive pulley 3930 in the second direction causes the closure cable 3850 to retract the preclamping collar 3840 out of engagement with the cam surface 3825 of the anvil 3824 to permit the anvil 3824 to move to an open position (by a spring or other means) to release the stapled tissue from the surgical end effector 3814.

Figure 77:
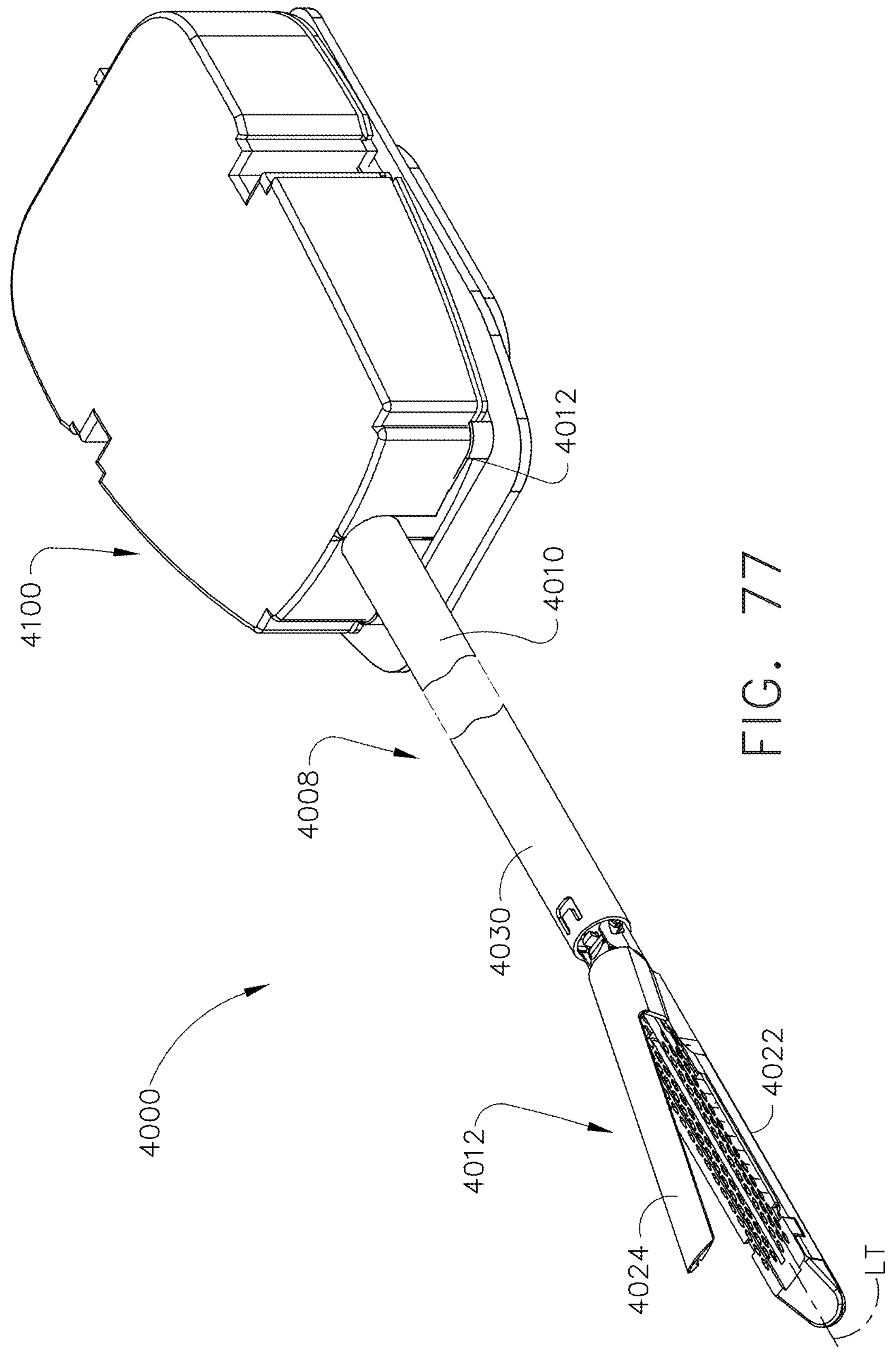
FIG. 77 is a perspective view of another surgical tool embodiment of the present invention.
Figure 78:
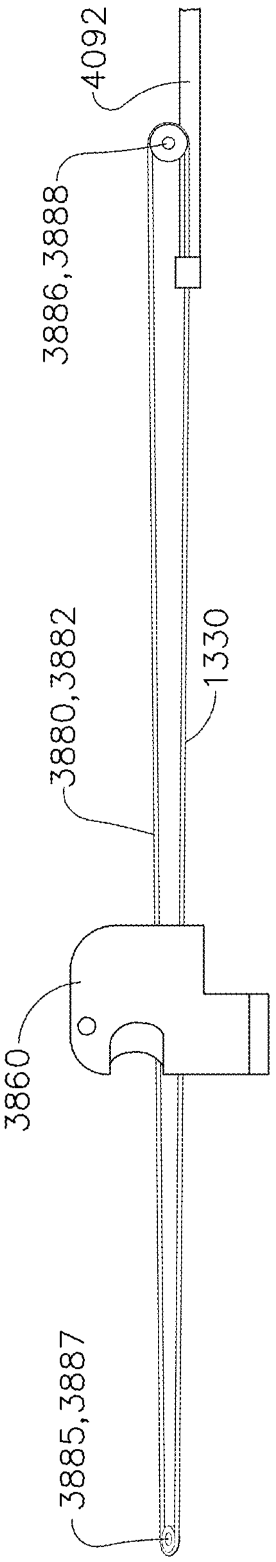
FIG. 78 is a side view of a portion of another cable-driven system embodiment for driving a cutting instrument employed in various surgical end effector embodiments of the present invention.
Figure 79:
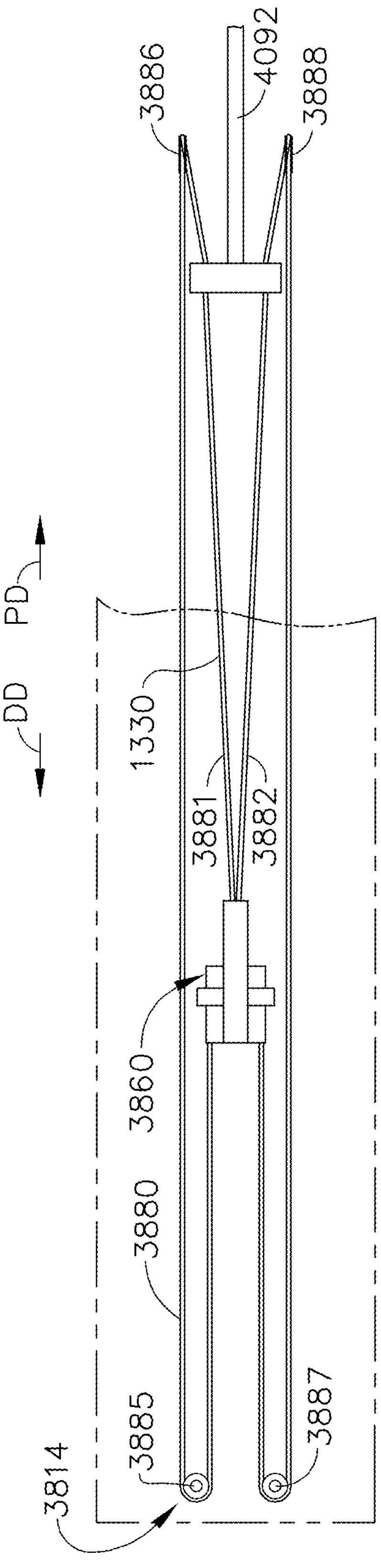
FIG. 79 is a top view of the cable-driven system embodiment of FIG. 78.
Figure 80:
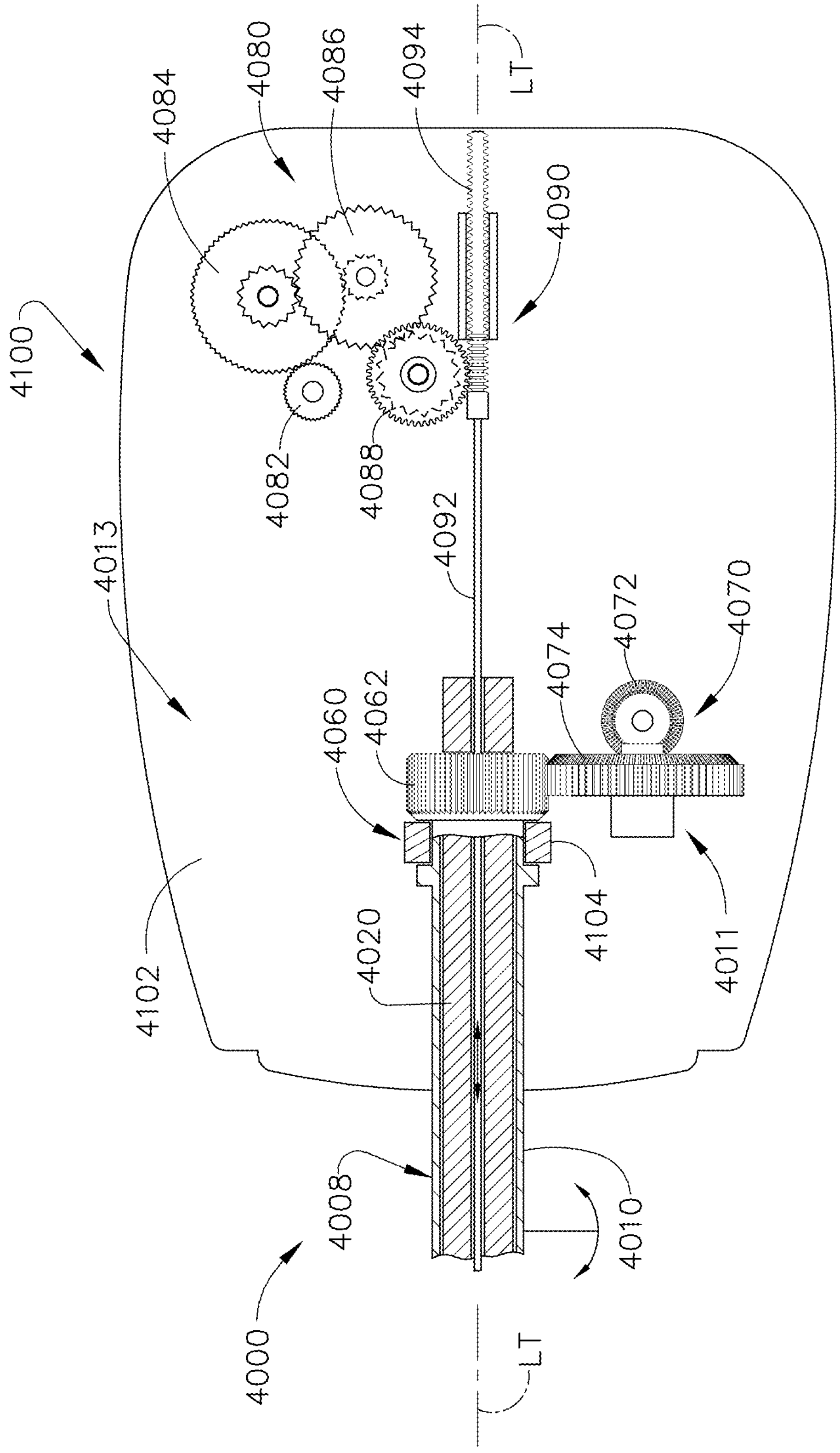
FIG. 80 is a top view of a tool mounting portion embodiment of another surgical tool embodiment of the present invention.

FIG. 77 illustrates a surgical tool 4000 that employs a gear driven firing bar 4092 as shown in FIGS. 78-80. This embodiment includes an elongated shaft assembly 4008 that extends from a tool mounting portion 4100. The tool mounting portion 4100 includes a tool mounting plate 4102 that operable supports a transmission arrangement 4103 thereon. The elongated shaft assembly 4008 includes a rotatable proximal closure tube 4010 that is rotatably journaled on a proximal spine member 4020 that is rigidly coupled to the tool mounting plate 4102. The proximal spine member 4020 has a distal end that is coupled to an elongated channel portion 4022 of a surgical end effector 4012. The surgical effector 4012 may be substantially similar to surgical end effector 3412 described above. In addition, the anvil 4024 of the surgical end effector 4012 may be opened and closed by a distal closure tube 4030 that operably interfaces with the proximal closure tube 4010. Distal closure tube 4030 is identical to distal closure tube 3430 described above. Similarly, proximal closure tube 4010 is identical to proximal closure tube segment 3410 described above.

Anvil 4024 is opened and closed by rotating the proximal closure tube 4010 in manner described above with respect to distal closure tube 3410. In at least one embodiment, the transmission arrangement comprises a closure transmission, generally designated as 4011. As will be further discussed below, the closure transmission 4011 is configured to receive a corresponding first rotary motion from the robotic system 1000 and convert that first rotary motion to a primary rotary motion for rotating the rotatable proximal closure tube 4010 about the longitudinal tool axis LT-LT. As can be seen in FIG. 80, a proximal end 4060 of the proximal closure tube 4010 is rotatably supported within a cradle arrangement 4104 that is attached to a tool mounting plate 4102 of the tool mounting portion 4100. A rotation gear 4062 is formed on or attached to the proximal end 4060 of the closure tube segment 4010 for meshing engagement with a rotation drive assembly 4070 that is operably supported on the tool mounting plate 4102. In at least one embodiment, a rotation drive gear 4072 is coupled to a corresponding first one of the driven discs or elements 1304 on the adapter side of the tool mounting plate 4102 when the tool mounting portion 4100 is coupled to the tool holder 1270. See FIGS. 10 and 80. The rotation drive assembly 4070 further comprises a rotary driven gear 4074 that is rotatably supported on the tool mounting plate 4102 in meshing engagement with the rotation gear 4062 and the rotation drive gear 4072. Application of a first rotary control motion from the robotic system 1000 through the tool holder 1270 and the adapter 1240 to the corresponding driven element 1304 will thereby cause rotation of the rotation drive gear 4072 by virtue of being operably coupled thereto. Rotation of the rotation drive gear 4072 ultimately results in the rotation of the closure tube segment 4010 to open and close the anvil 4024 as described above.

As indicated above, the end effector 4012 employs a cutting element 3860 as shown in FIGS. 78 and 79. In at least one non-limiting embodiment, the transmission arrangement 4103 further comprises a knife drive transmission that includes a knife drive assembly 4080. FIG. 80 illustrates one form of knife drive assembly 4080 for axially advancing the knife bar 4092 that is attached to such cutting element using cables as described above with respect to surgical tool 3800. In particular, the knife bar 4092 replaces the firing cable 3884 employed in an embodiment of surgical tool 3800. One form of the knife drive assembly 4080 comprises a rotary drive gear 4082 that is coupled to a corresponding second one of the driven discs or elements 1304 on the adapter side of the tool mounting plate 4102 when the tool mounting portion 4100 is coupled to the tool holder 1270. See FIGS. 10 and 80. The knife drive assembly 4080 further comprises a first rotary driven gear assembly 4084 that is rotatably supported on the tool mounting plate 4102. The first rotary driven gear assembly 4084 is in meshing engagement with a third rotary driven gear assembly 4086 that is rotatably supported on the tool mounting plate 4102 and which is in meshing engagement with a fourth rotary driven gear assembly 4088 that is in meshing engagement with a threaded portion 4094 of drive shaft assembly 4090 that is coupled to the knife bar 4092. Rotation of the rotary drive gear 4082 in a second rotary direction will result in the axial advancement of the drive shaft assembly 4090 and knife bar 4092 in the distal direction "DD". Conversely, rotation of the rotary drive gear 4082 in a secondary rotary direction (opposite to the second rotary direction) will cause the drive shaft assembly 4090 and the knife bar 4092 to move in the proximal direction. Movement of the firing bar 4092 in the proximal direction "PD" will drive the cutting element 3860 in the distal direction "DD". Conversely, movement of the firing bar 4092 in the distal direction "DD" will result in the movement of the cutting element 3860 in the proximal direction "PD".

Figure 83:
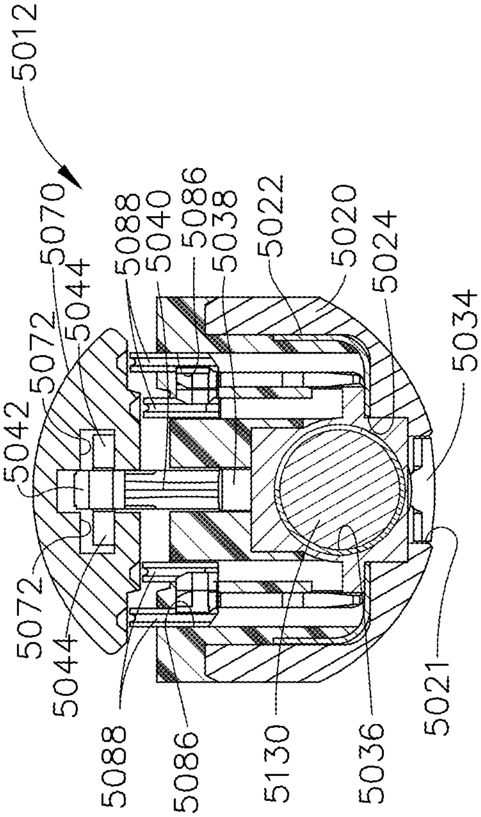
FIG. 83 is a cross-sectional end view of the surgical end effector of FIG. 82 taken along line 83-83 in FIG. 82.

FIGS. 81-87 illustrate yet another surgical tool 5000 that may be effectively employed in connection with a robotic system 1000. In various forms, the surgical tool 5000 includes a surgical end effector 5012 in the form of a surgical stapling instrument that includes an elongated channel 5020 and a pivotally translatable clamping member, such as an anvil 5070, which are maintained at a spacing that assures effective stapling and severing of tissue clamped in the surgical end effector 5012. As can be seen in FIG. 83, the elongated channel 5020 may be substantially U-shaped in cross-section and be fabricated from, for example, titanium, 203 stainless steel, 304 stainless steel, 416 stainless steel, 17-4 stainless steel, 17-7 stainless steel, 6061 or 7075 aluminum, chromium steel, ceramic, etc. A substantially U-shaped metal channel pan 5022 may be supported in the bottom of the elongated channel 5020 as shown.

Various embodiments include an actuation member in the form of a sled assembly 5030 that is operably supported within the surgical end effector 5012 and axially movable therein between a starting position and an ending position in response to control motions applied thereto. In some forms, the metal channel pan 5022 has a centrally-disposed slot 5024 therein to movably accommodate a base portion 5032 of the sled assembly 5030. The base portion 5032 includes a foot portion 5034 that is sized to be slidably received in a slot 5021 in the elongated channel 5020. See FIG. 104. As can be seen in FIGS. 82, 83, 86, and 87, the base portion 5032 of sled assembly 5030 includes an axially extending threaded bore 5036 that is configured to be threadedly received on a threaded drive shaft 5130 as will be discussed in further detail below. In addition, the sled assembly 5030 includes an upstanding support portion 5038 that supports a tissue cutting blade or tissue cutting instrument 5040. The upstanding support portion 5038 terminates in a top portion 5042 that has a pair of laterally extending retaining fins 5044 protruding therefrom. As shown in FIG. 83, the fins 5044 are positioned to be received within corresponding slots 5072 in anvil 5070. The fins 5044 and the foot 5034 serve to retain the anvil 5070 in a desired spaced closed position as the sled assembly 5030 is driven distally through the tissue clamped within the surgical end effector 5014. As can also be seen in FIGS. 85 and 87, the sled assembly 5030 further includes a reciprocatably or sequentially activatable drive assembly 5050 for driving staple pushers toward the closed anvil 5070.

Figure 84:
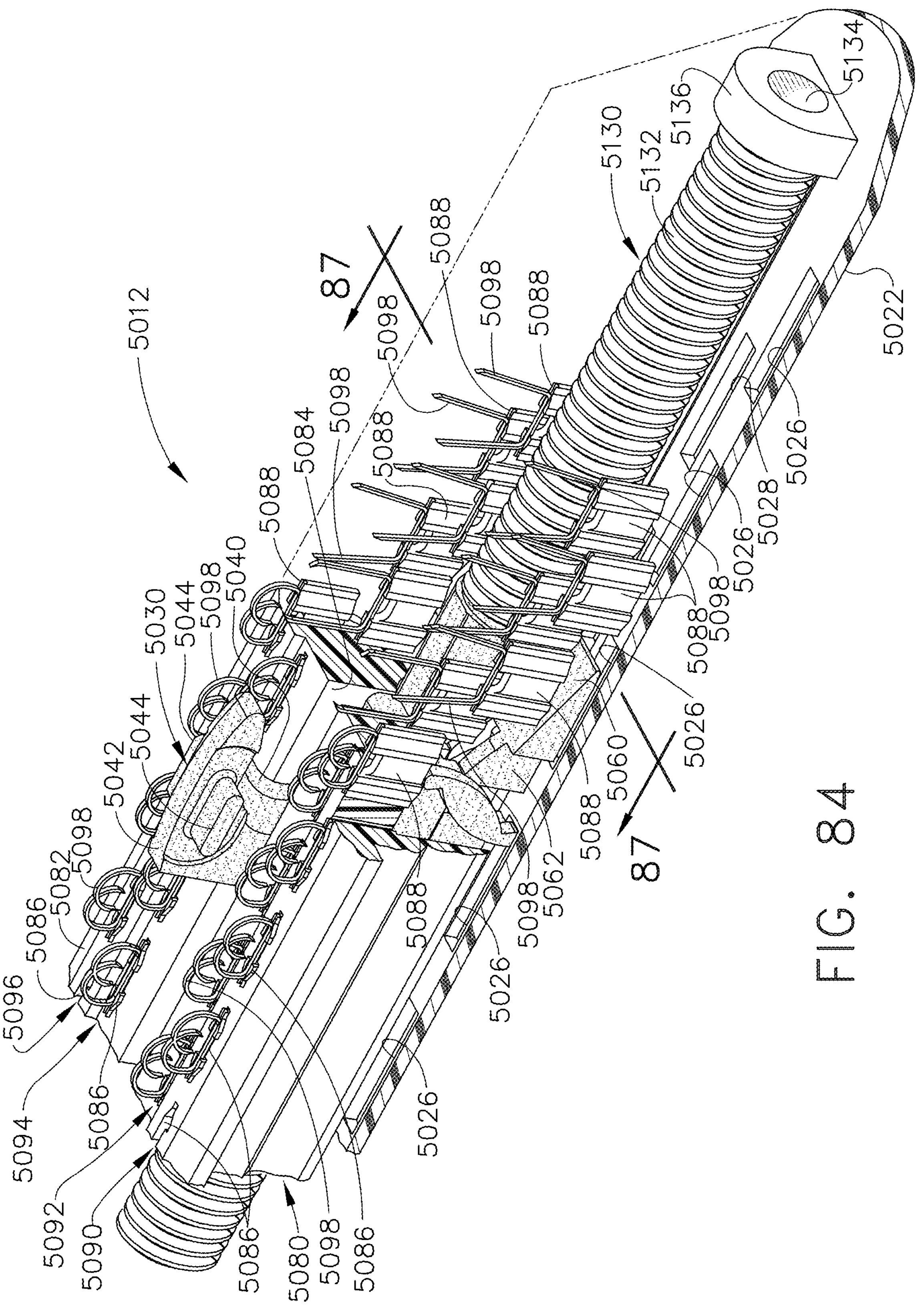
FIG. 84 is a perspective view of the surgical end effector of FIGS. 82 and 83 with portions thereof shown in cross-section.
Figure 85:
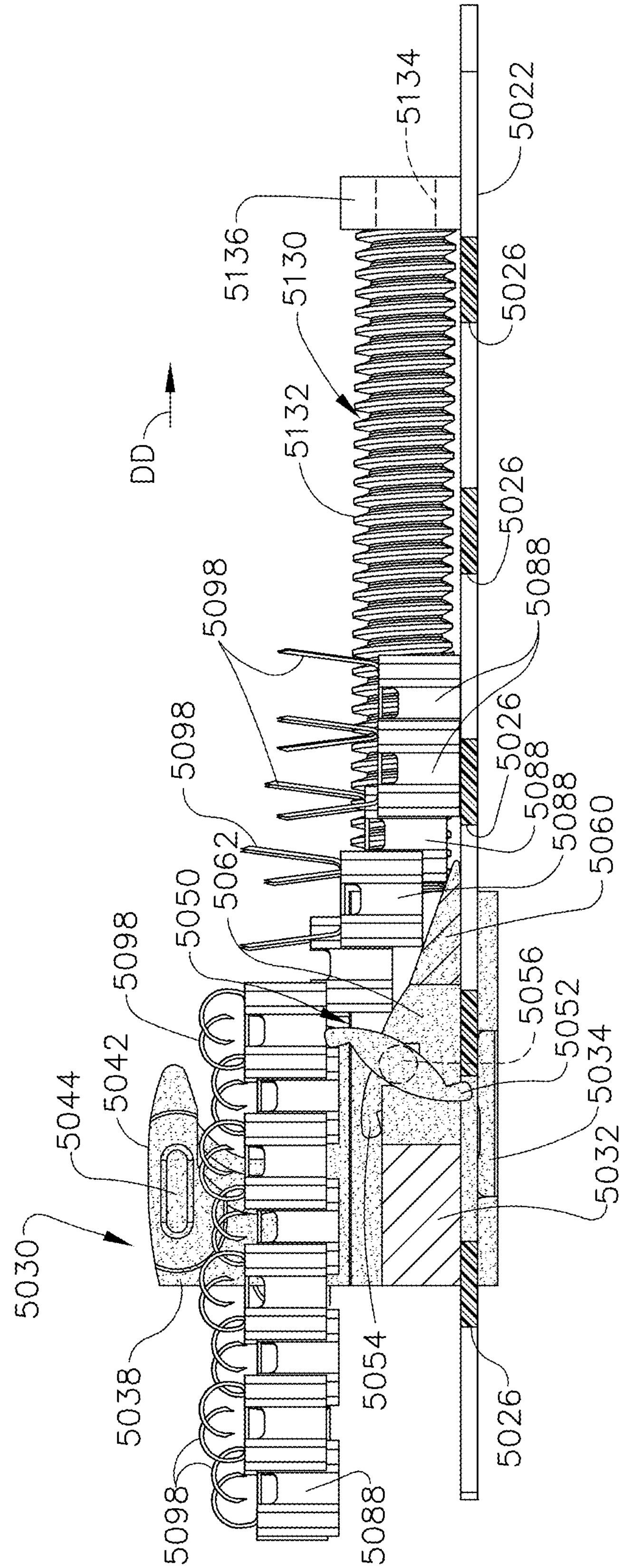
FIG. 85 is a side view of a portion of the surgical end effector of FIGS. 82-84.
Figure 87:
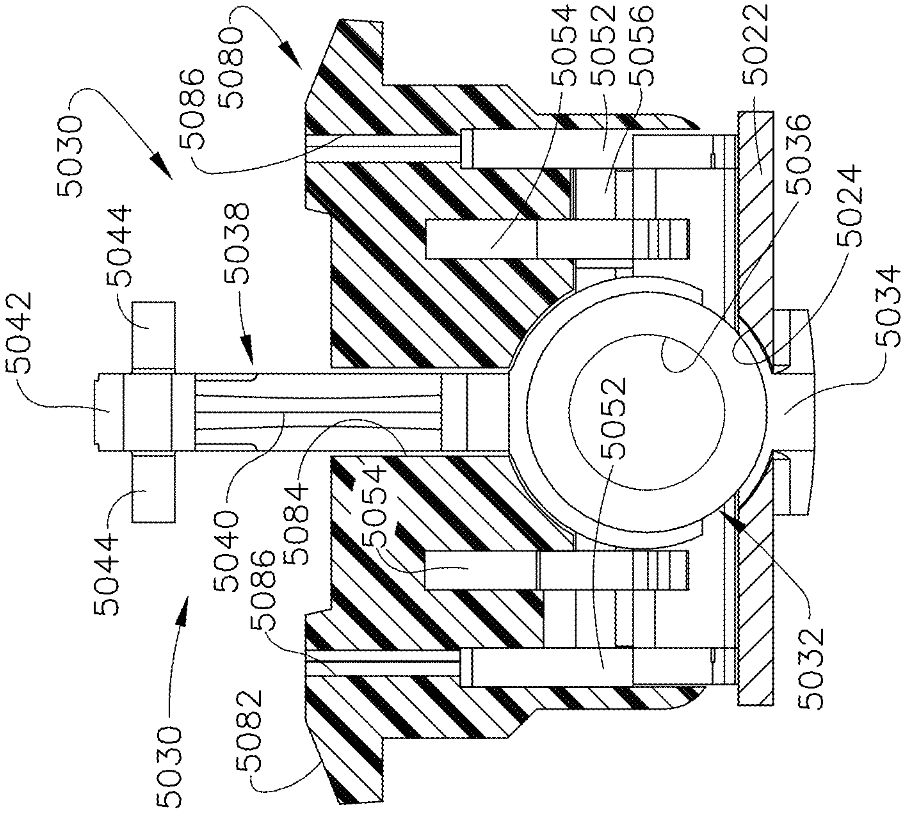
FIG. 87 is a cross-sectional view of the sled assembly embodiment of FIG. 86 and a portion of the elongated channel of FIG. 85.
Figure 86:
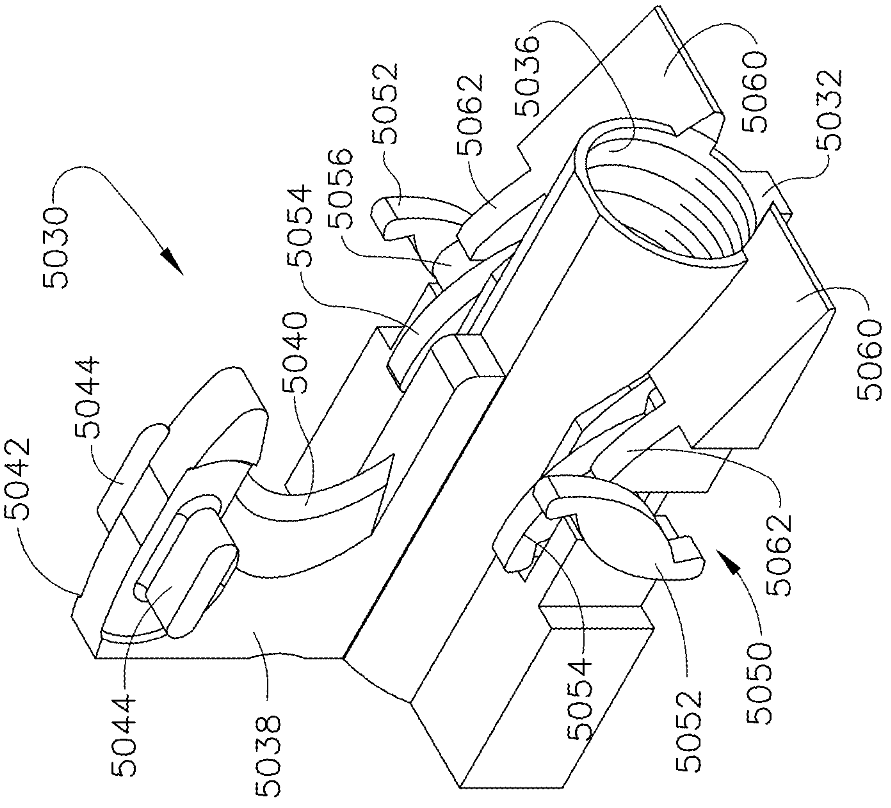
FIG. 86 is a perspective view of a sled assembly embodiment of various surgical tool embodiments of the present invention.

More specifically and with reference to FIGS. 83 and 84, the elongated channel 5020 is configured to operably support a surgical staple cartridge 5080 therein. In at least one form, the surgical staple cartridge 5080 comprises a body portion 5082 that may be fabricated from, for example, Vectra, Nylon (6/6 or 6/12) and include a centrally disposed slot 5084 for accommodating the upstanding support portion 5038 of the sled assembly 5030. See FIG. 83. These materials could also be filled with glass, carbon, or mineral fill of 10%-40%. The surgical staple cartridge 5080 further includes a plurality of cavities 5086 for movably supporting lines or rows of staple-supporting pushers 5088 therein. The cavities 5086 may be arranged in spaced longitudinally extending lines or rows 5090, 5092, 5094, 5096. For example, the rows 5090 may be referred to herein as first outboard rows. The rows 5092 may be referred to herein as first inboard rows. The rows 5094 may be referred to as second inboard rows and the rows 5096 may be referred to as second outboard rows. The first inboard row 5090 and the first outboard row 5092 are located on a first lateral side of the longitudinal slot 5084 and the second inboard row 5094 and the second outboard row 5096 are located on a second lateral side of the longitudinal slot 5084. The first staple pushers 5088 in the first inboard row 5092 are staggered in relationship to the first staple pushers 5088 in the first outboard row 5090. Similarly, the second staple pushers 5088 in the second outboard row 5096 are staggered in relationship to the second pushers 5088 in the second inboard row 5094. Each pusher 5088 operably supports a surgical staple 5098 thereon.

In various embodiments, the sequentially-activatable or reciprocatably-activatable drive assembly 5050 includes a pair of outboard drivers 5052 and a pair of inboard drivers 5054 that are each attached to a common shaft 5056 that is rotatably mounted within the base 5032 of the sled assembly 5030. The outboard drivers 5052 are oriented to sequentially or reciprocatingly engage a corresponding plurality of outboard activation cavities 5026 provided in the channel pan 5022. Likewise, the inboard drivers 5054 are oriented to sequentially or reciprocatingly engage a corresponding plurality of inboard activation cavities 5028 provided in the channel pan 5022. The inboard activation cavities 5028 are arranged in a staggered relationship relative to the adjacent outboard activation cavities 5026. See FIG. 84. As can also be seen in FIGS. 84 and 86, in at least one embodiment, the sled assembly 5030 further includes distal wedge segments 5060 and intermediate wedge segments 5062 located on each side of the bore 5036 to engage the pushers 5088 as the sled assembly 5030 is driven distally in the distal direction "DD". As indicated above, the sled assembly 5030 is threadedly received on a threaded portion 5132 of a drive shaft 5130 that is rotatably supported within the end effector 5012. In various embodiments, for example, the drive shaft 5130 has a distal end 5134 that is supported in a distal bearing 5136 mounted in the surgical end effector 5012. See FIGS. 83 and 84.

In various embodiments, the surgical end effector 5012 is coupled to a tool mounting portion 5200 by an elongated shaft assembly 5108. In at least one embodiment, the tool mounting portion 5200 operably supports a transmission arrangement generally designated as 5204 that is configured to receive rotary output motions from the robotic system. The elongated shaft assembly 5108 includes an outer closure tube 5110 that is rotatable and axially movable on a spine member 5120 that is rigidly coupled to a tool mounting plate 5201 of the tool mounting portion 5200. The spine member 5120 also has a distal end 5122 that is coupled to the elongated channel portion 5020 of the surgical end effector 5012.

In use, it may be desirable to rotate the surgical end effector 5012 about a longitudinal tool axis LT-LT defined by the elongated shaft assembly 5008. In various embodiments, the outer closure tube 5110 has a proximal end 5112 that is rotatably supported on the tool mounting plate 5201 of the tool drive portion 5200 by a forward support cradle 5203. The proximal end 5112 of the outer closure tube 5110 is configured to operably interface with a rotation transmission portion 5206 of the transmission arrangement 5204. In various embodiments, the proximal end 5112 of the outer closure tube 5110 is also supported on a closure sled 5140 that is also movably supported on the tool mounting plate 5201. A closure tube gear segment 5114 is formed on the proximal end 5112 of the outer closure tube 5110 for meshing engagement with a rotation drive assembly 5150 of the rotation transmission 5206. As can be seen in FIG. 102, the rotation drive assembly 5150, in at least one embodiment, comprises a rotation drive gear 5152 that is coupled to a corresponding first one of the driven discs or elements 1304 on the adapter side 1307 of the tool mounting plate 5201 when the tool drive portion 5200 is coupled to the tool holder 1270. The rotation drive assembly 5150 further comprises a rotary driven gear 5154 that is rotatably supported on the tool mounting plate 5201 in meshing engagement with the closure tube gear segment 5114 and the rotation drive gear 5152. Application of a first rotary control motion from the robotic system 1000 through the tool holder 1270 and the adapter 1240 to the corresponding driven element 1304 will thereby cause rotation of the rotation drive gear 5152. Rotation of the rotation drive gear 5152 ultimately results in the rotation of the elongated shaft assembly 5108 (and the end effector 5012) about the longitudinal tool axis LT-LT (represented by arrow "R" in FIG. 81).

Figure 81:
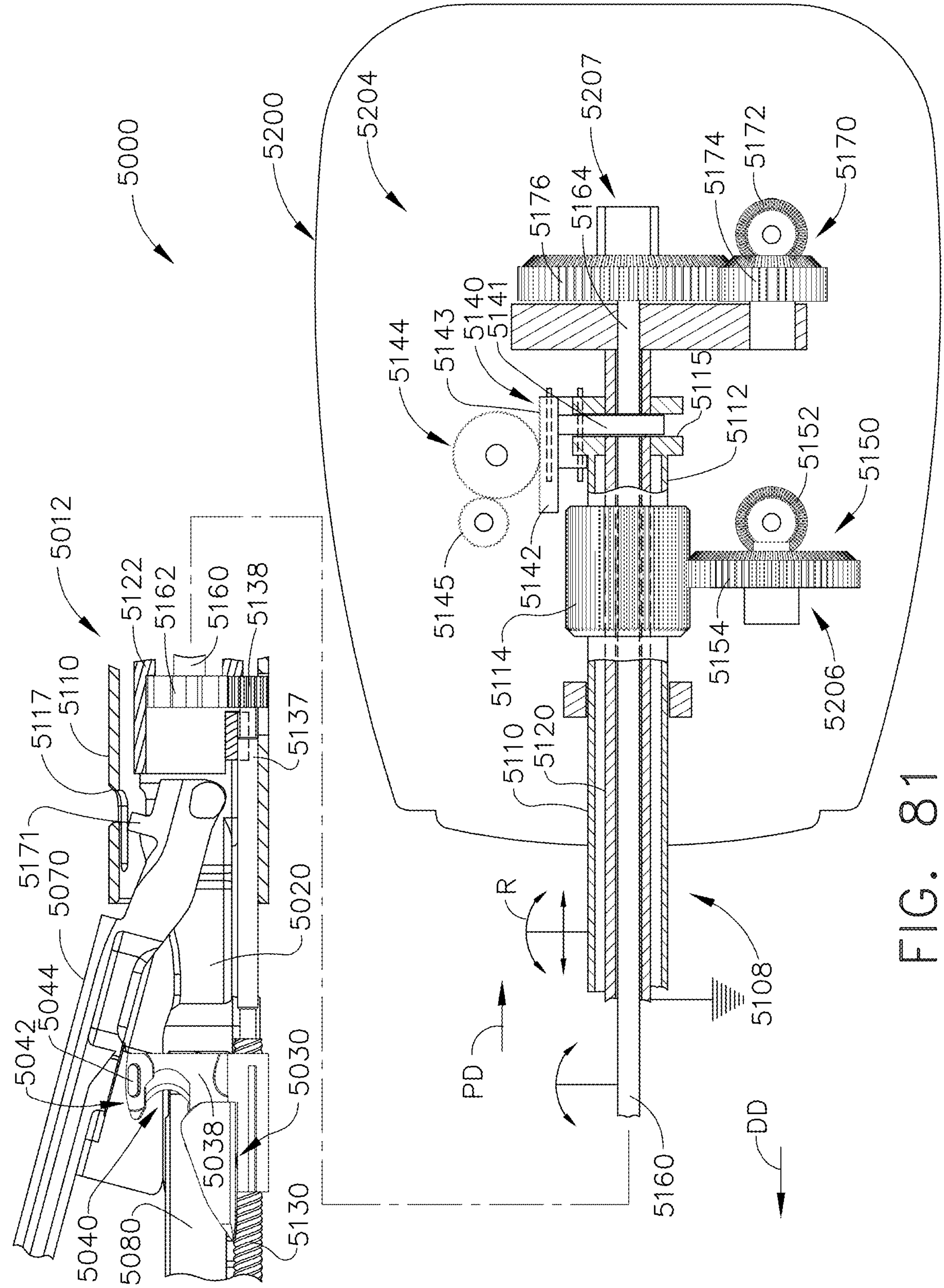
FIG. 81 is a top cross-sectional view of another surgical tool embodiment of the present invention.
Figure 82:
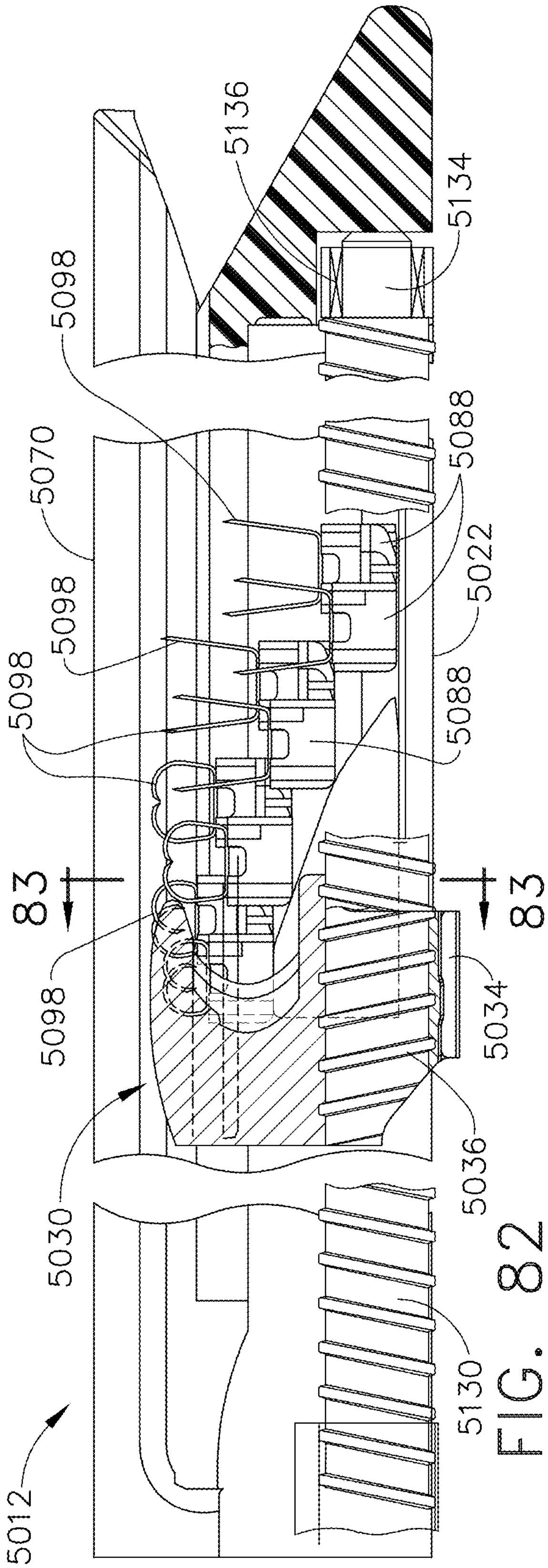
FIG. 82 is a cross-sectional view of a portion of a surgical end effector embodiment of a surgical tool embodiment of the present invention.

Closure of the anvil 5070 relative to the surgical staple cartridge 5080 is accomplished by axially moving the outer closure tube 5110 in the distal direction "DD". Such axial movement of the outer closure tube 5110 may be accomplished by a closure transmission portion 5144 of the transmission arrangement 5204. As indicated above, in various embodiments, the proximal end 5112 of the outer closure tube 5110 is supported by the closure sled 5140 which enables the proximal end 5112 to rotate relative thereto, yet travel axially with the closure sled 5140. In particular, as can be seen in FIG. 81, the closure sled 5140 has an upstanding tab 5141 that extends into a radial groove 5115 in the proximal end portion 5112 of the outer closure tube 5110. In addition, as was described above, the closure sled 5140 is slidably mounted to the tool mounting plate 5201. In various embodiments, the closure sled 5140 has an upstanding portion 5142 that has a closure rack gear 5143 formed thereon. The closure rack gear 5143 is configured for driving engagement with the closure transmission 5144.

In various forms, the closure transmission 5144 includes a closure spur gear 5145 that is coupled to a corresponding second one of the driven discs or elements 1304 on the adapter side 1307 of the tool mounting plate 5201. Thus, application of a second rotary control motion from the robotic system 1000 through the tool holder 1270 and the adapter 1240 to the corresponding second driven element 1304 will cause rotation of the closure spur gear 5145 when the interface 1230 is coupled to the tool mounting portion 5200. The closure transmission 5144 further includes a driven closure gear set 5146 that is supported in meshing engagement with the closure spur gear 5145 and the closure rack gear 5143. Thus, application of a second rotary control motion from the robotic system 1000 through the tool holder 1270 and the adapter 1240 to the corresponding second driven element 1304 will cause rotation of the closure spur gear 5145 and ultimately drive the closure sled 5140 and the outer closure tube 5110 axially. The axial direction in which the closure tube 5110 moves ultimately depends upon the direction in which the second driven element 1304 is rotated. For example, in response to one rotary closure motion received from the robotic system 1000, the closure sled 5140 will be driven in the distal direction "DD" and ultimately the outer closure tube 5110 will be driven in the distal direction as well. The outer closure tube 5110 has an opening 5117 in the distal end 5116 that is configured for engagement with a tab 5071 on the anvil 5070 in the manners described above. As the outer closure tube 5110 is driven distally, the proximal end 5116 of the closure tube 5110 will contact the anvil 5070 and pivot it closed. Upon application of an "opening" rotary motion from the robotic system 1000, the closure sled 5140 and outer closure tube 5110 will be driven in the proximal direction "PD" and pivot the anvil 5070 to the open position in the manners described above.

In at least one embodiment, the drive shaft 5130 has a proximal end 5137 that has a proximal shaft gear 5138 attached thereto. The proximal shaft gear 5138 is supported in meshing engagement with a distal drive gear 5162 attached to a rotary drive bar 5160 that is rotatably supported with spine member 5120. Rotation of the rotary drive bar 5160 and ultimately rotary drive shaft 5130 is controlled by a rotary knife transmission 5207 which comprises a portion of the transmission arrangement 5204 supported on the tool mounting plate 5210. In various embodiments, the rotary knife transmission 5207 comprises a rotary knife drive system 5170 that is operably supported on the tool mounting plate 5201. In various embodiments, the knife drive system 5170 includes a rotary drive gear 5172 that is coupled to a corresponding third one of the driven discs or elements 1304 on the adapter side of the tool mounting plate 5201 when the tool drive portion 5200 is coupled to the tool holder 1270. The knife drive system 5170 further comprises a first rotary driven gear 5174 that is rotatably supported on the tool mounting plate 5201 in meshing engagement with a second rotary driven gear 5176 and the rotary drive gear 5172. The second rotary driven gear 5176 is coupled to a proximal end portion 5164 of the rotary drive bar 5160.

Rotation of the rotary drive gear 5172 in a first rotary direction will result in the rotation of the rotary drive bar 5160 and rotary drive shaft 5130 in a first direction. Conversely, rotation of the rotary drive gear 5172 in a second rotary direction (opposite to the first rotary direction) will cause the rotary drive bar 5160 and rotary drive shaft 5130 to rotate in a second direction. 2400. Thus, rotation of the drive shaft 2440 results in rotation of the drive sleeve 2400.

One method of operating the surgical tool 5000 will now be described. The tool drive 5200 is operably coupled to the interface 1240 of the robotic system 1000. The controller 1001 of the robotic system 1000 is operated to locate the tissue to be cut and stapled between the open anvil 5070 and the surgical staple cartridge 5080. Once the surgical end effector 5012 has been positioned by the robot system 1000 such that the target tissue is located between the anvil 5070 and the surgical staple cartridge 5080, the controller 1001 of the robotic system 1000 may be activated to apply the second rotary output motion to the second driven element 1304 coupled to the closure spur gear 5145 to drive the closure sled 5140 and the outer closure tube 5110 axially in the distal direction to pivot the anvil 5070 closed in the manner described above. Once the robotic controller 1001 determines that the anvil 5070 has been closed by, for example, sensors in the surgical end effector 5012 and/or the tool drive portion 5200, the robotic controller 1001 system may provide the surgeon with an indication that signifies the closure of the anvil. Such indication may be, for example, in the form of a light and/or audible sound, tactile feedback on the control members, etc. Then the surgeon may initiate the firing process. In alternative embodiments, however, the robotic controller 1001 may automatically commence the firing process.

To commence the firing process, the robotic controller applies a third rotary output motion to the third driven disc or element 1304 coupled to the rotary drive gear 5172. Rotation of the rotary drive gear 5172 results in the rotation of the rotary drive bar 5160 and rotary drive shaft 5130 in the manner described above. Firing and formation of the surgical staples 5098 can be best understood from reference to FIGS. 82, 84, and 85. As the sled assembly 5030 is driven in the distal direction "DD" through the surgical staple cartridge 5080, the distal wedge segments 5060 first contact the staple pushers 5088 and start to move them toward the closed anvil 5070. As the sled assembly 5030 continues to move distally, the outboard drivers 5052 will drop into the corresponding activation cavity 5026 in the channel pan 5022. The opposite end of each outboard driver 5052 will then contact the corresponding outboard pusher 5088 that has moved up the distal and intermediate wedge segments 5060, 5062. Further distal movement of the sled assembly 5030 causes the outboard drivers 5052 to rotate and drive the corresponding pushers 5088 toward the anvil 5070 to cause the staples 5098 supported thereon to be formed as they are driven into the anvil 5070. It will be understood that as the sled assembly 5030 moves distally, the knife blade 5040 cuts through the tissue that is clamped between the anvil and the staple cartridge. Because the inboard drivers 5054 and outboard drivers 5052 are attached to the same shaft 5056 and the inboard drivers 5054 are radially offset from the outboard drivers 5052 on the shaft 5056, as the outboard drivers 5052 are driving their corresponding pushers 5088 toward the anvil 5070, the inboard drivers 5054 drop into their next corresponding activation cavity 5028 to cause them to rotatably or reciprocatingly drive the corresponding inboard pushers 5088 towards the closed anvil 5070 in the same manner. Thus, the laterally corresponding outboard staples 5098 on each side of the centrally disposed slot 5084 are simultaneously formed together and the laterally corresponding inboard staples 5098 on each side of the slot 5084 are simultaneously formed together as the sled assembly 5030 is driven distally. Once the robotic controller 1001 determines that the sled assembly 5030 has reached its distal most position-either through sensors or through monitoring the amount of rotary input applied to the drive shaft 5130 and/or the rotary drive bar 5160, the controller 1001 may then apply a third rotary output motion to the drive shaft 5130 to rotate the drive shaft 5130 in an opposite direction to retract the sled assembly 5030 back to its starting position. Once the sled assembly 5030 has been retracted to the starting position (as signaled by sensors in the end effector 5012 and/or the tool drive portion 5200), the application of the second rotary motion to the drive shaft 5130 is discontinued. Thereafter, the surgeon may manually activate the anvil opening process or it may be automatically commenced by the robotic controller 1001. To open the anvil 5070, the second rotary output motion is applied to the closure spur gear 5145 to drive the closure sled 5140 and the outer closure tube 5110 axially in the proximal direction. As the closure tube 5110 moves proximally, the opening 5117 in the distal end 5116 of the closure tube 5110 contacts the tab 5071 on the anvil 5070 to pivot the anvil 5070 to the open position. A spring may also be employed to bias the anvil 5070 to the open position when the closure tube 5116 has been returned to the starting position. Again, sensors in the surgical end effector 5012 and/or the tool mounting portion 5200 may provide the robotic controller 1001 with a signal indicating that the anvil 5070 is now open. Thereafter, the surgical end effector 5012 may be withdrawn from the surgical site.

Figure 88:
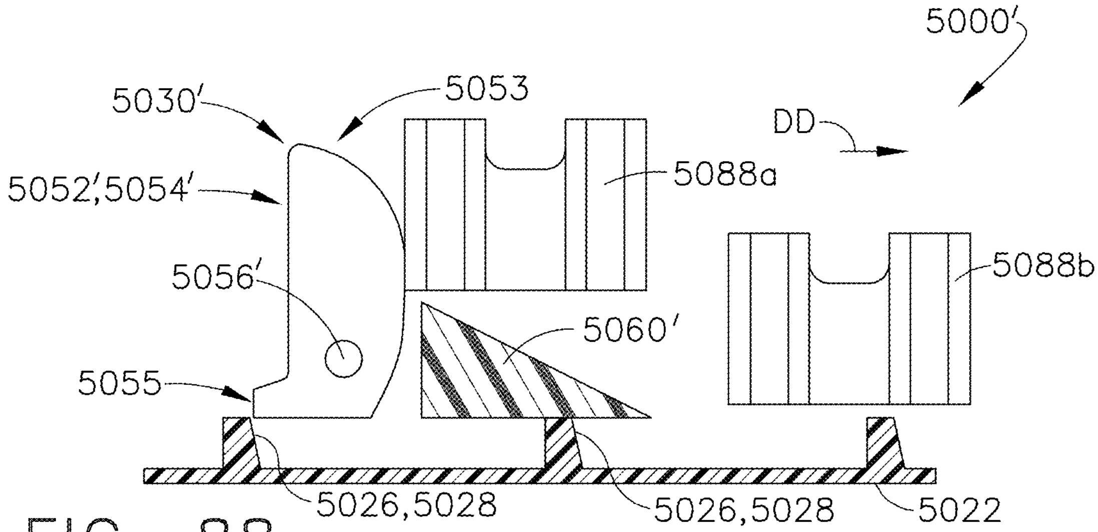
Figure 89:
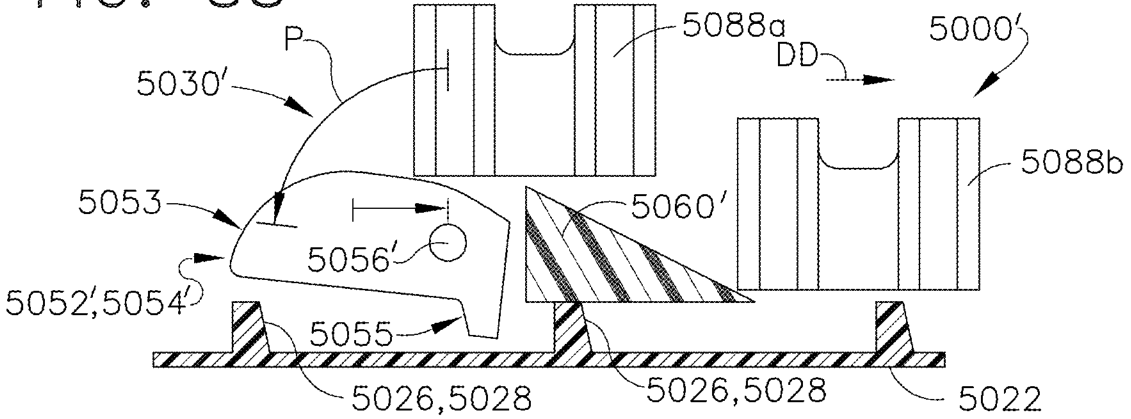

FIGS. 88-93 diagrammatically depict the sequential firing of staples in a surgical tool assembly 5000' that is substantially similar to the surgical tool assembly 5000 described above. In this embodiment, the inboard and outboard drivers 5052', 5054' have a cam-like shape with a cam surface 5053 and an actuator protrusion 5055 as shown in FIGS. 88-94. The drivers 5052', 5054' are journaled on the same shaft 5056' that is rotatably supported by the sled assembly 5030'. In this embodiment, the sled assembly 5030' has distal wedge segments 5060' for engaging the pushers 5088. FIG. 88 illustrates an initial position of two inboard or outboard drivers 5052', 5054' as the sled assembly 5030' is driven in the distal direction "DD". As can be seen in that Figure, the pusher 5088*a* has advanced up the wedge segment 5060' and has contacted the driver 5052', 5054'. Further travel of the sled assembly 5030' in the distal direction causes the driver 5052', 5054' to pivot in the "P" direction (FIG. 89) until the actuator portion 5055 contacts the end wall 5029*a* of the activation cavity 5026, 5028 as shown in FIG. 90. Continued advancement of the sled assembly 5030' in the distal direction "DD" causes the driver 5052', 5054' to rotate in the "D" direction as shown in FIG. 91. As the driver 5052', 5054' rotates, the pusher 5088*a* rides up the cam surface 5053 to the final vertical position shown in FIG. 113. When the pusher 5088*a* reaches the final vertical position shown in FIGS. 92 and 93, the staple (not shown) supported thereon has been driven into the staple forming surface of the anvil to form the staple.

FIGS. 95-100 illustrate a surgical end effector 5312 that may be employed for example, in connection with the tool mounting portion 1300 and shaft 2008 described in detail above. In various forms, the surgical end effector 5312 includes an elongated channel 5322 that is constructed as described above for supporting a surgical staple cartridge 5330 therein. The surgical staple cartridge 5330 comprises a body portion 5332 that includes a centrally disposed slot 5334 for accommodating an upstanding support portion 5386 of a sled assembly 5380. Sec FIGS. 95-97. The surgical staple cartridge body portion 5332 further includes a plurality of cavities 5336 for movably supporting staple-supporting pushers 5350 therein. The cavities 5336 may be arranged in spaced longitudinally extending rows 5340, 5342, 5344, 5346. The rows 5340, 5342 are located on one lateral side of the longitudinal slot 5334 and the rows 5344, 5346 are located on the other side of longitudinal slot 5334. In at least one embodiment, the pushers 5350 are configured to support two surgical staples 5352 thereon. In particular, each pusher 5350 located on one side of the elongated slot 5334 supports one staple 5352 in row 5340 and one staple 5352 in row 5342 in a staggered orientation. Likewise, each pusher 5350 located on the other side of the elongated slot 5334 supports one surgical staple 5352 in row 5344 and another surgical staple 5352 in row 5346 in a staggered orientation. Thus, every pusher 5350 supports two surgical staples 5352.

As can be further seen in FIGS. 95, 96, the surgical staple cartridge 5330 includes a plurality of rotary drivers 5360. More particularly, the rotary drivers 5360 on one side of the elongated slot 5334 are arranged in a single line 5370 and correspond to the pushers 5350 in lines 5340, 5342. In addition, the rotary drivers 5360 on the other side of the elongated slot 5334 are arranged in a single line 5372 and correspond to the pushers 5350 in lines 5344, 5346. As can be seen in FIG. 95, each rotary driver 5360 is rotatably supported within the staple cartridge body 5332. More particularly, each rotary driver 5360 is rotatably received on a corresponding driver shaft 5362. Each driver 5360 has an arcuate ramp portion 5364 formed thereon that is configured to engage an arcuate lower surface 5354 formed on each pusher 5350. See FIG. 100. In addition, each driver 5360 has a lower support portion 5366 extend therefrom to slidably support the pusher 5360 on the channel 5322. Each driver 5360 has a downwardly extending actuation rod 5368 that is configured for engagement with a sled assembly 5380.

As can be seen in FIG. 97, in at least one embodiment, the sled assembly 5380 includes a base portion 5382 that has a foot portion 5384 that is sized to be slidably received in a slot 5333 in the channel 5322. See FIG. 95. The sled assembly 5380 includes an upstanding support portion 5386 that supports a tissue cutting blade or tissue cutting instrument 5388. The upstanding support portion 5386 terminates in a top portion 5390 that has a pair of laterally extending retaining fins 5392 protruding therefrom. The fins 5392 are positioned to be received within corresponding slots (not shown) in the anvil (not shown). As with the above-described embodiments, the fins 5392 and the foot portion 5384 serve to retain the anvil (not shown) in a desired spaced closed position as the sled assembly 5380 is driven distally through the tissue clamped within the surgical end effector 5312. The upstanding support portion 5386 is configured for attachment to a knife bar 2200 (FIG. 16). The sled assembly 5380 further has a horizontally-extending actuator plate 5394 that is shaped for actuating engagement with each of the actuation rods 5368 on the pushers 5360.

Operation of the surgical end effector 5312 will now be explained with reference to FIGS. 95 and 96. As the sled assembly 5380 is driven in the distal direction "DD" through the staple cartridge 5330, the actuator plate 5394 sequentially contacts the actuation rods 5368 on the pushers 5360. As the sled assembly 5380 continues to move distally, the actuator plate 5394 sequentially contacts the actuator rods 5368 of the drivers 5360 on each side of the elongated slot 5334. Such action causes the drivers 5360 to rotate from a first unactuated position to an actuated portion wherein the pushers 5350 are driven towards the closed anvil. As the pushers 5350 are driven toward the anvil, the surgical staples 5352 thereon are driven into forming contact with the underside of the anvil. Once the robotic system 1000 determines that the sled assembly 5080 has reached its distal most position through sensors or other means, the control system of the robotic system 1000 may then retract the knife bar and sled assembly 5380 back to the starting position. Thereafter, the robotic control system may then activate the procedure for returning the anvil to the open position to release the stapled tissue.

FIGS. 101-105 depict one form of an automated reloading system embodiment of the present invention, generally designated as 5500. In one form, the automated reloading system 5500 is configured to replace a "spent" surgical end effector component in a manipulatable surgical tool portion of a robotic surgical system with a "new" surgical end effector component. As used herein, the term "surgical end effector component" may comprise, for example, a surgical staple cartridge, a disposable loading unit or other end effector components that, when used, are spent and must be replaced with a new component. Furthermore, the term "spent" means that the end effector component has been activated and is no longer useable for its intended purpose in its present state. For example, in the context of a surgical staple cartridge or disposable loading unit, the term "spent" means that at least some of the unformed staples that were previously supported therein have been "fired" therefrom. As used herein, the term "new" surgical end effector component refers to an end effector component that is in condition for its intended use. In the context of a surgical staple cartridge or disposable loading unit, for example, the term "new" refers to such a component that has unformed staples therein and which is otherwise ready for use.

In various embodiments, the automated reloading system 5500 includes a base portion 5502 that may be strategically located within a work envelope 1109 of a robotic arm cart 1100 (FIG. 2) of a robotic system 1000. As used herein, the term "manipulatable surgical tool portion" collectively refers to a surgical tool of the various types disclosed herein and other forms of surgical robotically-actuated tools that are operably attached to, for example, a robotic arm cart 1100 or similar device that is configured to automatically manipulate and actuate the surgical tool. The term "work envelope" as used herein refers to the range of movement of the manipulatable surgical tool portion of the robotic system. FIG. 2 generally depicts an area that may comprise a work envelope of the robotic arm cart 1100. Those of ordinary skill in the art will understand that the shape and size of the work envelope depicted therein is merely illustrative. The ultimate size, shape and location of a work envelope will ultimately depend upon the construction, range of travel limitations, and location of the manipulatable surgical tool portion. Thus, the term "work envelope" as used herein is intended to cover a variety of different sizes and shapes of work envelopes and should not be limited to the specific size and shape of the sample work envelope depicted in FIG. 2.

As can be seen in FIG. 101, the base portion 5502 includes a new component support section or arrangement 5510 that is configured to operably support at least one new surgical end effector component in a "loading orientation". As used herein, the term "loading orientation" means that the new end effector component is supported in such away so as to permit the corresponding component support portion of the manipulatable surgical tool portion to be brought into loading engagement with (i.e., operably seated or operably attached to) the new end effector component (or the new end effector component to be brought into loading engagement with the corresponding component support portion of the manipulatable surgical tool portion) without human intervention beyond that which may be necessary to actuate the robotic system. As will be further appreciated as the present Detailed Description proceeds, in at least one embodiment, the preparation nurse will load the new component support section before the surgery with the appropriate length and color cartridges (some surgical staple cartridges may support certain sizes of staples the size of which may be indicated by the color of the cartridge body) required for completing the surgical procedure. However, no direct human interaction is necessary during the surgery to reload the robotic endocutter. In one form, the surgical end effector component comprises a staple cartridge 2034 that is configured to be operably seated within a component support portion (elongated channel) of any of the various other end effector arrangements described above. For explanation purposes, new (unused) cartridges will be designated as "**2034*a*" and spent cartridges will be designated as "2034*b*". The Figures depict cartridges 2034*a*, 2034*b* designed for use with a surgical end effector 2012 that includes a channel 2022 and an anvil 2024, the construction and operation of which were discussed in detail above. Cartridges 2034*a*, 2034*b* are identical to cartridges 2034 described above. In various embodiments, the cartridges 2034*a*, 2034*b* are configured to be snappingly retained (i.e., loading engagement) within the channel 2022 of a surgical end effector 2012. As the present Detailed Description proceeds, however, those of ordinary skill in the art will appreciate that the unique and novel features of the automated cartridge reloading system 5500** may be effectively employed in connection with the automated removal and installation of other cartridge arrangements without departing from the spirit and scope of the present invention.

In the depicted embodiment, the term "loading orientation" means that the distal tip portion **2035*a* of the a new surgical staple cartridge 2034*a* is inserted into a corresponding support cavity 5512 in the new cartridge support section 5510 such that the proximal end portion 2037*a* of the new surgical staple cartridge 2034*a* is located in a convenient orientation for enabling the arm cart 1100 to manipulate the surgical end effector 2012 into a position wherein the new cartridge 2034*a* may be automatically loaded into the channel 2022 of the surgical end effector 2012. In various embodiments, the base 5502 includes at least one sensor 5504 which communicates with the control system 1003 of the robotic controller 1001 to provide the control system 1003 with the location of the base 5502 and/or the reload length and color doe each staged or new cartridge 2034*a***.

As can also be seen in the Figures, the base 5502 further includes a collection receptacle 5520 that is configured to collect spent cartridges **2034*b* that have been removed or disengaged from the surgical end effector 2012 that is operably attached to the robotic system 1000. In addition, in one form, the automated reloading system 5500 includes an extraction system 5530 for automatically removing the spent end effector component from the corresponding support portion of the end effector or manipulatable surgical tool portion without specific human intervention beyond that which may be necessary to activate the robotic system. In various embodiments, the extraction system 5530 includes an extraction hook member 5532. In one form, for example, the extraction hook member 5532 is rigidly supported on the base portion 5502. In one embodiment, the extraction hook member has at least one hook 5534 formed thereon that is configured to hookingly engage the distal end 2035 of a spent cartridge 2034*b* when it is supported in the elongated channel 2022 of the surgical end effector 2012. In various forms, the extraction hook member 5532 is conveniently located within a portion of the collection receptacle 5520 such that when the spent end effector component (cartridge 2034***b*) is brought into extractive engagement with the extraction hook member 5532, the spent end effector component (cartridge 2034*b*) is dislodged from the corresponding component support portion (elongated channel 2022), and falls into the collection receptacle 5020. Thus, to use this embodiment, the manipulatable surgical tool portion manipulates the end effector attached thereto to bring the distal end 2035 of the spent cartridge 2034*b* therein into hooking engagement with the hook 5534 and then moves the end effector in such a way to dislodge the spent cartridge 2034*b* from the elongated channel 2022.

In other arrangements, the extraction hook member 5532 comprises a rotatable wheel configuration that has a pair of diametrically-opposed hooks 5334 protruding therefrom. Sec FIGS. 101 and 104. The extraction hook member 5532 is rotatably supported within the collection receptacle 5520 and is coupled to an extraction motor 5540 that is controlled by the controller 1001 of the robotic system. This form of the automated reloading system 5500 may be used as follows. FIG. 103 illustrates the introduction of the surgical end effector 2012 that is operably attached to the manipulatable surgical tool portion 1200. As can be seen in that Figure, the arm cart 1100 of the robotic system 1000 locates the surgical end effector 2012 in the shown position wherein the hook end 5534 of the extraction member 5532 hookingly engages the distal end 2035 of the spent cartridge 2034*b* in the surgical end effector 2012. The anvil 2024 of the surgical end effector 2012 is in the open position. After the distal end 2035 of the spent cartridge 2034*b* is engaged with the hook end 5532, the extraction motor 5540 is actuated to rotate the extraction wheel 5532 to disengage the spent cartridge 2034*b* from the channel 2022. To assist with the disengagement of the spent cartridge 2034*b* from the channel 2022 (or if the extraction member 5530 is stationary), the robotic system 1000 may move the surgical end effector 2012 in an upward direction (arrow "U" in FIG. 104). As the spent cartridge 2034*b* is dislodged from the channel 2022, the spent cartridge 2034*b* falls into the collection receptacle 5520. Once the spent cartridge 2034*b* has been removed from the surgical end effector 2012, the robotic system 1000 moves the surgical end effector 2012 to the position shown in FIG. 105.

In various embodiments, a sensor arrangement 5533 is located adjacent to the extraction member 5532 that is in communication with the controller 1001 of the robotic system 1000. The sensor arrangement 5533 may comprise a sensor that is configured to sense the presence of the surgical end effector 2012 and, more particularly the tip 2035*b* of the spent surgical staple cartridge 2034*b* thereof as the distal tip portion 2035*b* is brought into engagement with the extraction member 5532. In some embodiments, the sensor arrangement 5533 may comprise, for example, a light curtain arrangement. However, other forms of proximity sensors may be employed. In such arrangement, when the surgical end effector 2012 with the spent surgical staple cartridge 2034*b* is brought into extractive engagement with the extraction member 5532, the sensor senses the distal tip 2035*b* of the surgical staple cartridge 2034*b* (e.g., the light curtain is broken). When the extraction member 5532 spins and pops the surgical staple cartridge 2034*b* loose and it falls into the collection receptacle 5520, the light curtain is again unbroken. Because the surgical end effector 2012 was not moved during this procedure, the robotic controller 1001 is assured that the spent surgical staple cartridge 2034*b* has been removed therefrom. Other sensor arrangements may also be successfully employed to provide the robotic controller 1001 with an indication that the spent surgical staple cartridge 2034*b* has been removed from the surgical end effector 2012.

As can be seen in FIG. 105, the surgical end effector 2012 is positioned to grasp a new surgical staple cartridge 2034*a* between the channel 2022 and the anvil 2024. More specifically, as shown in FIGS. 102 and 105, each cavity 5512 has a corresponding upstanding pressure pad 5514 associated with it. The surgical end effector 2012 is located such that the pressure pad 5514 is located between the new cartridge 2034*a* and the anvil 2024. Once in that position, the robotic system 1000 closes the anvil 2024 onto the pressure pad 5514 which serves to push the new cartridge 2034*a* into snapping engagement with the channel 2022 of the surgical end effector 2012. Once the new cartridge 2034*a* has been snapped into position within the elongated channel 2022, the robotic system 1000 then withdraws the surgical end effector 2012 from the automated cartridge reloading system 5500 for use in connection with performing another surgical procedure.

FIGS. 106-110 depict another automated reloading system 5600 that may be used to remove a spent disposable loading unit 3612 from a manipulatable surgical tool arrangement 3600 (FIGS. 53-66) that is operably attached to an arm cart 1100 or other portion of a robotic system 1000 and reload a new disposable loading unit 3612 therein. As can be seen in FIGS. 106 and 107, one form of the automated reloading system 5600 includes a housing 5610 that has a movable support assembly in the form of a rotary carrousel top plate 5620 supported thereon which cooperates with the housing 5610 to form a hollow enclosed area 5612. The automated reloading system 5600 is configured to be operably supported within the work envelop of the manipulatable surgical tool portion of a robotic system as was described above. In various embodiments, the rotary carrousel plate 5620 has a plurality of holes 5622 for supporting a plurality of orientation tubes 5660 therein. As can be seen in FIGS. 107 and 108, the rotary carrousel plate 5620 is affixed to a spindle shaft 5624. The spindle shaft 5624 is centrally disposed within the enclosed area 5612 and has a spindle gear 5626 attached thereto. The spindle gear 5626 is in meshing engagement with a carrousel drive gear 5628 that is coupled to a carrousel drive motor 5630 that is in operative communication with the robotic controller 1001 of the robotic system 1000.

Various embodiments of the automated reloading system 5600 may also include a carrousel locking assembly, generally designated as 5640. In various forms, the carrousel locking assembly 5640 includes a cam disc 5642 that is affixed to the spindle shaft 5624. The spindle gear 5626 may be attached to the underside of the cam disc 5642 and the cam disc 5642 may be keyed onto the spindle shaft 5624. In alternative arrangements, the spindle gear 5626 and the cam disc 5642 may be independently non-rotatably affixed to the spindle shaft 5624. As can be seen in FIGS. 107 and 108, a plurality of notches 5644 are spaced around the perimeter of the cam disc 5642. A locking arm 5648 is pivotally mounted within the housing 5610 and is biased into engagement with the perimeter of the cam disc 5642 by a locking spring 5649. As can be seen in FIG. 106, the outer perimeter of the cam disc 5642 is rounded to facilitate rotation of the cam disc 5642 relative to the locking arm 5648. The edges of each notch 5644 are also rounded such that when the cam disc 5642 is rotated, the locking arm 5648 is cammed out of engagement with the notches 5644 by the perimeter of the cam disc 5642.

Various forms of the automated reloading system 5600 are configured to support a portable/replaceable tray assembly 5650 that is configured to support a plurality of disposable loading units 3612 in individual orientation tubes 5660. More specifically and with reference to FIGS. 107 and 108, the replaceable tray assembly 5650 comprises a tray 5652 that has a centrally-disposed locator spindle 5654 protruding from the underside thereof. The locator spindle 5654 is sized to be received within a hollow end 5625 of spindle shaft 5624. The tray 5652 has a plurality of holes 5656 therein that are configured to support an orientation tube 5660 therein. Each orientation tube 5660 is oriented within a corresponding hole 5656 in the replaceable tray assembly 5650 in a desired orientation by a locating fin 5666 on the orientation tube 5660 that is designed to be received within a corresponding locating slot 5658 in the tray assembly 5650. In at least one embodiment, the locating fin 5666 has a substantially V-shaped cross-sectional shape that is sized to fit within a V-shaped locating slot 5658. Such arrangement serves to orient the orientation tube 5660 in a desired starting position while enabling it to rotate within the hole 5656 when a rotary motion is applied thereto. That is, when a rotary motion is applied to the orientation tube 5660 the V-shaped locating fin 5666 will pop out of its corresponding locating slot enabling the tube 5660 to rotate relative to the tray 5652 as will be discussed in further detail below. As can also be seen in FIGS. 106-108, the replaceable tray 5652 may be provided with one or more handle portions 5653 to facilitate transport of the tray assembly 5652 when loaded with orientation tubes 5660.

As can be seen in FIG. 110, each orientation tube 5660 comprises a body portion 5662 that has a flanged open end 5664. The body portion 5662 defines a cavity 5668 that is sized to receive a portion of a disposable loading unit 3612 therein. To properly orient the disposable loading unit 3612 within the orientation tube 5660, the cavity 5668 has a flat locating surface 5670 formed therein. As can be seen in FIG. 110, the flat locating surface 5670 is configured to facilitate the insertion of the disposable loading unit into the cavity 5668 in a desired or predetermined non-rotatable orientation. In addition, the end 5669 of the cavity 5668 may include a foam or cushion material 5672 that is designed to cushion the distal end of the disposable loading unit 3612 within the cavity 5668. Also, the length of the locating surface may cooperate with a sliding support member 3689 of the axial drive assembly 3680 of the disposable loading unit 3612 to further locate the disposable loading unit 3612 at a desired position within the orientation tube 5660.

The orientation tubes 5660 may be fabricated from Nylon, polycarbonate, polyethylene, liquid crystal polymer, 6061 or 7075 aluminum, titanium, 300 or 400 series stainless steel, coated or painted steel, plated steel, etc. and, when loaded in the replaceable tray 5662 and the locator spindle 5654 is inserted into the hollow end 5625 of spindle shaft 5624, the orientation tubes 5660 extend through corresponding holes 5662 in the carrousel top plate 5620. Each replaceable tray 5662 is equipped with a location sensor 5663 that communicates with the control system 1003 of the controller 1001 of the robotic system 1000. The sensor 5663 serves to identify the location of the reload system, and the number, length, color and fired status of each reload housed in the tray. In addition, an optical sensor or sensors 5665 that communicate with the robotic controller 1001 may be employed to sense the type/size/length of disposable loading units that are loaded within the tray 5662.

Various embodiments of the automated reloading system 5600 further include a drive assembly 5680 for applying a rotary motion to the orientation tube 5660 holding the disposable loading unit 3612 to be attached to the shaft 3700 of the surgical tool 3600 (collectively the "manipulatable surgical tool portion") that is operably coupled to the robotic system. The drive assembly 5680 includes a support yoke 5682 that is attached to the locking arm 5648. Thus, the support yoke 5682 pivots with the locking arm 5648. The support yoke 5682 rotatably supports a tube idler wheel 5684 and a tube drive wheel 5686 that is driven by a tube motor 5688 attached thereto. Tube motor 5688 communicates with the control system 1003 and is controlled thereby. The tube idler wheel 5684 and tube drive wheel 5686 are fabricated from, for example, natural rubber, sanoprene, isoplast, etc. such that the outer surfaces thereof create sufficient amount of friction to result in the rotation of an orientation tube 5660 in contact therewith upon activation of the tube motor 5688. The idler wheel 5684 and tube drive wheel 5686 are oriented relative to each other to create a cradle area 5687 therebetween for receiving an orientation tube 5060 in driving engagement therein.

In use, one or more of the orientation tubes 5660 loaded in the automated reloading system 5600 are left empty, while the other orientation tubes 5660 may operably support a corresponding new disposable loading unit 3612 therein. As will be discussed in further detail below, the empty orientation tubes 5660 are employed to receive a spent disposable loading unit 3612 therein.

The automated reloading system 5600 may be employed as follows after the system 5600 is located within the work envelope of the manipulatable surgical tool portion of a robotic system. If the manipulatable surgical tool portion has a spent disposable loading unit 3612 operably coupled thereto, one of the orientation tubes 5660 that are supported on the replaceable tray 5662 is left empty to receive the spent disposable loading unit 3612 therein. If, however, the manipulatable surgical tool portion does not have a disposable loading unit 3612 operably coupled thereto, each of the orientation tubes 5660 may be provided with a properly oriented new disposable loading unit 3612.

As described hereinabove, the disposable loading unit 3612 employs a rotary "bayonet-type" coupling arrangement for operably coupling the disposable loading unit 3612 to a corresponding portion of the manipulatable surgical tool portion. That is, to attach a disposable loading unit 3612 to the corresponding portion of the manipulatable surgical tool portion (3700—see FIG. 59, 60), a rotary installation motion must be applied to the disposable loading unit 3612 and/or the corresponding portion of the manipulatable surgical tool portion when those components have been moved into loading engagement with each other. Such installation motions are collectively referred to herein as "loading motions". Likewise, to decouple a spent disposable loading unit 3612 from the corresponding portion of the manipulatable surgical tool, a rotary decoupling motion must be applied to the spent disposable loading unit 3612 and/or the corresponding portion of the manipulatable surgical tool portion while simultaneously moving the spent disposable loading unit and the corresponding portion of the manipulatable surgical tool away from each other. Such decoupling motions are collectively referred to herein as "extraction motions".

To commence the loading process, the robotic system 1000 is activated to manipulate the manipulatable surgical tool portion and/or the automated reloading system 5600 to bring the manipulatable surgical tool portion into loading engagement with the new disposable loading unit 3612 that is supported in the orientation tube 5660 that is in driving engagement with the drive assembly 5680. Once the robotic controller 1001 (FIG. 1) of the robotic control system 1000 has located the manipulatable surgical tool portion in loading engagement with the new disposable loading unit 3612, the robotic controller 1001 activates the drive assembly 5680 to apply a rotary loading motion to the orientation tube 5660 in which the new disposable loading unit 3612 is supported and/or applies another rotary loading motion to the corresponding portion of the manipulatable surgical tool portion. Upon application of such rotary loading motions(s), the robotic controller 1001 also causes the corresponding portion of the manipulatable surgical tool portion to be moved towards the new disposable loading unit 3612 into loading engagement therewith. Once the disposable loading unit 3612 is in loading engagement with the corresponding portion of the manipulatable tool portion, the loading motions are discontinued and the manipulatable surgical tool portion may be moved away from the automated reloading system 5600 carrying with it the new disposable loading unit 3612 that has been operably coupled thereto.

To decouple a spent disposable loading unit 3612 from a corresponding manipulatable surgical tool portion, the robotic controller 1001 of the robotic system manipulates the manipulatable surgical tool portion so as to insert the distal end of the spent disposable loading unit 3612 into the empty orientation tube 5660 that remains in driving engagement with the drive assembly 5680. Thereafter, the robotic controller 1001 activates the drive assembly 5680 to apply a rotary extraction motion to the orientation tube 5660 in which the spent disposable loading unit 3612 is supported and/or applies a rotary extraction motion to the corresponding portion of the manipulatable surgical tool portion. The robotic controller 1001 also causes the manipulatable surgical tool portion to withdraw away from the spent rotary disposable loading unit 3612. Thereafter the rotary extraction motion(s) are discontinued.

After the spent disposable loading unit 3612 has been removed from the manipulatable surgical tool portion, the robotic controller 1001 may activate the carrousel drive motor 5630 to index the carrousel top plate 5620 to bring another orientation tube 5660 that supports a new disposable loading unit 3612 therein into driving engagement with the drive assembly 5680. Thereafter, the loading process may be repeated to attach the new disposable loading unit 3612 therein to the portion of the manipulatable surgical tool portion. The robotic controller 1001 may record the number of disposable loading units that have been used from a particular replaceable tray 5652. Once the controller 1001 determines that all of the new disposable loading units 3612 have been used from that tray, the controller 1001 may provide the surgeon with a signal (visual and/or audible) indicating that the tray 5652 supporting all of the spent disposable loading units 3612 must be replaced with a new tray 5652 containing new disposable loading units 3612.

FIGS. 111-116 depict another non-limiting embodiment of a surgical tool 6000 of the present invention that is well-adapted for use with a robotic system 1000 that has a tool drive assembly 1010 (FIG. 6) that is operatively coupled to a master controller 1001 that is operable by inputs from an operator (i.e., a surgeon). As can be seen in FIG. 111, the surgical tool 6000 includes a surgical end effector 6012 that comprises an endocutter. In at least one form, the surgical tool 6000 generally includes an elongated shaft assembly 6008 that has a proximal closure tube 6040 and a distal closure tube 6042 that are coupled together by an articulation joint 6100. The surgical tool 6000 is operably coupled to the manipulator by a tool mounting portion, generally designated as 6200. The surgical tool 6000 further includes an interface 6030 which may mechanically and electrically couple the tool mounting portion 6200 to the manipulator in the various manners described in detail above.

In at least one embodiment, the surgical tool 6000 includes a surgical end effector 6012 that comprises, among other things, at least one component 6024 that is selectively movable between first and second positions relative to at least one other component 6022 in response to various control motions applied to component 6024 as will be discussed in further detail below to perform a surgical procedure. In various embodiments, component 6022 comprises an elongated channel 6022 configured to operably support a surgical staple cartridge 6034 therein and component 6024 comprises a pivotally translatable clamping member, such as an anvil 6024. Various embodiments of the surgical end effector 6012 are configured to maintain the anvil 6024 and elongated channel 6022 at a spacing that assures effective stapling and severing of tissue clamped in the surgical end effector 6012. Unless otherwise stated, the end effector 6012 is similar to the surgical end effector 2012 described above and includes a cutting instrument (not shown) and a sled (not shown). The anvil 6024 may include a tab 6027 at its proximal end that interacts with a component of the mechanical closure system (described further below) to facilitate the opening of the anvil 6024. The elongated channel 6022 and the anvil 6024 may be made of an electrically conductive material (such as metal) so that they may serve as part of an antenna that communicates with sensor(s) in the end effector, as described above. The surgical staple cartridge 6034 could be made of a nonconductive material (such as plastic) and the sensor may be connected to or disposed in the surgical staple cartridge 6034, as was also described above.

As can be seen in FIG. 111, the surgical end effector 6012 is attached to the tool mounting portion 6200 by the elongated shaft assembly 6008 according to various embodiments. As shown in the illustrated embodiment, the elongated shaft assembly 6008 includes an articulation joint generally designated as 6100 that enables the surgical end effector 6012 to be selectively articulated about a first tool articulation axis AA1-AA1 that is substantially transverse to a longitudinal tool axis LT-LT and a second tool articulation axis AA2-AA2 that is substantially transverse to the longitudinal tool axis LT-LT as well as the first articulation axis AA1-AA1. See FIG. 112. In various embodiments, the elongated shaft assembly 6008 includes a closure tube assembly 6009 that comprises a proximal closure tube 6040 and a distal closure tube 6042 that are pivotably linked by a pivot links 6044 and 6046. The closure tube assembly 6009 is movably supported on a spine assembly generally designated as 6102.

As can be seen in FIG. 113, the proximal closure tube 6040 is pivotally linked to an intermediate closure tube joint 6043 by an upper pivot link 6044U and a lower pivot link 6044L such that the intermediate closure tube joint 6043 is pivotable relative to the proximal closure tube 6040 about a first closure axis CA1-CA1 and a second closure axis CA2-CA2. In various embodiments, the first closure axis CA1-CA1 is substantially parallel to the second closure axis CA2-CA2 and both closure axes CA1-CA1, CA2-CA2 are substantially transverse to the longitudinal tool axis LT-LT. As can be further seen in FIG. 134, the intermediate closure tube joint 6043 is pivotally linked to the distal closure tube 6042 by a left pivot link 6046L and a right pivot link 6046R such that the intermediate closure tube joint 6043 is pivotable relative to the distal closure tube 6042 about a third closure axis CA3-CA3 and a fourth closure axis CA4-CA4. In various embodiments, the third closure axis CA3-CA3 is substantially parallel to the fourth closure axis CA4-CA4 and both closure axes CA3-CA3, CA4-CA4 are substantially transverse to the first and second closure axes CA1-CA1, CA2-CA2 as well as to longitudinal tool axis LT-LT.

The closure tube assembly 6009 is configured to axially slide on the spine assembly 6102 in response to actuation motions applied thereto. The distal closure tube 6042 includes an opening 6045 which interfaces with the tab 6027 on the anvil 6024 to facilitate opening of the anvil 6024 as the distal closure tube 6042 is moved axially in the proximal direction "PD". The closure tubes 6040, 6042 may be made of electrically conductive material (such as metal) so that they may serve as part of the antenna, as described above. Components of the spine assembly 6102 may be made of a nonconductive material (such as plastic).

As indicated above, the surgical tool 6000 includes a tool mounting portion 6200 that is configured for operable attachment to the tool mounting assembly 1010 of the robotic system 1000 in the various manners described in detail above. As can be seen in FIG. 115, the tool mounting portion 6200 comprises a tool mounting plate 6202 that operably supports a transmission arrangement 6204 thereon. In various embodiments, the transmission arrangement 6204 includes an articulation transmission 6142 that comprises a portion of an articulation system 6140 for articulating the surgical end effector 6012 about a first tool articulation axis TA1-TA1 and a second tool articulation axis TA2-TA2. The first tool articulation axis TA1-TA1 is substantially transverse to the second tool articulation axis TA2-TA2 and both of the first and second tool articulation axes are substantially transverse to the longitudinal tool axis LT-LT. See FIG. 112.

To facilitate selective articulation of the surgical end effector 6012 about the first and second tool articulation axes TA1-TA1, TA2-TA2, the spine assembly 6102 comprises a proximal spine portion 6110 that is pivotally coupled to a distal spine portion 6120 by pivot pins 6122 for selective pivotal travel about TA1-TA1. Similarly, the distal spine portion 6120 is pivotally attached to the elongated channel 6022 of the surgical end effector 6012 by pivot pins 6124 to enable the surgical end effector 6012 to selectively pivot about the second tool axis TA2-TA2 relative to the distal spine portion 6120.

In various embodiments, the articulation system 6140 further includes a plurality of articulation elements that operably interface with the surgical end effector 6012 and an articulation control arrangement 6160 that is operably supported in the tool mounting member 6200 as will described in further detail below. In at least one embodiment, the articulation elements comprise a first pair of first articulation cables 6144 and 6146. The first articulation cables are located on a first or right side of the longitudinal tool axis. Thus, the first articulation cables are referred to herein as a right upper cable 6144 and a right lower cable 6146. The right upper cable 6144 and the right lower cable 6146 extend through corresponding passages 6147, 6148, respectively along the right side of the proximal spine portion 6110. See FIG. 137. The articulation system 6140 further includes a second pair of second articulation cables 6150, 6152. The second articulation cables are located on a second or left side of the longitudinal tool axis. Thus, the second articulation cables are referred to herein as a left upper articulation cable 6150 and a left articulation cable 6152. The left upper articulation cable 6150 and the left lower articulation cable 6152 extend through passages 6153, 6154, respectively in the proximal spine portion 6110.

As can be seen in FIG. 112, the right upper cable 6144 extends around an upper pivot joint 6123 and is attached to a left upper side of the elongated channel 6022 at a left pivot joint 6125. The right lower cable 6146 extends around a lower pivot joint 6126 and is attached to a left lower side of the elongated channel 6022 at left pivot joint 6125. The left upper cable 6150 extends around the upper pivot joint 6123 and is attached to a right upper side of the elongated channel 6022 at a right pivot joint 6127. The left lower cable 6152 extends around the lower pivot joint 6126 and is attached to a right lower side of the elongated channel 6022 at right pivot joint 6127. Thus, to pivot the surgical end effector 6012 about the first tool articulation axis TA1-TA1 to the left (arrow "L"), the right upper cable 6144 and the right lower cable 6146 must be pulled in the proximal direction "PD". To articulate the surgical end effector 6012 to the right (arrow "R") about the first tool articulation axis TA1-TA1, the left upper cable 6150 and the left lower cable 6152 must be pulled in the proximal direction "PD". To articulate the surgical end effector 6012 about the second tool articulation axis TA2-TA2, in an upward direction (arrow "U"), the right upper cable 6144 and the left upper cable 6150 must be pulled in the proximal direction "PD". To articulate the surgical end effector 6012 in the downward direction (arrow "DW") about the second tool articulation axis TA2-TA2, the right lower cable 6146 and the left lower cable 6152 must be pulled in the proximal direction "PD".

The proximal ends of the articulation cables 6144, 6146, 6150, 6152 are coupled to the articulation control arrangement 6160 which comprises a ball joint assembly that is a part of the articulation transmission 6142. More specifically and with reference to FIG. 116, the ball joint assembly 6160 includes a ball-shaped member 6162 that is formed on a proximal portion of the proximal spine 6110. Movably supported on the ball-shaped member 6162 is an articulation control ring 6164. As can be further seen in FIG. 116, the proximal ends of the articulation cables 6144, 6146, 6150, 6152 are coupled to the articulation control ring 6164 by corresponding ball joint arrangements 6166. The articulation control ring 6164 is controlled by an articulation drive assembly 6170. As can be most particularly seen in FIG. 116, the proximal ends of the first articulation cables 6144, 6146 are attached to the articulation control ring 6164 at corresponding spaced first points 6149, 6151 that are located on plane 6159. Likewise, the proximal ends of the second articulation cables 6150, 6152 are attached to the articulation control ring 6164 at corresponding spaced second points 6153, 6155 that are also located along plane 6159. As the present Detailed Description proceeds, those of ordinary skill in the art will appreciate that such cable attachment configuration on the articulation control ring 6164 facilitates the desired range of articulation motions as the articulation control ring 6164 is manipulated by the articulation drive assembly 6170.

In various forms, the articulation drive assembly 6170 comprises a horizontal articulation assembly generally designated as 6171. In at least one form, the horizontal articulation assembly 6171 comprises a horizontal push cable 6172 that is attached to a horizontal gear arrangement 6180. The articulation drive assembly 6170 further comprises a vertically articulation assembly generally designated as 6173. In at least one form, the vertical articulation assembly 6173 comprises a vertical push cable 6174 that is attached to a vertical gear arrangement 6190. As can be seen in FIGS. 115 and 116, the horizontal push cable 6172 extends through a support plate 6167 that is attached to the proximal spine portion 6110. The distal end of the horizontal push cable 6174 is attached to the articulation control ring 6164 by a corresponding ball/pivot joint 6168. The vertical push cable 6174 extends through the support plate 6167 and the distal end thereof is attached to the articulation control ring 6164 by a corresponding ball/pivot joint 6169.

The horizontal gear arrangement 6180 includes a horizontal driven gear 6182 that is pivotally mounted on a horizontal shaft 6181 that is attached to a proximal portion of the proximal spine portion 6110. The proximal end of the horizontal push cable 6172 is pivotally attached to the horizontal driven gear 6182 such that, as the horizontal driven gear 6172 is rotated about horizontal pivot axis HA, the horizontal push cable 6172 applies a first pivot motion to the articulation control ring 6164. Likewise, the vertical gear arrangement 6190 includes a vertical driven gear 6192 that is pivotally supported on a vertical shaft 6191 attached to the proximal portion of the proximal spine portion 6110 for pivotal travel about a vertical pivot axis VA. The proximal end of the vertical push cable 6174 is pivotally attached to the vertical driven gear 6192 such that as the vertical driven gear 6192 is rotated about vertical pivot axis VA, the vertical push cable 6174 applies a second pivot motion to the articulation control ring 6164.

The horizontal driven gear 6182 and the vertical driven gear 6192 are driven by an articulation gear train 6300 that operably interfaces with an articulation shifter assembly 6320. In at least one form, the articulation shifter assembly comprises an articulation drive gear 6322 that is coupled to a corresponding one of the driven discs or elements 1304 on the adapter side 1307 of the tool mounting plate 6202. See FIG. 10. Thus, application of a rotary input motion from the robotic system 1000 through the tool drive assembly 1010 to the corresponding driven element 1304 will cause rotation of the articulation drive gear 6322 when the interface 1230 is coupled to the tool holder 1270. An articulation driven gear 6324 is attached to a splined shifter shaft 6330 that is rotatably supported on the tool mounting plate 6202. The articulation driven gear 6324 is in meshing engagement with the articulation drive gear 6322 as shown. Thus, rotation of the articulation drive gear 6322 will result in the rotation of the shaft 6330. In various forms, a shifter driven gear assembly 6340 is movably supported on the splined portion 6332 of the shifter shaft 6330.

In various embodiments, the shifter driven gear assembly 6340 includes a driven shifter gear 6342 that is attached to a shifter plate 6344. The shifter plate 6344 operably interfaces with a shifter solenoid assembly 6350. The shifter solenoid assembly 6350 is coupled to corresponding pins 6352 by conductors 6352. See FIG. 115. Pins 6352 are oriented to electrically communicate with slots 1258 (FIG. 9) on the tool side 1244 of the adaptor 1240. Such arrangement serves to electrically couple the shifter solenoid assembly 6350 to the robotic controller 1001. Thus, activation of the shifter solenoid 6350 will shift the shifter driven gear assembly 6340 on the splined portion 6332 of the shifter shaft 6330 as represented by arrow "S" in FIGS. 115 and 116. Various embodiments of the articulation gear train 6300 further include a horizontal gear assembly 6360 that includes a first horizontal drive gear 6362 that is mounted on a shaft 6361 that is rotatably attached to the tool mounting plate 6202. The first horizontal drive gear 6362 is supported in meshing engagement with a second horizontal drive gear 6364. As can be seen in FIG. 116, the horizontal driven gear 6182 is in meshing engagement with the distal face portion 6365 of the second horizontal driven gear 6364.

Various embodiments of the articulation gear train 6300 further include a vertical gear assembly 6370 that includes a first vertical drive gear 6372 that is mounted on a shaft 6371 that is rotatably supported on the tool mounting plate 6202. The first vertical drive gear 6372 is supported in meshing engagement with a second vertical drive gear 6374 that is concentrically supported with the second horizontal drive gear 6364. The second vertical drive gear 6374 is rotatably supported on the proximal spine portion 6110 for travel therearound. The second horizontal drive gear 6364 is rotatably supported on a portion of said second vertical drive gear 6374 for independent rotatable travel thereon. As can be seen in FIG. 116, the vertical driven gear 6192 is in meshing engagement with the distal face portion 6375 of the second vertical driven gear 6374.

In various forms, the first horizontal drive gear 6362 has a first diameter and the first vertical drive gear 6372 has a second diameter. As can be seen in FIGS. 115 and 116, the shaft 6361 is not on a common axis with shaft 6371. That is, the first horizontal driven gear 6362 and the first vertical driven gear 6372 do not rotate about a common axis. Thus, when the shifter gear 6342 is positioned in a center "locking" position such that the shifter gear 6342 is in meshing engagement with both the first horizontal driven gear 6362 and the first vertical drive gear 6372, the components of the articulation system 6140 are locked in position. Thus, the shiftable shifter gear 6342 and the arrangement of first horizontal and vertical drive gears 6362, 6372 as well as the articulation shifter assembly 6320 collectively may be referred to as an articulation locking system, generally designated as 6380.

In use, the robotic controller 1001 of the robotic system 1000 may control the articulation system 6140 as follows. To articulate the end effector 6012 to the left about the first tool articulation axis TA1-TA1, the robotic controller 1001 activates the shifter solenoid assembly 6350 to bring the shifter gear 6342 into meshing engagement with the first horizontal drive gear 6362. Thereafter, the controller 1001 causes a first rotary output motion to be applied to the articulation drive gear 6322 to drive the shifter gear in a first direction to ultimately drive the horizontal driven gear 6182 in another first direction. The horizontal driven gear 6182 is driven to pivot the articulation ring 6164 on the ball-shaped portion 6162 to thereby pull right upper cable 6144 and the right lower cable 6146 in the proximal direction "PD". To articulate the end effector 6012 to the right about the first tool articulation axis TA1-TA1, the robotic controller 1001 activates the shifter solenoid assembly 6350 to bring the shifter gear 6342 into meshing engagement with the first horizontal drive gear 6362. Thereafter, the controller 1001 causes the first rotary output motion in an opposite direction to be applied to the articulation drive gear 6322 to drive the shifter gear 6342 in a second direction to ultimately drive the horizontal driven gear 6182 in another second direction. Such actions result in the articulation control ring 6164 moving in such a manner as to pull the left upper cable 6150 and the left lower cable 6152 in the proximal direction "PD". In various embodiments the gear ratios and frictional forces generated between the gears of the vertical gear assembly 6370 serve to prevent rotation of the vertical driven gear 6192 as the horizontal gear assembly 6360 is actuated.

To articulate the end effector 6012 in the upper direction about the second tool articulation axis TA2-TA2, the robotic controller 1001 activates the shifter solenoid assembly 6350 to bring the shifter gear 6342 into meshing engagement with the first vertical drive gear 6372. Thereafter, the controller 1001 causes the first rotary output motion to be applied to the articulation drive gear 6322 to drive the shifter gear 6342 in a first direction to ultimately drive the vertical driven gear 6192 in another first direction. The vertical driven gear 6192 is driven to pivot the articulation ring 6164 on the ball-shaped portion 6162 of the proximal spine portion 6110 to thereby pull right upper cable 6144 and the left upper cable 6150 in the proximal direction "PD". To articulate the end effector 6012 in the downward direction about the second tool articulation axis TA2-TA2, the robotic controller 1001 activates the shifter solenoid assembly 6350 to bring the shifter gear 6342 into meshing engagement with the first vertical drive gear 6372. Thereafter, the controller 1001 causes the first rotary output motion to be applied in an opposite direction to the articulation drive gear 6322 to drive the shifter gear 6342 in a second direction to ultimately drive the vertical driven gear 6192 in another second direction. Such actions thereby cause the articulation control ring 6164 to pull the right lower cable 6146 and the left lower cable 6152 in the proximal direction "PD". In various embodiments, the gear ratios and frictional forces generated between the gears of the horizontal gear assembly 6360 serve to prevent rotation of the horizontal driven gear 6182 as the vertical gear assembly 6370 is actuated.

In various embodiments, a variety of sensors may communicate with the robotic controller 1001 to determine the articulated position of the end effector 6012. Such sensors may interface with, for example, the articulation joint 6100 or be located within the tool mounting portion 6200. For example, sensors may be employed to detect the position of the articulation control ring 6164 on the ball-shaped portion 6162 of the proximal spine portion 6110. Such feedback from the sensors to the controller 1001 permits the controller 1001 to adjust the amount of rotation and the direction of the rotary output to the articulation drive gear 6322. Further, as indicated above, when the shifter drive gear 6342 is centrally positioned in meshing engagement with the first horizontal drive gear 6362 and the first vertical drive gear 6372, the end effector 6012 is locked in the articulated position. Thus, after the desired amount of articulation has been attained, the controller 1001 may activate the shifter solenoid assembly 6350 to bring the shifter gear 6342 into meshing engagement with the first horizontal drive gear 6362 and the first vertical drive gear 6372. In alternative embodiments, the shifter solenoid assembly 6350 may be spring activated to the central locked position.

In use, it may be desirable to rotate the surgical end effector 6012 about the longitudinal tool axis LT-LT. In at least one embodiment, the transmission arrangement 6204 on the tool mounting portion includes a rotational transmission assembly 6400 that is configured to receive a corresponding rotary output motion from the tool drive assembly 1010 of the robotic system 1000 and convert that rotary output motion to a rotary control motion for rotating the elongated shaft assembly 6008 (and surgical end effector 6012) about the longitudinal tool axis LT-LT. In various embodiments, for example, a proximal end portion 6041 of the proximal closure tube 6040 is rotatably supported on the tool mounting plate 6202 of the tool mounting portion 6200 by a forward support cradle 6205 and a closure sled 6510 that is also movably supported on the tool mounting plate 6202. In at least one form, the rotational transmission assembly 6400 includes a tube gear segment 6402 that is formed on (or attached to) the proximal end 6041 of the proximal closure tube 6040 for operable engagement by a rotational gear assembly 6410 that is operably supported on the tool mounting plate 6202. As can be seen in FIG. 115, the rotational gear assembly 6410, in at least one embodiment, comprises a rotation drive gear 6412 that is coupled to a corresponding second one of the driven discs or elements 1304 on the adapter side 1307 of the tool mounting plate 6202 when the tool mounting portion 6200 is coupled to the tool drive assembly 1010. See FIG. 10. The rotational gear assembly 6410 further comprises a first rotary driven gear 6414 that is rotatably supported on the tool mounting plate 6202 in meshing engagement with the rotation drive gear 6412. The first rotary driven gear 6414 is attached to a drive shaft 6416 that is rotatably supported on the tool mounting plate 6202. A second rotary driven gear 6418 is attached to the drive shaft 6416 and is in meshing engagement with tube gear segment 6402 on the proximal closure tube 6040. Application of a second rotary output motion from the tool drive assembly 1010 of the robotic system 1000 to the corresponding driven element 1304 will thereby cause rotation of the rotation drive gear 6412. Rotation of the rotation drive gear 6412 ultimately results in the rotation of the elongated shaft assembly 6008 (and the surgical end effector 6012) about the longitudinal tool axis LT-LT. It will be appreciated that the application of a rotary output motion from the tool drive assembly 1010 in one direction will result in the rotation of the elongated shaft assembly 6008 and surgical end effector 6012 about the longitudinal tool axis LT-LT in a first direction and an application of the rotary output motion in an opposite direction will result in the rotation of the elongated shaft assembly 6008 and surgical end effector 6012 in a second direction that is opposite to the first direction.

In at least one embodiment, the closure of the anvil 2024 relative to the staple cartridge 2034 is accomplished by axially moving a closure portion of the elongated shaft assembly 2008 in the distal direction "DD" on the spine assembly 2049. As indicated above, in various embodiments, the proximal end portion 6041 of the proximal closure tube 6040 is supported by the closure sled 6510 which comprises a portion of a closure transmission, generally depicted as 6512. As can be seen in FIG. 115, the proximal end portion 6041 of the proximal closure tube portion 6040 has a collar 6048 formed thereon. The closure sled 6510 is coupled to the collar 6048 by a yoke 6514 that engages an annular groove 6049 in the collar 6048. Such arrangement serves to enable the collar 6048 to rotate about the longitudinal tool axis LT-LT while still being coupled to the closure transmission 6512. In various embodiments, the closure sled 6510 has an upstanding portion 6516 that has a closure rack gear 6518 formed thereon. The closure rack gear 6518 is configured for driving engagement with a closure gear assembly 6520. See FIG. 115.

In various forms, the closure gear assembly 6520 includes a closure spur gear 6522 that is coupled to a corresponding second one of the driven discs or elements 1304 on the adapter side 1307 of the tool mounting plate 6202. See FIG. 10. Thus, application of a third rotary output motion from the tool drive assembly 1010 of the robotic system 1000 to the corresponding second driven element 1304 will cause rotation of the closure spur gear 6522 when the tool mounting portion 6202 is coupled to the tool drive assembly 1010. The closure gear assembly 6520 further includes a closure reduction gear set 6524 that is supported in meshing engagement with the closure spur gear 6522 and the closure rack gear 2106. Thus, application of a third rotary output motion from the tool drive assembly 1010 of the robotic system 1000 to the corresponding second driven element 1304 will cause rotation of the closure spur gear 6522 and the closure transmission 6512 and ultimately drive the closure sled 6510 and the proximal closure tube 6040 axially on the proximal spine portion 6110. The axial direction in which the proximal closure tube 6040 moves ultimately depends upon the direction in which the third driven element 1304 is rotated. For example, in response to one rotary output motion received from the tool drive assembly 1010 of the robotic system 1000, the closure sled 6510 will be driven in the distal direction "DD" and ultimately drive the proximal closure tube 6040 in the distal direction "DD". As the proximal closure tube 6040 is driven distally, the distal closure tube 6042 is also driven distally by virtue of its connection with the proximal closure tube 6040. As the distal closure tube 6042 is driven distally, the end of the closure tube 6042 will engage a portion of the anvil 6024 and cause the anvil 6024 to pivot to a closed position. Upon application of an "opening" out put motion from the tool drive assembly 1010 of the robotic system 1000, the closure sled 6510 and the proximal closure tube 6040 will be driven in the proximal direction "PD" on the proximal spine portion 6110. As the proximal closure tube 6040 is driven in the proximal direction "PD", the distal closure tube 6042 will also be driven in the proximal direction "PD". As the distal closure tube 6042 is driven in the proximal direction "PD", the opening 6045 therein interacts with the tab 6027 on the anvil 6024 to facilitate the opening thereof. In various embodiments, a spring (not shown) may be employed to bias the anvil 6024 to the open position when the distal closure tube 6042 has been moved to its starting position. In various embodiments, the various gears of the closure gear assembly 6520 are sized to generate the necessary closure forces needed to satisfactorily close the anvil 6024 onto the tissue to be cut and stapled by the surgical end effector 6012. For example, the gears of the closure transmission 6520 may be sized to generate approximately 70-120 pounds of closure forces.

In various embodiments, the cutting instrument is driven through the surgical end effector 6012 by a knife bar 6530. See FIG. 115. In at least one form, the knife bar 6530 is fabricated with a joint arrangement (not shown) and/or is fabricated from material that can accommodate the articulation of the surgical end effector 6102 about the first and second tool articulation axes while remaining sufficiently rigid so as to push the cutting instrument through tissue clamped in the surgical end effector 6012. The knife bar 6530 extends through a hollow passage 6532 in the proximal spine portion 6110.

In various embodiments, a proximal end 6534 of the knife bar 6530 is rotatably affixed to a knife rack gear 6540 such that the knife bar 6530 is free to rotate relative to the knife rack gear 6540. The distal end of the knife bar 6530 is attached to the cutting instrument in the various manners described above. As can be seen in FIG. 115, the knife rack gear 6540 is slidably supported within a rack housing 6542 that is attached to the tool mounting plate 6202 such that the knife rack gear 6540 is retained in meshing engagement with a knife drive transmission portion 6550 of the transmission arrangement 6204. In various embodiments, the knife drive transmission portion 6550 comprises a knife gear assembly 6560. More specifically and with reference to FIG. 115, in at least one embodiment, the knife gear assembly 6560 includes a knife spur gear 6562 that is coupled to a corresponding fourth one of the driven discs or elements 1304 on the adapter side 1307 of the tool mounting plate 6202. See FIG. 10. Thus, application of another rotary output motion from the robotic system 1000 through the tool drive assembly 1010 to the corresponding fourth driven element 1304 will cause rotation of the knife spur gear 6562. The knife gear assembly 6560 further includes a knife gear reduction set 6564 that includes a first knife driven gear 6566 and a second knife drive gear 6568. The knife gear reduction set 6564 is rotatably mounted to the tool mounting plate 6202 such that the first knife driven gear 6566 is in meshing engagement with the knife spur gear 6562. Likewise, the second knife drive gear 6568 is in meshing engagement with a third knife drive gear assembly 6570. As shown in FIG. 115, the second knife driven gear 6568 is in meshing engagement with a fourth knife driven gear 6572 of the third knife drive gear assembly 6570. The fourth knife driven gear 6572 is in meshing engagement with a fifth knife driven gear assembly 6574 that is in meshing engagement with the knife rack gear 6540. In various embodiments, the gears of the knife gear assembly 6560 are sized to generate the forces needed to drive the cutting instrument through the tissue clamped in the surgical end effector 6012 and actuate the staples therein. For example, the gears of the knife gear assembly 6560 may be sized to generate approximately 40 to 100 pounds of driving force. It will be appreciated that the application of a rotary output motion from the tool drive assembly 1010 in one direction will result in the axial movement of the cutting instrument in a distal direction and application of the rotary output motion in an opposite direction will result in the axial travel of the cutting instrument in a proximal direction.

As can be appreciated from the foregoing description, the surgical tool 6000 represents a vast improvement over prior robotic tool arrangements. The unique and novel transmission arrangement employed by the surgical tool 6000 enables the tool to be operably coupled to a tool holder portion 1010 of a robotic system that only has four rotary output bodies, yet obtain the rotary output motions therefrom to: (i) articulate the end effector about two different articulation axes that are substantially transverse to each other as well as the longitudinal tool axis; (ii) rotate the end effector 6012 about the longitudinal tool axis; (iii) close the anvil 6024 relative to the surgical staple cartridge 6034 to varying degrees to enable the end effector 6012 to be used to manipulate tissue and then clamp it into position for cutting and stapling; and (iv) firing the cutting instrument to cut through the tissue clamped within the end effector 6012. The unique and novel shifter arrangements of various embodiments of the present invention described above enable two different articulation actions to be powered from a single rotatable body portion of the robotic system.

The various embodiments of the present invention have been described above in connection with cutting-type surgical instruments. It should be noted, however, that in other embodiments, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, the present invention may be in laparoscopic instruments, for example. The present invention also has application in conventional endoscopic and open surgical instrumentation as well as robotic-assisted surgery.

FIG. 117 depicts use of various aspects of certain embodiments of the present invention in connection with a surgical tool 7000 that has an ultrasonically powered end effector 7012. The end effector 7012 is operably attached to a tool mounting portion 7100 by an elongated shaft assembly 7008. The tool mounting portion 7100 may be substantially similar to the various tool mounting portions described hereinabove. In one embodiment, the end effector 7012 includes an ultrasonically powered jaw portion 7014 that is powered by alternating current or direct current in a known manner. Such ultrasonically-powered devices are disclosed, for example, in U.S. Pat. No. 6,783,524, entitled ROBOTIC SURGICAL TOOL WITH ULTRASOUND CAUTERIZING AND CUTTING INSTRUMENT, the entire disclosure of which is herein incorporated by reference. In the illustrated embodiment, a separate power cord 7020 is shown. It will be understood, however, that the power may be supplied thereto from the robotic controller 1001 through the tool mounting portion 7100. The surgical end effector 7012 further includes a movable jaw 7016 that may be used to clamp tissue onto the ultrasonic jaw portion 7014. The movable jaw portion 7016 may be selectively actuated by the robotic controller 1001 through the tool mounting portion 7100 in anyone of the various manners herein described.

FIG. 118 illustrates use of various aspects of certain embodiments of the present invention in connection with a surgical tool 8000 that has an end effector 8012 that comprises a linear stapling device. The end effector 8012 is operably attached to a tool mounting portion 8100 by an elongated shaft assembly 3700 of the type and construction describe above. However, the end effector 8012 may be attached to the tool mounting portion 8100 by a variety of other elongated shaft assemblies described herein. In one embodiment, the tool mounting portion 8100 may be substantially similar to tool mounting portion 3750. However, various other tool mounting portions and their respective transmission arrangements describe in detail herein may also be employed. Such linear stapling head portions are also disclosed, for example, in U.S. Pat. No. 7,673,781, entitled SURGICAL STAPLING DEVICE WITH STAPLE DRIVER THAT SUPPORTS MULTIPLE WIRE DIAMETER STAPLES, the entire disclosure of which is herein incorporated by reference.

Various sensor embodiments described in U.S. Patent Application Publication No. 2011/0062212, now U.S. Pat. No. 8,167,185, the disclosure of which is herein incorporated by reference in its entirety, may be employed with many of the surgical tool embodiments disclosed herein. As was indicated above, the master controller 1001 generally includes master controllers (generally represented by 1003) which are grasped by the surgeon and manipulated in space while the surgeon views the procedure via a stereo display 1002. See FIG. 1. The master controllers 1001 are manual input devices which preferably move with multiple degrees of freedom, and which often further have an actuatable handle for actuating the surgical tools. Some of the surgical tool embodiments disclosed herein employ a motor or motors in their tool drive portion to supply various control motions to the tool's end effector. Such embodiments may also obtain additional control motion(s) from the motor arrangement employed in the robotic system components. Other embodiments disclosed herein obtain all of the control motions from motor arrangements within the robotic system.

Such motor powered arrangements may employ various sensor arrangements that are disclosed in the published U.S. patent application cited above to provide the surgeon with a variety of forms of feedback without departing from the spirit and scope of the present invention. For example, those master controller arrangements 1003 that employ a manually actuatable firing trigger can employ run motor sensor(s) to provide the surgeon with feedback relating to the amount of force applied to or being experienced by the cutting member. The run motor sensor(s) may be configured for communication with the firing trigger portion to detect when the firing trigger portion has been actuated to commence the cutting/stapling operation by the end effector. The run motor sensor may be a proportional sensor such as, for example, a rheostat or variable resistor. When the firing trigger is drawn in, the sensor detects the movement, and sends an electrical signal indicative of the voltage (or power) to be supplied to the corresponding motor. When the sensor is a variable resistor or the like, the rotation of the motor may be generally proportional to the amount of movement of the firing trigger. That is, if the operator only draws or closes the firing trigger in a small amount, the rotation of the motor is relatively low. When the firing trigger is fully drawn in (or in the fully closed position), the rotation of the motor is at its maximum. In other words, the harder the surgeon pulls on the firing trigger, the more voltage is applied to the motor causing greater rates of rotation. Other arrangements may provide the surgeon with a feed back meter 1005 that may be viewed through the display 1002 and provide the surgeon with a visual indication of the amount of force being applied to the cutting instrument or dynamic clamping member. Other sensor arrangements may be employed to provide the master controller 1001 with an indication as to whether a staple cartridge has been loaded into the end effector, whether the anvil has been moved to a closed position prior to firing, etc.

In alternative embodiments, a motor-controlled interface may be employed in connection with the controller 1001 that limit the maximum trigger pull based on the amount of loading (e.g., clamping force, cutting force, etc.) experienced by the surgical end effector. For example, the harder it is to drive the cutting instrument through the tissue clamped within the end effector, the harder it would be to pull/actuate the activation trigger. In still other embodiments, the trigger on the controller 1001 is arranged such that the trigger pull location is proportionate to the end effector-location/condition. For example, the trigger is only fully depressed when the end effector is fully fired.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A robotic stapler, comprising:

a shaft;

an end effector, comprising:

a first jaw; and a second jaw rotatable relative to the first jaw;

a staple firing driver movable distally through a staple firing stroke;

a first articulation joint, wherein the end effector is articulatable relative to the shaft about the first articulation joint in a first plane;

a second articulation joint, wherein the end effector is articulatable relative to the shaft about the second articulation joint in a second plane transverse to the first plane;

a first cable extending distally to the first articulation joint, wherein an actuation of the first cable is to generate a first articulation motion at the first articulation joint in the first plane;

a second cable extending distally to the second articulation joint, wherein an actuation of the second cable is to generate a second articulation motion at the second articulation joint in the second plane; and an articulation lock to simultaneously prevent the first articulation motion and the second articulation motion.

2. The robotic stapler of claim 1, wherein the articulation lock is biased toward a locked configuration.

3. The robotic stapler of claim 1, wherein the articulation lock comprises a solenoid.

4. The robotic stapler of claim 1, wherein the articulation lock comprises a spring.

5. The robotic stapler of claim 1, wherein the end effector further comprises a staple cartridge, wherein the staple cartridge comprises a plurality of staples.

6. The robotic stapler of claim 1, further comprising a firing beam comprising:

a first lateral cam configured to engage the first jaw; and a second lateral cam configured to engage the second jaw.

7. The robotic stapler of claim 6, further comprising a firing driver comprising a flexible portion, wherein the firing driver is configured to push the firing beam distally to fire staples, and wherein the firing driver extends through the first articulation joint and the second articulation joint.

8. The robotic stapler of claim 1, further comprising a proximal housing comprising a plurality of motor-driven drive inputs, wherein the shaft is rotatable relative to the proximal housing about a longitudinal shaft axis.

9. The robotic stapler of claim 8, wherein the articulation lock is internal to the proximal housing.

10. The robotic stapler of claim 1, wherein the articulation lock is electrically coupled to and driven by a robotic controller.

11. A robotic stapler, comprising:

a shaft defining a longitudinal axis;

an end effector, comprising:

a first jaw; and a second jaw rotatable relative to the first jaw;

a staple firing driver movable distally through a staple firing stroke;

an articulation region, wherein the end effector is articulatable relative to the longitudinal axis in a first direction, a second direction opposite the first direction, a third direction different than the first direction and the second direction, and a fourth direction opposite the third direction;

a plurality of actuation cables actuatable to generate articulations motions in the first direction, the second direction, the third direction, and the fourth direction; and an articulation lock to simultaneously prevent actuation of the plurality of actuation cables.

12. The robotic stapler of claim 11, wherein the articulation lock is biased toward a locked configuration.

13. The robotic stapler of claim 12, wherein the articulation lock comprises a solenoid.

14. The robotic stapler of claim 13, wherein the end effector further comprises a staple cartridge, wherein the staple cartridge comprises a plurality of staples.

15. The robotic stapler of claim 12, wherein the articulation lock comprises a spring.

16. The robotic stapler of claim 11, further comprising a proximal housing comprising a plurality of motor-driven drive inputs structured to receive drive inputs from a robot, wherein the shaft is rotatable relative to the proximal housing about a longitudinal shaft axis.

17. The robotic stapler of claim 16, wherein the articulation lock is internal to the proximal housing.

18. The robotic stapler of claim 11, wherein the articulation lock is electrically coupled to and driven by a robotic controller.

* * * * *